(12) United States Patent
Ostertag et al.

(10) Patent No.: US 11,744,861 B2
(45) Date of Patent: Sep. 5, 2023

(54) COMPOSITIONS AND METHODS FOR SELECTIVE ELIMINATION AND REPLACEMENT OF HEMATOPOIETIC STEM CELLS

(71) Applicant: Poseida Therapeutics, Inc., San Diego, CA (US)

(72) Inventors: Eric M. Ostertag, San Diego, CA (US); Devon Shedlock, San Diego, CA (US); Julian David Down, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 443 days.

(21) Appl. No.: 16/493,853

(22) PCT Filed: Mar. 13, 2018

(86) PCT No.: PCT/US2018/022169
§ 371 (c)(1),
(2) Date: Sep. 13, 2019

(87) PCT Pub. No.: WO2018/169948
PCT Pub. Date: Sep. 20, 2018

(65) Prior Publication Data
US 2020/0078402 A1 Mar. 12, 2020

Related U.S. Application Data

(60) Provisional application No. 62/596,062, filed on Dec. 7, 2017, provisional application No. 62/470,814, filed on Mar. 13, 2017.

(51) Int. Cl.
| | | |
|---|---|---|
| *A61K 35/17* | (2015.01) | |
| *A61K 9/00* | (2006.01) | |
| *A61K 31/664* | (2006.01) | |
| *A61K 31/7076* | (2006.01) | |
| *A61K 35/28* | (2015.01) | |
| *A61K 38/17* | (2006.01) | |
| *A61K 38/19* | (2006.01) | |
| *A61K 38/48* | (2006.01) | |
| *A61K 38/52* | (2006.01) | |
| *A61K 39/39* | (2006.01) | |
| *A61K 39/395* | (2006.01) | |
| *A61K 45/06* | (2006.01) | |
| *C12N 5/0783* | (2010.01) | |
| *C12N 9/12* | (2006.01) | |
| *C12N 9/22* | (2006.01) | |
| *C12N 15/11* | (2006.01) | |

(52) U.S. Cl.
CPC ............ *A61K 35/17* (2013.01); *A61K 9/0019* (2013.01); *A61K 9/0085* (2013.01); *A61K 31/664* (2013.01); *A61K 31/7076* (2013.01); *A61K 35/28* (2013.01); *A61K 38/177* (2013.01); *A61K 38/1774* (2013.01); *A61K 38/193* (2013.01); *A61K 38/4873* (2013.01); *A61K 38/52* (2013.01); *A61K 39/39* (2013.01); *A61K 39/3955* (2013.01); *A61K 45/06* (2013.01); *C12N 5/0636* (2013.01); *C12N 9/1241* (2013.01); *C12N 9/22* (2013.01); *C12N 15/11* (2013.01); *C12Y 207/07* (2013.01); *C12Y 304/22062* (2013.01); *C12Y 502/01008* (2013.01); *C12N 2310/20* (2017.05); *C12N 2510/00* (2013.01); *C12N 2800/80* (2013.01)

(58) Field of Classification Search
CPC ... A61K 35/17; A61K 38/177; A61K 38/1774
See application file for complete search history.

(56) References Cited

U.S. PATENT DOCUMENTS

| | | | |
|---|---|---|---|
| 4,656,134 | A | 4/1987 | Ringold |
| 4,683,195 | A | 7/1987 | Mullis et al. |
| 4,683,202 | A | 7/1987 | Mullis |
| 4,704,692 | A | 11/1987 | Ladner |
| 4,766,067 | A | 8/1988 | Biswas |
| 4,795,699 | A | 1/1989 | Tabor et al. |
| 4,800,159 | A | 1/1989 | Mullis et al. |

(Continued)

FOREIGN PATENT DOCUMENTS

| | | |
|---|---|---|
| CN | 105936649 B | 7/2019 |
| WO | WO 91/17271 A1 | 11/1991 |

(Continued)

OTHER PUBLICATIONS

US 5,733,746 A, 03/1998, Treco et al. (withdrawn)

(Continued)

*Primary Examiner* — Vanessa L Ford
*Assistant Examiner* — Sandra Dillahunt
(74) *Attorney, Agent, or Firm* — Cooley LLP; Ivor R. Elrifi; Matthew Pavao

(57) ABSTRACT

Disclosed are methods of eliminating at least on target cell in a subject, comprising administering to the subject an effective amount of a composition comprising a plurality of immune cells, wherein each immune cell of the plurality expresses one or more chimeric ligand receptor(s) (CLR(s)) that each specifically bind to a target ligand on the at least one target cell, wherein specifically binding of the one or more CLR(s) to the target activates the immune cell, and wherein the activated immune cell induces death of the target cell. Exemplary target cells include, but are not limited to, hematopoietic stem cells (HSCs).

19 Claims, 35 Drawing Sheets

Specification includes a Sequence Listing.

(56) References Cited

U.S. PATENT DOCUMENTS

| | | | |
|---|---|---|---|
| 4,889,818 A | 12/1989 | Gelfand et al. |
| 4,921,794 A | 5/1990 | Tabor et al. |
| 4,939,666 A | 7/1990 | Hardman |
| 4,946,778 A | 8/1990 | Ladner et al. |
| 4,965,188 A | 10/1990 | Mullis et al. |
| 4,994,370 A | 2/1991 | Silver et al. |
| 5,066,584 A | 11/1991 | Gyllensten et al. |
| 5,091,310 A | 2/1992 | Innis |
| 5,122,464 A | 6/1992 | Wilson et al. |
| 5,130,238 A | 7/1992 | Malek et al. |
| 5,142,033 A | 8/1992 | Innis |
| 5,168,062 A | 12/1992 | Stinski |
| 5,223,409 A | 6/1993 | Ladner et al. |
| 5,260,203 A | 11/1993 | Ladner et al. |
| 5,266,491 A | 11/1993 | Nagata et al. |
| 5,385,839 A | 1/1995 | Stinksi |
| 5,403,484 A | 4/1995 | Ladner et al. |
| 5,427,908 A | 6/1995 | Dower et al. |
| 5,455,030 A | 10/1995 | Ladner et al. |
| 5,518,889 A | 5/1996 | Ladner et al. |
| 5,534,621 A | 7/1996 | Ladner et al. |
| 5,571,698 A | 11/1996 | Ladner et al. |
| 5,576,195 A | 11/1996 | Robinson et al. |
| 5,580,717 A | 12/1996 | Dower et al. |
| 5,580,734 A | 12/1996 | Treco et al. |
| 5,595,898 A | 1/1997 | Robinson et al. |
| 5,618,920 A | 4/1997 | Robinson et al. |
| 5,641,670 A | 6/1997 | Treco et al. |
| 5,643,768 A | 7/1997 | Kawasaki |
| 5,656,730 A | 8/1997 | Lee |
| 5,658,754 A | 8/1997 | Kawasaki |
| 5,693,493 A | 12/1997 | Robinson et al. |
| 5,698,417 A | 12/1997 | Robinson et al. |
| 5,698,435 A | 12/1997 | Robinson et al. |
| 5,733,761 A | 3/1998 | Treco et al. |
| 5,750,373 A | 5/1998 | Garrard et al. |
| 5,763,733 A | 6/1998 | Whitlow et al. |
| 5,767,260 A | 6/1998 | Whitlow et al. |
| 5,770,359 A | 6/1998 | Wilson et al. |
| 5,827,739 A | 10/1998 | Wilson et al. |
| 5,837,500 A | 11/1998 | Ladner et al. |
| 5,856,456 A | 1/1999 | Whitlow et al. |
| 5,885,793 A | 3/1999 | Griffiths et al. |
| 2017/0157176 A1 | 6/2017 | Wang et al. |

FOREIGN PATENT DOCUMENTS

| | | |
|---|---|---|
| WO | WO 91/18980 A1 | 12/1991 |
| WO | WO 91/19818 A1 | 12/1991 |
| WO | WO 92/05258 A1 | 4/1992 |
| WO | WO 92/14843 A1 | 9/1992 |
| WO | WO 92/16221 A1 | 10/1992 |
| WO | WO 93/08278 A1 | 4/1993 |
| WO | WO 96/19256 A1 | 6/1996 |
| WO | WO 2008/067115 A2 | 6/2008 |
| WO | WO 2016/205554 A1 | 12/2016 |
| WO | WO-2016210293 A1 | 12/2016 |
| WO | WO-2017032777 A1 | 3/2017 |

OTHER PUBLICATIONS

Minagawa et al. PLOS One 11(12):e0166891, 2016 (Year: 2016).*
Paul. Fundamental Immunology, 3rd Edition, Raven Press, New York, Chapter 8, pp. 292-295, 1993 (Year: 1993).*
MacCallum et al. Journal of Molecular Biology, 262:732-745, 1996 (Year: 1996).*
Dotti et al. Immunology Reviews, 2014: 1-35, pp. 1-5 (Year: 2014).*
Minagawa et al. PLoS ONE 11(12): e0166891. doi:10.1371/journal.pone.0166891 (Year: 2016).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Dotti et al. Immunology Reviews, 2014: 257(1); 1-35 (Year: 2014).*
Minagawa et al. In vitro pre-clinical validation of suicide gene modified anti-CD33 refirected chimeric antigen receptor T-cells for acute myeloid leukemia. PLoS ONE 11(12): e0166891. doi:10.1371/journal. pone.0166891 (Year: 2016).*
Capellas, M. et al. (1997) "Enzymatic Condensation of Cholecystokinin CCK-8 (4-6) and CCK-8 (7-8) Peptide Fragments inOrganic Media" *Biotechnol Bioeng*, 56(4):456-463.
Chhabra, A. et al. (Aug. 10, 2016) "Hematopoietic stem cell transplantation in immunocompetent hosts without radiation or chemotherapy" *Science Transl Med*, 8(351):351ra105, 11 pages.
Cunningham, B.C. and J.A. Wells (Jun. 2, 1989) "High-Resolution Epitope Mapping of hGH-Receptor Interactions by Alaninie-Scanning Mutagenesis" *Science*, 244:1081-1085.
De Vos, A.M. et al. (1992) "Human Growth Hormone and Extracellular Domain of Its Receptor: Crystal Structure of the Complex" *Science*, 255:306-312.
Fesnak, A.D. et al. (Sep. 2016) "Engineered T cells: the promise and challenges of cancer immunotherapy" *Nat Rev Cancer*, 16(9):566-581.
Fisch, I. et al. (1992) "Site-Specific Modification of a Fragment of a Chimeric Monoclonal Antibody Using Reverse Proteolysis" *Bioconjugate Chem*, 3:147-153.
Gargett, T. and Brown, M.P. (Oct. 2014) "The inducible caspase-9 suicide gene system as a "safety switch" to limit on-target, off-tumor toxicities of chimeric antigen receptor T cells" *Front Pharmacol*, 5:Article 235, 7 pages.
Itoh, K. et al. (1996) "Application of Inverse Substrates to Trypsin-Catalyzed Peptide Synthesis" *Bioorg Chem*, 24(1):59-68.
Kumaran, S. et al. (1997) "Conformationally driven protease-catalyzed splicing of peptide segments: V8 protease-mediated synthesis of fragments derived from thermolysin and ribonuclease A" *Protein Sci*, 6(10):2233-2241.
Minagawa, K. et al. (Dec. 1, 2016) "In Vitro Pre-Clinical Validation of Suicide Gene Modified Anti-CD33 Redirected Chimeric Antigen Receptor T-Cells for Acute Myeloid Leukemia" *PLOS One*, e0166891, 25 pages.
Philip, B. et al. (2014) "A highly compact epitope-based marker/suicide gene for easier and safer T-cell therapy" *Blood*, 124(8):1277-1287.
Smith, L.J. et al. (1992) "Human Interleukin 4. The Solution Structure of a Four-helix Bundle Protein" *J Mol Biol*, 224:899-904.
Sprague, J. et al. (Feb. 1983) "Expression of a Recombinant DNA Gene Coding for the Vesicular Stomatitis Virus Nucleocapsid Protein" *J Virol*, 45:773-781.
Timberlake, N. et al. (Dec. 1, 2017) "The Application of 'Drug-Reversible' CAR-T Cells Directed Against Recipient Hematopoietic Cells As a Selective Conditioning Strategy for Stem Cell Transplantation" *Blood*, 130(Suppl. 1):1893 [online]. Retrieved from: https://ashpublications.org/blood/article/130/Supplement%201/1893/71519/The-Application-of-Drug-Reversible-CAR-T-Cells?searchresult=1; 2 printed pages.
Werlen, R.C. et al. (1994) "Site-Specific Conjugation of an Enzyme and an Antibody Fragment" *Bioconjugate Chem*, 5:411-417 (1994).
Zhou, X. et al. (2016) "Improving the safety of T-Cell therapies using an inducible caspase-9 gene" *Experimental Hematology*, 44(11):1013-1019.
Burgess et al. (1990). "Possible dissociation of the heparin-binding and mitogenic activities of heparin-binding (acidic fibroblast) growth factor-1 from its receptor-binding activities by site-directed mutagenesis of a single lysine residue." J. Cell Biol. 111:2129-2138.
Czechowicz, A. et al. "Efficient transplantation via antibody-based clearance of hematopoietic stem cell niches", Science, vol. 318, No. 5854, Nov. 1, 2007, pp. 1296-1299, DOI: 10.1126/SCIENCE. 1149726., with Supporting Online Material, 16 pages.
Lazar, E. et al. (1988) "Transforming Growth Factor alpha: Mutation of Aspartic Acid 47 and Leucine 48 Results in Different Biological Activities." Molecular and Cellular Biology, 8(3):1247-1252.
Vajdos, F.F. et al. (2002) "Comprehensive functional maps of the antigen-binding site of an anti-ErbB2 antibody obtained with shot-

(56) References Cited

OTHER PUBLICATIONS gun scanning mutagenesis" Journal of Molecular Biology, 320(2):415-428.

* cited by examiner

FIG. 5B

Color code: Heavy Chain; Light chain; linker c-kit ScFv (1)

QVQLKQSGAELVRPGASVKLSCKASGYTFTDYYINWVKQRPGQGLEWIARIYPGSGNTYYNEKFKGKATLTAEKSSSTAYMQLSSLT
SEDSAVYFCARGVYYFDYWGQGTTLTVSAGGGGSGGGGSGGGGSDIVMTQSQKFMSTSVGDRVSVTCKASQNVRTNVAWYQQ
KPGQSPKALIYSASYRYSGVPDRFTGSGSGTDFTLTISNVQSEDLADYFCQQYNSYPRTFGGGTKLEIKR c-kit ScFv (2)

DIVMTQSQKFMSTSVGDRVSVTCKASQNVRTNVAWYQQKPGQSPKALIYSASYRYSGVPDRFTGSGSGTDFTLTISNVQSEDLADY
FCQQYNSYPRTFGGGTKLEIKRGGGGSGGGGSGGGGSQVQLKQSGAELVRPGASVKLSCKASGYTFTDYYINWVKQRPGQGLEWI
ARIYPGSGNTYYNEKFKGKATLTAEKSSSTAYMQLSSLTSEDSAVYFCARGVYYFDYWGQGTTLTVSA c-kit ScFv (3)

QVQLKQSGAELVRPGASVKLSCKASGYTFTDYYINWVKQRPGQGLEWIARIYPGSGNTYYNEKFKGKATLTAEKSSSTAYMQLSSLT
SEDSAVYFCARGVYYFDYWGQGTTLTVSSGGGGSGGGGSGGGGSDIVMTQSQKFMSTSVGDRVSVTCKASQNVRTNVAWYQQ
KPGQSPKALIYSASYRYSGVPDRFTGSGSGTDFTLTISNVQSEDLADYFCQQYNSYPRTFGGGTKLEIKR c-kit ScFv (4)

DIVMTQSQKFMSTSVGDRVSVTCKASQNVRTNVAWYQQKPGQSPKALIYSASYRYSGVPDRFTGSGSGTDFTLTISNVQSEDLADY
FCQQYNSYPRTFGGGTKLEIKRGGGGSGGGGSGGGGSQVQLKQSGAELVRPGASVKLSCKASGYTFTDYYINWVKQRPGQGLEWI
ARIYPGSGNTYYNEKFKGKATLTAEKSSSTAYMQLSSLTSEDSAVYFCARGVYYFDYWGQGTTLTVSS c-kit ScFv (5)

EVQLLESGGGLVQPGGSLRLSCAASGFTFSNYLMSWVRQAPGKGLEWVSSIVPSGGFTHYADSVKGRFTISRDNSKNTLYLQMNSL
RAEDTAVYYCARLQTGSWRVHAFDIWGQGTMVTVSSGGGGSGGGGSGGGGSDIQMTQSPTSLSAFVGDRVTITCQASQDIGNY
LNWYQQKSGEPPKLLVYDASFLKGVPSRFSGSGSGTQYFLTIYSLQPEDFATYFCQHSDNLSVTFGGGTKVEVK c-kit ScFv (6)

DIQMTQSPTSLSAFVGDRVTITCQASQDIGNYLNWYQQKSGEPPKLLVYDASFLKKGVPSRFSGSGSGTQYFLTIYSLQPEDFATYFC
QHSDNLSVTFGGGTKVEVKGGGGSGGGGSGGGGSEVQLLESGGGLVQPGGSLRLSCAASGFTFSNYLMSWVRQAPGKGLEWVS
SIVPSGGFTHYADSVKGRFTISRDNSKNTLYLQMNSLRAEDTAVYYCARLQTGSWRVHAFDIWGQGTMVTVSS c-kit ScFv (7)

EVQLLESGGGLVQPGGSLRLSCAASGFTFSNYLMSWVRQAPGKGLEWVSSIVPSGGFTHYADSVKGRFTISRDNSKNTLYLQMNSL
RAEDTAVYYCARLQTGSWRVHAFDIWGQGTMVTVSSGGGGSGGGGSGGGGSDIQMTQSPTSLSAFVGDRVTITCQASQDIGNY
LNWYQQKSGEPPKLLVYDASFLKGVPSRFSGSGSGTQYFLTIYSLQPEDFATYFCQHSDNLSVTFGGGTKVEVK

FIG. 5C

-kit ScFv (8)

DIQMTQSPTSLSASVGDRVTITCQASQDIGNYLNWYQQKSGEPPKLLIYDASFLRKGVPSRFSGSGSGTQYFLTIYSLQPEDFATYFC
QHSDSLSVTFGGGTKVEVKGGGGSGGGGSGGGGSEVQLLESGGGLVQPGGSLRLSCAASGFTFSNYLMSWVRQAPGKGLEWVSS
IVPSGGFTHYADSVKGRFTISRDNSKNTLYLQMNSLRAEDTAVYYCARLQTGSWRVHAFDIWGQGTMVTVSS c-kit ligand (1)

MALPVTALLLPLALLLHAARPEGICRNRVTNNVKDVTKLVANLPKDYMITLKYVPGMDVLPSHCWISEMVVQLSDSLTDLLDKFSNIS
EGLSNYSIIDKLVNIVDDLVECVKENSSKDLKKSFKSPEPRLFTPEEFFRIFNRSIDAFKDFVVASETSDCVVSSTLSPEKDSRVSVTKPFM
LPPVAASSLRNDSSSSNRKAKNPPGDSSLH c-kit ligand (2)

MALPVTALLLPLALLLHAARPEGICRNRVTNNVKDVTKLVANLPKDYMITLKYVPGMDVLPSHCWISEMVVQLSDSLTDLLDKFSNIS
EGLSNYSIIDKLVNIVDDLVECVKENSSKDLKKSFKSPEPRLFTPEEFFRIFNRSIDAFKDFVVASETSDCVVSSTLSPEKGKAKNPPGDSS
LH

Mouse c-kit ligand

MALPVTALLLPLALLLHAARPKEICGNPVTDNVKDITKLVANLPNDYMITLNYVAGMDVLPSHCWLRDMVIQLSLSLTTLLDKFSNIS
EGLSNYSIIDKLGKIVDDLVLCMEENAPKNIKESPKRPETRSFTPEEFFSIFNRSIDAFKDFMVASDTSDCVLSSTLGPEKDSRVSVTKPF
MLPPVAASSLRNDSSSSNRKAAKAPEDSGLQ

CD133 ScFv (1)

EVKLVESGPELKKPGETVKISCKASGYTFTDYSMHWVNQAPGKGLKWMGWINTETGEPSYADDFKGRFAFSLETSASTAYLQINNL
KNEDTATYFCATDYGDYFDYWGQGTTLTVSSGGGGSGGGGSGGGGSDIVLSQSPAIMSASPGEKVTISCSASSSVSYMYWYQQKP
GSSPKPWIYRTSNLASGVPARFSGSGSGTSYSLTISSMEAEDAATYYCQQYHSYPPTFGAGTKLELK

CD133 ScFv (2)

EVKLVESGPELKKPGETVKISCKASGYTFTDYSMHWVNQAPGKGLKWMGWINTETGEPSYADDFKGRFAFSLETSASTAYLQINNL
KNEDTATYFCATDYGDYFDYWGQGTTLTVSSSGGGGSGGGGGGSSRQSLDIVLSQSPAIMSASPGEKVTISCSASSSVSYMYWYQ
QKPGSSPKPWIYRTSNLASGVPARFSGSGSGTSYSLTISSMEAEDAATYYCQQYHSYPPTFGAGTKLELK

CD133 ScFv (3)

DIVLSQSPAIMSASPGEKVTISCSASSSVSYMYWYQQKPGSSPKPWIYRTSNLASGVPARFSGSGSGTSYSLTISSMEAEDAATYYCQ
QYHSYPPTFGAGTKLELKGGGGSGGGGSGGGGSEVKLVESGPELKKPGETVKISCKASGYTFTDYSMHWVNQAPGKGLKWMGWI
NTETGEPSYADDFKGRFAFSLETSASTAYLQINNLKNEDTATYFCATDYGDYFDYWGQGTTLTVSS

FIG. 5D

CD133 ScFv (4)

DIVLSQSPAIMSASPGEKVTISCSASSSVSYMYWYQQKPGSSPKPWIYRTSNLASGVPARFSGSGSGTSYSLTISSMEAEDAATYYCQ
QYHSYPPTFGAGTKLELKSSGGGGSGGGGGGSSRSSLEVKLVESGPELKKPGETVKISCKASGYTFTDYSMHWVNQAPGKGLKWM
GWINTETGEPSYADDFKGRFAFSLETSASTAYLQINNLKNEDTATYFCATDYGDYFDYWGQGTTLTVSS

CD133 ScFv (5)

EVKLVESGPELKKPGETVKISCKASGYTFTDYSMHWVNQAPGKGLKWMGWINTETGEPSYADDFKGRFAFSLETSASTAYLQINNL
KNEDTATYFCATDYGDYFDYWGQGTTLTVSSGGGGSGGGGSGGGGSDIVLTQSPAIMSASPGEKVTISCSASSSVSYMYWYQQKP
GQPPRLLIYLVSNLESGVPARFSGSGSGTDFTLNIHPVEEEDAATYYCQQYHSYPPTFGAGTKLEIK

CD133 ScFv (6)

EVKLVESGPELKKPGETVKISCKASGYTFTDYSMHWVNQAPGKGLKWMGWINTETGEPSYADDFKGRFAFSLETSASTAYLQINNL
KNEDTATYFCATDYGDYFDYWGQGTTLTVSSSGGGGSGGGGGGSSRSSLDIVLTQSPAIMSASPGEKVTISCSASSSVSYMYWYQ
QKPGQPPRLLIYLVSNLESGVPARFSGSGSGTDFTLNIHPVEEEDAATYYCQQYHSYPPTFGAGTKLEIK

CD133 ScFv (7)

DIVLTQSPAIMSASPGEKVTISCSASSSVSYMYWYQQKPGQPPRLLIYLVSNLESGVPARFSGSGSGTDFTLNIHPVEEEDAATYYCQ
QYHSYPPTFGAGTKLEIKGGGGSGGGGSGGGGSEVKLVESGPELKKPGETVKISCKASGYTFTDYSMHWVNQAPGKGLKWMGWI
NTETGEPSYADDFKGRFAFSLETSASTAYLQINNLKNEDTATYFCATDYGDYFDYWGQGTTLTVSS

CD133 ScFv (8)

DIVLTQSPAIMSASPGEKVTISCSASSSVSYMYWYQQKPGQPPRLLIYLVSNLESGVPARFSGSGSGTDFTLNIHPVEEEDAATYYCQ
QYHSYPPTFGAGTKLEIKSSGGGGSGGGGGGSSRSSLEVKLVESGPELKKPGETVKISCKASGYTFTDYSMHWVNQAPGKGLKWM
GWINTETGEPSYADDFKGRFAFSLETSASTAYLQINNLKNEDTATYFCATDYGDYFDYWGQGTTLTVSS

Example CAR sequence with all signaling domains included (CD133 ScFV (2) used as example):

Color code: CD8a leader peptide; VL; Linker; VH; CD8 hinge; CD8a TM domain; 41BB costimulatory domain; CD3zeta chain MALPVTALLLPLALLLHAARPDIVLSQSPAIMSASPGEKVTISCSASSSVSYMYWYQQKPGSSPKPWIYRTSNLASGVPARFSGSGSGTS
YSLTISSMEAEDAATYYCQQYHSYPPTFGAGTKLELKSSGGGGSGGGGGGSSRSSLEVKLVESGPELKKPGETVKISCKASGYTFTDYS
MHWVNQAPGKGLKWMGWINTETGEPSYADDFKGRFAFSLETSASTAYLQINNLKNEDTATYFCATDYGDYFDYWGQGTTLTVSS
TTTPAPRPPTPAPTIASQPLSLRPEACRPAAGGAVHTRGLDFACDIYIWAPLAGTCGVLLLSLVITLYCKRGRKKLLYIFKQPFMRPVQT
TQEEDGCSCRFPEEEEGGCELRVKFSRSADAPAYKQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR*

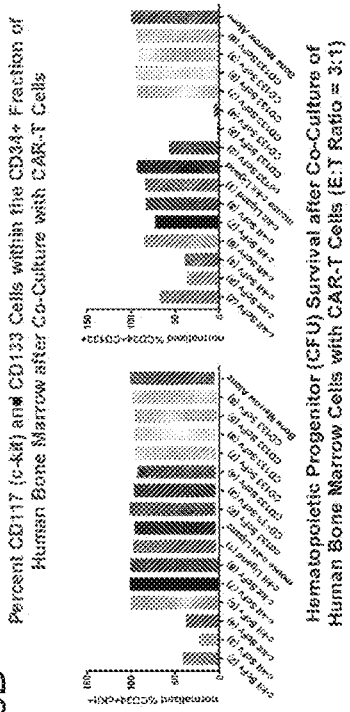
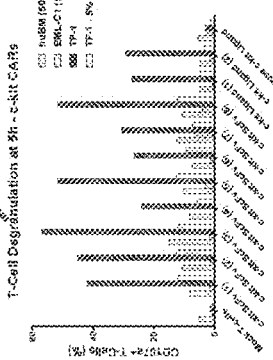
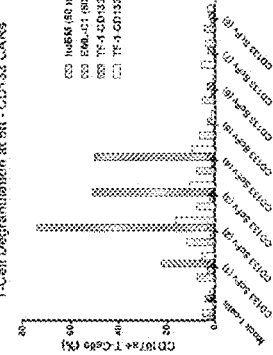
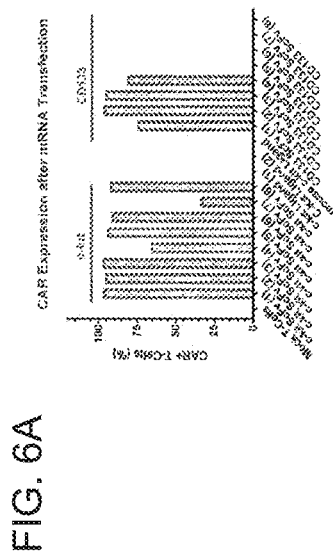
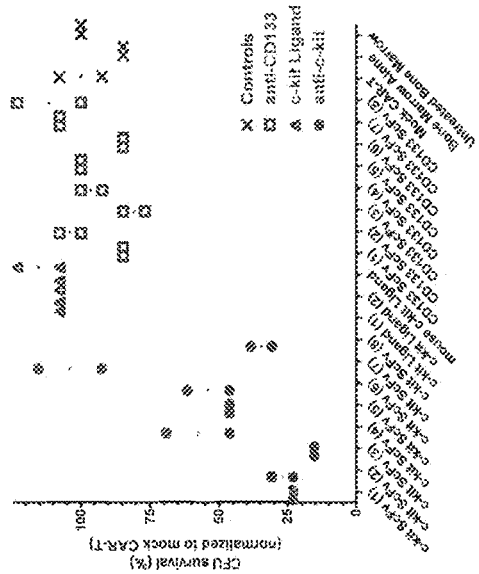
FIG. 6A  FIG. 6B  FIG. 6C  FIG. 6D  FIG. 6E

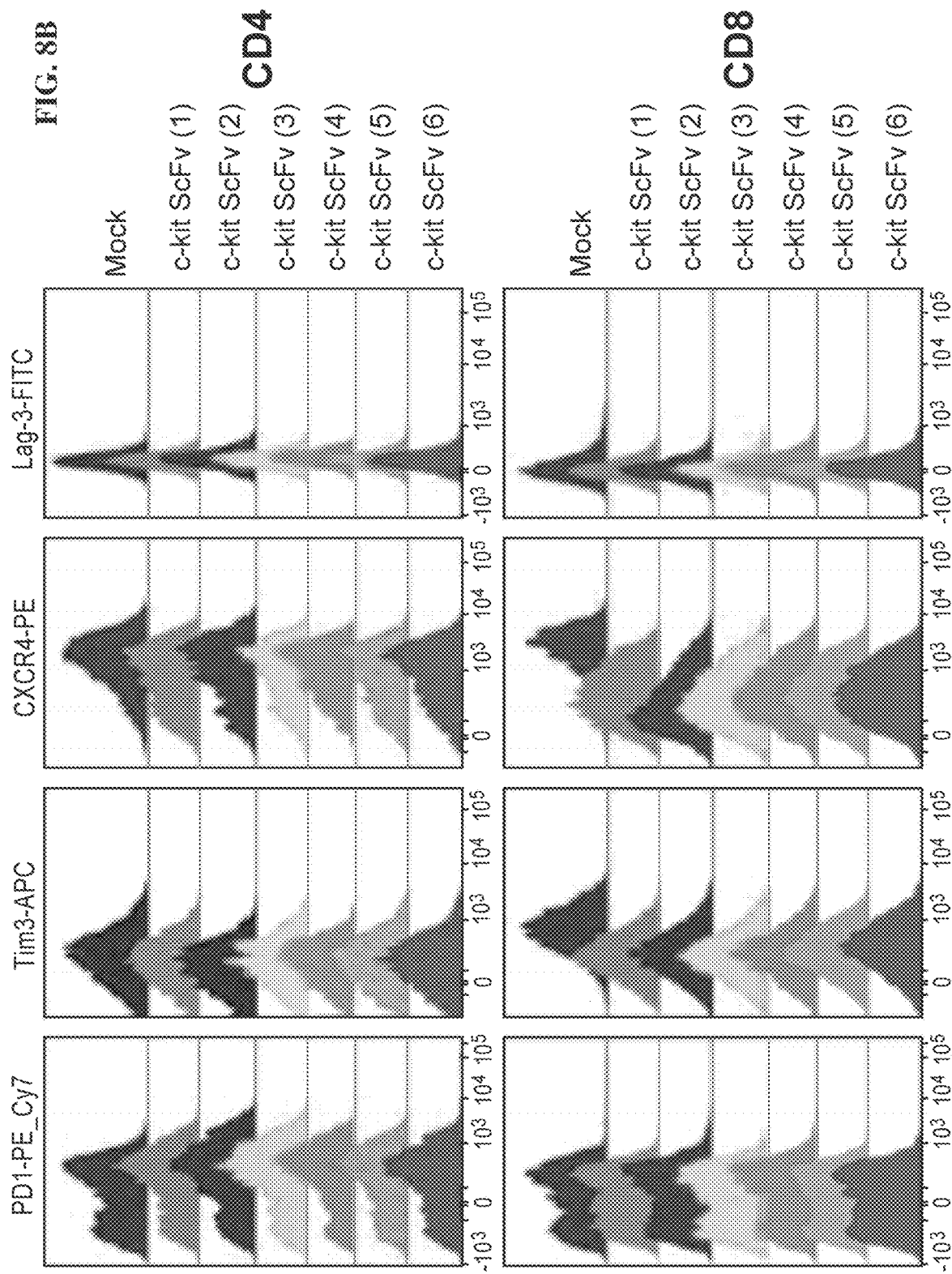

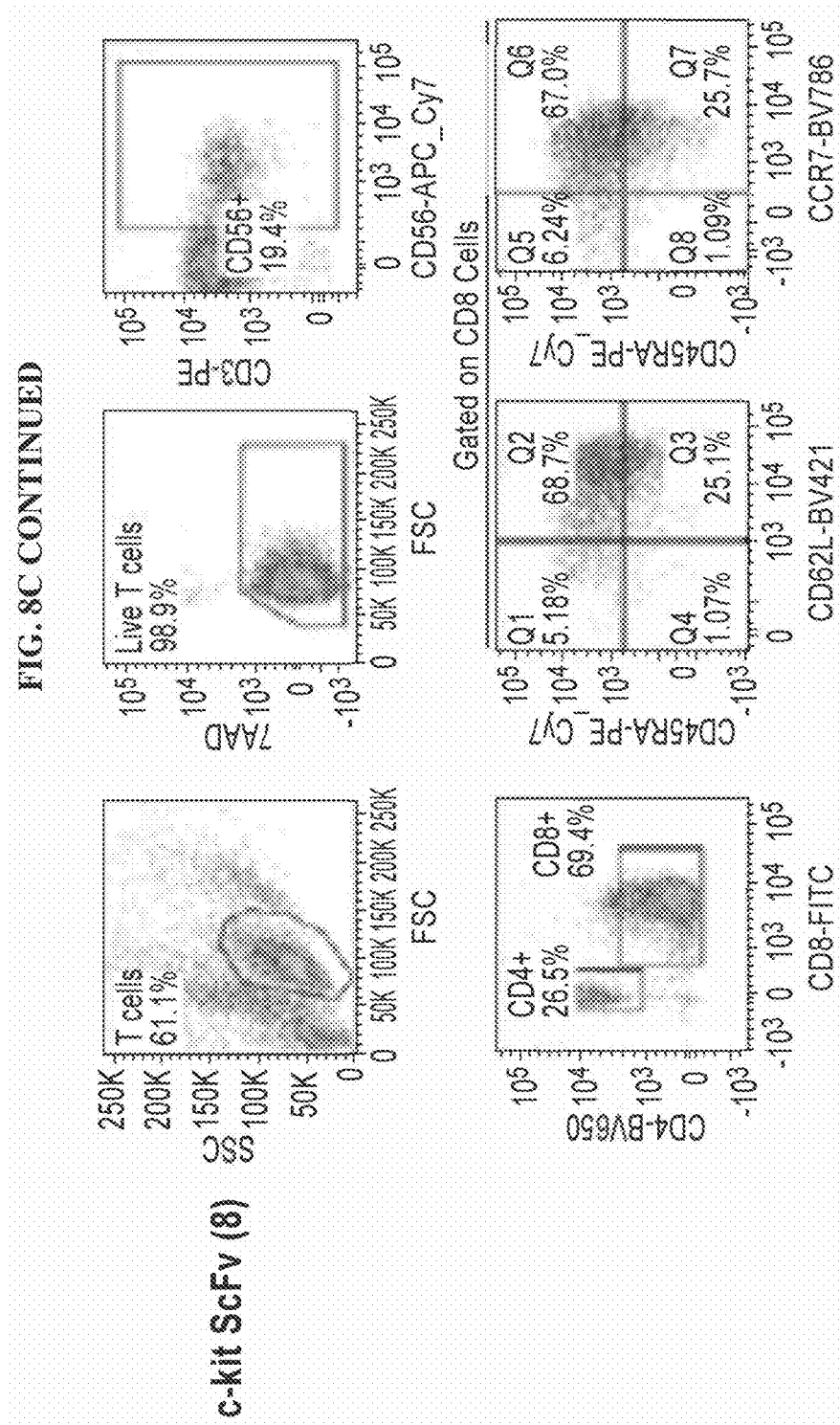

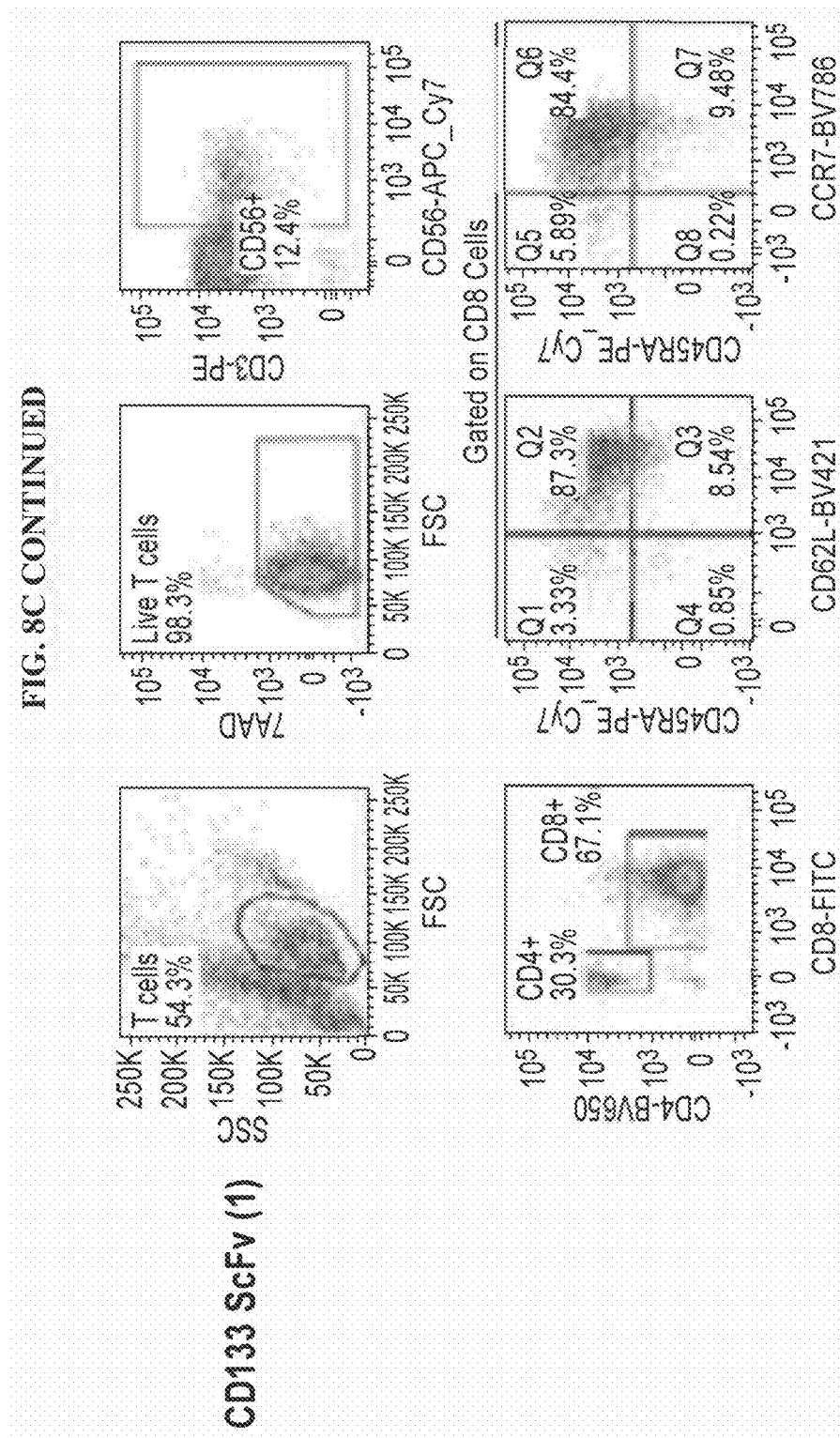

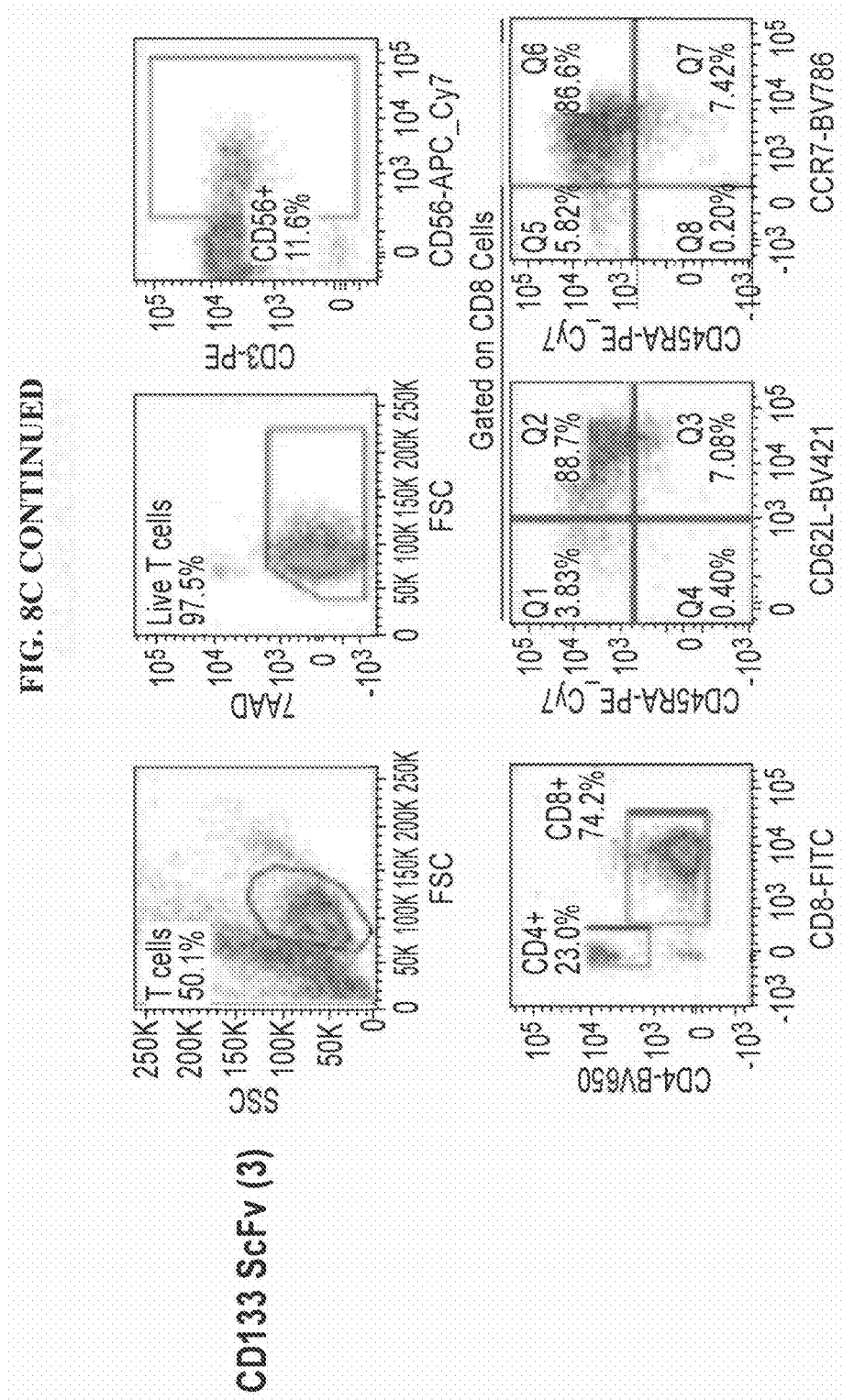

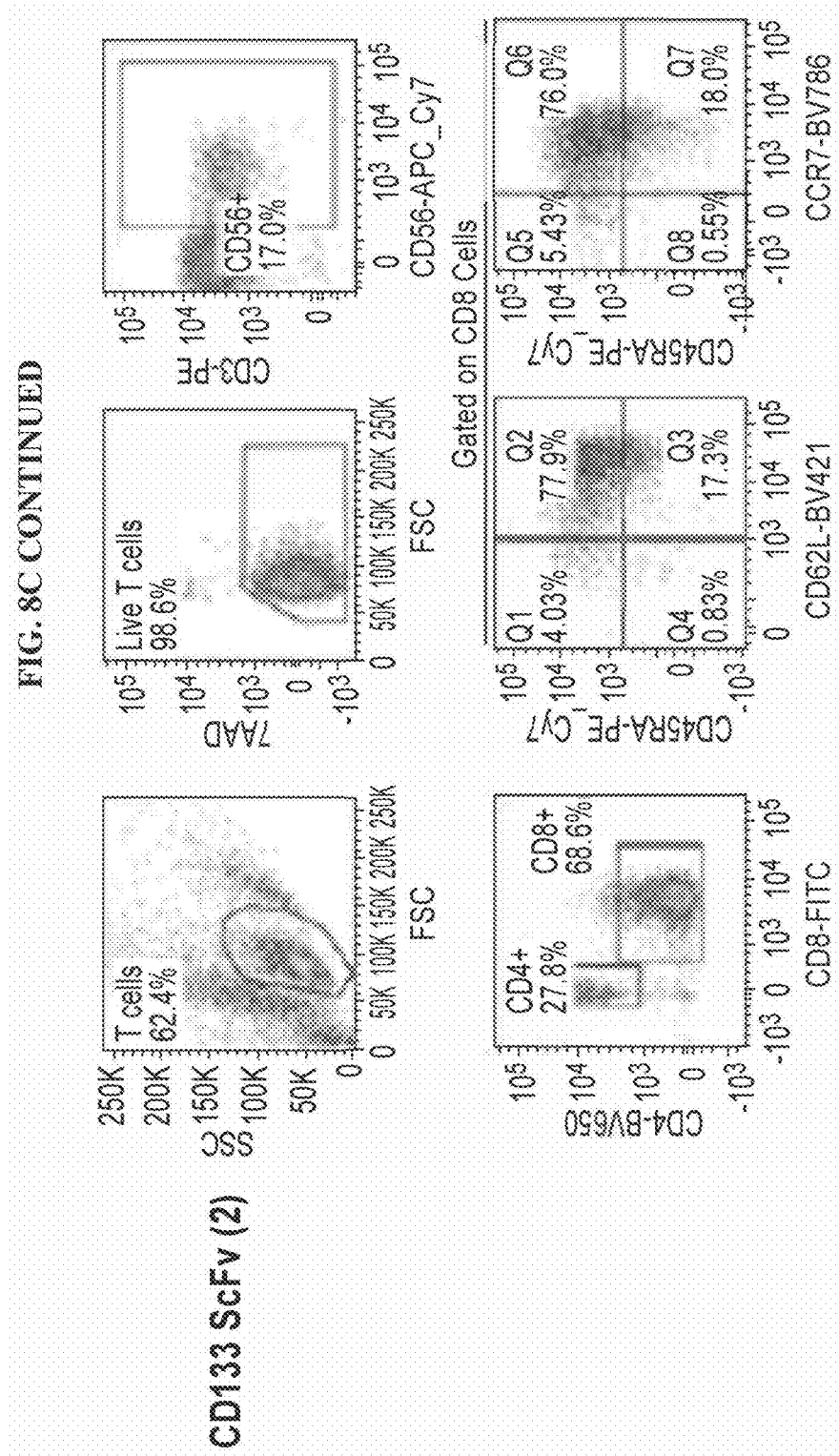

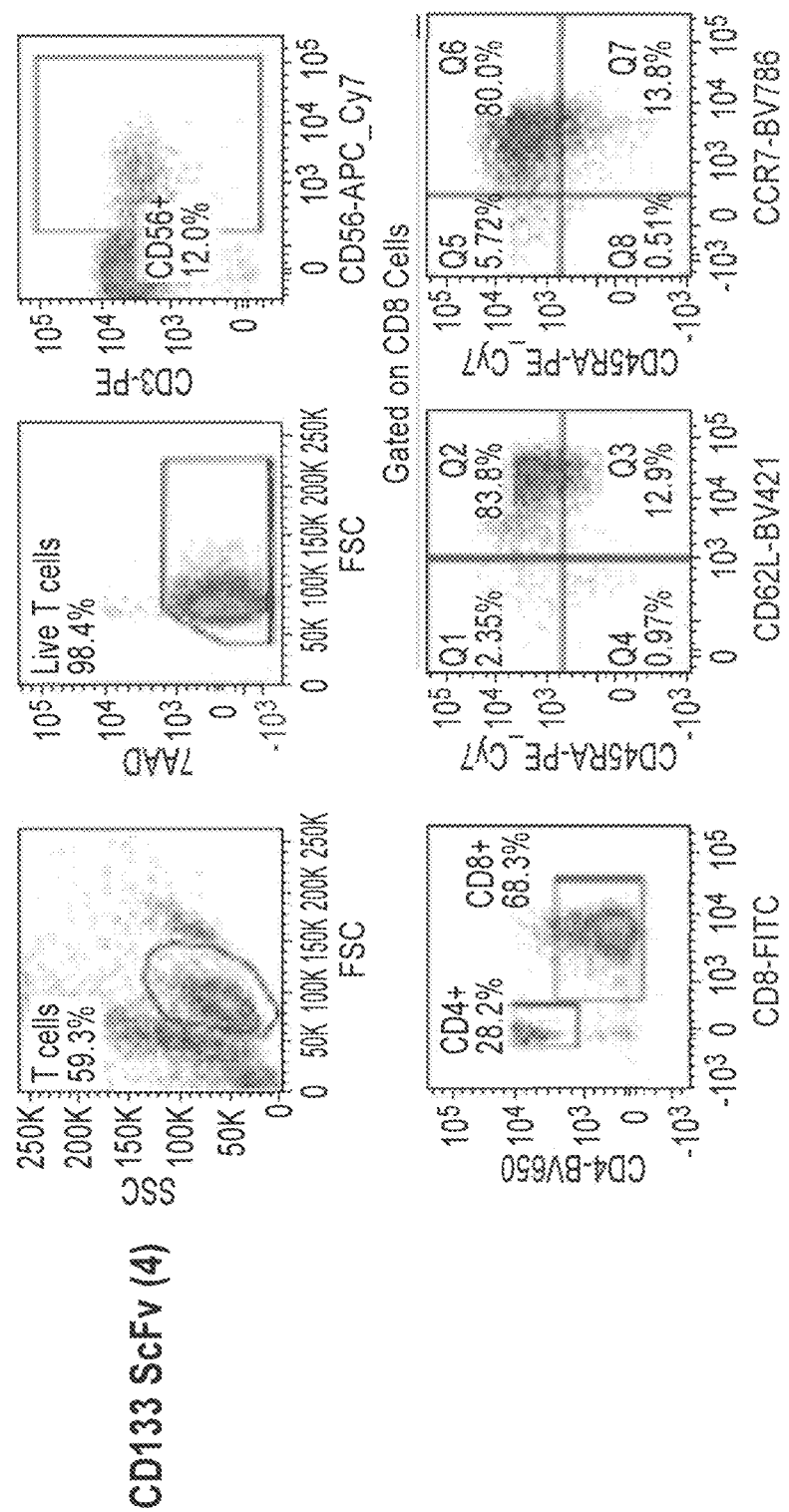

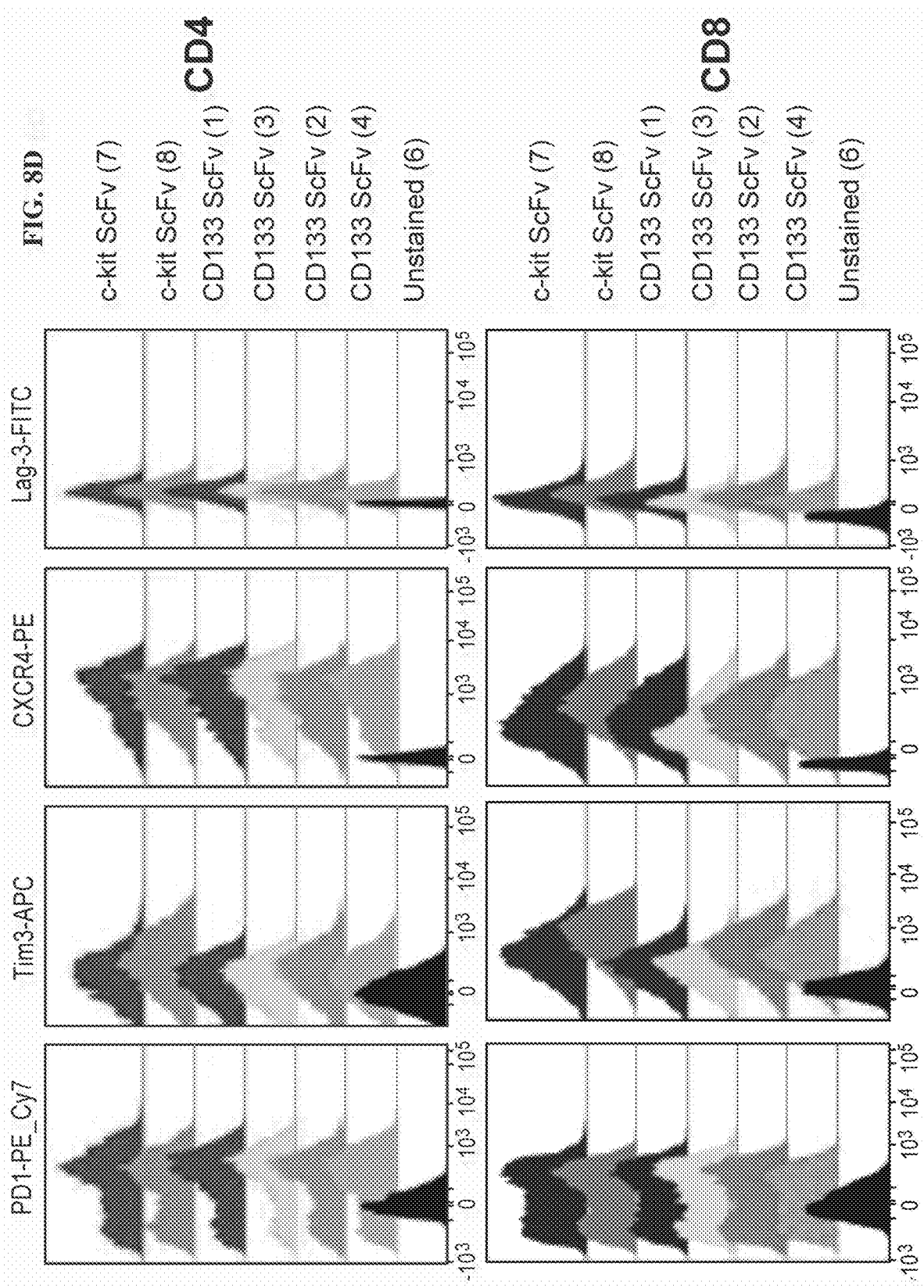

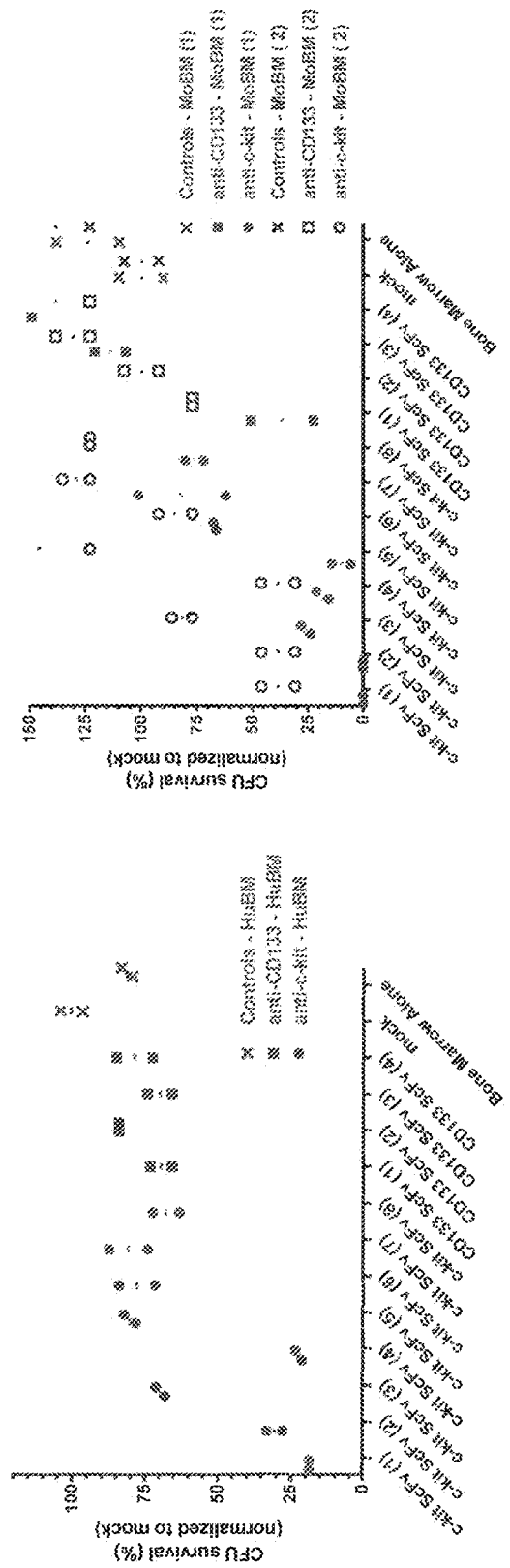
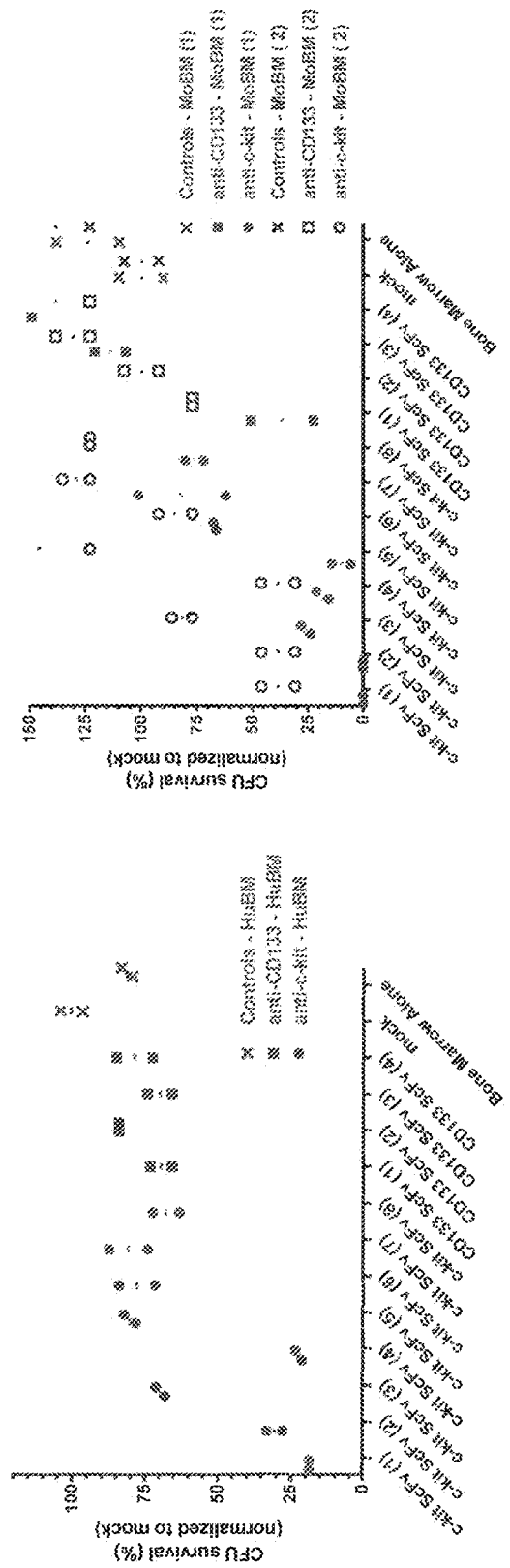
FIG. 9A Hematopoietic Progenitor (CFU) Survival after Co-Culture of Human Bone Marrow with CAR-T Cells (E:T Ratio = 3:1)
FIG. 9B Hematopoietic Progenitor (CFU) Survival after Co-Culture of Rhesus Macaque Bone Marrow with CAR-T Cells (E:T Ratio = 3:1)

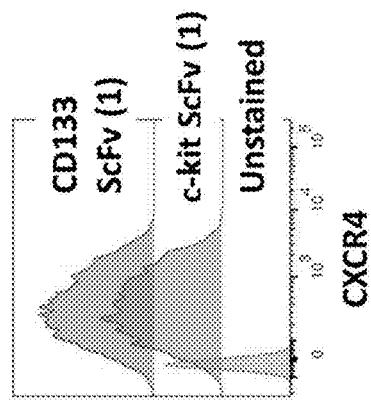
FIG. 12B
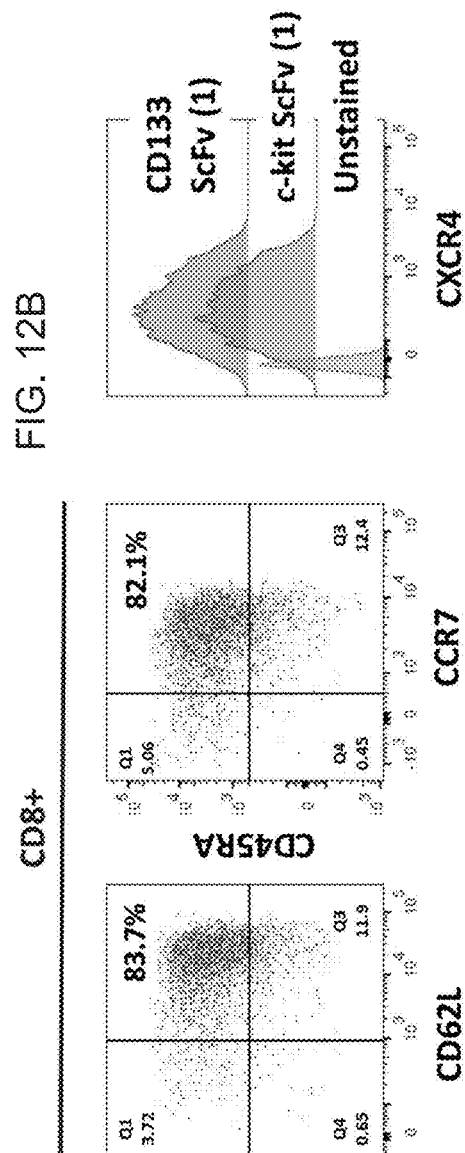
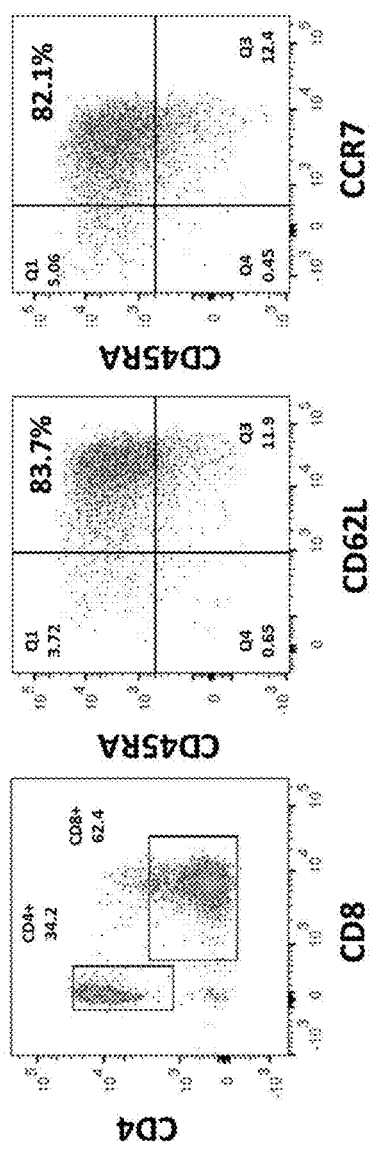
FIG. 12A

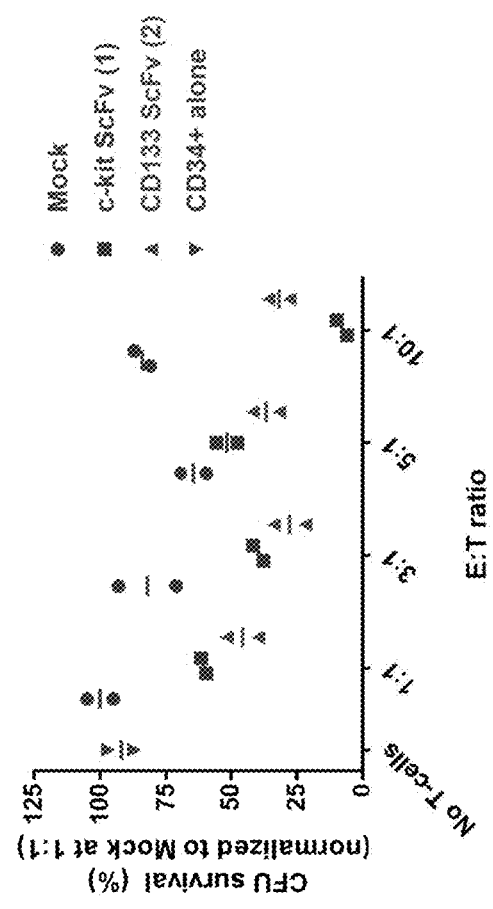
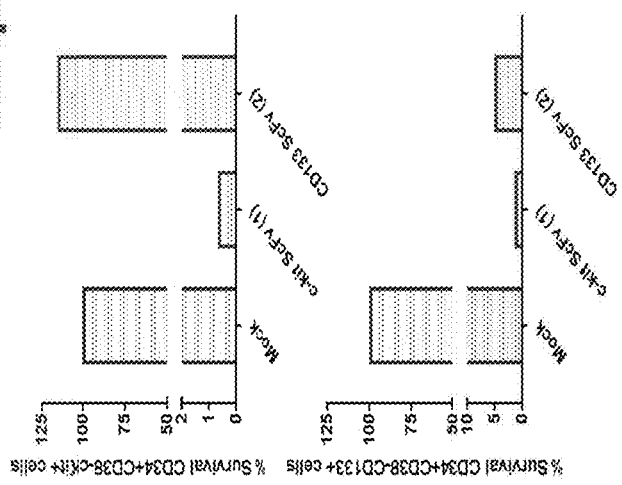
FIG. 13A
FIG. 13B

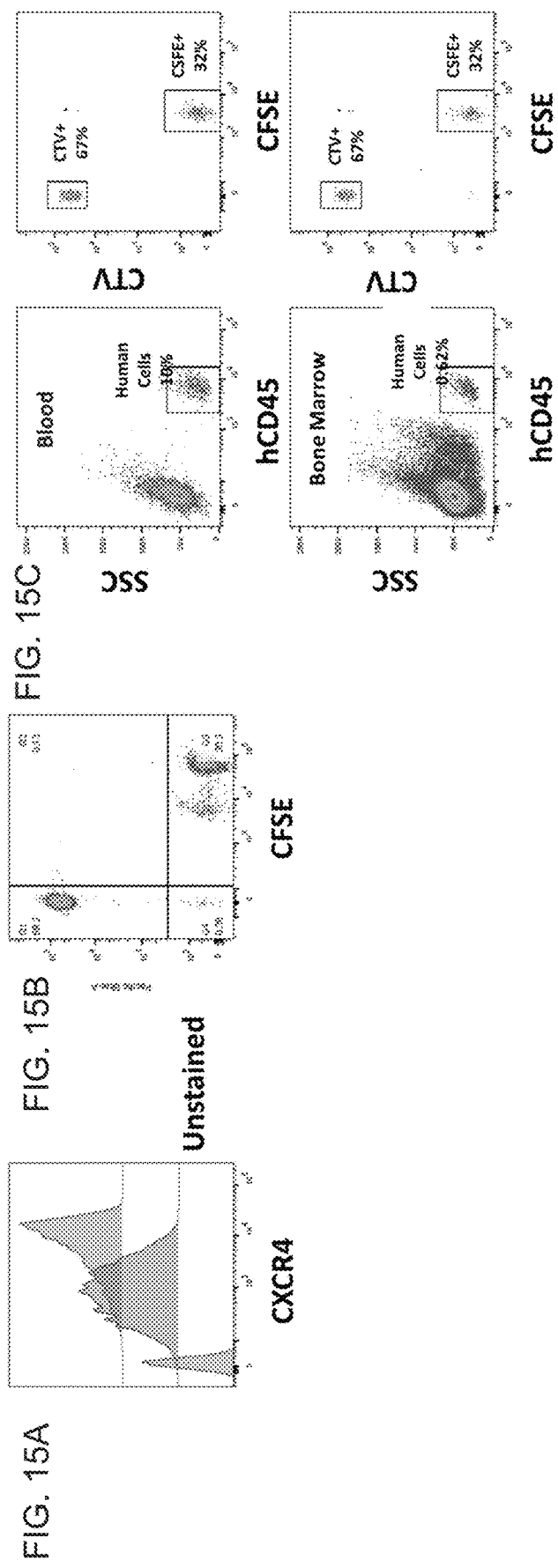

COMPOSITIONS AND METHODS FOR SELECTIVE ELIMINATION AND REPLACEMENT OF HEMATOPOIETIC STEM CELLS

CROSS-REFERENCE TO RELATED APPLICATIONS

This application is a U.S. national phase filing under 35 U.S.C. § 371 of International Application No. PCT/US2018/022169, filed on Mar. 13, 2018, which claims priority to, and the benefit of U.S. provisional application No. U.S. Ser. No. 62/470,814, filed on Mar. 13, 2017, and U.S. Ser. No. 62/596,062, filed on Dec. 7, 2017. The contents of each of the aforementioned patent applications are incorporated by reference in their entireties.

The contents of the text file named "POTH-026 N01US SeqListing ST25.txt", which was created on Sep. 12, 2019, and is 229 KB in size, are hereby incorporated by reference in their entirety.

FIELD OF THE DISCLOSURE

The disclosure is directed to molecular biology, and more, specifically, to cells expressing chimeric ligand receptors that selectively target hematopoietic stem cells (HSCs), methods of making and using the same.

BACKGROUND

There has been a long-felt but unmet need in the art for a method of selectively eliminating endogenous hematopoietic stem cells (HSCs) in a subject prior to replacement of these endogenous HSCs with a therapeutic HSC composition (for example, in the context of a bone marrow transplant). The disclosure provides compositions and methods of selectively eliminating endogenous hematopoietic stem cells (HSCs) in a subject.

SUMMARY

The disclosure provides a method of eliminating at least one target cell in a subject, comprising administering to the subject an effective amount of a composition comprising a plurality of immune cells, wherein each immune cell of the plurality expresses one or more chimeric ligand receptor(s) (CLR(s)) that each specifically bind to a target ligand on the at least one target cell, wherein specifically binding of the one or more CLR(s) to the target ligand activates the immune cell, and wherein the activated immune cell induces death of the target cell. In certain embodiments, the method further comprises the step of eliminating the plurality of immune cells.

The disclosure provides a method of transplanting an immune system of a subject, comprising: (a) administering to the subject an effective amount of a composition comprising a plurality of immune cells, wherein each immune cell of the plurality expresses one or more chimeric ligand receptor(s) (CLR(s)) that each specifically bind to a target ligand on the at least one target cell, wherein specifically binding of the one or more CLR(s) to the target ligand activates the immune cell, and wherein the activated immune cell induces death of the target cell; (b) eliminating the plurality of immune cells; and (c) administering to the subject an effective amount of a composition comprising a plurality of therapeutic hematopoietic stem cells (HSCs).

As used herein, the term "therapeutic HSCs" is meant to describe a plurality or population of HSCs that are administered to a subject following selective elimination of target cells of the disclosure. Therapeutic HSCs may include heathy or disease-free autologous or allogeneic HSCs that replace the eliminated target HSCs. Alternatively, therapeutic HSCs may include HSCs that differ from the target HSCs in a clinically-relevant manner to improve HSC function, to condition a niche or microenvironment, to condition another cell or cell type, or to tolerize the subject's immune system for a subsequent transplant with cells, tissue, or organs from the same source as the therapeutic HSCs. Therapeutic HSCs may be isolated or derived from any human source, including, but not limited to, the subject of the methods of the disclosure, a twin (for example, who does not carry one or more sporadic mutation(s) of the subject, a genetically-related individual or a combination of genetically-related individuals, and an individual with a compatible MHCI/MHCII profile or a combination of individuals with compatible MHCI/MHCII profiles. Therapeutic HSCs may include autologous or allogeneic HSCs that do not include one or more genetic or epigenetic markers of a disease or disorder. In certain embodiments, therapeutic HSCs are not genetically modified. In certain embodiments, therapeutic HSCs are genetically modified. Therapeutic HSCs may be genetically modified to eliminate one or more genetic or epigenetic markers of a disease or disorder. Alternatively, or in addition, therapeutic HSCs may be genetically modified to express on the cell surface or to secrete one or more ions, small molecules, peptides, or proteins to affect the activity of another cell or cell type (e.g. a cancer cell, a stem cell or progenitor cell (an osteoblast, a mesenchymal stem cell, a neural progenitor cell or glial cell), or an immune cell) or to condition a particular biological niche or microenvironment (an extracellular matrix, an injury site, a stem cell niche) to create more favorable conditions for engraftment of the therapeutic HSCs. Furthermore, therapeutic HSCs may be genetically modified to contain an inducible proapoptotic polypeptide of the disclosure (i.e. a safety switch) in the event that, for example, that one or more of the therapeutic HSCs is incompatible with the subject's immune system or undergoes a malignant transformation. In certain embodiments, therapeutic HSCs are administered to a subject to tolerize the subject's immune system to a subsequent transplant of a cell, tissue, graft or organ derived from the same donor as the therapeutic HSCs. Once therapeutic HSCs tolerize the subject's immune system, the immune system will be hyporeactive to the subsequent transplant and should not reject the subsequent transplant.

In certain embodiments of the methods of the disclosure, inducing death of the target cell comprises inducing cytolysis of the target cell.

In certain embodiments of the methods of the disclosure, the at least one target cell is a plurality of target cells.

In certain embodiments of the methods of the disclosure, the at least one target cell is a plurality of target cells. In certain embodiments, the at least one target cell or the plurality of target cells comprises a hematopoietic stem cell (HSC).

In certain embodiments of the methods of the disclosure, the at least one target cell is a plurality of target cells. In certain embodiments, the at least one target cell or the plurality of target cells comprises an immune cell. In certain embodiments, the immune cell is a T lymphocyte (T cell). In certain embodiments, the T cell expresses CD4 or CD8.

In certain embodiments of the methods of the disclosure, the at least one target cell is a plurality of target cells. In certain embodiments, the at least one target cell or the plurality of target cells comprises an immune cell. In certain embodiments, the immune cell is a T lymphocyte (T cell). In certain embodiments, the T cell is a helper T (TH) cell. In certain embodiments, the helper T cell (TH) is a type I helper T ($T_H$) cell. In certain embodiments, the helper T cell ($T_H$) is a type 2 helper T ($T_H2$) cell. In certain embodiments, the helper T cell ($T_H$) is a T helper 17 ($T_H17$) cell.

In certain embodiments of the methods of the disclosure, the at least one target cell is a plurality of target cells. In certain embodiments, the at least one target cell or the plurality of target cells comprises an immune cell. In certain embodiments, the immune cell is a T lymphocyte (T cell). In certain embodiments, the T cell is a regulatory T ($T_{REG}$) cell. In certain embodiments, the T cell is an induced regulatory T ($iT_{REG}$) cell or a natural regulatory T ($nT_{REG}$) cell. In certain embodiments, the T cell is an induced regulatory T ($iT_{REG}$) cell. In certain embodiments, the T cell is a natural regulatory T ($nT_{REG}$) cell.

In certain embodiments of the methods of the disclosure, the at least one target cell is a plurality of target cells. In certain embodiments, the at least one target cell or the plurality of target cells comprises an immune cell. In certain embodiments, the immune cell is a natural killer (NK) cell.

In certain embodiments of the methods of the disclosure, the at least one target cell is a plurality of target cells. In certain embodiments, the at least one target cell or the plurality of target cells comprises an HSC and an immune cell. In certain embodiments, including those in which the at least one target cell or the plurality of target cells comprises an HSC and an immune cell, the at least one target cell or the plurality of target cells comprises an HSC cell and a T cell or a NK cell. In certain embodiments, including those in which the at least one target cell or the plurality of target cells comprises an HSC and an immune cell, the at least one target cell or the plurality of target cells comprises an HSC cell and a T cell and a NK cell. In certain embodiments, wherein the at least one target cell or the plurality of target cells comprises an HSC, wherein the at least one target cell or the plurality of target cells further comprises an immune cell, and wherein the subject is at risk of rejecting the composition comprising the plurality of immune cells, each expressing one or more CLR(s). In certain embodiments, wherein the at least one target cell or the plurality of target cells comprises an HSC, wherein the at least one target cell or the plurality of target cells further comprises an immune cell, and wherein the subject is at risk of rejecting the composition comprising the plurality of therapeutic HSCs.

In certain embodiments of the methods of the disclosure, the composition comprising a plurality of immune cells is allogeneic. In certain embodiments, the allogeneic composition is derived from a healthy donor.

In certain embodiments of the methods of the disclosure, the composition comprising a plurality of immune cells is autologous. In certain embodiments, including those embodiments wherein the composition comprising a plurality of immune cells is autologous, the subject has a disease or disorder and the autologous composition is derived from a biological sample obtained from the subject prior to development of the disease or disorder, during a period of remission from the disease or disorder, or following treatment for the disease or disorder.

In certain embodiments of the methods of the disclosure, at least one immune cell of the plurality of immune cells comprises a genetic modification and wherein the genetic modification reduces or inhibits expression of a T-cell receptor or a major histocompatability complex (MHC). In certain embodiments, a portion of the immune cells of the plurality of immune cells comprises a genetic modification and wherein the genetic modification reduces or inhibits expression of a T-cell receptor or a major histocompatability complex (MHC). In certain embodiments, the portion comprises at least 2%, 5%, 10%, 15%, 20%, 25%, 30%, 35%, 40%, 45%, 50%, 55%, 60%, 65%, 70%, 75%, 80%, 85%, 90%, 95%, 99% or any percentage in between of the plurality of immune cells. In certain embodiments, each immune cell of the plurality of immune cells comprises a genetic modification and wherein the genetic modification reduces or inhibits expression of a T-cell receptor (TCR) or a major histocompatability complex (MHC). In certain embodiments, the MHC consists of or comprises MHC I, MHC II or a combination thereof. In certain embodiments, the MHC consists of or comprises MHC I. In certain embodiments, the MHC consists of or comprises MHC II. In certain embodiments, the genetic modification is a single strand break, a double strand break, a sequence deletion, a sequence insertion, a sequence substitution or any combination thereof. In certain embodiments, the sequence deletion, the sequence insertion, the sequence substitution or the combination thereof comprise(s) a sequence encoding an intron, an exon, a promoter, an enhancer, a transcriptional repressor, a CpG site or any combination thereof. In certain embodiments, the genetic modification comprises a sequence encoding a β-2 microglobulin (β2M) and wherein the genetic modification reduces or inhibits expression of a MHC I. In certain embodiments, the genetic modification comprises a sequence encoding an HLA-DRα, a CIITA or a combination thereof and wherein the genetic modification reduces or inhibits expression of a MHC II. In certain embodiments, the genetic modification comprises a sequence encoding an α chain (TCRα), a β chain (TCRβ), or a combination thereof and wherein the genetic modification reduces or inhibits expression of a TCR.

In certain embodiments of the methods of the disclosure, including those wherein at least one immune cell of the plurality of immune cells comprises a genetic modification and wherein the genetic modification reduces or inhibits expression of a T-cell receptor or a major histocompatability complex (MHC), the genetic modification is introduced by a composition comprising a DNA binding domain and an endonuclease domain. In certain embodiments, the DNA binding domain comprises a guide RNA. In certain embodiments, the DNA binding domain comprises a sequence isolated or derived from a Cas9, a Transcription Activator-Like Effector Nuclease (TALEN), a Centromere and Promoter Factor 1 (Cpf1) or a zinc-finger nuclease (ZFN). In certain embodiments, the Cas9 is a catalytically-inactive Cas9 (dCas9) or a short and catalytically-inactive Cas9 (dsCas9).

In certain embodiments, the dCas9 of the disclosure comprises a dCas9 isolated or derived from Staphyloccocus *pyogenes*. In certain embodiments, the dCas9 comprises a dCas9 with substitutions at positions 10 and 840 of the amino acid sequence of the dCas9 which inactivate the catalytic site. In certain embodiments, these substitutions are D10A and H840A. In certain embodiments, the "X" residue at position 1 of the dCas9 sequence is a methionine (M). In certain embodiments, the amino acid sequence of the dCas9 comprises the sequence of (SEQ ID NO: 3)

```
   1  XDKKYSIGLA IGTNSVGWAV ITDEYKVPSK KFKVLGNTDR HSIKKNLIGA LLFDSGETAE
  61  ATRLKRTARR RYTRRKNRIC YLQEIFSNEM AKVDDSFFHR LEESFLVEED KKHERHPIFG
 121  NIVDEVAYHE KYPTIYHLRK KLVDSTDKAD LRLIYLALAH MIKFRGHFLI EGDLNPDNSD
 181  VDKLFIQLVQ TYNQLFEENP INASGVDAKA ILSARLSKSR RLENLIAQLP GEKKNGLFGN
 241  LIALSLGLTP NFKSNFDLAE DAKLQLSKDT YDDDLDNLLA QIGDQYADLF LAAKNLSDAI
 301  LLSDILRVNT EITKAPLSAS MIKRYDEHHQ DLTLLKALVR QQLPEKYKEI FFDQSKNGYA
 361  GYIDGGASQE EFYKFIKPIL EKMDGTEELL VKLNREDLLR KQRTFDNGSI PHQIHLGELH
 421  AILRRQEDFY PFLKDNREKI EKILTFRIPY YVGPLARGNS RFAWMTRKSE ETITPWNFEE
 481  VVDKGASAQS FIERMTNFDK NLPNEKVLPK HSLLYEYFTV YNELTKVKYV TEGMRKPAFL
 541  SGEQKKAIVD LLFKTNRKVT VKQLKEDYFK KIECFDSVEI SGVEDRFNAS LGTYHDLLKI
 601  IKDKDFLDNE ENEDILEDIV LTLTLFEDRE MIEERLKTYA HLFDDKVMKQ LKRRRYTGWG
 661  RLSRKLINGI RDKQSGKTIL DFLKSDGFAN RNFMQLIHDD SLTFKEDIQK AQVSGQGDSL
 721  HEHIANLAGS PAIKKGILQT VKVVDELVKV MGRHKPENIV IEMARENQTT QKGQKNSRER
 781  MKRIEEGIKE LGSQILKEHP VENTQLQNEK LYLYYLQNGR DMYVDQELDI NRLSDYDVDA
 841  IVPQSFLKDD SIDNKVLTRS DKNRGKSDNV PSEEVVKKMK NYWRQLLNAK LITQRKFDNL
 901  TKAERGGLSE LDKAGFIKRQ LVETRQITKH VAQILDSRMN TKYDENDKLI REVKVITLKS
 961  KLVSDFRKDF QFYKVREINN YHHAHDAYLN AVVGTALIKK YPKLESEFVY GDYKVYDVRK
1021  MIAKSEQEIG KATAKYFFYS NIMNFFKTEI TLANGEIRKR PLIETNGETG EIVWDKGRDF
1081  ATVRKVLSMP QVNIVKKTEV QTGGFSKESI LPKRNSDKLI ARKKDWDPKK YGGFDSPTVA
1141  YSVLVVAKVE KGKSKKLKSV KELLGITIME RSSFEKNPID FLEAKGYKEV KKDLITKLPK
1201  YSLFELENGR KRMLASAGEL QKGNELALPS KYVNFLYLAS HYEKLKGSPE DNEQKQLFVE
1261  QHKHYLDEII EQISEFSKRV ILADANLDKV LSAYNKHRDK PIREQAENII HLFTLTNLGA
1321  PAAFKYFDTT IDRKRYTSTK EVLDATLIHQ SITGLYETRI DLSQLGGD.
```

In certain embodiments, the dCas9 of the disclosure comprises a dCas9 isolated or derived from *Staphylococcus aureus*. In certain embodiments, the dCas9 comprises a dCas9 with substitutions at positions 10 and 580 of the amino acid sequence of the dCas9 which inactivate the catalytic site. In certain embodiments, these substitutions are D10A and N580A. In certain embodiments, the dCas9 is a small and inactive Cas9 (dSaCas9). In certain embodiments, the amino acid sequence of the dSaCas9 comprises the sequence of:

(SEQ ID NO: 4)

```
   1  mkrnyilglA igitsvgygi idyetrdvid agvrlfkean venneqrrsk rgarrlkrrr
  61  rhriqrvkkl lfdynlltdh selsginpye arvkglsqkl seeefsaall hlakrrgvhn
 121  vneveedtgn elstkeqisr nskaleekyv aelqlerlkk dgevrgsinr fktsdyvkea
 181  kqllkvqkay hqldqsfidt yidlletrrt yyegpgegsp fgwkdikewy emlmghctyf
 241  peelrsvkya ynadlynaln dlnnlvitrd enekleyyek fqiienvfkq kkkptlkqia
 301  keilvneedi kgyrvtstgk peftnlkvyh dikditarke iienaelldq iakiltiyqs
 361  sediqeeltn lnseltqeei eqisnlkgyt gthnlslkai nlildelwht ndnqiaifnr
 421  lklvpkkvdl sqqkeipttl vddfilspvv krsfiqsikv inaiikkygl pndiiielar
 481  eknskdaqkm inemqkrnrq tnerieeiir ttgkenakyl iekiklhdmq egkclyslea
 541  ipledllnnp fnyevdhiip rsvsfdnsfn nkvlvkqeeA skkgnrtpfq ylsssdskis
 601  yetfkkhiln lakgkgrisk tkkeylleer dinrfsvqkd finrnlvdtr yatrglmnll
 661  rsyfrvnnld vkvksinggf tsflrrkwkf kkernkgykh haedaliian adfifkewkk
```

```
721   ldkakkvmen qmfeekqaes mpeieteqey keifitphqi khikdfkdyk yshrvdkkpn 781   relindtlys trkddkgntl ivnnlnglyd kdndklkkli nkspekllmy hhdpqtyqkl 841   klimeqygde knplykyyee tgnyltkysk kdngpvikki kyygnklnah lditddypns 901   rnkvvklslk pyrfdvyldn gvykfvtvkn ldvikkenyy evnskcyeea kklkkisnqa 961   efiasfynnd likingelyr vigvnndlln rievnmidit yreylenmnd krppriikti 1021  asktqsikky stdilgnlye vkskkhpqii kkg.
```

In certain embodiments, the endonuclease domain comprises a sequence isolated or derived from a Cas9, a Transcription Activator-Like Effector Nuclease (TALEN), or a type IIS endonuclease. In certain embodiments, the type IIS endonuclease is AciI, MnlI, AlwI, BbvI, BccI, BceAI, BsmAI, BsmFI, BspCNI, BsrI, BtsCI, HgaI, HphI, HpyAV, MboII, MylI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpul0I, BspQI, SapI, BaeI, BsaXI, CspCI, BfiI, MboII, Acc36I, FokI or Clo051. In certain embodiments, the type IIS endonuclease is Clo051. In certain embodiments, the DNA binding domain and the endonuclease domain are covalently or non-covalently linked. In certain embodiments, the DNA binding domain and the endonuclease domain are covalently linked as a fusion protein.

In certain embodiments of the methods of the disclosure, including those wherein at least one immune cell of the plurality of immune cells comprises a genetic modification and wherein the genetic modification reduces or inhibits expression of a T-cell receptor or a major histocompatability complex (MHC), the plurality of immune cells comprises resting cells, activated cells or a combination thereof. In certain embodiments, the plurality of immune cells comprises activated cells. In certain embodiments, the plurality of immune cells comprises resting cells. In certain embodiments, the plurality of immune cells comprises resting CAR-T cells, activated CAR-T cells or a combination thereof. In certain embodiments, the plurality of immune cells comprises activated CAR-T cells. In certain embodiments, the plurality of immune cells comprises resting CAR-T cells.

In certain embodiments of the methods of the disclosure, at least one of the immune cells of the plurality of immune cells expresses two or more chimeric ligand receptor(s) (CLR(s)) that each specifically bind to a target ligand on the at least one target cell. In certain embodiments, a portion of the immune cells of the plurality of immune cells expresses two or more chimeric ligand receptor(s) (CLR(s)) that each specifically bind to a target ligand on the at least one target cell. In certain embodiments, the portion comprises at least 2%, 5%, 10%, 15%, 20%, 25%, 30%, 35%, 40%, 45%, 50%, 55%, 60%, 65%, 70%, 75%, 80%, 85%, 90%, 95%, 99% or any percentage in between of the plurality of immune cells. In certain embodiments, each immune cell of the plurality of immune cells expresses two or more chimeric ligand receptor(s) (CLR(s)) that each specifically bind to a target ligand on the at least one target cell. In certain embodiments, for example, a first CAR specifically binds to a first target ligand, a second CAR specifically binds to a second target ligand and the first target ligand and the second target ligand are not identical. In certain embodiments, the first target ligand and the second target ligand are not homologous. In certain embodiments, a third or subsequent CAR specifically binds to a third or subsequent target ligand. In certain embodiments, the first target ligand, the second target ligand, and third or subsequent target ligand are not identical. In certain embodiments, the first target ligand, the second target ligand, and third or subsequent target ligand are not homologous.

In certain embodiments of the methods of the disclosure, the at least one target cell or the plurality of target cells comprises an HSC and the target ligand on the target HSC comprises one or more of c-KIT/CD117, CD45, CD34, Thy1/CD90, c-mpl/CD110, CD133, CD49f, ABCG2/CD338, carbonic anhydrase IX/CA9, CD123 and CD150. In certain embodiments, at least one of the plurality of immune cells that eliminate a target HSC comprises a CAR that specifically binds to c-KIT, and, optionally, the CAR comprises the amino acid sequence of malpvtalllplalllhaarpegicmrvtnnvkdvtklvanlpkdymitlkyvpgmdvlpshcwisemvvqlsdsltdlldkfsni seglsnysiidklvnivddlvecvkensskdlkksfkspeprlftpeeffrifnrsidafkdfvvasetsdcvvsstlspekdsrvsvtk pfmlppvaasslrndssssnrkaknppgdsslhtttpaprpptpaptiasqplslrpeacrpaaggavhtrgldfacdiyiwaplagt cgvlllslvitlyckrgrkkllyifkqpfmrpvqttqeedgcscrfpeeeeggcelrvkfsrsadapaykqgqnqlynelnlgrreey dvldkrrgrdpemggkprrknpgeglynelqkdkmaeayseigmkgerrrgkghdglyqglstatkdtydalhmgalppr (SEQ ID NO: 5). In certain embodiments, at least one of the plurality of immune cells that eliminate a target HSC comprises a CAR that specifically binds to c-KIT, and, optionally, the CAR comprises the amino acid sequence of malpvtalllplalllhaarpegicmrvtnnvkdvtklvanlpkdymitlkyvpgmdvlpshcwisemvvqlsdsltdlldkfsni seglsnysiidklvnivddlvecvkensskdlkksfkspeprlftpeeffrifnrsidafkdfvvasetsdcvvsstlspekgkaknpp gdsslhtttpaprpptpaptiasqplslrpeacrpaaggavhtrgldfacdiyiwaplagtcgvlllslvitlyckrgrkkllyifkqpfm rpvqttgeedgcscrfpeeeeggcelrvkfsrsadapaykqgqnglynelnlgrreeydvldkrrgrdpemggkprrknpqegly nelqkdkmaeayseigmkgerrrgkghdglyqglstatkdtydalhmgalppr (SEQ ID NO: 6). In certain embodiments, at least one of the plurality of immune cells that eliminate a target HSC comprises a CAR that specifically binds to c-KIT, and, optionally, the CAR comprises the amino acid sequence of malpvtalllplalllhaarpmaqvqlveswggvaqpgrslrlscaasgftfssfamhwvrqapgkglewvavtsydgsneyya dsvkgrftisrdnskntlylqmnslraedtavyycakamvrgvtfgdldywgqgtlvtvssggggsggggsggggsseltqdpav svalgqtvritcqgdslrsyyaswyqqkpeqapvlviygensrpsgipdrfsgsssgntasltitgaqaedeadyycnsrdssgthlr vfgggtkltvlgttttpaprpptpaptiasqplslrpeacrpaaggavhtrgldfacdiyiwaplagtcgvlllslvitlyckrgrkkllyif kqpfmrpvqttgeedgcscrfpeeeeggcelrvkfsrsadapaykqgqnglynelnlgrreeydvldkrrgrdpemggkprrkn pqeglynelqkdkmaeayseigmkgerrrgkghdglyqglstatkdtydalhmqalppr (SEQ ID NO: 7), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpmaqvqlveswggvaqpgrslrlscaasgftfssfamhwvrqapgkglewvavtsydgsneyy a dsvkgrftisrdnskntlylqmnslraedtavyycakamvrgvtfgdldywgqgtlvtvssggggsggggsggggsseltqdpav svalgqtvrktcqgdslksyy aswyqqkpgqapvlviygensrpsgipdrfsgsssgntasltitgaqaedeadyy ccsratggyh rifgggtkltvlgttttpaprpptpaptiasqplslrpeacrpaaggavhtrgldfacdiyiwaplagtcgvlllslvitly ckrgrkkllyifkqpfmrpvqttgeedgcscrfpeeeeggcelrvkfsrsadapaykqgqnqlynelnlgrreey dvldkrrgrdpemggkprrkn pqeglynelqkdkmaeayseigmkgerrrgkghdglyqglstatkdtydalhmqalppr (SEQ ID NO: 8), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of Malpvtalllplalllhaarpmaqvklgesgggglvqpggslrlscaasgftfdsyamswvrqapgkglewvsyitsssstiyyvds vkgrftisrdnaknslylqmnslrdedtavyycarlrnsegywyfdlwgrgtlvtvssggggsggggsggggsgsaltqdpavsv algqtvritcqgdslrsyfaswyqqkpgqapllvmygqnirpsgipdrfsgsssgnsasltitgaqaedeadyycnsrdssynhwv fgggtkltvlgtttpaprpptpaptiasqplslrpeacrpaaggavhtrgldfacdiyiwaplagtcgvlllslvitlyckrgrkkllyifk qpfmrpvqttgeedgcscrfpeeeeggcelrvkfsrsadapaykqgqnglynelnlgrreeydvldkrrgrdpemggkprrknp geglynelqkdkmaeayseigmkgerrrgkghdglyqglstatkdtydalhmqalppr (SEQ ID NO: 9), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpmaqvklgesggglvqpggslrlscaasgftfdsyamswvrqapgkglewvsyitsssstiyyvds vkgrftisrdnaknslylqmnslrdedtavyycarlrnsegywyfdlwgrgtlvtvssggggsggggsggggsgsvltqdpavsv algqtvritcqgdslrsyyaswyqqkpgqapllvmygenirpsgipdrfsgstsgnsasltitgaqaedeadyycnsrdssgnhln wvfgggtkltvlgtttpaprpptpaptiasqplslrpeacrpaaggavhtrgldfacdiyiwaplagtcgvlllslvitlyckrgrkkly ifkqpfmrpvqttqeedgcscrfpeeeeggcelrvkfsrsadapaykqgqnglynelnlgrreeydvldkrrgrdpemggkprrk npgeglynelqkdkmaeayseigmkgerrrgkghdglyqglstatkdtydalhmqalppr (SEQ ID NO: 10), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpqvqlkqsgaelvrpgasvklsckasgytftdyyinwvkqrpgqglewiariypgsgntyynekfk gkatltaekssstaymqlssltsedsavyfcargvyyfdywgqgttltvsaggggsggggsggggsdivmtqspslsaf vgdrvtitcqasqdignylnwyqqksgeppkllvydasflkkgvpsrfsgsgsgtqyfltiyslqpedfatyfcqhsdnlsvtfgggt svtckasqnvrtnvawyqqkpgqspkaliysasyrysgvpdrftgsgstdftltisnvqsedladyfcqqynsyprtfgggtklei krtttpaprpptpaptiasqplslrpeacrpaaggavhtrgldfacdiyiwaplagtcgvlllslvitlyckrgrkkllyifkqpfmrpv qttqeedgcscrfpeeeeggcelrvkfsrsadapaykqgqnglynelnlgrreey dvldkrrgrdpemggkprrknpgeglynel qkdkmaeayseigmkgerrrgkghdglyqglstatkdtydalhmqalppr (SEQ ID NO: 11), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpdivmtqsqkfmstsvgdrvsvtckasqnvrtnvawyqqkpgqspkaliysasyrysgvpdrftgs gsgtdftltisnvqsedladyfcqqynsyprtfgggtkleikrggggsggggsggggsqvqlkqsgaelvrpgasvklsckasgytf tdyyinwvkgrpgqglewiariypgsgntyynekfkgkatltaeksssaymqlssltsedsavyfcargvyyfdywgqgttltvs atttpaprpptpaptiasqplslrpeacrpaaggavhtrgldfacdiyiwaplagtcgvlllslvitlyckrgrkkllyifkqpfmrpvqt tqeedgcscrfpeeeeggcelrvkfsrsadapaykqgqnqlynelnlgrreeydvldkrrgrdpemggkprrknpqeglynelqk dkmaeayseigmkgerrrgkghdglyqglstatkdtydalhmqalppr (SEQ ID NO: 12), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpqvqlkqsgaelvrpgasvklsckasgytftdyyinwvkqrpgqglewiariypgsgntyynekfk gkatltaekssstaymqlssltsedsavyfcargvyyfdywgqgttltvssggggsggggsggggsdivmtqsqkfmstsvgdrv svtckasqnvrtnvawyqqkpgqspkaliysasyrysgvpdrftgsgstdftltisnvqsedladyfcqqynsyprtfgggtklei krtttpaprpptpaptiasqplslrpeacrpaaggavhtrgldfacdiyiwaplagtcgvlllslvitlyckrgrkkllyifkqpfmrpv qttqeedgcscrfpeeeeggcelrvkfsrsadapaykqgqnglynelnlgrreeydvldkrrgrdpemggkprrknpgeglynel qkdkmaeayseigmkgerrrgkghdglyqglstatkdtydalhmqalppr (SEQ ID NO: 13), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpdivmtqsqkfmstsvgdrvsvtckasqnvrtnvawyqqkpgqspkaliysasyrysgvpdrftgs gsgtdftltisnvqsedladyfcqqynsyprtfgggtkleikrggggsggggsggggsqvqlkqsgaelvrpgasvklsckasgytf tdyyinwvkgrpgqglewiariypgsgntyynekfkgkatltaeksssaymqlssltsedsavyfcargvyyfdywgqgttltvs stttpaprpptpaptiasqplslrpeacrpaaggavhtrgldfacdiyiwaplagtcgvlllslvitlyckrgrkkllyifkqpfmrpvqt tqeedgcscrfpeeeeggcelrvkfsrsadapaykqgqnqlynelnlgrreeydvldkrrgrdpemggkprrknpqeglynelqk dkmaeayseigmkgerrrgkghdglyqglstatkdtydalhmqalppr (SEQ ID NO: 14), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpevqllesggglvqpggslrlscaasgftfsnylmswvrqapgkglewvssivpsggfthy adsvkg rftisrdnskntlylqmnslraedtavyy carlqtgswrvhafdiwgqgtmvtvssggggsggggsggggsdigmtqsptslsaf vgdrvtitcqasqdignylnwyqqksgeppkllvydasflkkgvpsrfsgsgsgtqyfltiyslqpedfatyfcqhsdnlsvtfgggt kvevktttpaprpptpaptiasqplslrpeacrpaaggavhtrgldfacdiyiwaplagtcgvlllslvitly ckrgrkkllyifkqpfm rpvqttgeedgcscrfpeeeeggcelrvkfsrsadapaykqgqnglynelnlgrreey dvldkrrgrdpemggkprrknpqegly nelqkdkmaeayseigmkgerrrgkghdglyqglstatkdtydalhmqalppr (SEQ ID NO: 15), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpdigmtqsptslsafvgdrvtitcqasqdignylnwyqqksgeppkllvydasflkkgvpsrfsgsgs gtqyfltiyslqpedfatyfcqhsdnlsvtfgggtkvevkggggsggggsggggsevqllesggglvqpggslrlscaasgftfsnyl mswvrqapgkglewvssivpsggfthyadsvkgrftisrdnskntlylqmnslraedtavyycarlqtgswrvhafdiwgqgtm vtvssttfpaprpptpaptiasqplslrpeacrpaaggavhtrgldfacdiyiwaplagtcgvlllslvitlyckrgrkkllyifkqpfmr pvqttqeedgcscrfpeeeeggcelrvkfsrsadapaykqgqnglynelnlgrreeydvldkrrgrdpemggkprrknpgegly nelqkdkmaeayseigmkgerrrgkghdglyqglstatkdtydalhmgalppr (SEQ ID NO: 16), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpevqllesggglvqpggslrlscaasgftfsnylmswvrqapgkglewvssivpsggfthyadsvkg rftisrdnskntlylqmnslraedtavyycarlqtgswrvhafdiwgqgtmvtvssggggsggggsggggsdigmtqsptslsaf vgdrvtitcqasqdignynlwyqqksgeppkllvydasflkkgvpsrfsgsgsgtqyfltiyslqpedfatyfcqhsdslsvtfgggt kvevkttfpaprpptpaptiasqplslrpeacrpaaggavhtrgldfacdiyiwaplagtcgvlllslvitlyckrgrkkllyifkqpfm rpvqttqeedgcscrfpeeeeggcelrvkfsrsadapaykqgqnglynelnlgrreeydvldkrrgrdpemggkprrknpqegly nelqkdkmaeayseigmkgerrrgkghdglyqglstatkdtydalhmgalppr (SEQ ID NO: 17), wherein the sequence comprises a scFv that specifically binds to c-KIT. In certain embodiments, at least one of the plurality of immune cells that eliminate a target HSC comprises a CAR that specifically binds to c-KIT, and, optionally, the CAR comprises the amino acid sequence of malpvtalllplalllhaarpdigmtqsptslsafvgdrvtitcqasqdignynlwyqqksgeppkllvydasflkkgvpsrfsgsgs gtqyfltiyslqpedfatyfcqhsdslsvtfgggtkvevkggggsggggsggggsevqllesggglvqpggslrlscaasgftfsnyl mswvrqapgkglewvssivpsggfthy adsvkgrftisrdnskntlylqmnslraedtavyy carlqtgswrvhafdiwgqgtm vtvssttfpaprpptpaptiasqplslrpeacrpaaggavhtrgldfacdiyiwaplagtcgvlllslvitlyckrgrkkllyifkqpfmr pvqttqeedgcscrfpeeeeggcelrvkfsrsadapaykqgqnglynelnlgrreey dvldkrrgrdpemggkprrknpgegly nelqkdkmaeayseigmkgerrrgkghdglyqglstatkdtydalhmgalppr (SEQ ID NO: 18), wherein the sequence comprises a scFv that specifically binds to c-KIT. In certain embodiments, at least one of the plurality of immune cells that eliminate a target HSC comprises a CAR that specifically binds to CD133, and, optionally, the CAR comprises the amino acid sequence of malpvtalllplalllhaarpgpggrarhcslpvssnhvcisrgeghhilqcqlkcklyvlvpaepgsspkpwiyrtsnlasgvparf sgsgsgtsysltissmeaedaatyycqqyhsypptfgagtklelkssggggsggggggssrsslevklvesgpelkkpgetvkisc kasgytftdysmhwvngapgkglkwmgwintetgepsyaddfkgrfafsletsastaylqinnlknedtatyfcatdygdyfdy wgqgttltvssakttppsvtsgqagqhhhhhhgaypydvpdyastttpaprpptpaptiasqplslrpeacrpaaggavhtrgldfa cdiyiwaplagtcgvlllslvitlyckrgrkklly-ifkqpfmrpvqttqeedgcscrfpeeeeggcelrvkfsrsadapaykqggnql ynelnlgrreeydvldkrrgrdpemggkprrknpgeglynelqkdkmaeayseigmkgerrrgkghdglyqglstatkdtydal hmgalppr (SEQ ID NO: 19), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpevklvesgpelkkpgetvkisckasgytftdysmhwvngapgkglkwmgwintetgepsyadd fkgrfafsletsastaylqinnlknedtatyfcatdygdyfdywgqgtltltvssggggsggggsggggsdivlsqspaimsaspgek vtiscsasssvsymywyqqkpgsspkpwiyrtsnlasgvparfsgsgsgtsysltissmeaedaatyycqqyhsypptfgagtkl elktttpaprpptpaptiasqplslrpeacrpaaggavhtrgldfacdiyiwaplagtcgvlllslvitlyckrgrkkllyifkqpfmrpv qttgeedgcscrfpeeeeggcelrvkfsrsadapaykqgqnglynelnlgrreeydvldkrrgrdpemggkprrknpgeglynel qkdkmaeayseigmkgerrrgkghdglyqglstatkdtydalhmgalppr (SEQ ID NO: 20), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpevklvesgpelkkpgetvkisck-asgytftdysmhwvngapgkglkwmgwintetgepsyadd fkgrfafsletsastaylqinnlknedtatyfcatdygdyfdywgqgttltvssssggggsggggggssrssldivlsqspaimsasp gekvtiscsasssvsymywyqqkpgsspkpwiyrtsnlasgvparfsgsgsgtsysltissmeaedaatyycqqyhsypptfga gtklelktttpaprpptpaptiasqplslrpeacrpaaggavhtrgldfacdiyiwaplagtcgvlllslvitlyckrgrkkllyifkqpf mrpvqttgeedgcscrfpeeeeggcelrvkfsrsadapaykqgqnglynelnlgrreeydvldkrrgrdpemggkprrknpqeg lynelqkdkmaeayseigmkgerrrgkghdglyqglstatkdtydalhmgalppr (SEQ ID NO: 21), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpdivlsqspaimsaspgekvtiscsasssvsymywyqqkpgsspkpwiyrtsnlasgvparfsgsg sgtsysltissmeaedaatyycqqyhsypptfgagtklelkggggsggggsggggsevklvesgpelkkpgetvkisckasgytft dysmhwvngapgkglkwmgwintetgepsyaddfkgrfafsletsastaylqinnlknedtatyfcatdygdyfdywgqttlt vssttfpaprpptpaptiasqplslrpeacrpaaggavhtrgldfacdiyiwaplagtcgvlllslvitlyckrgrkkllyifkqpfmrpv qttgeedgcscrfpeeeeggcelrvkfsrsadapaykqgqnglynelnlgrreey dvldkrrgrdpemggkprrknpgeglynel qkdkmaeayseigmkgerrrgkghdglyqglstatkdtydalhmgalppr (SEQ ID NO: 22), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpdivlsqspaimsaspgekvtiscsasssvsymywyqqkpgsspkpwiyrtsnlasgvparfsgsg sgtsysltissmeaedaatyycqqyhsypptfgagtklelkssggggsggggggssrsslevklvesgpelkkpgetvkisckasg ytftdysmhwvngapgkglkwmgwintetgepsyaddfkgrfafsletsastaylqinnlknedtatyfcatdygdyfdywgq gttltvssttfpaprpptpaptiasqplslrpeacrpaaggavhtrgldfacdiyiwaplagtcgvlllslvitlyckrgrkkllyifkqpf mrpvqttgeedgcscrfpeeeeggcelrvkfsrsadapaykqgqnglynelnlgrreeydvldkrrgrdpemggkprrknpqeg lynelqkdkmaeayseigmkgerrrgkghdglyqglstatkdtydalhmgalppr (SEQ ID NO: 23), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpevklvesgpelkkpgetvkisck-asgytftdysmhwvngapgkglkwmgwintetgepsyadd fkgrfafsletsastaylqinnlknedtatyfcatdygdyfdywgqgttltvssggggsggggsggggsdivltqspaimsaspgek vtiscsasssvsymywyqqkpgqpprlliylvsnlesgvparfsgsgsgtdftlnihpveeedaatyycqqyhsypptfgagtklei ktttpaprpptpaptiasqplslrpeacrpaaggavhtrgldfacdiyi- waplagtcgvlllslvitlyckrgrkkllyifkqpfmrpvqt tqeedgcscrfpeeeeggcelrvkfsrsadapaykqgqnqlynelnlgrreey- dvldkrrgrdpemggkprrknpqeglynelqk dkmaeaysei- gmkgerrrgkghdglyqglstatkdtydalhmgalppr (SEQ ID NO: 24), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpevklvesgpelkkpgetvkisck- asgytftdysmhwvngapgkglkwmgwintetgepsy add fkgrfafs- letsastaylqinnlknedtatyfcatdygdyfdywgqgt- tltvsssgggsgggggssrssldivltqspaimsaspg ekvtiscsasssvsymywyqqkpgqpprlliylvsn- lesgvparfsgsgsgtdftlnihpveeedaatyycqqyhsypptfgagtk leiktttpaprpptpaptiasqplslrpeacrpaaggavhtrgldfacdiyi- waplagtcgvlllslvitlyckrgrkkllyifkqpfmrp vqtt- geedgcscrfpeeeeggcelrvkfsrsadapaykqgqnqlynelnlgrreey- dvldkrrgrdpemggkprrknpqeglyne lqkdkmaeayseigmkgerrrgkghdglyqglstatkdtydalhmgalppr (SEQ ID NO: 25), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpdivltqspaim- saspgekvtiscsasssvsymywyqqkpgqpprlliylvsn- lesgvparfsgsgs gtdftlnihpveeedaatyycqqyhsypptfgagtkleikggggsggggsgggg- sevklvesgpelkkpgetvkisckasgytftd ysmhwvn- gapgkglkwmgwintetgepsyaddfkgrfafsletsastaylqinnlkned- tatyfcatdygdyfdywgqgttlty sstttpaprpptpaptiasqplslrpeacrpaaggavhtrgldfacdiyi- waplagtcgvlllslvitlyckrgrkkllyifkqpfmrpvq ttgeedgcscrfpeeeeggcelrvkfsrsadapaykqgqnqlynelnlgrreey- dvldkrrgrdpemggkprrknpqeglynelq kdkmaeaysei- gmkgerrrgkghdglyqglstatkdtydalhmgalppr (SEQ ID NO: 26), wherein the sequence comprises a scFv that specifically binds to CD133. In certain embodiments, at least one of the plurality of immune cells that eliminate a target HSC comprises a CAR that specifically binds to CD133, and, optionally, the CAR comprises the amino acid sequence of malpvtalllplalllhaarpdivltqspaimsaspgekvtiscsasssvsy- mywyqqkpgqpprlliylvsnlesgvparfsgsgs gtdftlnihpveeedaatyycqqyhsypptfgagtkleikssggggsggg- gggsrsslevklvesgpelkkpgetvkisckasgy tftdysmhwvn- gapgkglkwmgwintetgepsyaddfkgrfafsletsastaylqinnlkned- tatyfcatdygdyfdywgqgt tltvsstttpaprpptpaptiasqplslrpeacr- paaggavhtrgldfacdiyiwaplagtcgvlllslvitlyckrgrkkllyifkqpfmr pvqttgeedgcscrfpeeeeggcelrvkfsrsadapaykqgqnqlynelnlgr- reeydvldkrrgrdpemggkprrknpqegly nelqkdkmaeaysei- gmkgerrrgkghdglyqglstatkdtydalhmgalppr (SEQ ID NO: 27), wherein the sequence comprises a scFv that specifically binds to CD133.

In certain embodiments of the methods of the disclosure, the at least one target cell or the plurality of target cells comprises an immune cell and the target ligand on the target immune cell comprises one or more of CD3, CD4, CD8, CD25, FoxP3, TCRα, TCRβ, TCRαβ, TCRγλ, CD52, NK1.1, CD16, CD30, CD31, CD3ε, CD56, CD94, NKG2A, NKG2C, NKp30, NKp44, NKp46, CD9, CD103, and KIR.

In certain embodiments of the methods of the disclosure, the at least one target cell or the plurality of target cells comprises an HSC and an immune cell, the target ligand on the target HSC comprises one or more of c-KIT/CD117, CD45, CD34, Thy1/CD90, c-mpl/CD110, CD133, CD49f, ABCG2/CD338, carbonic anhydrase IX/CA9, CD123 and CD150, and the target ligand on the target immune cell comprises one or more of CD3, CD4, CD8, CD25, FoxP3, TCRα, TCRβ, TCRαβ, TCRγλ, CD52, NK1.1, CD16, CD30, CD31, CD3ε, CD56, CD94, NKG2A, NKG2C, NKp30, NKp44, NKp46, CD9, CD103, and KIR.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ligand recognition region comprises one or more of a protein scaffold, a Centyrin, a single chain variable fragment (scFv), a VHH, an immunoglobulin and an antibody mimetic. In certain embodiments, the immunoglobulin is an antibody for fragment thereof of an IgA, IgD, IgE, IgG, or IgM isotype. In certain embodiments, the antibody fragment is a complementarity determining region (CDR), a heavy chain CDR (including CDR1, CDR2 and/or CDR3), a light chain CDR (including CDR1, CDR2 and/or CDR3), an antigen-binding fragment (Fab), a variable domain (Fv), a heavy chain variable region, a light chain variable region, a complete heavy chain, a complete light chain, one or more constant domains, an Fc (crystallizable fragment) or any combination thereof. In certain embodiments, the antibody mimetic comprises one or more of an affibody, an afflilin, an affimer, an affitin, an alphabody, an anticalin, and avimer, a Designed Ankyrin Repeat Protein (DARPin), a Fynomer, a Kunitz domain peptide, and a monobody. In certain embodiments, at least one of the CLR(s) is bi-specific. In certain embodiments, each of the CLR(s) is bi-specific. In certain embodiments, at least one of the CLR(s) is tri-specific. In certain embodiments, each of the CLR(s) is tri-specific.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the signal peptide comprises a sequence encoding a human CD2, CD3δ, CD3ε, CD3γ, CD3ζ, CD4, CD8α, CD19, CD28, 4-1BB or GM-CSFR signal peptide.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the hinge comprises a sequence derived from a human CD8a, IgG4, and/or CD4 sequence.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the transmembrane domain comprises a sequence encoding a human CD2, CD3δ, CD3R, CD3γ, CD3ζ, CD4, CD8a, CD19, CD28, 4-1BB or GM-CSFR transmembrane domain.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the endodomain comprises a human CD3ζ endodomain.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the endodomain comprises a human CD3ζ endodomain. In certain embodiments, the at least one costimulatory domain comprises a human 4-1BB, a human CD28, a human CD40, a human ICOS, a human MyD88, a human OX-40 intracellular segment or any combination thereof. In certain embodiments, the at least one costimulatory domain comprises a human CD28 and/or a human 4-1BB costimulatory domain. In certain embodiments, the 4-1BB costimulatory domain is located between the transmembrane domain and the CD28 costimulatory domain.

In certain embodiments of the methods of the disclosure, the at least one immune cell of the composition comprising the plurality of immune cells comprises a split CLR. In certain embodiments, the split CLR comprises two or more CLR(s) having distinct intracellular domains that, when expressed simultaneously in the at least one immune cell, increase or decrease the activity of the immune cell compared to an immune cell that does not express the split CLR or an immune cell that does not express a CLR.

In certain embodiments of the methods of the disclosure, the at least one immune cell of the composition comprising the plurality of immune cells comprises a split CLR. In certain embodiments, including those wherein the simultaneous expression increases the activity of the immune cell, the split CLR comprises (a) a first CLR comprising an ectodomain comprising a ligand recognition region, a transmembrane domain, and an endodomain consisting of a primary intracellular signaling domain, and (b) a second CLR comprising an ectodomain comprising a ligand recognition region, a transmembrane domain, and an endodomain consisting of a secondary intracellular signalling domain. In certain embodiments, the primary intracellular signaling domain comprises a human CD3(endodomain. In certain embodiments, the secondary intracellular signaling domain comprises a human 4-1BB, a human CD28, a human CD40, a human ICOS, a human MyD88, or a human OX-40 intracellular segment. In certain embodiments, the secondary intracellular signaling domain comprises a human 4-1BB and a human CD28.

In certain embodiments of the methods of the disclosure, the at least one immune cell of the composition comprising the plurality of immune cells comprises a split CLR. In certain embodiments, including those wherein the simultaneous expression decreases the activity of the immune cell, the split CLR comprises (a) a first CLR comprising an ectodomain comprising a ligand recognition region, a transmembrane domain, and an endodomain comprising of a primary intracellular signaling domain a secondary intracellular signalling domain, and (b) a second CLR comprising an ectodomain comprising a ligand recognition region, a transmembrane domain, and an endodomain consisting of an inhibitory intracellular signalling domain. In certain embodiments, the primary intracellular signaling domain comprises a human CD3ζ endodomain and the secondary intracellular signaling domain comprises a human 4-1BB, a human CD28, a human CD40, a human ICOS, a human MyD88, or a human OX-40 intracellular segment. In certain embodiments, the primary intracellular signaling domain comprises a human CD3ζ endodomain and the secondary intracellular signaling domain comprises a human 4-1BB and a human CD28. In certain embodiments, the inhibitory intracellular signalling domain comprises a signaling domain derived from PD1, CTLA4, LAG3, B7-H1, B7-1, CD160, BTLA, PD1H, LAIR1, TIM1, TIM3, TIM4, 2B4, and TIGIT. Additional intracellular signaling components from these inhibitory intracellular signalling domains and other molecules that may be used in whole or in part, include, but are not limited to, ITIM, ITSM, YVKM, PP2A, SHP2, KIEELE, and Y265. In certain embodiments, the second CLR selectively binds a target on a non-target cell, thereby inducing the second CLR to inhibit the activity of the first CLR. In certain embodiments, the second CLR to inhibits the ability of the first CLR to induce death in the target or non-target cell.

In certain embodiments of the methods of the disclosure, the one or more CLR(s) bind a ligand with an affinity selected from a $K_D$ of less than or equal to $10^{-9}$M, less than or equal to $10^{-0}$M, less than or equal to $10^{-11}$M, less than or equal to $10^{-2}$M, less than or equal to $10^{-13}$M, less than or equal to $10^{-14}$M, and less than or equal to $10^{-15}$M. In certain embodiments, the $K_D$ is determined by surface plasmon resonance.

In certain embodiments of the methods of the disclosure, the composition comprising a plurality of immune cells further comprises at least one pharmaceutically acceptable carrier.

In certain embodiments of the methods of the disclosure, the composition comprising a plurality of immune cells further comprises at least one pharmaceutically acceptable carrier.

In certain embodiments of the methods of the disclosure, the method further comprises administering to the subject a mobilizing composition. In certain embodiments, the composition comprising a plurality of immune cells each comprising one or more CLR(s) and the mobilizing composition are administered sequentially. In certain embodiments, wherein the mobilizing composition is administered before the composition comprising a plurality of immune cells each comprising one or more CLR(s) is administered. In certain embodiments, the mobilizing composition is administered a period of time before Figure the composition comprising a plurality of immune cells each comprising one or more CLR(s) is administered, wherein the period of time is sufficient to permit a migration of HSCs from the bone marrow to, for example, the circulating blood to increase access of the composition comprising a plurality of immune cells to the target HSCs. In certain embodiments, the mobilizing composition is administered between 1 and 7 days, inclusive of the endpoints, before the composition comprising a plurality of immune cells each comprising one or more CLR(s) is administered. In certain embodiments, the mobilizing composition comprises granulocyte colony stimulating factor (G-CSF), plerixafor or a combination thereof.

In certain embodiments of the methods of the disclosure, the method further comprises administering to the subject an effective amount of a preconditioning composition to enhance engraftment of the composition comprising a plurality of immune cells each expressing one or more CLR(s) or efficiency of elimination of at least one target cell by the composition comprising a plurality of immune cells each expressing one or more CLR(s). In certain embodiments, the preconditioning composition suppresses the immune system. In certain embodiments, the preconditioning composition comprises a chemotherapy, a radiation therapy (including, but not limited to, local radiation and whole-body radiation), an autoimmune therapy, or an anti-rejection drug. In certain embodiments, the preconditioning composition does not comprise radiation therapy, local radiation or whole-body radiation. In certain embodiments, the preconditioning composition comprises one or more of a lymphoablative agent, a myeloablative agent, a chemotherapeutic agent or a combination thereof. In certain embodiments, the preconditioning composition comprises a lymphoablative agent. Exemplary lymphoablative agents include, but are not limited to, cyclophosphamide and fludarabine. In certain embodiments, the preconditioning composition comprises a myeloablative agent. Exemplary myeloablative agents include, but are not limited to, low dose and/or local radiation therapy. In certain embodiments, the preconditioning composition comprises a chemotherapeutic agent selected from the group consisting of busulphan, treosulphan, melphalan, and thiotepa.

In certain embodiments of the methods of the disclosure, the method further comprises administering to the subject an effective amount of a preconditioning composition to enhance engraftment of the composition comprising a plurality of immune cells each expressing one or more CLR(s) or efficiency of elimination of at least one target cell by the composition comprising a plurality of immune cells each expressing one or more CLR(s). In certain embodiments, the preconditioning composition is administered to the subject before the composition comprising a plurality of immune cells each expressing one or more CLR(s) is administered to the subject. In certain embodiments, the preconditioning composition is administered to the subject 1 minute, 2 minutes, 5 minutes, 10 minutes, 15 minutes, 20 minutes, 25 minutes, 30 minutes, 35 minutes, 40 minutes, 45 minutes, 50 minutes, 55 minutes, 60 minutes or any number of minutes in between before the composition comprising a plurality of immune cells each expressing one or more CLR(s) is administered to the subject. In certain embodiments, the preconditioning composition is administered to the subject 1 hour, 2 hours, 4 hours, 6 hours, 8 hours, 12 hours, 16 hours, 18 hours, 24 hours or any number of hours in between before the composition comprising a plurality of immune cells each expressing one or more CLR(s) is administered to the subject.

In certain embodiments of the methods of the disclosure, at least one immune cell of the plurality of immune cells is pre-irradiated prior to administration to the subject. In certain embodiments of the methods of the disclosure, a portion of the immune cells of the plurality of immune cells is pre-irradiated prior to administration to the subject. In certain embodiments, the portion comprises at least 2%, 5%, 10%, 15%, 20%, 25%, 30%, 35%, 40%, 45%, 50%, 55%, 60%, 65%, 70%, 75%, 80%, 85%, 90%, 95%, 99% or any percentage in between of the plurality of immune cells. In certain embodiments, each immune cell of the plurality of immune cells is pre-irradiated prior to administration to the subject.

In certain embodiments of the methods of the disclosure, including those wherein at least one or wherein each immune cell of the plurality of immune cells is pre-irradiated prior to administration to the subject, the step of eliminating the plurality of immune cells comprises administering to the subject an effective amount of the plurality of pre-irradiated immune cells, thereby preventing proliferation and/or shortening survival of the plurality of pre-irradiated immune cells.

In certain embodiments of the methods of the disclosure, each immune cell of the plurality of immune cells comprises an inducible caspase polypeptide or a sequence encoding an inducible caspase polypeptide. In certain embodiments, the inducible caspase polypeptide comprises (a) a ligand binding region, (b) a linker, and (c) a truncated caspase 9 polypeptide. In certain embodiments, the inducible caspase polypeptide does not comprise a non-human sequence.

In certain embodiments of the methods of the disclosure, including those wherein each immune cell of the plurality of immune cells comprises an inducible caspase polypeptide or a sequence encoding an inducible caspase polypeptide, the step of eliminating the plurality of immune cells comprises administering an effective amount of an induction agent to the subject to induce the caspase polypeptide, thereby initiating death of the immune cell.

In certain embodiments of the methods of the disclosure, each HSC of the plurality of therapeutic HSCs comprises an inducible caspase polypeptide or a sequence encoding an inducible caspase polypeptide. In certain embodiments, the inducible caspase polypeptide comprises (a) a ligand binding region, (b) a linker, and (c) a truncated caspase 9 polypeptide. In certain embodiments, the inducible caspase polypeptide does not comprise a non-human sequence. In certain embodiments, the method further comprises administering to the subject a composition comprising an induction agent, thereby initiating death of the plurality of therapeutic HSCs.

In certain embodiments of the methods of the disclosure, including those wherein each immune cell of the plurality of immune cells comprises an inducible caspase polypeptide or a sequence encoding an inducible caspase polypeptide, the composition comprising a plurality of immune cells each comprising one or more CLR(s) further comprises an induction agent. In certain embodiments of the methods of the disclosure, including those wherein each immune cell of the plurality of immune cells comprises an inducible caspase polypeptide or a sequence encoding an inducible caspase polypeptide, the composition comprising a plurality of plurality of therapeutic HSCs further comprises an induction agent.

In certain embodiments of the methods of the disclosure, at least one HSC of the plurality of therapeutic HSCs comprises a genetic modification. In certain embodiments, a portion of the HSCs of the plurality of therapeutic HSCs comprise a genetic modification. In certain embodiments, the portion comprises at least 2%, 5%, 10%, 15%, 20%, 25%, 30%, 35%, 40%, 45%, 50%, 55%, 60%, 65%, 70%, 75%, 80%, 85%, 90%, 95%, 99% or any percentage in between of the plurality of therapeutic HSCs. In certain embodiments, each HSC of the plurality of therapeutic HSCs comprise a genetic modification.

In certain embodiments of the methods of the disclosure, including those wherein at least one HSC of the plurality of therapeutic HSCs comprises a genetic modification, the genetic modification is a single strand break, a double strand break, a sequence deletion, a sequence insertion, a sequence substitution or any combination thereof. In certain embodiments, the sequence deletion, the sequence insertion, the sequence substitution or the combination thereof comprise(s) a sequence encoding an intron, an exon, a promoter, an enhancer, a transcriptional repressor, a CpG site or any combination thereof. In certain embodiments of the methods of the disclosure, including those wherein at least one HSC of the plurality of therapeutic HSCs comprises a genetic modification, the genetic modification is introduced by a composition comprising a DNA binding domain and an endonuclease domain. In certain embodiments, the DNA binding domain comprises a guide RNA. In certain embodiments, the DNA binding domain comprises a sequence isolated or derived from a Cas9, a Transcription Activator-Like Effector Nuclease (TALEN), a Centromere and Promoter Factor 1 (Cpf1) or a zinc-finger nuclease (ZFN).

In certain embodiments, the dCas9 of the disclosure comprises a dCas9 isolated or derived from Staphyloccocus pyogenes. In certain embodiments, the dCas9 comprises a dCas9 with substitutions at positions 10 and 840 of the amino acid sequence of the dCas9 which inactivate the catalytic site. In certain embodiments, these substitutions are D10A and H840A. In certain embodiments, the "X" residue at position 1 of the dCas9 sequence is a methionine (M). In certain embodiments, the amino acid sequence of the dCas9 comprises the sequence of.

```
                                                              (SEQ ID NO: 28)
   1 XDKKYSIGLA IGTNSVGWAV ITDEYKVPSK KFKVLGNTDR HSIKKNLIGA LLFDSGETAE

61 ATRLKRTARR RYTRRKNRIC YLQEIFSNEM AKVDDSFFHR LEESFLVEED KKHERHPIFG

121 NIVDEVAYHE KYPTIYHLRK KLVDSTDKAD LRLIYLALAH MIKFRGHFLI EGDLNPDNSD

181 VDKLFIQLVQ TYNQLFEENP INASGVDAKA ILSARLSKSR RLENLIAQLP GEKKNGLFGN

241 LIALSLGLTP NFKSNFDLAE DAKLQLSKDT YDDDLDNLLA QIGDQYADLF LAAKNLSDAI

301 LLSDILRVNT EITKAPLSAS MIKRYDEHHQ DLTLLKALVR QQLPEKYKEI FFDQSKNGYA

361 GYIDGGASQE EFYKFIKPIL EKMDGTEELL VKLNREDLLR KQRTFDNGSI PHQIHLGELH

421 AILRRQEDFY PFLKDNREKI EKILTFRIPY YVGPLARGNS RFAWMTRKSE ETITPWNFEE

481 VVDKGASAQS FIERMTNFDK NLPNEKVLPK HSLLYEYFTV YNELTKVKYV TEGMRKPAFL

541 SGEQKKAIVD LLFKTNRKVT VKQLKEDYFK KIECFDSVEI SGVEDRFNAS LGTYHDLLKI

601 IKDKDFLDNE ENEDILEDIV LTLTLFEDRE MIEERLKTYA HLFDDKVMKQ LKRRRYTGWG

661 RLSRKLINGI RDKQSGKTIL DFLKSDGFAN RNFMQLIHDD SLTFKEDIQK AQVSGQGDSL

721 HEHIANLAGS PAIKKGILQT VKVVDELVKV MGRHKPENIV IEMARENQTT QKGQKNSRER

781 MKRIEEGIKE LGSQILKEHP VENTQLQNEK LYLYYLQNGR DMYVDQELDI NRLSDYDVDA

841 IVPQSFLKDD SIDNKVLTRS DKNRGKSDNV PSEEVVKKMK NYWRQLLNAK LITQRKFDNL

901 TKAERGGLSE LDKAGFIKRQ LVETRQITKH VAQILDSRMN TKYDENDKLI REVKVITLKS

961 KLVSDFRKDF QFYKVREINN YHHAHDAYLN AVVGTALIKK YPKLESEFVY GDYKVYDVRK

1021 MIAKSEQEIG KATAKYFFYS NIMNFFKTEI TLANGEIRKR PLIETNGETG EIVWDKGRDF

1081 ATVRKVLSMP QVNIVKKTEV QTGGFSKESI LPKRNSDKLI ARKKDWDPKK YGGFDSPTVA

1141 YSVLVVAKVE KGKSKKLKSV KELLGITIME RSSFEKNPID FLEAKGYKEV KKDLIIKLPK

1201 YSLFELENGR KRMLASAGEL QKGNELALPS KYVNFLYLAS HYEKLKGSPE DNEQKQLFVE

1261 QHKHYLDEII EQISEFSKRV ILADANLDKV LSAYNKHRDK PIREQAENII HLFTLTNLGA

1321 PAAFKYFDTT IDRKRYTSTK EVLDATLIHQ SITGLYETRI DLSQLGGD.
```

In certain embodiments, the dCas9 of the disclosure comprises a dCas9 isolated or derived from Staphylococcus aureus. In certain embodiments, the dCas9 comprises a dCas9 with substitutions at positions 10 and 580 of the amino acid sequence of the dCas9 which inactivate the catalytic site. In certain embodiments, these substitutions are D10A and N580A. In certain embodiments, the dCas9 is a small and inactive Cas9 (dSaCas9). In certain embodiments, the amino acid sequence of the dSaCas9 comprises the sequence of:

```
                                                              (SEQ ID NO: 29)
  1 mkrnyilglA igitsvgygi idyetrdvid agvrlfkean vennegrrsk rgarrlkrrr 61 rhriqrvkkl lfdynlltdh selsginpye arvkglsqkl seeefsaall hlakrrgvhn
```

```
121 vneveedtgn elstkeqisr nskaleekyv aelqlerlkk dgevrgsinr fktsdyvkea 181 kqllkvqkay hqldqsfidt yidlletrrt yyegpgegsp fgwkdikewy emlmghctyf 241 peelrsvkya ynadlynaln dlnnlvitrd enekleyyek fqiienvfkq kkkptlkqia 301 keilvneedi kgyrvtstgk peftnlkvyh dikditarke iienaelldq iakiltiyqs 361 sediqeeltn lnseltqeei eqisnlkgyt gthnlslkai nlildelwht ndnqiaifnr 421 lklvpkkvdl sqqkeipttl vddfilspvv krsfiqsikv inaiikkygl pndiiielar 481 eknskdaqkm inemqkrnrq tnerieeiir ttgkenakyl iekiklhdmq egkclyslea 541 ipledllnnp fnyevdhiip rsvsfdnsfn nkvlvkqeeA skkgnrtpfq ylsssdskis 601 yetfkkhiln lakgkgrisk tkkeylleer dinrfsvqkd finrnlvdtr yatrglmnll 661 rsyfrvnnld vkvksinggf tsflrrkwkf kkernkgykh haedaliian adfifkewkk 721 ldkakkvmen qmfeekqaes mpeieteqey keifitphqi khikdfkdyk yshrvdkkpn 781 relindtlys trkddkgntl ivnnlnglyd kdndklkkli nkspekllmy hhdpqtyqkl 841 klimeqygde knplykyyee tgnyltkysk kdngpvikki kyygnklnah lditddypns 901 rnkvvklslk pyrfdvyldn gvykfvtvkn ldvikkenyy evnskcyeea kklkkisnqa 961 efiasfynnd likingelyr vigvnndlln rievnmidit yreylenmnd krppriikti 1021 asktqsikky stdilgnlye vkskkhpqii kkg.
```

In certain embodiments, the endonuclease domain comprises a sequence isolated or derived from a Cas9, a Transcription Activator-Like Effector Nuclease (TALEN), or a type IIS endonuclease. In certain embodiments, the type IIS endonuclease is AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the type IIS endonuclease is Clo051. In certain embodiments, the DNA binding domain and the endonuclease domain are covalently or non-covalently linked. In certain embodiments, the DNA binding domain and the endonuclease domain are covalently linked as a fusion protein. In certain embodiments of the disclosure, the nuclease domain may comprise, consist essentially of or consist of a dSaCas9 and Clo051. An exemplary Clo051 nuclease domain may comprise, consist essentially of or consist of, the amino acid sequence of:

(SEQ ID NO: 34)
EGIKSNISLLKDELRGQISHISHEYLSLIDLAFDSKQNRLFEMKVLELLV

NEYGFKGRHLGGSRKPDGIVYSTTLEDNFGIIVDTKAYSEGYSLPISQAD

EMERYVRENSNRDEEVNPNKWWENFSEEVKKYYFVFISGSFKGKFEEQLR

RLSMTTGVNGSAVNVVNLLLGAEKIRSGEMTIEELERAMFNNSEFILKY.

An exemplary dCas9-Clo051 nuclease domain may comprise, consist essentially of or consist of, the amino acid sequence of (Clo051 sequence underlined (SEQ ID NO: 34), linker bold italics, dCas9 sequence in italics):

(SEQ ID NO: 30)
MAPKKKRKV<u>EGIKSNISLLKDELRGQISHISHEYLSLIDLAFDSKQNRLF

EMKVLELLVNEYGFKGRHLGGSRKPDGIVYSTTLEDNFGIIVDTKAYSEG

YSLPISQADEMERYVRENSNRDEEVNPNKWWENFSEEVKKYYFVFISGSF

KGKFEEQLRRLSMTTGVNGSAVNVVNLLLGAEKIRSGEMTIEELERAMFN

NSEFILKY</u>    *DKKYSIGLAIGTNSVGWAVITDEYKVPSKKFKVLGNT*

*DRHSIKKNLIGALLFDSGETAEATRLKRTARRRYTRRKNRICYLQEIFSN*

*EMAKVDDSFFHRLEESFLVEEDKKHERHPIFGNIVDEVAYHEKYPTIYHL*

*RKKLVDSTDKADLRLIYLALAHMIKFRGHFLIEGDLNPDNSDVDKLFIQL*

*VQTYNQLFEENPINASGVDAKAILSARLSKSRRLENLIAQLPGEKKNGLF*

*GNLIALSLGLTPNFKSNFDLAEDAKLQLSKDTYDDDLDNLLAQIGDQYAD*

*LFLAAKNLSDAILLSDILRVNTEITKAPLSASMIKRYDEHHQDLTLLKAL*

*VRQQLPEKYKEIFFDQSKNGYAGYIDGGASQEEFYKFIKPILEKMDGTEE*

*LLVKLNREDLLRKQRTFDNGSIPHQIHLGELHAILRRQEDFYPFLKDNRE*

*KIEKILTFRIPYYVGPLARGNSRFAWMTRKSEETITPWNFEEVVDKGASA*

*QSFIERMTNFDKNLPNEKVLPKHSLLYEYFTVYNELTKVKYVTEGMRKPA*

*FLSGEQKKAIVDLLFKTNRKVTVKQLKEDYFKKIECFDSVEISGVEDRFN*

*ASLGTYHDLLKIIKDKDFLDNEENEDILEDIVLTLTLFEDREMIEERLKT*

*YAHLFDDKVMKQLKRRRYTGWGRLSRKLINGIRDKQSGKTILDFLKSDG*

*FANRNFMQLIHDDSLTFKEDIQKAQVSGQGDSLHEHIANLAGSPAIKKG*

*ILQTVKVVDELVKVMGRHKPENIVIEMARENQTTQKGQKNSRERMKRIE*

*EGIKELGSQILKEHPVENTQLQNEKLYLYYLQNGRDMYVDQELDINRLS*

*DYDVDAIVPQSFLKDDSIDNKVLTRSDKNRGKSDNVPSEEVVKKMKNYW*

*RQLLNAKLITQRKFDNLTKAERGGLSELDKAGFIKRQLVETRQITKHVA*

```
QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGDGSPKK

KRKVSS.
```

In certain embodiments of the methods of the disclosure, including those wherein at least one HSC of the plurality of therapeutic HSCs comprises a genetic modification, the genetic modification is introduced by induction of a homologous recombination, insertion of a single-stranded oligodeoxynucleotide (ssODN) or a transposition event. In certain embodiments, the genetic modification results in the insertion of a sequence. In certain embodiments, the transposition event results in the insertion of a functional transgene. In certain embodiments, a transposon comprises the functional transgene and wherein the transposon is a piggyBac transposon. In certain embodiments, the HSC comprising the transposon further comprises a super piggyBac transposase.

In certain embodiments of the methods of the disclosure, at least one target HSC comprises a genetic modification, the genetic modification is introduced by induction of a homologous recombination, insertion of a single-stranded oligodeoxynucleotide (ssODN) or a transposition event. In certain embodiments, the genetic modification results in the insertion of a sequence. In certain embodiments, the transposition event results in the insertion of a functional and/or therapeutic transgene. In certain embodiments, a transposon comprises the functional and/or therapeutic transgene and wherein the transposon is a piggyBac transposon. In certain embodiments, the at least one target HSC comprising the transposon further comprises a super piggyBac transposase. In certain embodiments, the at least one target HSC is an endogenous HSC of the subject.

The disclosure provides a composition comprising the transposon the disclosure. In certain embodiments, the composition may further comprise a plasmid comprising a sequence encoding a transposase enzyme. The sequence encoding a transposase enzyme may be an mRNA sequence.

Transposons of the disclosure may comprise piggyBac transposons. Transposase enzymes of the disclosure may include piggyBac transposases or compatible enzymes. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

```
                                                                (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substution at one or more of positions 30, 165, 282, or 538 of the sequence:

```
                                                                (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV
```

```
241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments, the transposase enzyme is a piggyBac™ (PB) transposase enzyme that comprises or consists of an amino acid sequence having an amino acid substution at two or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at three or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at each of the following positions 30, 165, 282, and 538 of the sequence of SEQ ID NO: 1. In certain embodiments, the amino acid substution at position 30 of the sequence of SEQ ID NO: 1 is a substitution of a valine (V) for an isoleucine (I). In certain embodiments, the amino acid substution at position 165 of the sequence of SEQ ID NO: 1 is a substitution of a serine (S) for a glycine (G). In certain embodiments, the amino acid substution at position 282 of the sequence of SEQ ID NO: 1 is a substitution of a valine (V) for a methionine (M). In certain embodiments, the amino acid substution at position 538 of the sequence of SEQ ID NO: 1 is a substitution of a lysine (K) for an asparagine (N).

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 1 wherein the amino acid substution at position 30 is a substitution of a valine (V) for an isoleucine (I), the amino acid substution at position 165 is a substitution of a serine (S) for a glycine (G), the amino acid substution at position 282 is a substitution of a valine (V) for a methionine (M), and the amino acid substution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

```
                                                              (SEQ ID NO: 2)
  1 MGSSLDDEHI LSALLQSDDE LVGEDSDSEV SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTSATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RVYIPNKPSK YGIKILMMCD

301 SGTKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPKEV

541 PGTSDDSTEE PVMKKRTYCT YCPSKIRRKA NASCKKCKKV ICREHNIDMC QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 1 or SEQ ID NO: 2. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 1 or SEQ ID NO: 2 is a substitution of an asparagine (N) for a serine (S). In certain embodiments, the amino acid substitution at position 46 of SEQ ID NO: 1 or SEQ ID NO: 2 is a substitution of a serine (S) for an alanine (A). In certain embodiments, the amino acid substitution at position 46 of SEQ ID NO: 1 or SEQ ID NO: 2 is a substitution of a threonine (T) for an alanine (A). In certain embodiments, the amino acid substitution at position 82 of SEQ ID NO: 1 or SEQ ID NO: 2 is a substitution of a tryptophan (W) for an isoleucine (I). In certain embodiments, the amino acid substitution at position 103 of SEQ ID NO: 1 or SEQ ID NO: 2 is a substitution of a proline (P) for a serine (S). In certain embodiments, the amino acid substitution at position 119 of SEQ ID NO: 1 or SEQ ID NO: 2 is a substitution of a proline (P) for an arginine (R). In certain embodiments, the amino acid substitution at position 125 of SEQ ID NO: 1 or SEQ ID NO: 2 is a substitution of an alanine (A) a cysteine (C). In certain embodiments, the amino acid substitution at position 125 of SEQ ID NO: 1 or SEQ ID NO: 2 is a substitution of a leucine (L) for a cysteine (C). In certain embodiments, the amino acid substitution at position 177 of SEQ ID NO: 1 or SEQ ID NO: 2 is a substitution of a lysine (K) for a tyrosine (Y). In certain embodiments, the amino acid substitution at position 177 of SEQ ID NO: 1 or SEQ ID NO: 2 is a substitution of a histidine (H) for a tyrosine (Y). In certain embodiments, the amino acid substitution at position 180 of SEQ ID NO: 1 or SEQ ID NO: 2 is a substitution of a leucine (L) for a phenylalanine (F). In certain embodiments, the amino acid substitution at position 180 of SEQ ID NO: 1 or SEQ ID NO: 2 is a substitution of an isoleucine (I) for a phenylalanine (F). In certain embodiments, the amino acid substitution at position 180 of SEQ ID NO: 1 or SEQ ID NO: 2 is a substitution of a valine (V) for a phenylalanine (F). In certain embodiments, the amino acid substitution at position 185 of SEQ ID NO: 1 or SEQ ID NO: 2 is a substitution of a leucine (L) for a methionine (M). In certain embodiments, the amino acid substitution at position 187 of SEQ ID NO: 1 or SEQ ID NO: 2 is a substitution of a glycine (G) for an alanine (A). In certain embodiments, the amino acid substitution at position 200 of SEQ ID NO: 1 or SEQ ID NO: 2 is a substitution of a tryptophan (W) for a phenylalanine (F).In certain embodiments, the amino acid substitution at position 207 of SEQ ID NO: 1 or SEQ ID NO: 2 is a substitution of a proline (P) for a valine (V). In certain embodiments, the amino acid substitution at position 209 of SEQ ID NO: 1 or SEQ ID NO: 2 is a substitution of a phenylalanine (F) for a valine (V). In certain embodiments, the amino acid substitution at position 226 of SEQ ID NO: 1 or SEQ ID NO: 2 is a substitution of a phenylalanine (F) for a methionine (M). In certain embodiments, the amino acid substitution at position 235 of SEQ ID NO: 1 or SEQ ID NO: 2 is a substitution of an arginine (R) for a leucine (L). In certain embodiments, the amino acid substitution at position 240 of SEQ ID NO: 1 or SEQ ID NO: 1 is a substitution of a lysine (K) for a valine (V). In certain embodiments, the amino acid substitution at position 241 of SEQ ID NO: 1 or SEQ ID NO: 2 is a substitution of a leucine (L) for a phenylalanine (F). In certain embodiments, the amino acid substitution at position 243 of SEQ ID NO: 1 or SEQ ID NO: 2 is a substitution of a lysine (K) for a proline (P). In certain embodiments, the amino acid substitution at position 258 of SEQ ID NO: 1 or SEQ ID NO: 2 is a substitution of a serine (S) for an asparagine (N). In certain embodiments, the amino acid substitution at position 296 of SEQ ID NO: 1 or SEQ ID NO: 2 is a substitution of a tryptophan (W) for a leucine (L). In certain embodiments, the amino acid substitution at position 296 of SEQ ID NO: 1 or SEQ ID NO: 2 is a substitution of a tyrosine (Y) for a leucine (L). In certain embodiments, the amino acid substitution at position 296 of SEQ ID NO: 1 or SEQ ID NO: 2 is a substitution of a phenylalanine (F) for a leucine (L). In certain embodiments, the amino acid substitution at position 298 of SEQ ID NO: 1 or SEQ ID NO: 2 is a substitution of a leucine (L) for a methionine (M). In certain embodiments, the amino acid substitution at position 298 of SEQ ID NO: 1 or SEQ ID NO: 2 is a substitution of an alanine (A) for a methionine (M). In certain embodiments, the amino acid substitution at position 298 of SEQ ID NO: 1 or SEQ ID NO: 2 is a substitution of a valine (V) for a methionine (M). In certain embodiments, the amino acid substitution at position 311 of SEQ ID NO: 1 or SEQ ID NO: 2 is a substitution of an isoleucine (I) for a proline (P). In certain embodiments, the amino acid substitution at position 311 of SEQ ID NO: 1 or SEQ ID NO: 2 is a substitution of a valine for a proline (P). In certain embodiments, the amino acid substitution at position 315 of SEQ ID NO: 1 or SEQ ID NO: 2 is a substitution of a lysine (K) for an arginine (R).In certain embodiments, the amino acid substitution at position 319 of SEQ ID NO: 1 or SEQ ID NO: 2 is a substitution of a glycine (G) for a threonine (T). In certain embodiments, the amino acid substitution at position 327 of SEQ ID NO: 1 or SEQ ID NO: 2 is a substitution of an arginine (R) for a tyrosine (Y). In certain embodiments, the amino acid substitution at position 328 of SEQ ID NO: 1 or SEQ ID NO: 2 is a substitution of a valine (V) for a tyrosine (Y). In certain embodiments, the amino acid substitution at position 340 of SEQ ID NO: 1 or SEQ ID NO: 2 is a substitution of a glycine (G) for a cysteine (C). In certain embodiments, the amino acid substitution at position 340 of SEQ ID NO: 1 or SEQ ID NO: 2 is a substitution of a leucine (L) for a cysteine (C). In certain embodiments, the amino acid substitution at position 421 of SEQ ID NO: 1 or SEQ ID NO: 2 is a substitution of a histidine (H) for the aspartic acid (D). In certain embodiments, the amino acid substitution at position 436 of SEQ ID NO: 1 or SEQ ID NO: 2 is a substitution of an isoleucine (I) for a valine (V). In certain embodiments, the amino acid substitution at position 456 of SEQ ID NO: 1 or SEQ ID NO: 2 is a substitution of a tyrosine (Y) for a methionine (M). In certain embodiments, the amino acid substitution at position 470 of SEQ ID NO: 1 or SEQ ID NO: 2 is a substitution of a phenylalanine (F) for a leucine (L). In certain embodiments, the amino acid substitution at position 485 of SEQ ID NO: 1 or SEQ ID NO: 2 is a substitution of a lysine (K) for a serine (S). In certain embodiments, the amino acid substitution at position 503 of SEQ ID NO: 1 or SEQ ID NO: 2 is a substitution of a leucine (L) for a methionine (M). In certain embodiments, the amino acid substitution at position 503 of SEQ ID NO: 1 or SEQ ID NO: 2 is a substitution of an isoleucine (I) for a methionine (M). In certain embodiments, the amino acid substitution at position 552 of SEQ ID NO: 1 or SEQ ID NO: 2 is a substitution of a lysine (K) for a valine (V). In certain embodiments, the amino acid substitution at position 570 of SEQ ID NO: 1 or SEQ ID NO: 2 is a substitution of a threonine (T) for an alanine (A). In certain embodiments, the amino acid substitution at position 591 of SEQ ID NO: 1 or SEQ ID NO: 2 is a substitution of a proline (P) for a glutamine (Q). In certain embodiments, the amino acid substitution at position 591 of SEQ ID NO: 1 or SEQ ID NO: 2 is a substitution of an arginine (R) for a glutamine (Q). In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 1 or SEQ ID NO: 2. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 1 or SEQ ID NO: 2. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 1 or SEQ ID NO: 2. In certain embodiments, the amino acid substitution at position 103 of SEQ ID NO: 1 or SEQ ID NO: 2 is a substitution of a proline (P) for a serine (S). In certain embodiments, the amino acid substitution at position 194 of SEQ ID NO: 1 or SEQ ID NO: 2 is a substitution of a valine (V) for a methionine (M). In certain embodiments, the amino acid substitution at position 372 of SEQ ID NO: 1 or SEQ ID NO: 2 is a substitution of an alanine (A) for an arginine (R). In certain embodiments, the amino acid substitution at position 375 of SEQ ID NO: 1 or SEQ ID NO: 2 is a substitution of an alanine (A) for a lysine (K). In certain embodiments, the amino acid substitution at position 450 of SEQ ID NO: 1 or SEQ ID NO: 2 is a substitution of an asparagine (N) for an aspartic acid (D). In certain embodiments, the amino acid substitution at position 509 of SEQ ID NO: 1 or SEQ ID NO: 2 is a substitution of a glycine (G) for a serine (S). In certain embodiments, the amino acid substitution at position 570 of SEQ ID NO: 1 or SEQ ID NO: 2 is a substitution of a serine (S) for an asparagine (N). In certain embodiments, the piggyBac™ transposase enzyme may comprise a substitution of a valine (V) for a methionine (M) at position 194 of SEQ ID NO: 1. In certain embodiments, including those embodiments wherein the piggyBac™ transposase enzyme may comprise a substitution of a valine (V) for a methionine (M) at position 194 of SEQ ID NO: 1, the piggyBac™ transposase enzyme may further comprise an amino acid substitution at positions 372, 375 and 450 of the sequence of SEQ ID NO: 1 or SEQ ID NO: 2. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, and a substitution of an alanine (A) for a lysine (K) at position 375 of SEQ ID NO: 1. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, a substitution of an alanine (A) for a lysine (K) at position 375 of SEQ ID NO: 1 and a substitution of an asparagine (N) for an aspartic acid (D) at position 450 of SEQ ID NO: 1.

In certain embodiments of the methods of the disclosure, the subject is human.

In certain embodiments of the methods of the disclosure, the subject has an immune system disease or disorder or the subject is at risk of developing an immune system disease or disorder.

In certain embodiments of the methods of the disclosure, the subject has an autoimmune disease or disorder. In certain embodiments, the autoimmune disease or disorder is acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal & neuronal neuropathies, Balo disease, Behcet's disease, bullous pemphigoid, cardiomyopathy, Castleman disease, Celiac disease, Chagas disease, chronic inflammatory demyelinating polyneuropathy (CIDP), chronic recurrent multifocal ostomyelitis (CRMO), Churg-Strauss syndrome, cicatricial pemphigoid/ benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, Granulomatosis with Polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD) Lupus (SLE, Lyme disease, chronic Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH) Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I autoimmune polyglandular syndrome, type II autoimmune polyglandular syndrome, type III autoimmune polyglandular syndrome, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), susac's syndrome, sympathetic ophthalmia, Takayasu's arteritis, temporal arteritis/Giant cell arteritis, thrombocytopenic purpura (TTP), Tolosa-Hunt syndrome, transverse myelitis, type 1 diabetes, ulcerative colitis, undifferentiated connective tissue disease (UCTD), uveitis, vasculitis, vesiculobullous dermatosis or vitiligo.

In certain embodiments of the methods of the disclosure, the subject is immunocompromised.

In certain embodiments of the methods of the disclosure, the subject has an inflammatory disorder.

In certain embodiments of the methods of the disclosure, the subject has an immune system disease or disorder or the subject is at risk of developing an immune system disease or disorder. In certain embodiments, the subject has a genetic or epigenetic marker for the immune system disease or disorder. In certain embodiments, the immune system disease or disorder is induced a medical intervention.

In certain embodiments of the methods of the disclosure, the subject has a genetic or epigenetic marker for the immune system disease or disorder.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC).

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is cancer. In certain embodiments, the cancer is a lymphoma, a leukemia, a myeloma or a malignant immunoproliferative disease. In certain embodiments, the lymphoma is Hodgkin lymphoma, Non-Hodgkin lymphoma, anaplastic large cell lymphoma, angioimmunoblastic T-cell lymphoma (AILT), hepatosplenic T-cell lymphoma, B-cell lymphoma, reticuloendotheliosis, reticulosis, microglioma, diffuse large B-cell lymphoma, follicular lymphoma, mucosa-associated lymphatic tissue lymphoma, B-cell chronic lymphocytic leukemia, mantle cell lymphoma (MCL), Burkitt lymphoma, mediastinal large B cell lymphoma, Waldenstrom's macroglobulinemia, nodal marginal zone B cell lymphoma, splenic marginal zone lymphoma (SMZL), intravascular large B-cell lymphoma, primary effusion lymphoma, lymphomatoid granulomatosis or nodular lymphocyte predominant Hodgkin's lymphoma.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is cancer. In certain embodiments, the cancer is a lymphoma, a leukemia, a myeloma or a malignant immunoproliferative disease. In certain embodiments, the leukemia is plasma cell leukemia (PCL), acute erythraemia and erythroleukaemia, acute erythremic myelosis, acute erythroid leukemia, Heilmeyer-Schoner disease, acute megakaryoblastic leukemia (AMKL), mast cell leukemia, panmyelosis, acute panmyelosis with myelofibrosis (APMF), lymphosarcoma cell leukemia, blastic phase chronic myelogenous leukemia, stem cell leukemia, accelerated phase chronic myelogenous leukemia, acute myeloid leukemia (AML), polycythemia vera, acute promyelocytic leukemia, acute basophilic leukemia, acute eosinophilic leukemia, acute lymphoblastic leukemia, acute monocytic leukemia, acute myeloblastic leukemia with maturation, acute myeloid dendritic cell leukemia, adult T-cell leukemia/lymphoma, aggressive NK-cell leukemia, B-cell prolymphocytic leukemia, B-cell chronic lymphocytic leukemia, B-cell leukemia, chronic myelogenous leukemia, chronic myelomonocytic leukemia, chronic neutrophilic leukemia, chronic lymphocytic leukemia, hairy cell leukemia or chronic idiopathic myelofibrosis.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is cancer. In certain embodiments, the cancer is a lymphoma, a leukemia, a myeloma or a malignant immunoproliferative disease. In certain embodiments, the myeloma is multiple myeloma, Kahler's disease, myelomatosis, solitary myeloma, plasma cell leukemia, extramedullary plasmacytoma, malignant plasma cell tumour or plasmacytoma.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is cancer. In certain embodiments, the cancer is a lymphoma, a leukemia, a myeloma or a malignant immunoproliferative disease. In certain embodiments, the malignant immunoproliferative disease is alpha heavy chain disease or gamma heavy chain disease.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is an anemia. In certain embodiments, the anemia is a hemolytic anemia, an autoimmune hemolytic anemia, a congenital hemolytic anemia, an aplastic anemia, a P-thalassemia, a congenital erythroid aplasia, a congenital dyserythropoietic anemia, a glucose-6-phosphate dehydrogenase deficiency, a Fanconi anemia, a hereditary spherocytosis, a hereditary elliptocytosis, a hereditary pyropoikilocytosis, a hereditary persistence of fetal hemoglobin, a hereditary stomatocytosis, a hexokinase deficiency, a hyperanaemia, a hypochromic anemia, an ineffective erythropoiesis, a macrocytic anemia, a megaloblastic anemia, a myelophthisic anemia, a neuroacanthocytosis, a choreaacanthocytosis, a paroxysmal nocturnal hemoglobinuria, a pyruvate kinase deficiency, a Rh deficiency syndrome, a sickle-cell disease, a sideroblastic anemia, a stomatocytic ovalocytosis, a thalassemia, a triosephosphate isomerase (TPI) deficiency or a warm autoimmune hemolytic anemia.

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is a clotting disorder or a hemorrhagic condition. In certain embodiments, the disease or disorder is a clotting disorder. In certain embodiments, the clotting disorder is a defibrination syndrome, a protein C deficiency, a protein S deficiency, Factor V Leiden, thrombocytosis, thrombosis, recurrent thrombosis, antiphospholipid syndrome, primary antiphospholipid syndrome or thrombotic thrombocytopenic purpura (TTP).

In certain embodiments of the methods of the disclosure, the subject has a genetic or epigenetic marker for a disease or disorder that manifests in a blood cell, an immune cell circulating in the blood, a bone marrow cell or a precursor cell thereof. In certain embodiments, the precursor cell is a hematopoietic stem cell (HSC). In certain embodiments, the disease or disorder is a clotting disorder or a hemorrhagic condition. In certain embodiments, the disease or disorder is a hemorrhagic condition. In certain embodiments, the hemorrhagic condition is thrombocytopenia, hemophilia, hemophilia A, hemophilia B, hemophilia C, Von Willebrand disease (vWD), hereditary Von Willebrand disease (vWD), vWD type 1, vWD type 2, vWD type 3, Glanzmann's thrombasthenia or Wiskott-Aldrich syndrome (WAS).

In certain embodiments of the methods of the disclosure, the subject has a genetic or epigenetic marker for a disease or disorder that manifests in a secondary target cell that may be contacted by the composition comprising a plurality of therapeutic HSCs. In certain embodiments, the secondary target cell is a stem cell or a progenitor cell. In certain embodiments, the stem cell is a somatic stem cell. In certain embodiments, the stem cell is a target HSC, a mesenchymal stem cell, an epidermal stem cell, an epithelial stem cell, a neural stem cell. In certain embodiments, the secondary target cell is a differentiated cell. In certain embodiments, the differentiated cell is a red blood cell, a white blood cell, a monocyte, a granulocyte, a platelet, or a dendritic cell.

In certain embodiments of the methods of the disclosure, the subject has a genetic or epigenetic marker for a disease or disorder that manifests in a secondary target cell that may be contacted by the composition comprising a plurality of therapeutic HSCs. In certain embodiments, the secondary target cell is a stem cell or a progenitor cell. In certain embodiments, the progenitor cell is an osteoblast. In certain embodiments, the at least one HSC of the composition comprising a plurality of therapeutic HSCs is modified to secrete a ligand, peptide or protein that enhances an activity of an osteoblast. In certain embodiments, the composition comprising a plurality of therapeutic HSCs treats or prevents a disease or disorder associated with aberrant osteoblast function. In certain embodiments, the subject has one or more genetic or epigenetic markers for the disease or disorder associated with aberrant osteoblast function. In certain embodiments, the disease or disorder associated with aberrant osteoblast function is Paget's disease, hypophosphatasia or ostesopetrosis.

In certain embodiments of the methods of the disclosure, the subject has a genetic or epigenetic marker for a disease or disorder that manifests in a secondary target cell that may be contacted by the composition comprising a plurality of therapeutic HSCs. In certain embodiments, the secondary target cell is a differentiated cell. In certain embodiments, the differentiated cell is a red blood cell, a white blood cell, a monocyte, a granulocyte, a platelet, or a dendritic cell. In certain embodiments, the at least one HSC of the composition comprising a plurality of therapeutic HSCs is modified to secrete a ligand, peptide or protein that enhances an activity of a granulocyte. In certain embodiments, the composition comprising a plurality of therapeutic HSCs treats or prevents a disease or disorder associated with aberrant granulocyte function. In certain embodiments, the subject has one or more genetic or epigenetic markers for the disease or disorder associated with aberrant granulocyte function. In certain embodiments, the disease or disorder associated with aberrant granulocyte function is Chronic Granulomatous Disease.

In certain embodiments of the methods of the disclosure, the subject has an immune system disease or disorder or the subject is at risk of developing an immune system disease or disorder. In certain embodiments, the immune system disease or disorder is induced a medical intervention. In certain embodiments, the subject is at risk of developing an immune system disease or disorder due to a past, present or future medical intervention.

In certain embodiments of the methods of the disclosure, the subject has an immune system disease or disorder or the subject is at risk of developing an immune system disease or disorder. In certain embodiments, the immune system disease or disorder was induced by an infection. In certain embodiments, the subject is at risk of developing an immune system disease or disorder due to a past, present or potential infection. In certain embodiments, the infection is viral, bacterial and/or microbial. In certain embodiments, the infection is viral. In certain embodiments, the infection is viral and the subject becomes immunocompromised as a result of the infection. In certain embodiments, the subject was exposed to or infected with HIV. In certain embodiments, the subject has developed AIDS. In certain embodiments, the infection is viral. In certain embodiments, the infection is viral and the subject develops cancer.

In certain embodiments of the methods of the disclosure, administration of the composition comprising the plurality of immune cells is systemic. In certain embodiments, the composition is administered via an intravenous route.

In certain embodiments of the methods of the disclosure, administration of the composition comprising the plurality of immune cells is local. In certain embodiments, the composition is administered via an intraosseous, intraspinal or intracerebral infusion.

In certain embodiments of the methods of the disclosure, administration of the composition comprising the plurality of therapeutic HSCs is systemic. In certain embodiments, the composition is administered via an intravenous route.

In certain embodiments of the methods of the disclosure, administration of the composition comprising the plurality of therapeutic HSCs is local. In certain embodiments, the composition is administered via an intraosseous infusion.

In certain embodiments of the methods of the disclosure, the composition comprising a plurality of therapeutic HSCs further comprises at least one pharmaceutically acceptable carrier. In certain embodiments, the composition comprising a plurality of therapeutic HSCs further comprises an induction agent.

In certain embodiments of the methods of the disclosure, at least one HSC of the plurality of therapeutic HSCs is genetically modified. In certain embodiments, each HSC of the plurality of therapeutic HSCs is genetically modified.

In certain embodiments of the methods of the disclosure, at least one HSC of the plurality of therapeutic HSCs is genetically modified. In certain embodiments, each HSC of the plurality of therapeutic HSCs is genetically modified. In certain embodiments of the methods of the disclosure, the subject has an immune disease or disorder and wherein the plurality of therapeutic HSCs improves a sign or symptom of the immune disease or disorder. In certain embodiments, at least one HSC of the plurality of therapeutic HSCs is genetically modified to improve a sign or symptom of the immune disease or disorder of the subject. In certain embodiments, each HSC of the plurality of therapeutic HSCs is genetically modified to improve a sign or symptom of the immune disease or disorder of the subject.

In certain embodiments of the methods of the disclosure, the subject has a genetic or epigenetic marker for a disease or disorder that manifests in a blood cell, an immune cell circulating in the blood, a bone marrow cell or a precursor cell thereof and the plurality of therapeutic HSCs improves a sign or symptom of the disease or disorder. In certain embodiments, the disease or disorder is a clotting disorder.

In certain embodiments, at least one HSC of the plurality of therapeutic HSCs has been modified to secrete a protein that improves a sign or symptom of the clotting disorder. In certain embodiments, a majority of HSCs of the plurality of therapeutic HSCs have been modified to secrete a protein that improves a sign or symptom of the clotting disorder. In certain embodiments, each HSC of the plurality of therapeutic HSCs has been modified to secrete a protein that improves a sign or symptom of the clotting disorder. In certain embodiments, the at least one HSC, the majority of HSCs or each HSC of the plurality of therapeutic HSCs are modified to secrete a protein that improves a sign or symptom of the clotting disorder. In certain embodiments, the at least one HSC, the majority of HSCs or each HSC of the plurality of therapeutic HSCs are modified to secrete one or more clotting factors.

In certain embodiments of the methods of the disclosure, the subject has a genetic or epigenetic marker for a glycogen storage disease or disorder and the plurality of therapeutic HSCs improves a sign or symptom of the glycogen storage disease or disorder. In certain embodiments, the glycogen storage disease or disorder is glycogen storage disease (GSD) type 0, GSD type I, GSD type II, GSD type III, GSD type IV, GSD type V, GSD type VI, GSD type VII, GSD type IX, GSD type X, GSD type XI, GSD type XII or GSD type XIII. In certain embodiments, at least one HSC, a majority of HSCs or each HSC of the plurality of therapeutic HSCs are modified to secrete one or more of glycogen synthase, glucose-6-phosphatase, acid alpha-glucosidase, glycogen debranching enzyme, glycogen branching enzyme, muscle glycogen phosphorylase, liver glycogen phosphorylase, muscle phosphofructokinase, phosphorylase kinase, glucose transporter GLUT2, Aldolase A or 0-enolase and wherein the plurality of therapeutic HSCs improves a sign or symptom of GSD type 0, GSD type I, GSD type II, GSD type III, GSD type IV, GSD type V, GSD type VI, GSD type VII, GSD type IX, GSD type X, GSD type XI, GSD type XII or GSD type XIII, respectively.

In certain embodiments of the methods of the disclosure, the subject has a genetic or epigenetic marker for the immune system disease or disorder, at least one HSC, a portion of the HSCs or each HSC the plurality of therapeutic HSCs comprise a genetic modification and the at least one HSC, the portion of the HSCs or each HSC the plurality of therapeutic HSCs does not comprise the genetic or epigenetic marker. In certain embodiments, the genetic modification removed the genetic or epigenetic marker.

In certain embodiments of the methods of the disclosure, at least one HSC of the composition comprising a plurality of therapeutic HSCs is autologous. In certain embodiments, each HSC of the composition comprising a plurality of therapeutic HSCs is autologous. In certain embodiments, at least one genetically-modified HSC of the composition comprising a plurality of therapeutic HSCs is autologous. In certain embodiments, each genetically-modified HSC of the composition comprising a plurality of therapeutic HSCs is autologous.

In certain embodiments of the methods of the disclosure, at least one HSC of the composition comprising a plurality of therapeutic HSCs is allogeneic. In certain embodiments, each HSC of the composition comprising a plurality of therapeutic HSCs is allogeneic. In certain embodiments, at least one genetically-modified HSC of the composition comprising a plurality of therapeutic HSCs is allogeneic. In certain embodiments, each genetically-modified HSC of the composition comprising a plurality of therapeutic HSCs is allogeneic.

In certain embodiments of the methods of the disclosure, the method treats or prevents the onset or progression of graft-versus-host disease (GvHD). In certain embodiments, treating GvHD comprises reducing a sign or symptom of GvHD. In certain embodiments, the GvHD is acute GvHD. In certain embodiments, the GvHD is chronic GvHD. In certain embodiments, the sign or symptom of GvHD comprises a skin rash, skin blistering, nausea, vomiting, abdominal cramps, diarrhea, loss of appetite, jaundice, dry mouth, dry throat, excessive dry mouth, excessive dry throat, ulcers of mouth or throat, dryness bronchial tissues, dryness of endothelial tissues, dryness of surface tissues, loss of patches of skin, skin discoloration, skin scarring, reduced joint mobility coincident with skin scarring, hair loss coincident with skin injury, loss of tear formation leading to dry eye or any combination thereof.

In certain embodiments of the methods of the disclosure, including those wherein the method treats or prevents the onset or progression of graft-versus-host disease (GvHD), the subject is a transplant recipient. In certain embodiments, the composition comprising a plurality of therapeutic HSCs is administered to the subject before the administration of the transplant and wherein the plurality of therapeutic HSCs and the transplant are isolated or derived from the same donor. In certain embodiments, the method further comprises a period following administration of the composition comprising a plurality of therapeutic HSCs sufficient for tolerization of the subject's immune system to the transplant. In certain embodiments, the transplant comprises a cell, a tissue, a tissue graft, an organ, an organ graft or any combination thereof. In certain embodiments, the organ is a solid organ.

BRIEF DESCRIPTION OF THE DRAWINGS

FIG. 5B is a series of sequences of exemplary c-kit ScFv(1) (SEQ ID NO: 69), c-kit ScFv (2) (SEQ ID NO: 70), c-kit ScFv (3) (SEQ ID NO: 71), c-kit ScFv (4) (SEQ ID NO: 72), c-kit ScFv (5) (SEQ ID NO: 73), c-kit ScFv (6) (SEQ ID NO: 74) and c-kit ScFv (7) (SEQ ID NO: 75) that may be used in the exemplary CAR depitcted in FIG. 5A.

FIG. 5C is a series of sequences of exemplary c-kit ScFv (8) (SEQ ID NO: 76); exemplary c-kit ligand (1) (SEQ ID NO: 77), c-kit ligand (2) (SEQ ID NO: 78) and Mouse c-kit ligand (SEQ ID NO: 79); and exemplary CD133 scFv(1) (SEQ ID NO: 80), CD133 scFv(2) (SEQ ID NO: 81) and CD133 scFv(3) (SEQ ID NO: 82) that may be used in the exemplary CAR depitcted in FIG. 5A.

FIG. 5D is a series of sequences of exemplary CD133 scFv(4) (SEQ ID NO: 83), CD133 scFv(5) (SEQ ID NO: 84), CD133 scFv(6) (SEQ ID NO: 85), CD133 scFv(7) (SEQ ID NO: 86) and CD133 scFv(8) (SEQ ID NO: 87) that may be used in the exemplary CAR depicted in FIG. 5A. A sequence of an exemplary CAR CAR depicted in FIG. 5A is also provided (SEQ ID NO: 88).

FIGS. 6A-6E is a series of graphs depicting results of evaluating the in vitro efficacy of CAR-T cells in specifically targeting human hematopoietic cells expressing either c-kit (CD117) or prominin-1 (CD133). CD3/CD28-stimulated pan T cells isolated from human peripheral blood were electroporated with mRNA encoding each of the CAR candidates directed against either c-kit or CD133 (FIG. 5). On the day after introduction of the mRNAs, the CAR expression from antibody-directed ScFv sequences was determined from anti-mouse IgG staining and flow cytometry (FIG. 6A). The activation of the effector CAR-T cells in the presence of the target cells (effector to target cell ratio of 3:1) was demonstrated through degranulation according to CD107a expression at 5 hours. TF-1 cells that endogenously and uniformly express c-kit elicited highest activation of CAR-T cells directed against c-kit with less activation when mixed at a 5% proportion with non-c-kit expressing Raji cells (FIG. 6B). CAR-T cell activation was similarly seen for co-cultures with human bone marrow cells but no significant activation beyond the mock CAR-T control cells was observed following coculture with the mouse c-kit expressing EML-C1 cell line (FIG. 6B). TF-1 cells were rendered CD133 expression following electroporation of CD133 encoded mRNA as determined by anti-CD133 antibody staining and flow cytometry (data not shown). These transfected cells enabled activation of CAR-T cells carrying four of eight anti-CD133 ScFv sequences. Less anti-CD133 CAR-T stimulation was shown for CD133 expressing TF-1 cells mixed at a 5% proportion with non-CD133 expressing Raji cells or for human bone marrow cells (FIG. 6C). Following co-culture of the CAR-T cells with human bone marrow for 2 days (effector to target cell ratio of 3:1), the cells were either stained with anti-human CD34, CD 117 and CD133 antibodies and analyzed by flow cytometry or plated in methylcellulose cultures supplemented with human growth factors (MethoCult™, H4434) for the generation of hematopoietic colonies (CFUs) over 12 days. Flow cytometric analysis within the CD34 positive population showed a decrease in the proportion of c-kit positive cells for 3 of the 6 anti-c-kit CAR-T cell candidates and a decrease in proportion of CD133 positive cells for 3 of 7 anti-CD133 CAR-T candidates (FIG. 6D). The CFU survival assay showed depletion of functional hematopoietic progenitors by up to 85% for 7 of the 8 anti-c-kit CAR-T cell candidates (FIG. 6E).

FIGS. 9A-9B is a pair of graphs depicting the percent survival of bone marrow hematopoietic progenitors following targeting by piggyBac (PB) transposed CAR-T cells. Following co-culture of the CAR-T cells with human or monkey (Rhesus macaque) bone marrow cells for 2 days (effector to target cell ratio of 3:1), the cells were plated in methylcellulose cultures supplemented with human growth factors (MethoCult™, H4434) for the generation of hematopoietic colonies (CFUs) over 12 days. The CFU survival assay showed depletion of human functional hematopoietic progenitors by over 70% for 3 of the 8 anti-c-kit CAR-T cell candidates (FIG. 9A). CAR-T cells encoding for these same anti-c-kit ScFv sequences also depleted hematopoietic progenitors from monkey bone marrow to demonstrate cross-reactivity with this species.

(FIG. 11A) a constitutive promoter is used to drive the tri-cistronic cassette consisting of a safety switch, the chimeric antigen receptor (CAR), and a selection gene with flanking chromatin insulators; (FIG. 11B) pan T cells are isolated from an apheresis product, and then electroporated with anti-CD117 or anti-CD133 CAR piggyBac™ transposon plasmid DNA and in vitro transcribed piggyBac™ transposase mRNA. The electroporated cells are then activated, expanded, and selected prior to freezing. The process yields>$1 \times 10^9$ cells with >95% CAR expression.

FIGS. 12A-12B are a series of graphs depicting an exemplary PB CAR-T phenotype: PB CAR-T cells directed against CD 117 and CD133 antigens were evaluated by flow cytometry for typical T-cell markers following the manufacturing process. (FIG. 12A) Expression CD4, CD8 and memory markers demonstrating the stem cell memory phenotype of PB CAR-T cells; (FIG. 12B) PB CAR-T cells express CXCR4, a marker commonly associated with bone marrow homing.

FIGS. 13A-13B is a series of graphs depicting an exemplary activity of anti-CD 117 or -CD133 CAR-T cells against the CD34+CD38—progenitor population and CFUs from mobilized peripheral blood CD34+ cells: CD34+ cells isolated from human mobilized peripheral blood were incubated with anti-c-kit and CD133 CAR-T cells for 48 hours followed by FACS phenotyping of remaining cells (FIG. 13A) and CFU survival assay (FIG. 13B). The anti-CD117 CAR-T depleted>95% of ckit+ and CD133+ cells from the primitive CD34+CD38-population, while the anti-CD133 CAR-T depleted>90% of CD133+ cells from this population (FIG. 13A). Both the anti-CD 117 and -CD133 CAR-T cells also reduced colony formation at all E:T ratios tested.

FIGS. 15A-15C is a series of graphs depicting Bone Marrow Homing of PB CAR-T Cells: PB CAR-T cells were cultured with (+) or without (−) factors to increase CXCR4 expression. Cells from each treatment group were labeled separately, mixed, and injected IV into 4-week old, irradiated NSG mice. (FIG. 15A) CXCR4 expression increases after 24h culture with added factors; (FIG. 15B) input cell ratio; (FIG. 15C) 16h after injection cells, CAR-T cells, regardless of treatment, were found at equal ratios in the blood and bone marrow.

DETAILED DESCRIPTION

Figure 1:
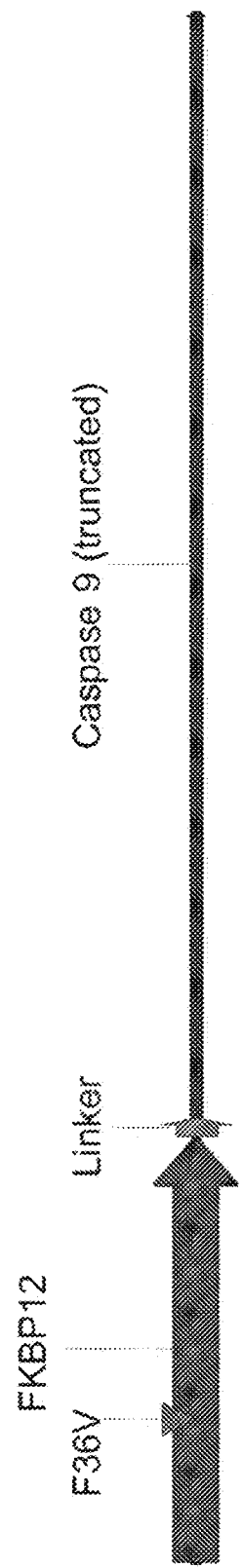
FIG. 1 is a schematic diagram depicting an exemplary inducible truncated caspase 9 polypeptide of the disclosure.

The compositions and methods of the disclosure utilize genetically modified immune cells that express chimeric ligand/antigen receptors (CLRs/CARs) to selectively eliminate target cells in a subject. Furthermore, the compositions and methods of the disclosure enable the selective elimination of these CLR/CAR-expressing immune cells once they have selective eliminated target cells. Of particular interest, the compositions and methods of the disclosure enable the subsequent transplantation of therapeutic cells that may have also been genetically modified to correct a genetic defect present in the subject's native cells that were selectively destroyed, to replace the cell population that was selectively destroyed or to supplement the subject's native cell populations to treat genetic, immune, and blood-based disorders, including cancer.

The compositions and methods of the disclosure provide a 'drug-reversible' CAR-T cell or plurality of cells directed against recipient hematopoietic cells as a selective conditioning strategy for stem cell transplantation. The transplant of autologous or allogeneic hematopoietic stem cells (HSCs) has the proven ability to treat a wide array of malignant and non-malignant hematological diseases. The preparative regimen, however, routinely entails aggressive and genotoxic treatment with total body irradiation and/or chemotherapy, which brings severe and even life-threatening complications that limit its broader application. Previous experimental studies have established that depletion of recipient HSCs is an essential requirement of these conditioning regimens in allowing successful engraftment of the composite donor HSCs. Animal and clinical studies have also indicated that alloreactive anti-HSC donor T cells additionally facilitate stem cell engraftment, but this is often accompanied by the risks of GvHD. This has prompted the consideration of alternative conditioning methods for the depletion of HSCs with less toxic side-effects, such as anti-c-kit and anti-CD45 antibody-directed treatments. In this way, more precise HSC targeting may also be achieved by the application of short-lived, genetically engineered chimeric antigen receptor (CAR)-T cells for stem cell transplantation conditioning.

We developed a novel and controllable CAR-T approach for recipient HSC targeting via genetic modification using the non-viral piggyBac™ (PB) transposon system. As opposed to viral vector delivery systems, the relatively large carrying capacity of PB allows the stable introduction of at least three separate genes encoded within the same tri-cistronic transgene cassette. This includes a second-generation CAR that targets either human c-kit (CD 117) or prominin-1 (CD133), markers known to be antigenically expressed on the surface of HSCs. In addition, a drug resistance element serves as a selection gene that, in combination with a non-genotoxic drug, provides an effective method of CAR-T cell purification during manufacture. Importantly, a small molecule drug-inducible safety switch gene is also included to facilitate rapid in vivo clearance of the CAR-T cells after depletion of recipient HSCs and prior to donor HSC transplant. Lastly, as a result of the manufacturing process, the majority of the CAR-T cells express chemokine receptors such as CXCR4 that can allow more selective trafficking to the bone marrow (BM) for eradication of resident HSCs.

To select a lead candidate from a panel of anti-HSC CAR constructs, CD3/CD28 stimulated T cells from human peripheral blood were first electroporated with mRNA encoding each of the CAR candidates directed against either c-kit or CD133. CAR surface expression was confirmed in transfected T cells by flow cytometry. In vitro functional assays were performed by co-culturing mRNA-transfected CAR-T cells with mouse or human cell lines (EML-C1, TF-1 and K562), expressing either c-kit or CD133, as well as mouse and human primary BM cells. Lead CAR candidates were identified from their specific activation of the CAR-T cells through degranulation according to CD107a expression and secretion of IFNγ. Furthermore, those CARs were also capable of selectively depleting c-kit or CD133 positive cells. Interestingly, some mRNA-transfected CAR-T cells retained effector activity against target c-kit+ TF-1 cells even in the presence of its soluble ligand, stem cell factor. Next, lead CAR candidates were co-expressed with the selection and drug-inducible safety switch genes in the same tri-cistronic transgene and then stably delivered to T cells using PB. The manufacturing process yielded CAR-T cells that were mainly of the T memory stem cell (Tscm) phenotype, as determined by positive expression of CD62L and CD45RA, and also expressed high levels of the CXCR4 chemokine receptor. Similar to the mRNA-transfected CAR-T cells, these stably-transposed cells were capable of extensive effector capabilities including specific depletion of c-kit or CD133 expressing target cells.

Future studies will evaluate PB-produced lead anti-HSC CAR-T cells in immune-deficient NSG mice with pre-established xenogeneic human hematopoietic chimerism, along with standard busulfan or radiation conditioning controls. This approach constitutes a novel targeted biological therapy that is envisaged to lead the way towards minimally toxic transplant regimens for depletion of endogenous HSCs in the BM and to procure their replacement with engrafted allogeneic or gene-corrected stem cells.

Need for Alternative Conditioning Therapies prior to HSC Transplants: More than 5,000 patients per year in the U.S. are treated with myeloablative conditioning regimens prior to HSC transplants. Most of these conditioning regimens consist of high doses of genotoxic radiation or busulfan that are primarily applied as HSC-depleting agents but are limited by major life-threatening complications. Monoclonal antibodies directed against antigens expressed on HSCs such as c-kit and CD45 have been considered as alternatives. CAR-T cells may provide more effective, selective and safer depletion of HSC residing in the bone marrow. PiggyBac™-produced CAR-T cells is a non-viral system with a large cargo capacity that allows introduction of multiple genes including those for selection and a safety switch that can clear CAR-T cells prior to donor HSC transplant. PB CAR-T cells also exhibit a stem-cell memory (SCM) phenotype for enhanced in vivo potency and may better home to bone marrow.

PB CAR-T cells targeted against CD117 or CD133 deplete hematopoietic progenitor cells from human and monkey bone marrow, and primitive CAFCs from human CD34+ cells. PB CAR-T cells exhibit a stem cell memory phenotype and naturally express CXCR4, although expression can be increased by 24 hr culture with added factors. PB CAR-T cells successfully home to bone marrow within 16 hours after injection. This data supports the use of PB CAR-T cells to target endogenous HSCs in the BM as a minimal non-genotoxic HSC transplant regimen.

The hematopoietic system is maintained by a rare population of primitive hematopoietic stem cells (HSCs) that are defined by the key feature of self-renewal, as well as the ability to generate multi-lineage progenitor populations that ultimately give rise to the functioning cells of blood and immune system. The normal mammalian hematopoietic system is largely distributed around the adult body within the bone marrow and consists of quiescent stem cells and lineage-committed progenitors. The progenitors in turn give rise to differentiated cells with defined function, such as erythrocytes, monocytes, granulocytes, platelets, dendritic cells, B cells and T cells. The proliferative potential of HSCs is thus considerable as they have the unique ability to perpetuate themselves by self-renewal. Methods for distinguishing stem cell lineage and developmental potential have used phenotypic and functional characteristics. The defining feature of a hematopoietic stem cell (HSC) that has been found to be useful is the ability of HSCs to repopulate the hematopoietic system of a recipient after transplantation, particularly after whole body irradiation treatment. Accordingly, it is important to effectively deplete or inactivate host HSCs in treating diseases involving HSCs, such as cancers, immune disorders, and transplant rejection. However, this has proven difficult, particularly because the frequency of HSCs is extremely low (estimated to be only 1 to 2 per so 100,000 bone marrow cells in competitive repopulation experiments, making these cells more difficult to target and eradicate. Current treatments typically involve administration of high doses of cytotoxic agents, which ablate not just HSCs, but many cells in the hematopoietic system. These therapies have clear drawbacks and severe toxic side effects. Accordingly, improved treatments for depleting HSCs, (e.g., prior to transplantation of donor HSCs to establish complete or mixed hematopoietic cell chimerism) would be beneficial.

Clinically, bone marrow and hematopoietic stem cell transplantation are widely used as a means of providing patients with the capacity to generate blood cells, usually where the patient has been depleted of endogenous stem cells by high-dose chemotherapy or radiation. Bone marrow and peripheral blood are currently used as sources of autologous and allogeneic stem cells. In the future, cultured stem cells, including those derived from embryonic stem cells and induced pluripotent stem cells (iPSCs), may provide an alternative to HSCs for transplants.

Graft failure or poor graft function may be caused by administration of myelosuppressive drugs, graft-versus-host disease, and infections in the early post-transplant period. Poor engraftment may also result from microenvironment or marrow stroma dysfunction related to the patient's underlying disease or prior therapy.

When a recipient is properly conditioned to receive a donor graft, an active state of unresponsiveness is seen with respect to the lymphoid cells' response to a specific ligand such as an MHC marker or pattern of ligands as a result of their interactions with that ligand or ligands. Specific tolerance is achieved. Hosts which receive complete allogeneic donor bone marrow transplants accept a renal allograft from the same donor without immunosuppression. However, full allogeneic bone marrow transplantation as currently practiced utilizing extensive myeloablative conditioning is limited in its applicability to patients of a particular age range and medical history. Myeloablative conditioning regimes including high doses of whole body irradiation are often used in HSC transplantation in conjunction with treatments designed to prevent immunological rejection (e.g., cyclophosphamide). Such conditioning is used for procuring engraftment of transplanted allogeneic donor HSCs in the recipient. However, these treatments can have undesired side effects, such as toxicity (e.g. enteritis, pneumonitis, nephrotoxicity, hyperlipidemia, myelosuppression) and the complications of aggravated GVHD and immunodeficiency (for example, infection and malignancy) on the recipient. These side effects are thought to be due in part to cytokine-induced adverse reactions and can result in damage to the recipient's organ systems. Therefore, less toxic pre- and post-transplant conditioning regimens are highly desirable. The disclosure provides compositions and methods for the selective elimination and replacement of HSCs that do not induce any of the negative side effects that result from existing therapeutic uses.

Compositions and methods are provided for the engraftment of HSCs, where endogenous stem cells are selectively ablated by adoptively transferring specific CAR-T effector cells, thereby opening a niche for the engraftment of donor stem cells. Selective ablation substantially eliminates endogenous stem cells in the targeted tissue, without general ablation of cells in the tissue. The efficiency of engraftment is significantly enhanced by selective ablation, as compared to engraftment obtained without pretreatment. Such selective ablation allows improved function of the targeted tissue during the engraftment period, compared to methods involving non-selective ablation. Thus, the methods of the disclosure provide effective HSC engraftment without the use of existing, non-selective, ablation methods (e.g. radiation or chemotherapy). Radiation and chemotherapy ablate differentiated cells involved in the function of the targeted tissue (e.g. on progenitor populations that maintain peripheral blood cell numbers), induce undesirable side effects upon other tissues (e.g. on cells of the gastrointestinal epithelium, lung, liver and kidneys) and increase the risk of secondary malignancies.

In certain embodiments of the methods of the disclosure, selective ablation is accomplished by administering CAR-T cells capable of specific depletion of endogenous HSCs to the patient prior to transplantation of donor stem cells. Following ablation, and after a period of time sufficient to substantially eliminate the HSC ablative CAR-T cells from the patient, an effective dose of donor stem cells are introduced to the patient.

The compositions and methods of the disclosure provide a non-toxic or relatively less-toxic conditioning regimen, when compared to the established non-selective ablation methods (e.g. radiation and chemotherapy) for establishing mixed hematopoietic cell chimerism for the following non-limiting exemplary uses: (a) in the treatment of malignant and non-malignant diseases, particularly those of the blood; (b) in the promotion of immunological acceptance for cellular, tissue, and/or solid organ transplantation; (c) to prevent or reduce graft-versus-host disease (GvHD); (d) to provide a platform for administering donor-leukocyte infusions (DLI); (e) in the treatment of enzyme deficiency diseases; (f) in the treatment of autoimmune diseases; and (g) congenital diseases affecting HSC derivatives.

Stem Cell Microenvironments

The interaction of stem cells with their microenvironment provides important cues for maintenance, proliferation and differentiation. This physical environment in which stem cells reside may be referred to as the stem cell microenvironment, or niche. The stromal and other cells involved in this niche provide soluble and bound factors, which have a multitude of effects in HSC regulation.

Various models have been proposed for the interaction between stem cell and niche. In its simplest form, a model has been suggested where, when a stem cell divides, only one daughter remains in the niche and the other daughter cell leaves the niche to differentiate.

A particular advantage of the compositions and methods of the disclosure is the ability to activate CLR/CAR expressing T cells only within close proximity or only within a specified microenvironment. This physical selectivity minimizes the effect of compositions of the disclosure on cells, niches, and microenvironments that are not targets of a given therapy.

Moreover, because a microenvironment may be defined by the secretome of one or more target cells, the CLR/CAR expressing immune cells of the disclosure may be modified such that the CLR/CAR is only activated once the CLR/CAR expressing immune cell of the disclosure contacts a secreted protein or contacts a secreted protein at a given concentration. Furthermore, the CLR/CAR expressing immune cells of the disclosure may be modified such that the CLR/CAR is deactivated or eliminated upon contacting an apoptosis induction agent of the disclosure or a component of the endogenous secretome of a non-target cell.

Microenvironments of the disclosure may be defined by the expression of proteins on the surface of one or more target cells. Accordingly, the CLR/CAR expressing immune cells of the disclosure may be modified such that the CLR/CAR is only activated once the CLR/CAR expressing immune cell of the disclosure contacts one or more cell-surface bound protein(s) on a target cell. Furthermore, the CLR/CAR expressing immune cells of the disclosure may be modified such that the CLR/CAR is deactivated or eliminated upon contacting an apoptosis induction agent of the disclosure or a cell surface bound protein of a non-target cell.

For example, CLR/CAR expressing immune cells of the disclosure may be modified to express CLRs/CARs that specifically bind to one or more ligands on a target cancer cell, but may also require binding of one or more secreted proteins (e.g. one or more cytokines, one or more factors to induce vascularization, one or more factors to break down the extracellular matrix, etc.) present in the target cancer cells microenvironment to be activated. As in the digital world, this two-factor authentication system ensures that the CLR/CAR expressing immune cells of the disclosure eliminate only target cells and do not negatively impact non-target cells or non-target environments. As described above, should one or more of the required signals not match the target cell and target microenvironment, CLR/CAR expressing immune cells of the disclosure may be modified to induce apoptosis rather than risk elimination of a non-target cell. Superior to the digital world, the CLR/CAR expressing immune cells of the disclosure may be modified to require multifactor authentications from, for example, at least 2, 3, 4, 5, 6, 7, 8, 9, 10, 11, 12, 13, 14, 15, 16, 17, 18, 19 or 20 distinct ligands (which may include cell surface bound ligands, secreted ligands or a combination thereof). As used herein, the term ligand may be used to describe any sequence, nucleic acid or amino acid, to which the CARs of the disclosure specifically bind.

Chimeric Ligand/Antigen Receptors (CLRs/CARs)

The terms "chimeric ligand receptor (CLR)" and "chimeric antigen receptor (CAR)" are used interchangeably throughout the disclosure. Chimeric receptors of the disclosure may specifically binds to target antigens and/or target ligands of the disclosure.

Exemplary CLR(s)/CAR(s) of the disclosure comprise (a) an ectodomain comprising a ligand recognition region, (b) a transmembrane domain, and (c) an endodomain comprising at least one costimulatory domain. In certain embodiments, the ligand recognition region comprises one or more of a protein scaffold, a Centyrin, a single chain variable fragment (scFv), a VHH, an immunoglobulin and an antibody mimetic. In certain embodiments, the immunoglobulin is an antibody for fragment thereof of an IgA, IgD, IgE, IgG, or IgM isotype. In certain embodiments, the antibody fragment is a complementarity determining region (CDR), a heavy chain CDR (including CDR1, CDR2 and/or CDR3), a light chain CDR (including CDR1, CDR2 and/or CDR3), an antigen-binding fragment (Fab), a variable domain (Fv), a heavy chain variable region, a light chain variable region, a complete heavy chain, a complete light chain, one or more constant domains, an Fc (crystallizable fragment) or any combination thereof. In certain embodiments, the antibody mimetic comprises one or more of an affibody, an afflilin, an affimer, an affitin, an alphabody, an anticalin, and avimer, a Designed Ankyrin Repeat Protein (DARPin), a Fynomer, a Kunitz domain peptide, and a monobody. In certain embodiments, at least one of the CLR(s) is bi-specific. In certain embodiments, each of the CLR(s) is bi-specific. In certain embodiments, at least one of the CLR(s) is tri-specific. In certain embodiments, each of the CLR(s) is tri-specific.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the signal peptide comprises a sequence encoding a human CD2, CD3δ, CD3ε, CD3γ, CD3ζ, CD4, CD8α, CD19, CD28, 4-1BB or GM-CSFR signal peptide.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the hinge comprises a sequence derived from a human CD8a, IgG4, and/or CD4 sequence.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the transmembrane domain comprises a sequence encoding a human CD2, CD3δ, CD3R, CD3γ, CD3ζ, CD4, CD8α, CD19, CD28, 4-1BB or GM-CSFR transmembrane domain.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the endodomain comprises a human CD3ζ endodomain.

In certain embodiments of the methods of the disclosure, each of the one or more CLR(s) comprises (a) an ectodomain comprising a ligand recognition region, (b) a transmembrane domain, and (c) an endodomain comprising at least one costimulatory domain. In certain embodiments, the ectodomain of (a) further comprises a signal peptide. In certain embodiments, the ectodomain of (a) further comprises a hinge between the ligand recognition region and the transmembrane domain. In certain embodiments, the endodomain comprises a human CD3ζ endodomain. In certain embodiments, the at least one costimulatory domain comprises a human 4-1BB, a human CD28, a human CD40, a human ICOS, a human MyD88, a human OX-40 intracellular segment or any combination thereof. In certain embodiments, the at least one costimulatory domain comprises a human CD28 and/or a human 4-1BB costimulatory domain. In certain embodiments, the 4-1BB costimulatory domain is located between the transmembrane domain and the CD28 costimulatory domain.

In certain embodiments of the methods of the disclosure, the at least one immune cell of the composition comprising the plurality of immune cells comprises a split CLR/CAR. In certain embodiments, the split CLR/CAR comprises two or more CLR(s)/CAR(s) having distinct intracellular domains that, when expressed simultaneously in the at least one immune cell, increase or decrease the activity of the immune cell compared to an immune cell that does not express the split CLR/CAR or an immune cell that does not express a CLR/CAR.

In certain embodiments of the methods of the disclosure, the at least one immune cell of the composition comprising the plurality of immune cells comprises a split CLR/CAR. In certain embodiments, including those wherein the simultaneous expression increases the activity of the immune cell, the split CLR/CAR comprises (a) a first CLR/CAR comprising an ectodomain comprising a ligand recognition region, a transmembrane domain, and an endodomain consisting of a primary intracellular signaling domain, and (b) a second CLR/CAR comprising an ectodomain comprising a ligand recognition region, a transmembrane domain, and an endodomain consisting of a secondary intracellular signalling domain. In certain embodiments, the primary intracellular signaling domain comprises a human CD3ζ endodomain. In certain embodiments, the secondary intracellular signaling domain comprises a human 4-1BB, a human CD28, a human CD40, a human ICOS, a human MyD88, or a human OX-40 intracellular segment. In certain embodiments, the secondary intracellular signaling domain comprises a human 4-1BB and a human CD28.

In certain embodiments of the methods of the disclosure, the at least one immune cell of the composition comprising the plurality of immune cells comprises a split CLR/CAR. In certain embodiments, including those wherein the simultaneous expression decreases the activity of the immune cell, the split CLR/CAR comprises (a) a first CLR/CAR comprising an ectodomain comprising a ligand recognition region, a transmembrane domain, and an endodomain comprising of a primary intracellular signaling domain a secondary intracellular signalling domain, and (b) a second CLR/CAR comprising an ectodomain comprising a ligand recognition region, a transmembrane domain, and an endodomain consisting of an inhibitory intracellular signalling domain. In certain embodiments, the primary intracellular signaling domain comprises a human CD3ζ endodomain and the secondary intracellular signaling domain comprises a human 4-1BB, a human CD28, a human CD40, a human ICOS, a human MyD88, or a human OX-40 intracellular segment. In certain embodiments, the primary intracellular signaling domain comprises a human CD3ζ endodomain and the secondary intracellular signaling domain comprises a human 4-1BB and a human CD28. In certain embodiments, the inhibitory intracellular signalling domain comprises a signaling domain derived from PD1, CTLA4, LAG3, B7-H1, B7-1, CD160, BTLA, PD1H, LAIR1, TIM1, TIM3, TIM4, 2B4, and TIGIT. Additional intracellular signaling components from these inhibitory intracellular signalling domains and other molecules that may be used in whole or in part, include, but are not limited to, ITIM, ITSM, YVKM, PP2A, SHP2, KIEELE, and Y265. In certain embodiments, the second CLR/CAR selectively binds a target on a non-target cell, thereby inducing the second CLR/CAR to inhibit the activity of the first CLR/CAR. In certain embodiments, the second CLR/CAR to inhibits the ability of the first CLR/CAR to induce death in the target or non-target cell.

In certain embodiments of the methods of the disclosure, the one or more CLR(s)/CAR(s) bind a ligand with an affinity selected from a $K_D$ of less than or equal to $10^{-9}$M, less than or equal to $10^{-10}$M, less than or equal to $10^{-11}$M, less than or equal to $10^{-12}$M, less than or equal to $10^{-13}$M, less than or equal to $10^{-14}$M, and less than or equal to $10^{-15}$M. In certain embodiments, the $K_D$ is determined by surface plasmon resonance.

Scaffold Proteins

Protein scaffolds of the disclosure may be derived from a fibronectin type III (FN3) repeat protein, encoding or complementary nucleic acids, vectors, host cells, compositions, combinations, formulations, devices, and methods of making and using them. In a preferred embodiment, the protein scaffold is comprised of a consensus sequence of multiple FN3 domains from human Tenascin-C(hereinafter "Tenascin"). In a further preferred embodiment, the protein scaffold of the present invention is a consensus sequence of 15 FN3 domains. The protein scaffolds of the disclosure can be designed to bind various molecules, for example, a cellular target protein. In a preferred embodiment, the protein scaffolds of the disclosure can be designed to bind an epitope of a wild type and/or variant form of a ligand.

Protein scaffolds of the disclosure may include additional molecules or moieties, for example, the Fc region of an antibody, albumin binding domain, or other moiety influencing half-life. In further embodiments, the protein scaffolds of the disclosure may be bound to a nucleic acid molecule that may encode the protein scaffold.

The disclosure provides at least one method for expressing at least one protein scaffold based on a consensus sequence of multiple FN3 domains, in a host cell, comprising culturing a host cell as described herein under conditions wherein at least one protein scaffold is expressed in detectable and/or recoverable amounts.

The disclosure provides at least one composition comprising (a) a protein scaffold based on a consensus sequence of multiple FN3 domains and/or encoding nucleic acid as described herein; and (b) a suitable and/or pharmaceutically acceptable carrier or diluent.

The disclosure provides a method of generating libraries of a protein scaffold based on a fibronectin type III (FN3) repeat protein, preferably, a consensus sequence of multiple FN3 domains and, more preferably, a consensus sequence of multiple FN3 domains from human Tenascin. The library is formed by making successive generations of scaffolds by altering (by mutation) the amino acids or the number of amino acids in the molecules in particular positions in portions of the scaffold, e.g., loop regions. Libraries can be generated by altering the amino acid composition of a single loop or the simultaneous alteration of multiple loops or additional positions of the scaffold molecule. The loops that are altered can be lengthened or shortened accordingly. Such libraries can be generated to include all possible amino acids at each position, or a designed subset of amino acids. The library members can be used for screening by display, such as in vitro or CIS display (DNA, RNA, ribosome display, etc.), yeast, bacterial, and phage display.

Protein scaffolds of the disclosure provide enhanced biophysical properties, such as stability under reducing conditions and solubility at high concentrations; they may be expressed and folded in prokaryotic systems, such as *E. coli*, in eukaryotic systems, such as yeast, and in in vitro transcription/translation systems, such as the rabbit reticulocyte lysate system.

The disclosure provides a method of generating a scaffold molecule that binds to a particular target by panning the scaffold library of the invention with the target and detecting binders. In other related aspects, the disclosure comprises screening methods that may be used to generate or affinity mature protein scaffolds with the desired activity, e.g., capable of binding to target proteins with a certain affinity. Affinity maturation can be accomplished by iterative rounds of mutagenesis and selection using systems, such as phage display or in vitro display. Mutagenesis during this process may be the result of site directed mutagenesis to specific scaffold residues, random mutagenesis due to error-prone PCR, DNA shuffling, and/or a combination of these techniques.

The disclosure provides an isolated, recombinant and/or synthetic protein scaffold based on a consensus sequence of fibronectin type III (FN3) repeat protein, including, without limitation, mammalian-derived scaffold, as well as compositions and encoding nucleic acid molecules comprising at least one polynucleotide encoding protein scaffold based on the consensus FN3 sequence. The disclosure further includes, but is not limited to, methods of making and using such nucleic acids and protein scaffolds, including diagnostic and therapeutic compositions, methods and devices.

The protein scaffolds of the disclosure offer advantages over conventional therapeutics, such as ability to administer locally, orally, or cross the blood-brain barrier, ability to express in *E. Coli* allowing for increased expression of protein as a function of resources versus mammalian cell expression ability to be engineered into bispecific or tandem molecules that bind to multiple targets or multiple epitopes of the same target, ability to be conjugated to drugs, polymers, and probes, ability to be formulated to high concentrations, and the ability of such molecules to effectively penetrate diseased tissues and tumors.

Moreover, the protein scaffolds possess many of the properties of antibodies in relation to their fold that mimics the variable region of an antibody. This orientation enables the FN3 loops to be exposed similar to antibody complementarity determining regions (CDRs). They should be able to bind to cellular targets and the loops can be altered, e.g., affinity matured, to improve certain binding or related properties.

Three of the six loops of the protein scaffold of the disclosure correspond topologically to the complementarity determining regions (CDRs 1-3), i.e., ligand-binding regions, of an antibody, while the remaining three loops are surface exposed in a manner similar to antibody CDRs. These loops span at or about residues 13-16, 22-28, 38-43, 51-54, 60-64, and 75-81 of SEQ ID NO: 1. Preferably, the loop regions at or about residues 22-28, 51-54, and 75-81 are altered for binding specificity and affinity. One or more of these loop regions are randomized with other loop regions and/or other strands maintaining their sequence as backbone portions to populate a library and potent binders can be selected from the library having high affinity for a particular protein target. One or more of the loop regions can interact with a target protein similar to an antibody CDR interaction with the protein.

Scaffolds of the disclosure may comprise an antibody mimetic.

The term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be a ligand. Antibody mimetics may provide superior properties over antibodies including, but not limited to, superior solubility, tissue penetration, stability towards heat and enzymes (e.g. resistance to enzymatic degradation), and lower production costs. Exemplary antibody mimetics include, but are not limited to, an affibody, an afflilin, an affimer, an affitin, an alphabody, an anticalin, and avimer (also known as avidity multimer), a DARPin (Designed Ankyrin Repeat Protein), a Fynomer, a Kunitz domain peptide, and a monobody.

Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

Affilin molecules of the disclosure comprise a protein scaffold produced by modification of exposed amino acids of, for example, either gamma-B crystallin or ubiquitin. Affilin molecules functionally mimic an antibody's affinity to ligand, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target ligand sequence or ligand.

Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

Affitin molecules of the disclosure comprise an artificial protein scaffold, the structure of which may be derived, for example, from a DNA binding protein (e.g. the DNA binding protein Sac7d). Affitins of the disclosure selectively bind a target sequence, which may be the entirety or part of a ligand. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In certain embodiments of the disclosure, an affitin molecule may be used as a specific inhibitor of an enzyme. Affitin molecules of the disclosure may include heat-resistant proteins or derivatives thereof.

Alphabody molecules of the disclosure may also be referred to as Cell-Penetrating Alphabodies (CPAB). Alphabody molecules of the disclosure comprise small proteins (typically of less than 10 kDa) that bind to a variety of target sequences (including ligands). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In preferred embodiments, anticalin molecules of the disclosure comprise a barrel structure comprising eight antiparallel beta-strands pairwise connected by loops and an attached alpha helix.

Avimer molecules of the disclosure comprise an artificial protein that specifically binds to a target sequence (which may also be a ligand). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

DARPins (Designed Ankyrin Repeat Proteins) of the disclosure comprise genetically-engineered, recombinant, or chimeric proteins having high specificity and high affinity for a target sequence. In certain embodiments, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

Fynomers of the disclosure comprise small binding proteins (about 7 kDa) derived from the human Fyn SH3 domain and engineered to bind to target sequences and molecules with equal affinity and equal specificity as an antibody.

Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

Monobodies of the disclosure are small proteins (comprising about 94 amino acids and having a mass of about 10 kDa) comparable in size to a single chain antibody. These genetically engineered proteins specifically bind target sequences including ligands. Monobodies of the disclosure may specifically target one or more distinct proteins or target sequences. In preferred embodiments, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof, contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Multispecific monobodies may be optimized by modifying the loops BC and FG. Monobodies of the disclosure may comprise an adnectin.

Such a method can comprise administering an effective amount of a composition or a pharmaceutical composition comprising at least one scaffold protein to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

Production and Generation of Scaffold Proteins

At least one scaffold protein of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., N.Y., N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., N.Y. (1994-2001); Colligan et al., Current Protocols in Protein Science, John Wiley & Sons, N.Y., N.Y., (1997-2001).

Amino acids from a scaffold protein can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, scaffold proteins can be engineered with retention of high affinity for the ligand and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate scaffold protein to bind its ligand. In this way, residues can be selected and combined from the parent and reference sequences so that the desired characteristic, such as affinity for the target ligand(s), is achieved. Alternatively, or in addition to, the above procedures, other suitable methods of engineering can be used.

Screening of Scaffold Proteins

Screening protein scaffolds for specific binding to similar proteins or fragments can be conveniently achieved using nucleotide (DNA or RNA display) or peptide display libraries, for example, in vitro display. This method involves the screening of large collections of peptides for individual members having the desired function or structure. The displayed nucleotide or peptide sequences can be from 3 to 5000 or more nucleotides or amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5,427,908, 5,580,717, assigned to Affymax; 5,885,793, assigned to Cambridge Antibody Technologies; 5,750,373, assigned to Genentech, 5,618,920, 5,595,898, 5,576,195, 5,698,435, 5,693,493, 5,698,417, assigned to Xoma, Colligan, supra; Ausubel, supra; or Sambrook, supra.

The protein scaffolds of the disclosure can bind human or other mammalian proteins with a wide range of affinities ($K_D$). In a preferred embodiment, at least one protein scaffold of the present invention can optionally bind to a target ligand with high affinity, for example, with a $K_D$ equal to or less than about 10-7 M, such as but not limited to, 0.1-9.9 (or any range or value therein)×10-8, 10-9, 10-10, 10-11, 10-12, 10-13, 10-14, 10-15 or any range or value therein, as determined by surface plasmon resonance or the Kinexa method, as practiced by those of skill in the art.

The affinity or avidity of a protein scaffold for a ligand can be determined experimentally using any suitable method. (See, for example, Berzofsky, et al., "Antibody-Ligand Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular protein scaffold-ligand interaction can vary if measured under different conditions (e.g., salt concentration, pH). Thus, measurements of affinity and other ligand-binding parameters (e.g., $K_D$, Kon, Koff) are preferably made with standardized solutions of protein scaffold and ligand, and a standardized buffer, such as the buffer described herein.

Competitive assays can be performed with the protein scaffold of the disclosure in order to determine what proteins, antibodies, and other antagonists compete for binding to a target protein with the protein scaffold of the present invention and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to the target protein is separated from the unbound sample, for example, by decanting (where the protein/antibody was preinsolubilized) or by centrifuging (where the protein/antibody was precipitated after the competitive reaction). Also, the competitive binding may be determined by whether function is altered by the binding or lack of binding of the protein scaffold to the target protein, e.g., whether the protein scaffold molecule inhibits or potentiates the enzymatic activity of, for example, a label. ELISA and other functional assays may be used, as well known in the art.

Centyrins and CARTyrins

The disclosure provides a chimeric ligand/antigen receptor (CLR/CAR) comprising: (a) an ectodomain comprising a ligand recognition region, wherein the ligand recognition region comprises at least one Centyrin; (b) a transmembrane domain, and (c) an endodomain comprising at least one costimulatory domain. As used throughout the disclosure, a CLR/CAR comprising a Centyrin is referred to as a CARTyrin. In certain embodiments, the ligand recognition region may comprise two Centyrins to produce a bi-specific or tandem CLR/CAR. In certain embodiments, the ligand recognition region may comprise three Centyrins to produce a tri-specific CLR/CAR. In certain embodiments, the ectodomain may further comprise a signal peptide. Alternatively, or in addition, in certain embodiments, the ectodomain may further comprise a hinge between the ligand recognition region and the transmembrane domain.

The disclosure provides a chimeric ligand/antigen receptor (CLR/CAR) comprising: (a) an ectodomain comprising a ligand recognition region, wherein the ligand recognition region comprises at least one protein scaffold or antibody mimetic; (b) a transmembrane domain, and (c) an endodomain comprising at least one costimulatory domain. In certain embodiments, the ligand recognition region may comprise two scaffold proteins or antibody mimetics to produce a bi-specific or tandem CLR/CAR. In certain embodiments, the ligand recognition region may comprise three protein scaffolds or antibody mimetics to produce a tri-specific CLR/CAR. In certain embodiments, the ectodomain may further comprise a signal peptide. Alternatively, or in addition, in certain embodiments, the ectodomain may further comprise a hinge between the ligand recognition region and the transmembrane domain.

In certain embodiments of the CLRs/CARs of the disclosure, the signal peptide may comprise a sequence encoding a human CD2, CD3δ, CD3ε, CD3γ, CD3ζ, CD4, CD8α, CD19, CD28, 4-1BB or GM-CSFR signal peptide. In certain embodiments of the CLRs/CARs of the disclosure, the signal peptide may comprise a sequence encoding a human CD8α signal peptide. The human CD8α signal peptide may comprise an amino acid sequence comprising MALPVTALLLPLALLLHAARP (SEQ ID NO: 31). The human CD8α signal peptide may comprise an amino acid sequence comprising MALPVTALLLPLALLLHAARP (SEQ ID NO: 31) or a sequence having at least 70%, 80%, 90%, 95%, or 99% identity to the an amino acid sequence comprising MALPVTALLLPLALLLHAARP (SEQ ID NO: 31). The human CD8α signal peptide may be encoded by a nucleic acid sequence comprising atggcactgccagtcaccgccctgctgctgcctctggctctgctgctgcacgcagctagacca (SEQ ID NO: 32).

In certain embodiments of the CLRs/CARs of the disclosure, the transmembrane domain may comprise a sequence encoding a human CD2, CD3δ, CD3ε, CD3γ, CD3ζ, CD4, CD8α, CD19, CD28, 4-1BB or GM-CSFR transmembrane domain. In certain embodiments of the CLRs/CARs of the disclosure, the transmembrane domain may comprise a sequence encoding a human CD8α transmembrane domain. The CD8α transmembrane domain may comprise an amino acid sequence comprising IYIWAPLAGTCGVLLLSLVITLYC (SEQ ID NO: 33) or a sequence having at least 70%, 80%, 90%, 95%, or 99% identity to the amino acid sequence comprising IYIWAPLAGTCGVLLLSLVITLYC (SEQ ID NO: 33). The CD8α transmembrane domain may be encoded by the nucleic acid sequence comprising atctacattgggcaccactggccgggacctgtggagtgctgctgctgagcctggtcatcacactgtactgc (SEQ ID NO: 35).

In certain embodiments of the CLRs/CARs of the disclosure, the endodomain may comprise a human CD3ζ endodomain.

In certain embodiments of the CLRs/CARs of the disclosure, the at least one costimulatory domain may comprise a human 4-1BB, CD28, CD40, ICOS, MyD88, OX-40 intracellular segment, or any combination thereof. In certain embodiments of the CLRs/CARs of the disclosure, the at least one costimulatory domain may comprise a CD28 and/or a 4-1BB costimulatory domain. The CD28 costimulatory domain may comprise an amino acid sequence comprising RVKFSRSADAPAYKQGQNQLYNELNLGRREEYDVLDKRRGRDPEMGGKPRRKNPQE GLYNELQKDKMAEAYSEIGMKGERRRGKGHDG-LYQGLSTATKDTYDALHMQALPP R (SEQ ID NO: 36) or a sequence having at least 70%, 80%, 90%, 95%, or 99% identity to the amino acid sequence comprising RVKFSRSADAPAYKQGQNQLYNELNLGRREEYDVLDKRR-GRDPEMGGKPRRKNPQE GLYNELQKDKMAEAYSEI-GMKGERRRGKGHDGLYQGLSTATKDTYDALHM-QALPP R(SEQ ID NO: 36). The CD28 costimulatory domain may be encoded by the nucleic acid sequence comprising cgcgtgaagtttagtcgatcagcagatgccccagcttacaaacagggacagaaccagctgtataacgagctgaatctgggccgccga gagaatatgacgtgctggataagcgcgagaggacgcgacccgaaatgggaggcaagcccaggcgcaaaaaccctcaggaagg cctgtataacgagctgcagaaggacaaaatggcagaagcctattctgagatcggcatgaaggggggagcgacggagaggcaaagg gcacgatgggctgtaccagggactgagcaccgccacaaaggacacctatgatgctctg-
catatgcaggcactgcctccaagg (SEQ ID NO: 37). The 4-1BB costimulatory domain may comprise an amino acid sequence comprising KRGRKKLLY-IFKQPFMRPVQTTQEEDGCSCRFPEEEEGGCEL (SEQ ID NO: 38) or a sequence having at least 70%, 80%, 90%, 95%, or 99% identity to the amino acid sequence comprising KRGRKKLLY-IFKQPFMRPVQTTQEEDGCSCRFPEEEEGGCEL (SEQ ID NO: 38). The 4-1BB costimulatory domain may be encoded by the nucleic acid sequence comprising aagagaggcaggaagaaactgctgtatattttcaaacagcccttcatgcgccccgtgcagactacccaggaggaagacgggtgctcc tgtcgat-tccctgaggaagaggaaggcgggtgtgagctg (SEQ ID NO: 39). The 4-1BB costimulatory domain may be located between the transmembrane domain and the CD28 costimulatory domain.

In certain embodiments of the CLRs/CARs of the disclosure, the hinge may comprise a sequence derived from a human CD8α, IgG4, and/or CD4 sequence. In certain embodiments of the CLRs/CARs of the disclosure, the hinge may comprise a sequence derived from a human CD8α sequence. The hinge may comprise a human CD8α amino acid sequence comprising TTTPAPRPPTPAPTIA-SQPLSLRPEACRPAAGGAVHTRGLDFACD (SEQ ID NO: 40) or a sequence having at least 70%, 80%, 90%, 95%, or 99% identity to the amino acid sequence comprising TTTPAPRPPTPAPTIASQPLSLRPEACRPAAGGAVHTR-GLDFACD (SEQ ID NO: 40). The human CD8α hinge amino acid sequence may be encoded by the nucleic acid sequence comprising actaccacaccagcacctagaccac-caactccagctccaaccatcgcgagtcagcccctgagtctgagacct-gaggcctgcaggcc agctgcaggag-gagctgtgcacaccaggggcctggacttcgcctgcgac (SEQ ID NO: 41).

Centyrins of the disclosure may comprise a protein scaffold, wherein the scaffold is capable of specifically binding a ligand. Centyrins of the disclosure may comprise a protein scaffold comprising a consensus sequence of at least one fibronectin type III (FN3) domain, wherein the scaffold is capable of specifically binding a ligand. The at least one fibronectin type III (FN3) domain may be derived from a human protein. The human protein may be Tenascin-C. The consensus sequence may comprise LPAPKNLVVSEVTED-SLRLSWTAPDAAFDSFLIQYQESEKVGEAINLTVPGS-ERSYDL TGLKPGTEYTVSIYGVKGGHRSNPLSAEFTT (SEQ ID NO: 42) or MLPAPKNLVVSEVTED-SLRLSWTAPDAAFDSFLIQYQESEKVGEAINLTVPGS-ERSYD LTGLKPGTEYTVSIYGVKGGHRSNPLSAEFTT (SEQ ID NO: 43). The consensus sequence may encoded by a nucleic acid sequence comprising atgctgcctgcac-caaagaacctggtgtggtgtctcatgtgacagaggatagtgccagactgt-catggactgctcccgacgcagccttcg atagttttatcatcgtgtaccgggagaa-catcgaaaccggcgaggccattgtcctgacagtgccagggtccgaacgctct-tatgacctg acagatctgaagccccggaactgagtactatgtgca-gatcgccggcgtcaaaggaggcaatatcagcttccctctgtccgcaatcttcac caca (SEQ ID NO: 44). The consensus sequence may be modified at one or more positions within (a) a A-B loop comprising or consisting of the amino acid residues TEDS (SEQ ID NO: 63) at positions 13-16 of the consensus sequence; (b) a B-C loop comprising or consisting of the amino acid residues TAPDAAF (SEQ ID NO: 64) at positions 22-28 of the consensus sequence; (c) a C-D loop comprising or consisting of the amino acid residues SEKVGE (SEQ ID NO: 65) at positions 38-43 of the consensus sequence; (d) a D-E loop comprising or consisting of the amino acid residues GSER (SEQ ID NO: 66) at positions 51-54 of the consensus sequence; (e) a E-F loop comprising or consisting of the amino acid residues GLKPG (SEQ ID NO: 67) at positions 60-64 of the consensus sequence; (f) a F-G loop comprising or consisting of the amino acid residues KGGHRSN (SEQ ID NO: 68) at positions 75-81 of the consensus sequence; or (g) any combination of (a)-(f). Centyrins of the disclosure may comprise a consensus sequence of at least 5 fibronectin type III (FN3) domains, at least 10 fibronectin type III (FN3) domains or at least 15 fibronectin type III (FN3) domains. The scaffold may bind a ligand with at least one affinity selected from a $K_D$ of less than or equal to $10^{-9}$M, less than or equal to $10^{-10}$M, less than or equal to $10^{-11}$M, less than or equal to $10^{-12}$M, less than or equal to $10^{-13}$M, less than or equal to $10^{-14}$M, and less than or equal to $10^{-15}$M. The $K_D$ may be determined by surface plasmon resonance.

The disclosure provides a composition comprising the CLR/CAR of the disclosure and at least one pharmaceutically acceptable carrier.

The disclosure provides a transposon comprising the CLR/CAR of the disclosure.

Transposons of the disclosure may comprise a selection gene for identification, enrichment and/or isolation of cells that express the transposon. Exemplary selection genes encode any gene product (e.g. transcript, protein, and enzyme) essential for cell viability and survival. Exemplary selection genes encode any gene product (e.g. transcript, protein, enzyme) essential for conferring resistance to a drug challenge against which the cell is sensitive (or which could be lethal to the cell) in the absence of the gene product encoded by the selection gene. Exemplary selection genes encode any gene product (e.g. transcript, protein, and enzyme) essential for viability and/or survival in a cell media lacking one or more nutrients essential for cell viability and/or survival in the absence of the selection gene. Exemplary selection genes include, but are not limited to, neo (conferring resistance to neomycin), DHFR (encoding Dihydrofolate Reductase and conferring resistance to Methotrexate), TYMS (encoding Thymidylate Synthetase), MGMT (encoding 0(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), and NKX2.2 (encoding NK2 Homeobox 2).

Transposons of the disclosure be episomally maintained or integrated into the genome of the recombinant/modified cell. The transposon may be part of a two component piggyBac system that utilizes a transposon and transposase for enhanced non-viral gene transfer. In certain embodiments of this method, the transposon is a plasmid DNA transposon with a sequence encoding the chimeric ligand/antigen receptor flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase.

In certain embodiments of the methods of the disclosure, the transposon is a plasmid DNA transposon with a sequence encoding the ligand/antigen receptor flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

sequence of SEQ ID NO: 1 is a substitution of a valine (V) for an isoleucine (I). In certain embodiments, the amino acid substution at position 165 of the sequence of SEQ ID NO: 1 is a substitution of a serine (S) for a glycine (G). In certain embodiments, the amino acid substution at position 282 of the sequence of SEQ ID NO: 1 is a substitution of a valine (V) for a methionine (M). In certain embodiments, the

```
                                                                    (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substution at one or more of positions 30, 165, 282, or 538 of the sequence:

amino acid substution at position 538 of the sequence of SEQ ID NO: 1 is a substitution of a lysine (K) for an asparagine (N).

In certain embodiments of the methods of the disclosure, the transposase enzyme is a Super piggyBac™ (SPB) trans-

```
                                                                    (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments, the transposase enzyme is a piggyBac™ (PB) transposase enzyme that comprises or consists of an amino acid sequence having an amino acid substution at two or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at three or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at each of the following positions 30, 165, 282, and 538 of the sequence of SEQ ID NO: 1. In certain embodiments, the amino acid substution at position 30 of the posase enzyme. In certain embodiments, the Super piggyBac™ (SPB) transposase enzymes of the disclosure may comprise or consist of the amino acid sequence of the sequence of SEQ ID NO: 1 wherein the amino acid substution at position 30 is a substitution of a valine (V) for an isoleucine (I), the amino acid substution at position 165 is a substitution of a serine (S) for a glycine (G), the amino acid substution at position 282 is a substitution of a valine (V) for a methionine (M), and the amino acid substution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

```
                                                              (SEQ ID NO: 2)
  1 MGSSLDDEHI LSALLQSDDE LVGEDSDSEV SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTSATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RVYIPNKPSK YGIKILMMCD

301 SGTKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPKEV

541 PGTSDDSTEE PVMKKRTYCT YCPSKIRRKA NASCKKCKKV ICREHNIDMC QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 1 or SEQ ID NO: 2. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 1 or SEQ ID NO: 2 is a substitution of an asparagine (N) for a serine (S). In certain embodiments, the amino acid substitution at position 46 of SEQ ID NO: 1 or SEQ ID NO: 2 is a substitution of a serine (S) for an alanine (A). In certain embodiments, the amino acid substitution at position 46 of SEQ ID NO: 1 or SEQ ID NO: 2 is a substitution of a threonine (T) for an alanine (A). In certain embodiments, the amino acid substitution at position 82 of SEQ ID NO: 1 or SEQ ID NO: 2 is a substitution of a tryptophan (W) for an isoleucine (I). In certain embodiments, the amino acid substitution at position 103 of SEQ ID NO: 1 or SEQ ID NO: 2 is a substitution of a proline (P) for a serine (S). In certain embodiments, the amino acid substitution at position 119 of SEQ ID NO: 1 or SEQ ID NO: 2 is a substitution of a proline (P) for an arginine (R). In certain embodiments, the amino acid substitution at position 125 of SEQ ID NO: 1 or SEQ ID NO: 2 is a substitution of an alanine (A) a cysteine (C). In certain embodiments, the amino acid substitution at position 125 of SEQ ID NO: 1 or SEQ ID NO: 2 is a substitution of a leucine (L) for a cysteine (C). In certain embodiments, the amino acid substitution at position 177 of SEQ ID NO: 1 or SEQ ID NO: 2 is a substitution of a lysine (K) for a tyrosine (Y). In certain embodiments, the amino acid substitution at position 177 of SEQ ID NO: 1 or SEQ ID NO: 2 is a substitution of a histidine (H) for a tyrosine (Y). In certain embodiments, the amino acid substitution at position 180 of SEQ ID NO: 1 or SEQ ID NO: 2 is a substitution of a leucine (L) for a phenylalanine (F). In certain embodiments, the amino acid substitution at position 180 of SEQ ID NO: 1 or SEQ ID NO: 2 is a substitution of an isoleucine (I) for a phenylalanine (F). In certain embodiments, the amino acid substitution at position 180 of SEQ ID NO: 1 or SEQ ID NO: 2 is a substitution of a valine (V) for a phenylalanine (F). In certain embodiments, the amino acid substitution at position 185 of SEQ ID NO: 1 or SEQ ID NO: 2 is a substitution of a leucine (L) for a methionine (M). In certain embodiments, the amino acid substitution at position 187 of SEQ ID NO: 1 or SEQ ID NO: 2 is a substitution of a glycine (G) for an alanine (A). In certain embodiments, the amino acid substitution at position 200 of SEQ ID NO: 1 or SEQ ID NO: 2 is a substitution of a tryptophan (W) for a phenylalanine (F). In certain embodiments, the amino acid substitution at position 207 of SEQ ID NO: 1 or SEQ ID NO: 2 is a substitution of a proline (P) for a valine (V). In certain embodiments, the amino acid substitution at position 209 of SEQ ID NO: 1 or SEQ ID NO: 2 is a substitution of a phenylalanine (F) for a valine (V). In certain embodiments, the amino acid substitution at position 226 of SEQ ID NO: 1 or SEQ ID NO: 2 is a substitution of a phenylalanine (F) for a methionine (M). In certain embodiments, the amino acid substitution at position 235 of SEQ ID NO: 1 or SEQ ID NO: 2 is a substitution of an arginine (R) for a leucine (L). In certain embodiments, the amino acid substitution at position 240 of SEQ ID NO: 1 or SEQ ID NO: 1 is a substitution of a lysine (K) for a valine (V). In certain embodiments, the amino acid substitution at position 241 of SEQ ID NO: 1 or SEQ ID NO: 2 is a substitution of a leucine (L) for a phenylalanine (F). In certain embodiments, the amino acid substitution at position 243 of SEQ ID NO: 1 or SEQ ID NO: 2 is a substitution of a lysine (K) for a proline (P). In certain embodiments, the amino acid substitution at position 258 of SEQ ID NO: 1 or SEQ ID NO: 2 is a substitution of a serine (S) for an asparagine (N). In certain embodiments, the amino acid substitution at position 296 of SEQ ID NO: 1 or SEQ ID NO: 2 is a substitution of a tryptophan (W) for a leucine (L). In certain embodiments, the amino acid substitution at position 296 of SEQ ID NO: 1 or SEQ ID NO: 2 is a substitution of a tyrosine (Y) for a leucine (L). In certain embodiments, the amino acid substitution at position 296 of SEQ ID NO: 1 or SEQ ID NO: 2 is a substitution of a phenylalanine (F) for a leucine (L). In certain embodiments, the amino acid substitution at position 298 of SEQ ID NO: 1 or SEQ ID NO: 2 is a substitution of a leucine (L) for a methionine (M). In certain embodiments, the amino acid substitution at position 298 of SEQ ID NO: 1 or SEQ ID NO: 2 is an substitution of an alanine (A) for a methionine (M). In certain embodiments, the amino acid substitution at position 298 of SEQ ID NO: 1or SEQ ID NO: 2 is a substitution of a valine (V) for a methionine (M). In certain embodiments, the amino acid substitution at position 311 of SEQ ID NO: 1 or SEQ ID NO: 2 is a substitution of an isoleucine (I) for a proline (P). In certain embodiments, the amino acid substitution at position 311 of SEQ ID NO: 1 or SEQ ID NO: 2 is a substitution of a valine for a proline (P). In certain embodiments, the amino acid substitution at position 315 of SEQ ID NO: 1 or SEQ ID NO: 2 is a substitution of a lysine (K) for an arginine (R).In certain embodiments, the amino acid substitution at position 319 of SEQ ID NO: 1 or SEQ ID NO: 2 is a substitution of a glycine (G) for a threonine (T). In certain embodiments, the amino acid substitution at position 327 of SEQ ID NO: 1 or SEQ ID NO: 2 is a substitution of an arginine (R) for a tyrosine (Y). In certain embodiments, the amino acid substitution at position 328 of SEQ ID NO: 1 or SEQ ID NO: 2 is a substitution of a valine (V) for a tyrosine (Y). In certain embodiments, the amino acid substitution at position 340 of SEQ ID NO: 1 or SEQ ID NO: 2 is a substitution of a glycine (G) for a cysteine (C). In certain embodiments, the amino acid substitution at position 340 of SEQ ID NO: 1 or SEQ ID NO: 2 is a substitution of a leucine (L) for a cysteine (C). In certain embodiments, the amino acid substitution at position 421 of SEQ ID NO: 1 or SEQ ID NO: 2 is a substitution of a histidine (H) for the aspartic acid (D). In certain embodiments, the amino acid substitution at position 436 of SEQ ID NO: 1 or SEQ ID NO: 2 is a substitution of an isoleucine (I) for a valine (V). In certain embodiments, the amino acid substitution at position 456 of SEQ ID NO: 1 or SEQ ID NO: 2 is a substitution of a tyrosine (Y) for a methionine (M). In certain embodiments, the amino acid substitution at position 470 of SEQ ID NO: 1 or SEQ ID NO: 2 is a substitution of a phenylalanine (F) for a leucine (L). In certain embodiments, the amino acid substitution at position 485 of SEQ ID NO: 1 or SEQ ID NO: 2 is a substitution of a lysine (K) for a serine (S). In certain embodiments, the amino acid substitution at position 503 of SEQ ID NO: 1 or SEQ ID NO: 2 is a substitution of a leucine (L) for a methionine (M). In certain embodiments, the amino acid substitution at position 503 of SEQ ID NO: 1 or SEQ ID NO: 2 is a substitution of an isoleucine (I) for a methionine (M). In certain embodiments, the amino acid substitution at position 552 of SEQ ID NO: 1 or SEQ ID NO: 2 is a substitution of a lysine (K) for a valine (V). In certain embodiments, the amino acid substitution at position 570 of SEQ ID NO: 1 or SEQ ID NO: 2 is a substitution of a threonine (T) for an alanine (A). In certain embodiments, the amino acid substitution at position 591 of SEQ ID NO: 1 or SEQ ID NO: 2 is a substitution of a proline (P) for a glutamine (Q). In certain embodiments, the amino acid substitution at position 591 of SEQ ID NO: 1 or SEQ ID NO: 2 is a substitution of an arginine (R) for a glutamine (Q). In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 1 or SEQ ID NO: 2. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 1 or SEQ ID NO: 2. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 1 or SEQ ID NO: 2. In certain embodiments, the amino acid substitution at position 103 of SEQ ID NO: 1 or SEQ ID NO: 2 is a substitution of a proline (P) for a serine (S). In certain embodiments, the amino acid substitution at position 194 of SEQ ID NO: 1 or SEQ ID NO: 2 is a substitution of a valine (V) for a methionine (M). In certain embodiments, the amino acid substitution at position 372 of SEQ ID NO: 1 or SEQ ID NO: 2 is a substitution of an alanine (A) for an arginine (R). In certain embodiments, the amino acid substitution at position 375 of SEQ ID NO: 1 or SEQ ID NO: 2 is a substitution of an alanine (A) for a lysine (K). In certain embodiments, the amino acid substitution at position 450 of SEQ ID NO: 1 or SEQ ID NO: 2 is a substitution of an asparagine (N) for an aspartic acid (D). In certain embodiments, the amino acid substitution at position 509 of SEQ ID NO: 1 or SEQ ID NO: 2 is a substitution of a glycine (G) for a serine (S). In certain embodiments, the amino acid substitution at position 570 of SEQ ID NO: 1 or SEQ ID NO: 2 is a substitution of a serine (S) for an asparagine (N). In certain embodiments, the piggyBac™ transposase enzyme may comprise a substitution of a valine (V) for a methionine (M) at position 194 of SEQ ID NO: 1. In certain embodiments, including those embodiments wherein the piggyBac™ transposase enzyme may comprise a substitution of a valine (V) for a methionine (M) at position 194 of SEQ ID NO: 1, the piggyBac™ transposase enzyme may further comprise an amino acid substitution at positions 372, 375 and 450 of the sequence of SEQ ID NO: 1 or SEQ ID NO: 2. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, and a substitution of an alanine (A) for a lysine (K) at position 375 of SEQ ID NO: 1. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, a substitution of an alanine (A) for a lysine (K) at position 375 of SEQ ID NO: 1 and a substitution of an asparagine (N) for an aspartic acid (D) at position 450 of SEQ ID NO: 1.

Inducible Proapoptotic Polypeptides

Inducible proapoptotic polypeptides of the disclosure are superior to existing inducible polypeptides because the inducible proapoptotic polypeptides of the disclosure are far less immunogenic. While inducible proapoptotic polypeptides of the disclosure are recombinant polypeptides, and, therefore, non-naturally occurring, the sequences that are recombined to produce the inducible proapoptotic polypeptides of the disclosure do not comprise non-human sequences that the host human immune system could recognize as "non-self" and, consequently, induce an immune response in the subject receiving an inducible proapoptotic polypeptide of the disclosure, a cell comprising the inducible proapoptotic polypeptide or a composition comprising the inducible proapoptotic polypeptide or the cell comprising the inducible proapoptotic polypeptide.

Transposons of the disclosure may comprise an inducible proapoptotic polypeptide comprising (a) a ligand binding region, (b) a linker, and (c) a proapoptotic polypeptide, wherein the inducible proapoptotic polypeptide does not comprise a non-human sequence. In certain embodiments, the non-human sequence comprises a restriction site. In certain embodiments, the ligand binding region may be a multimeric ligand binding region. Inducible proapoptotic polypeptides of the disclosure may also be referred to as an "iC9 safety switch". In certain embodiments, transposons of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, transposons of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, transposons of the disclosure may comprise an inducible caspase polypeptide comprising (a) a ligand binding region, (b) a linker, and (c) a truncated caspase 9 polypeptide, wherein the inducible proapoptotic polypeptide does not comprise a non-human sequence. In certain embodiments of the inducible proapoptotic polypeptides, inducible caspase polypeptides or truncated caspase 9 polypeptides of the disclosure, the ligand binding region may comprise a FK506 binding protein 12 (FKBP12) polypeptide. In certain embodiments, the amino acid sequence of the ligand binding region that comprise a FK506 binding protein 12 (FKBP12) polypeptide may comprise a modification at position 36 of the sequence. The modification may be a substitution of valine (V) for phenylalanine (F) at position 36 (F36V). In certain embodiments, the FKBP12 polypeptide is encoded by an amino acid sequence comprising GVQVETISPGDGRTFPKRGQTCVVHYTGMLEDGKKVDSSRDRNKPFKFMLGKQEVI RGWEEGVAQMSVGQRAKLTISPDYAYGATGHPGIIPPHATLVFDVELLKLE (SEQ ID NO: 45). In certain embodiments, the FKBP12 polypeptide is encoded by a nucleic acid sequence comprising GGGGTCCAGGTCGAGACTATTTCACCAGGGGATGGGCGAACATTTCCAAAAAGG GGCCAGACTTGCGTCGTGCATTACACCGGGATGCTGGAGGACGGGAAGAAAGTG GACAGCTCCAGGGATCGCAACAAGCCCTTCAAGTTCATGCTGGGAAAGCAGGAA GTGATCCGAGGATGGGAGGAAGGCGTGGCACAGATGTCAGTCGGCCAGCGGGCC AAACTGACCATTAGCCCTGACTACGCTTATGGAGCAACAGGCCACCCAGGGATC ATTCCCCCTCATGCCACCCTGGTCTTCGAT GTGGAACTGCTGAAGCTGGAG (SEQ ID NO: 46). In certain embodiments, the induction agent specific for the ligand binding region may comprise a FK506 binding protein 12 (FKBP12) polypeptide having a substitution of valine (V) for phenylalanine (F) at position 36 (F36V) comprises AP20187 and/or AP1903, both synthetic drugs.

In certain embodiments of the inducible proapoptotic polypeptides, inducible caspase polypeptides or truncated caspase 9 polypeptides of the disclosure, the linker region is encoded by an amino acid comprising GGGGS (SEQ ID NO: 47) or a nucleic acid sequence comprising GGAGGAGGAGGATCC (SEQ ID NO: 48). In certain embodiments, the nucleic acid sequence encoding the linker does not comprise a restriction site.

In certain embodiments of the truncated caspase 9 polypeptides of the disclosure, the truncated caspase 9 polypeptide is encoded by an amino acid sequence that does not comprise an arginine (R) at position 87 of the sequence. Alternatively, or in addition, in certain embodiments of the inducible proapoptotic polypeptides, inducible caspase polypeptides or truncated caspase 9 polypeptides of the disclosure, the truncated caspase 9 polypeptide is encoded by an amino acid sequence that does not comprise an alanine (A) at position 282 the sequence. In certain embodiments of the inducible proapoptotic polypeptides, inducible caspase polypeptides or truncated caspase 9 polypeptides of the disclosure, the truncated caspase 9 polypeptide is encoded by an amino acid comprising GFGDVGALESLRGNADLAYISLMEPCGHCLIINNVNFCRESGLRTRTGSNIDCEKLRR RFSSLHFMVEVKGDLTAKKMVLALLELAQQDHGALDCCVVVILSHGCQASHLQFPG AVYGTDGCPVSVEKIVNIFNGTSCPSLGGKPKLFFIQACGGEQKDHGFEVASTSPEDE SPGSNPEPDATPFQEGLRTFDQLDAISSLPTPSDIFVSYSTFPGFVSWRDPKSGSWYVE TLDDIFEQWAHSEDLQSLLLRVANAVSVKGIYKQMPGCNFLRKKLFFKTS (SEQ ID NO: 49) or a nucleic acid sequence comprising TTTGGGGACGTGGGGGCCCTGGAGTCTCTGCGAGGAAATGCCGATCTGGCTTACA TCCTGAGCATGGAACCCTGCGGCCACTGTCTGATCATTAACAATGTGAACTTCTG CAGAGAAAGCGGACTGCGAACACGGACTGGCTCCAATATTGACTGTGAGAAGCT GCGGAGAAGGTTCTCTAGTCTGCACTTTATGGTCGAAGTGAAAGGGGATCTGACC GCCAAGAAAATGGTGCTGGCCCTGCTGGAGCTGGCTCAGCAGGACCATGGAGCT CTGGATTGCTGCGTGGTCGTGATCCTGTCCCACGGGTGCCAGGCTTCTCATCTGC AGTTCCCCGGAGCAGTGTACGGAACAGACGGCTGTCCTGTCAGCGTGGAGAAGA TCGTCAACATCTTCAACGGCACTTCTTGCCCTAGTCTGGGGGGAAAGCCAAAAACT GTTCTTTATCCAGGCCTGTGGCGGGGAACAGAAAGATCACGGCTTCGAGGTGGC CAGCACCAGCCCTGAGGACGAATCACCAGGGAGCAACCCTGAACCAGATGCAAC TCCATTCCAGGAGGGACTGAGGACCTTTGACCAGCTGGATGCTATCTCAAGCCTG CCCACTCCTAGTGACATTTTCGTGTCTTACAGTACCTTCCCAGGCTTTGTCTCATG GCGCGATCCCAAGTCAGGGAGCTGGTACGTGGAGACACTGGACGACATCTTTGA ACAGTGGGCCCATTCAGAGGACCTGCAGAGCCTGCTGCTGCGAGTGGCAAACGC TGTCTCTGTGAAGGGCATCTACAAACAGATGCCCGGGTGCTTCAATTTTCTGAGA AAGAAACTGTTCTTTAAGACTTCC (SEQ ID NO: 50).

In certain embodiments of the inducible proapoptotic polypeptides, wherein the polypeptide comprises a truncated caspase 9 polypeptide, the inducible proapoptotic polypeptide is encoded by an amino acid sequence comprising GVQVETISPGDGRTFPKRGQTCVVHYTGMLEDGKKVDSSRDRNKPFKFMLGKQEVI RGWEEGVAQMSVGQRAKLTISPDYAYGATGHPGIIPPHATLVFDVELLKLEGGGGS GFGDVGALESLRGNADLAYISLMEPCGHCLIINNVNFCRESGLRTRTGSNIDCEKLRR RFSSLHFMVEVKGDLTAKKMVLALLELAQQDHGALDCCVVVILSHGCQASHLQFPG AVYGTDGCPVSVEKIVNIFNGTSCPSLGGKPKLFFIQACGGEQKDHGFEVASTSPEDE SPGSNPEPDATPFQEGLRTFDQL DAISSLPTPSDIFVSYSTFPGFVSWRDPKSGSWYVETLDDIFEQWAHSEDLQSLLLRVANAVSVKGIYKQMPGCNFLRKKLFFKTS (SEQ ID NO: 51) or the nucleic acid sequence comprising GGGGTCCAGGTCGAGACTATTTCACCAGGGGATGGGCGAACATTTCCAAAAAGG GGCCAGACTTGCGTCGTGCATTACACCGGGATGCTGGAGGACGGGAAGAAAGTGGACAGCTCCAGGGATCGCAACAAGCCCTTCAAGTTCATGCTGGGAAAGCAGGAAGTGATCCGAGGATGGGAGGAAGGCGTGGCACAGATGTCAGTCGGCCAGCGGGCC AAACTGACCATTAGCCCTGACTACGCTTATGGAGCAACAGGCCACCCAGGGATCATTCCCCCTCATGCCACCCTGGTCTTCGATGTGGAACTGCTGAAGCTGGAGGGAG GAGGAGGATCCGAATTTGGGGACGTGGGGGCCCTGGAGTCTCTGCGAGGAAATGCCGATCTGGCTTACATCCTGAGCATGGAACCCTGCGGCCACTGTCTGATCATTAA CAATGTGAACTTCTGCAGAGAAAGCGGACTGCGAACACGGACTGGCTCCAATAT TGACTGTGAGAAGCTGCGGAGAAGGTTCTCTAGTCTGCACTTTATGGTCGAAGTG AAAGGGGATCTGACCGCCAAGAAAATGGTGCTGGCCCTGCTGGAGCTGGCTCAG CAGGACCATGGAGCTCTGGATTGCTGCGTGGTCGTGATCCTGTCCCACGGGTGCCAGGCTTCTCATCTGCAGTTCCCCGGAGCAGTGTACGGAACAGACGGCTGTCCTGTCAGCGTGGAGAAGATCGTCAACATCTTCAACGGCACTTCTTGCCCTAGTCTGGGGGGAAAGCCAAAACTGTTCTTTATCCAGGCCTGTGGCGGGGAACAGAAAGATCAC GGCTTCGAGGTGGCCAGCACCAGCCCTGAGGACGAATCACCAGGGAGCAACCCT GAACCAGATGCAACTCCATTCCAGGAGGGACTGAGGACCTTTGACCAGCTGGATGCTATCTCAAGCCTGCCCACTCCTAGTGACATTTTCGTGTCTTACAGTACCTTCCC AGGCTTTGTCTCATGGCGCGATCCCAAGTCAGGGAGCTGGTACGTGGAGACACTGGACGACATCTTTGAACAGTGGGCCCATTCAGAGGACCTGCAGAGCCTGCTGCTGCGAGTGGCAAACGCTGTCTCTGTGAAGGGCATCTACAAACAGATGCCCGGGTG CTTCAATTTTCTGAGAAAGAAACTGTTCTTTAAGACTTCC (SEQ ID NO: 52).

Transposons and Transposases

Transposons of the disclosure may comprise at least one self-cleaving peptide(s) located, for example, between one or more of a protein scaffold, Centyrin or CARTyrin of the disclosure and a selection gene of the disclosure. Transposons of the disclosure may comprise at least one self-cleaving peptide(s) located, for example, between one or more of a protein scaffold, Centyrin or CARTyrin of the disclosure and an inducible proapoptotic polypeptide of the disclosure. Transposons of the disclosure may comprise at least two self-cleaving peptide(s), a first self-cleaving peptide located, for example, upstream or immediately upstream of an inducible proapoptotic polypeptide of the disclosure and a second first self-cleaving peptide located, for example, downstream or immediately upstream of an inducible proapoptotic polypeptide of the disclosure.

The at least one self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 53) or a sequence having at least 70%, 80%, 90%, 95%, or 99% identity to the amino acid sequence comprising EGRGSLLTCGDVEENPGP (SEQ ID NO: 53). A GSG-T2A peptide may comprise an amino acid sequence comprising GSGEGRGSLLTCGDVEENPGP (SEQ ID NO: 54) or a sequence having at least 70%, 80%, 90%, 95%, or 99% identity to the amino acid sequence comprising GSGEGRGSLLTCGDVEENPGP (SEQ ID NO: 54). A GSG-T2A peptide may comprise a nucleic acid sequence comprising ggatctggagagggaaggggaagcctgctgacctgtggagacgtggaggaaaacccaggacca (SEQ ID NO: 55). An E2A peptide may comprise an amino acid sequence comprising QCTNYALLKLAGDVESNPGP (SEQ ID NO: 56) or a sequence having at least 70%, 80%, 90%, 95%, or 99% identity to the amino acid sequence comprising QCTNYALLKLAGDVESNPGP (SEQ ID NO: 56). A GSG-E2A peptide may comprise an amino acid sequence comprising GSGQCTNYALLKLAGDVESNPGP (SEQ ID NO: 57) or a sequence having at least 70%, 80%, 90%, 95%, or 99% identity to the amino acid sequence comprising GSGQCTNYALLKLAGDVESNPGP (SEQ ID NO: 57). An F2A peptide may comprise an amino acid sequence comprising VKQTLNFDLLKLAGDVESNPGP (SEQ ID NO: 58) or a sequence having at least 70%, 80%, 90%, 95%, or 99% identity to the amino acid sequence comprising VKQTLNFDLLKLAGDVESNPGP (SEQ ID NO: 58). A GSG-F2A peptide may comprise an amino acid sequence comprising GSGVKQTLNFDLLKLAGDVESNPGP (SEQ ID NO: 59) or a sequence having at least 70%, 80%, 90%, 95%, or 99% identity to the amino acid sequence comprising GSGVKQTLNFDLLKLAGDVESNPGP (SEQ ID NO: 59). A P2A peptide may comprise an amino acid sequence comprising ATNFSLLKQAGDVEENPGP (SEQ ID NO: 60) or a sequence having at least 70%, 80%, 90%, 95%, or 99% identity to the amino acid sequence comprising ATNFSLLKQAGDVEENPGP (SEQ ID NO: 60). A GSG-P2A peptide may comprise an amino acid sequence comprising GSGATNFSLLKQAGDVEENPGP (SEQ ID NO: 61) or a sequence having at least 70%, 80%, 90%, 95%, or 99% identity to the amino acid sequence comprising GSGATNFSLLKQAGDVEENPGP (SEQ ID NO: 61).

Transposons of the disclosure may comprise a first and a second self-cleaving peptide, the first self-cleaving peptide located, for example, upstream of one or more of a protein scaffold, Centyrin or CARTyrin of the disclosure the second self-cleaving peptide located, for example, downstream of the one or more of a protein scaffold, Centyrin or CARTyrin of the disclosure. The first and/or the second self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 53) or a sequence having at least 70%, 80%, 90%, 95%, or 99% identity to the amino acid sequence comprising EGRGSLLTCGDVEENPGP (SEQ ID NO: 53). A GSG-T2A peptide may comprise an amino acid sequence comprising GSGEGRGSLLTCGDVEENPGP (SEQ ID NO: 54) or a sequence having at least 70%, 80%, 90%, 95%, or 99% identity to the amino acid sequence comprising GSGEGRGSLLTCGDVEENPGP (SEQ ID NO: 54). A GSG-T2A peptide may comprise a nucleic acid sequence comprising ggatctggagagggaaggggaagcctgctgacctgtggagacgtggaggaaaacccaggacca (SEQ ID NO: 55). An E2A peptide may comprise an amino acid sequence comprising QCTNYALLKLAGDVESNPGP (SEQ ID NO: 56) or a sequence having at least 70%, 80%, 90%, 95%, or 99% identity to the amino acid sequence comprising QCTNYALLKLAGDVESNPGP (SEQ ID NO: 56). A GSG-E2A peptide may comprise an amino acid sequence comprising GSGQCTNYALLKLAGDVESNPGP (SEQ ID NO: 57) or a sequence having at least 70%, 80%, 90%, 95%, or 99% identity to the amino acid sequence comprising GSGQCTNYALLKLAGDVESNPGP (SEQ ID NO: 57). An F2A peptide may comprise an amino acid sequence comprising VKQTLNFDLLKLAGDVESNPGP (SEQ ID NO: 58) or a sequence having at least 70%, 80%, 90%, 95%, or 99% identity to the amino acid sequence comprising VKQTLNFDLLKLAGDVESNPGP (SEQ ID NO: 58). A GSG-F2A peptide may comprise an amino acid sequence comprising GSGVKQTLNFDLLKLAGDVESNPGP (SEQ ID NO: 59) or a sequence having at least 70%, 80%, 90%, 95%, or 99% identity to the amino acid sequence comprising GSGVKQTLNFDLLKLAGDVESNPGP (SEQ ID NO: 59). A P2A peptide may comprise an amino acid sequence comprising ATNFSLLKQAGDVEENPGP (SEQ ID NO: 60) or a sequence having at least 70%, 80%, 90%, 95%, or 99% identity to the amino acid sequence comprising ATNFSLLKQAGDVEENPGP (SEQ ID NO: 60). A GSG-P2A peptide may comprise an amino acid sequence comprising GSGATNFSLLKQAGDVEENPGP (SEQ ID NO: 61) or a sequence having at least 70%, 80%, 90%, 95%, or 99% identity to the amino acid sequence comprising GSGATNFSLLKQAGDVEENPGP (SEQ ID NO: 61).

The disclosure provides a composition comprising the transposon the disclosure. In certain embodiments, the composition may further comprise a plasmid comprising a sequence encoding a transposase enzyme. The sequence encoding a transposase enzyme may be an mRNA sequence.

Transposons of the disclosure may comprise piggyBac transposons. Transposase enzymes of the disclosure may include piggyBac transposases or compatible enzymes. In certain embodiments of this method, the transposon is a plasmid DNA transposon with a sequence encoding the chimeric ligand/antigen receptor flanked by two cis-regulatory insulator elements. In certain embodiments, the transposon is a piggyBac transposon. Transposase enzymes of the disclosure may include piggyBac transposases or compatible enzymes. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

```
                                                            (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substution at one or more of positions 30, 165, 282, or 538 of the sequence:

```
                                                            (SEQ ID NO: 1)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN
```

```
481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments, the transposase enzyme is a piggyBac™ (PB) transposase enzyme that comprises or consists of an amino acid sequence having an amino acid substution at two or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at three or more of positions 30, 165, 282, or 538 of the sequence of SEQ ID NO: 1. In certain embodiments, the transposase enzyme is a piggyBac™ (PB) transposase enzyme that comprises or consists of an amino acid sequence having an amino acid substution at each of the following positions 30, 165, 282, and 538 of the sequence of SEQ ID NO: 1. In certain embodiments, the amino acid substution at position 30 of the sequence of SEQ ID NO: 1 is a substitution of a valine (V) for an isoleucine (I). In certain embodiments, the amino acid substution at position 165 of the sequence of SEQ ID NO: 1 is a substitution of a serine (S) for a glycine (G). In certain embodiments, the amino acid substution at position 282 of the sequence of SEQ ID NO: 1 is a substitution of a valine (V) for a methionine (M). In certain embodiments, the amino acid substution at position 538 of the sequence of SEQ ID NO: 1 is a substitution of a lysine (K) for an asparagine (N).

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 1 wherein the amino acid substution at position 30 is a substitution of a valine (V) for an isoleucine (I), the amino acid substution at position 165 is a substitution of a serine (S) for a glycine (G), the amino acid substution at position 282 is a substitution of a valine (V) for a methionine (M), and the amino acid substution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 1 or SEQ ID NO: 2. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 1 or SEQ ID NO: 2 is a substitution of an asparagine (N) for a serine (S). In certain embodiments, the amino acid substitution at position 46 of SEQ ID NO: 1 or SEQ ID NO: 2 is a substitution of a serine (S) for an alanine (A). In certain embodiments, the amino acid substitution at position 46 of SEQ ID NO: 1 or SEQ ID NO: 2 is a substitution of a threonine (T) for an alanine (A). In certain embodiments, the amino acid substitution at position 82 of SEQ ID NO: 1 or SEQ ID NO: 2 is a substitution of a tryptophan (W) for an isoleucine (I). In certain embodiments, the amino acid substitution at position 103 of SEQ ID NO: 1 or SEQ ID NO: 2 is a substitution of a proline (P) for a serine (S). In certain embodiments, the amino acid substitution at position 119 of SEQ ID NO: 1 or SEQ ID NO: 2 is a substitution of a proline (P) for an arginine (R). In certain embodiments, the amino acid substitution at position 125 of SEQ ID NO: 1 or SEQ ID NO: 2 is a substitution of an alanine (A) a cysteine (C). In certain embodiments, the amino acid substitution at position 125 of SEQ ID NO: 1 or SEQ ID NO: 2 is a substitution of a leucine (L) for a cysteine (C). In certain embodiments, the amino acid substitution at position 177 of SEQ ID NO: 1 or SEQ ID NO: 2 is a substitution of a lysine (K) for a tyrosine (Y). In certain embodiments, the amino acid substitution at

```
                                                                    (SEQ ID NO: 2)
  1 MGSSLDDEHI LSALLQSDDE LVGEDSDSEV SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFPT DEIISEIVKW TNAEISLKRR ESMTSATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RVYIPNKPSK YGIKILMMCD

301 SGTKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPKEV

541 PGTSDDSTEE PVMKKRTYCT YCPSKIRRKA NASCKKCKKV ICREHNIDMC QSCF.
``` position 177 of SEQ ID NO: 1 or SEQ ID NO: 2 is a substitution of a histidine (H) for a tyrosine (Y). In certain embodiments, the amino acid substitution at position 180 of SEQ ID NO: 1 or SEQ ID NO: 2 is a substitution of a leucine (L) for a phenylalanine (F). In certain embodiments, the amino acid substitution at position 180 of SEQ ID NO: 1 or SEQ ID NO: 2 is a substitution of an isoleucine (I) for a phenylalanine (F). In certain embodiments, the amino acid substitution at position 180 of SEQ ID NO: 1 or SEQ ID NO: 2 is a substitution of a valine (V) for a phenylalanine (F). In certain embodiments, the amino acid substitution at position 185 of SEQ ID NO: 1 or SEQ ID NO: 2 is a substitution of a leucine (L) for a methionine (M). In certain embodiments, the amino acid substitution at position 187 of SEQ ID NO: 1 or SEQ ID NO: 2 is a substitution of a glycine (G) for an alanine (A). In certain embodiments, the amino acid substitution at position 200 of SEQ ID NO: 1 or SEQ ID NO: 2 is a substitution of a tryptophan (W) for a phenylalanine (F). In certain embodiments, the amino acid substitution at position 207 of SEQ ID NO: 1 or SEQ ID NO: 2 is a substitution of a proline (P) for a valine (V). In certain embodiments, the amino acid substitution at position 209 of SEQ ID NO: 1 or SEQ ID NO: 2 is a substitution of a phenylalanine (F) for a valine (V). In certain embodiments, the amino acid substitution at position 226 of SEQ ID NO: 1 or SEQ ID NO: 2 is a substitution of a phenylalanine (F) for a methionine (M). In certain embodiments, the amino acid substitution at position 235 of SEQ ID NO: 1 or SEQ ID NO: 2 is a substitution of an arginine (R) for a leucine (L). In certain embodiments, the amino acid substitution at position 240 of SEQ ID NO: 1 or SEQ ID NO: 1 is a substitution of a lysine (K) for a valine (V). In certain embodiments, the amino acid substitution at position 241 of SEQ ID NO: 1 or SEQ ID NO: 2 is a substitution of a leucine (L) for a phenylalanine (F). In certain embodiments, the amino acid substitution at position 243 of SEQ ID NO: 1 or SEQ ID NO: 2 is a substitution of a lysine (K) for a proline (P). In certain embodiments, the amino acid substitution at position 258 of SEQ ID NO: 1 or SEQ ID NO: 2 is a substitution of a serine (S) for an asparagine (N). In certain embodiments, the amino acid substitution at position 296 of SEQ ID NO: 1 or SEQ ID NO: 2 is a substitution of a tryptophan (W) for a leucine (L). In certain embodiments, the amino acid substitution at position 296 of SEQ ID NO: 1 or SEQ ID NO: 2 is a substitution of a tyrosine (Y) for a leucine (L). In certain embodiments, the amino acid substitution at position 296 of SEQ ID NO: 1 or SEQ ID NO: 2 is a substitution of a phenylalanine (F) for a leucine (L). In certain embodiments, the amino acid substitution at position 298 of SEQ ID NO: 1 or SEQ ID NO: 2 is a substitution of a leucine (L) for a methionine (M). In certain embodiments, the amino acid substitution at position 298 of SEQ ID NO: 1 or SEQ ID NO: 2 is a substitution of an alanine (A) for a methionine (M). In certain embodiments, the amino acid substitution at position 298 of SEQ ID NO: 1 or SEQ ID NO: 2 is a substitution of a valine (V) for a methionine (M). In certain embodiments, the amino acid substitution at position 311 of SEQ ID NO: 1 or SEQ ID NO: 2 is a substitution of an isoleucine (I) for a proline (P). In certain embodiments, the amino acid substitution at position 311 of SEQ ID NO: 1 or SEQ ID NO: 2 is a substitution of a valine for a proline (P). In certain embodiments, the amino acid substitution at position 315 of SEQ ID NO: 1 or SEQ ID NO: 2 is a substitution of a lysine (K) for an arginine (R). In certain embodiments, the amino acid substitution at position 319 of SEQ ID NO: 1 or SEQ ID NO: 2 is a substitution of a glycine (G) for a threonine (T). In certain embodiments, the amino acid substitution at position 327 of SEQ ID NO: 1 or SEQ ID NO: 2 is a substitution of an arginine (R) for a tyrosine (Y). In certain embodiments, the amino acid substitution at position 328 of SEQ ID NO: 1 or SEQ ID NO: 2 is a substitution of a valine (V) for a tyrosine (Y). In certain embodiments, the amino acid substitution at position 340 of SEQ ID NO: 1 or SEQ ID NO: 2 is a substitution of a glycine (G) for a cysteine (C). In certain embodiments, the amino acid substitution at position 340 of SEQ ID NO: 1 or SEQ ID NO: 2 is a substitution of a leucine (L) for a cysteine (C). In certain embodiments, the amino acid substitution at position 421 of SEQ ID NO: 1 or SEQ ID NO: 2 is a substitution of a histidine (H) for the aspartic acid (D). In certain embodiments, the amino acid substitution at position 436 of SEQ ID NO: 1 or SEQ ID NO: 2 is a substitution of an isoleucine (I) for a valine (V). In certain embodiments, the amino acid substitution at position 456 of SEQ ID NO: 1 or SEQ ID NO: 2 is a substitution of a tyrosine (Y) for a methionine (M). In certain embodiments, the amino acid substitution at position 470 of SEQ ID NO: 1 or SEQ ID NO: 2 is a substitution of a phenylalanine (F) for a leucine (L). In certain embodiments, the amino acid substitution at position 485 of SEQ ID NO: 1 or SEQ ID NO: 2 is a substitution of a lysine (K) for a serine (S). In certain embodiments, the amino acid substitution at position 503 of SEQ ID NO: 1 or SEQ ID NO: 2 is a substitution of a leucine (L) for a methionine (M). In certain embodiments, the amino acid substitution at position 503 of SEQ ID NO: 1 or SEQ ID NO: 2 is a substitution of an isoleucine (I) for a methionine (M). In certain embodiments, the amino acid substitution at position 552 of SEQ ID NO: 1 or SEQ ID NO: 2 is a substitution of a lysine (K) for a valine (V). In certain embodiments, the amino acid substitution at position 570 of SEQ ID NO: 1 or SEQ ID NO: 2 is a substitution of a threonine (T) for an alanine (A). In certain embodiments, the amino acid substitution at position 591 of SEQ ID NO: 1 or SEQ ID NO: 2 is a substitution of a proline (P) for a glutamine (Q). In certain embodiments, the amino acid substitution at position 591 of SEQ ID NO: 1 or SEQ ID NO: 2 is a substitution of an arginine (R) for a glutamine (Q). In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 1 or SEQ ID NO: 2. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 1 or SEQ ID NO: 2. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 1 or SEQ ID NO: 2. In certain embodiments, the amino acid substitution at position 103 of SEQ ID NO: 1 or SEQ ID NO: 2 is a substitution of a proline (P) for a serine (S). In certain embodiments, the amino acid substitution at position 194 of SEQ ID NO: 1 or SEQ ID NO: 2 is a substitution of a valine (V) for a methionine (M). In certain embodiments, the amino acid substitution at position 372 of SEQ ID NO: 1 or SEQ ID NO: 2 is a substitution of an alanine (A) for an arginine (R). In certain embodiments, the amino acid substitution at position 375 of SEQ ID NO: 1 or SEQ ID NO: 2 is a substitution of an alanine (A) for a lysine (K). In certain embodiments, the amino acid substitution at position 450 of SEQ ID NO: 1 or SEQ ID NO: 2 is a substitution of an asparagine (N) for an aspartic acid (D). In certain embodiments, the amino acid substitution at position 509 of SEQ ID NO: 1 or SEQ ID NO: 2 is a substitution of a glycine (G) for a serine (S). In certain embodiments, the amino acid substitution at position 570 of SEQ ID NO: 1 or SEQ ID NO: 2 is a substitution of a serine (S) for an asparagine (N). In certain embodiments, the piggyBac™ transposase enzyme may comprise a substitution of a valine (V) for a methionine (M) at position 194 of SEQ ID NO: 1. In certain embodiments, including those embodiments wherein the piggyBac™ transposase enzyme may comprise a substitution of a valine (V) for a methionine (M) at position 194 of SEQ ID NO: 1, the piggyBac™ transposase enzyme may further comprise an amino acid substitution at positions 372, 375 and 450 of the sequence of SEQ ID NO: 1 or SEQ ID NO: 2. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, and a substitution of an alanine (A) for a lysine (K) at position 375 of SEQ ID NO: 1. In certain embodiments, the piggyBac™ transposase enzyme may comprise a substitution of a valine (V) for a methionine (M) at position 194 of SEQ ID NO: 1, a substitution of an alanine (A) for an arginine (R) at position 372 of SEQ ID NO: 1, a substitution of an alanine (A) for a lysine (K) at position 375 of SEQ ID NO: 1 and a substitution of an asparagine (N) for an aspartic acid (D) at position 450 of SEQ ID NO: 1.

Vectors

The disclosure provides a vector comprising the CAR of the disclosure. In certain embodiments, the vector is a viral vector. The vector may be a recombinant vector.

Viral vectors of the disclosure may comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV). Exemplary adeno-associated viruses and recombinant adeno-associated viruses of the disclosure comprise two or more inverted terminal repeat (ITR) sequences located in cis next to a sequence encoding a protein scaffold, Centyrin or CARTyrin of the disclosure. Exemplary adeno-associated viruses and recombinant adeno-associated viruses of the disclosure include, but are not limited to all serotypes (e.g. AAV1, AAV2, AAV3, AAV4, AAV5, AAV6, AAV7, AAV8, and AAV9). Exemplary adeno-associated viruses and recombinant adeno-associated viruses of the disclosure include, but are not limited to, self-complementary AAV (scAAV) and AAV hybrids containing the genome of one serotype and the capsid of another serotype (e.g. AAV2/5, AAV-DJ and AAV-DJ8). Exemplary adeno-associated viruses and recombinant adeno-associated viruses of the disclosure include, but are not limited to, rAAV-LK03.

Viral vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Viral vectors of the disclosure may comprise an inducible proapoptotic polypeptide comprising (a) a ligand binding region, (b) a linker, and (c) a proapoptotic polypeptide, wherein the inducible proapoptotic polypeptide does not comprise a non-human sequence. In certain embodiments, the non-human sequence comprises a restriction site. In certain embodiments, the ligand binding region may be a multimeric ligand binding region. Inducible proapoptotic polypeptides of the disclosure may also be referred to as an "iC9 safety switch". In certain embodiments, viral vectors of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, viral vectors of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, viral vectors of the disclosure may comprise an inducible caspase polypeptide comprising (a) a ligand binding region, (b) a linker, and (c) a truncated caspase 9 polypeptide, wherein the inducible proapoptotic polypeptide does not comprise a non-human sequence. In certain embodiments of the inducible proapoptotic polypeptides, inducible caspase polypeptides or truncated caspase 9 polypeptides of the disclosure, the ligand binding region may comprise a FK506 binding protein 12 (FKBP12) polypeptide. In certain embodiments, the amino acid sequence of the ligand binding region that comprise a FK506 binding protein 12 (FKBP12) polypeptide may comprise a modification at position 36 of the sequence. The modification may be a substitution of valine (V) for phenylalanine (F) at position 36 (F36V). In certain embodiments, the FKBP12 polypeptide is encoded by an amino acid sequence comprising GVQVETISPGDGRTFPKRGQTCVVHYTGMLEDGK-KVDSSRDRNKPFKFMLGKQEVI RGWEEGVAQMSVGQRAKLTISPDYAYGATGHPGIIP-PHATLVFDVELLKLE (SEQ ID NO: 45). In certain embodiments, the FKBP12 polypeptide is encoded by a nucleic acid sequence comprising GGGGTCCAGGTCGA-GACTATTTCACCAGGGGATGGGCGAACATTTC-CAAAAAGG GGCCAGACTTGCGTCGTGCATTA-CACCGGGATGCTGGAGGACGGGAAGAAAGTG GACAGCTCCAGGGATCGCAACAAGCCCTT-CAAGTTCATGCTGGGAAAGCAGGAA GTGATCCGAGGATGGGAGGAAGGCGTGGCACA-GATGTCAGTCGGCCAGCGGGCC AAACTGACCATT-AGCCCTGACTACGCTTATGGAGCAACAGGC-CACCCAGGGATC ATTCCCCCTCATGCCACCCTGGTCTTCGAT GTG-GAACTGCTGAAGCTGGAG (SEQ ID NO: 46). In certain embodiments, the induction agent specific for the ligand binding region may comprise a FK506 binding protein 12 (FKBP12) polypeptide having a substitution of valine (V) for phenylalanine (F) at position 36 (F36V) comprises AP20187 and/or AP1903, both synthetic drugs.

In certain embodiments of the inducible proapoptotic polypeptides, inducible caspase polypeptides or truncated caspase 9 polypeptides of the disclosure, the linker region is encoded by an amino acid comprising GGGGS (SEQ ID NO: 47) or a nucleic acid sequence comprising GGAGGAGGAGGATCC (SEQ ID NO: 48). In certain embodiments, the nucleic acid sequence encoding the linker does not comprise a restriction site.

In certain embodiments of the truncated caspase 9 polypeptides of the disclosure, the truncated caspase 9 polypeptide is encoded by an amino acid sequence that does not comprise an arginine (R) at position 87 of the sequence. Alternatively, or in addition, in certain embodiments of the inducible proapoptotic polypeptides, inducible caspase polypeptides or truncated caspase 9 polypeptides of the disclosure, the truncated caspase 9 polypeptide is encoded by an amino acid sequence that does not comprise an alanine (A) at position 282 the sequence. In certain embodiments of the inducible proapoptotic polypeptides, inducible caspase polypeptides or truncated caspase 9 polypeptides of the disclosure, the truncated caspase 9 polypeptide is encoded by an amino acid comprising GFGDVGALESLRGNADLAYISLMEPCGHCLIINNVNFCRESGLRTRTG-SNIDCEKLRR RFSSLHFMVEVKGDLTAKKMVLALLELAQQDHGALDCCVVVILSHGCQASHLQFPG AVYGTDGCPVS-VEKIVNIFNGTSCPSLGGKPKLFFIQACGGEQKDHGFEVASTSPEDE SPGSNPEPDATPFQEGLRTFDQLDAISSLPTPSDIFVSYSTFPGFVSWRDPKSGSWYVE TLDDIFEQWAHSEDLQSLLLRVA-NAVSVKGIYKQMPGCNFLRKKLFFKTS (SEQ ID NO: 49) or a nucleic acid sequence comprising TTTGGGGACGTGGGGGCCCTGGAGTCTCTGCGAG-GAAATGCCGATCTGGCTTACA TCCTGAGCATG-GAACCCTGCGGCCACTGTCTGATCATTAACAATGT-GAACTTCTG CAGAGAAAGCGGACTGCGAACACGGACTGGCTC-CAATATTGACTGTGAGAAGCT GCG-GAGAAGGTTCTCTAGTCTGCACTT-TATGGTCGAAGTGAAAGGGGATCTGACC GCCAAGAAAATGGTGCTGGCCCTGCTG-GAGCTGGCTCAGCAGGACCATGGAGCT CTGGAT-TGCTGCGTGGTCGTGATCCTGTCC-CACGGGTGCCAGGCTTCTCATCTGC AGTTCCCCGGAGCAGTGTACGGAACA-GACGGCTGTCCTGTCAGCGTGGAGAAGA TCGT-CAACATCTT-CAACGGCACTTCTTGCCCTAGTCTGGGGGGAAAGC-CAAAACT GTTCTTTATCCAGGCCTGTGGCGGGGAACAGAAA-GATCACGGCTTCGAGGTGGC CAGCACCAGCCCT-GAGGACGAATCACCAGGGAGCAACCCTGAACCA-GATGCAAC TCCATTCCAGGAGGGACT-GAGGACCTTTGACCAGCTGGATGCTATCT-CAAGCCTG CCCACTCCTAGTGACATTTTCGTGTCT-TACAGTACCTTCCCAGGCTTTGTCTCATG GCGCGATCCCAAGTCAGGGAGCTGGTACGTGGA-GACACTGGACGACATCTTTGA ACAGTGGGCCCAT-TCAGAGGACCTGCAGAGCCTGCTGCTGCGAGT-GGCAAACGC TGTCTCTGTGAAGGGCATCTA-CAAACAGATGCCCGGGTGCTTCAATTTTCTGAGA AAGAAACTGTTCTTTAAGACTTCC (SEQ ID NO: 50).

In certain embodiments of the inducible proapoptotic polypeptides, wherein the polypeptide comprises a truncated caspase 9 polypeptide, the inducible proapoptotic polypeptide is encoded by an amino acid sequence comprising GVQVETISPGDGRTFPKRGQTCVVHYTGMLEDG-KKVDSSRDRNKPFKFMLGKQEVI RGWEEGVAQMSVGQRAKLTISPDYAYGATGHPGIIP-PHATLVFDVELLKLEGGGGGS GFGDVGALESLRG-NADLAYISLMEPCGHCLIINNVNFCRESGLRTRTG-SNIDCEKLRR RFSSLHFMVEVKGDLTAKKMVLALLE-LAQQDHGALDCCVVVILSHGCQASHLQFPG AVYGTDGCPVS-VEKIVNIFNGTSCPSLGGKPKLFFIQACGGEQKD-HGFEVASTSPEDE SPGSNPEPDATPFQEGLRTFDQL-DAISSLPTPSDIFVSYSTFPGFVSWRDPKSGSWYVE TLDDIFEQWAHSEDLQSLLLRVA-NAVSVKGIYKQMPGCNFLRKKLFFKTS (SEQ ID NO: 51) or the nucleic acid sequence comprising GGGGTCCAGGTCGAGACTATTTCACCAGGG-GATGGGCGAACATTTCCAAAAAGG GGCCA-GACTTGCGTCGTGCATTACACCGGGATGCTG-GAGGACGGGAAGAAAGTG GACAGCTCCAGGGATCGCAACAAGCCCTT-CAAGTTCATGCTGGGAAAGCAGGAA GTGATCCGAGGATGGGAGGAAGGCGTGGCACA-GATGTCAGTCGGCCAGCGGGCC AAACTGACCATT-AGCCCTGACTACGCTTATGGAGCAACAGGC-CACCCAGGGATC ATTCCCCTCATGCCACCCTGGTCTTCGATGTG-GAACTGCTGAAGCTGGAGGGAG GAGGAG-GATCCGAATTTGGGGACGTGGGGGCCCTG-GAGTCTCTGCGAGGAAATG CCGATCTGGCTTACATCCTGAGCATG-GAACCCTGCGGCCACTGTCTGATCATTAA CAATGT-GAACTTCTGCAGAGAAAGCGGACTGCGAACAC-GGACTGGCTCCAATAT TGACTGTGAGAAGCTGCG-GAGAAGGTTCTCTAGTCTGCACTT-TATGGTCGAAGTG AAAGGGGATCTGACCGC-CAAGAAAATGGTGCTGGCCCTGCTGGAGCTGG-CTCAG CAGGACCATGGAGCTCTGGAT-TGCTGCGTGGTCGTGATCCTGTCCCACGGGTGCC AGGCTTCTCATCTGCAGTTCCCCG-GAGCAGTGTACGGAACAGACCGGCTGTCCTGT CAGCGTGGAGAAGATCGTCAACATCTT-CAACGGCACTTCTTGCCCTAGTCTGGGG GGAAAGCCAAAACTGTTCTT-TATCCAGGCCTGTGGCGGGGAACAGAAAGATCAC GGCTTCGAGGTGGCCAGCACCAGCCCT-GAGGACGAATCACCAGGGAGCAACCCT GAACCA-GATGCAACTCCATTCCAGGAGGGACT-GAGGACCTTTGACCAGCTGGAT GCTATCTCAAGCCTGCCCACTCCTAGTGACAT-TTTCGTGTCTTACAGTACCTTCCC AGGCTTTGTCT-CATGGCGCGATCCCAAGTCAGG-GAGCTGGTACGTGGAGACACT GGACGACATCTTTGAACAGTGGGCCCAT-TCAGAGGACCTGCAGAGCCTGCTGCT GCGAGTGGCAAACGCTGTCTCTGTGAAGGGCATC-TACAAACAGATGCCCGGGTG CTTCAATTTTCT-GAGAAAGAAACTGTTCTTTAAGACTTCC (SEQ ID NO: 52).

Viral vectors of the disclosure may comprise at least one self-cleaving peptide. In some embodiments, the vector may comprise at least one self-cleaving peptide and wherein a self-cleaving peptide is located between a CAR and a selection gene. In some embodiments, the vector may comprise at least one self-cleaving peptide and wherein a first self-cleaving peptide is located upstream of a CAR and a second self-cleaving peptide is located downstream of a CAR. Viral vectors of the disclosure may comprise at least one self-cleaving peptide(s) located, for example, between one or more of a protein scaffold, Centyrin or CARTyrin of the disclosure and an inducible proapoptotic polypeptide of the disclosure. Viral vectors of the disclosure may comprise at least two self-cleaving peptide(s), a first self-cleaving peptide located, for example, upstream or immediately upstream of an inducible proapoptotic polypeptide of the disclosure and a second first self-cleaving peptide located, for example, downstream or immediately upstream of an inducible proapoptotic polypeptide of the disclosure. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 53) or a sequence having at least 70%, 80%, 90%, 95%, or 99% identity to the amino acid sequence comprising EGRGSLLTCGDVEENPGP (SEQ ID NO: 53). A GSG-T2A peptide may comprise an amino acid sequence comprising GSGEGRGSLLTCGDVEENPGP (SEQ ID NO: 54) or a sequence having at least 70%, 80%, 90%, 95%, or 99% identity to the amino acid sequence comprising GSGEGRGSLLTCGDVEENPGP (SEQ ID NO: 54). A GSG-T2A peptide may comprise a nucleic acid sequence comprising ggatctggagagggaaggggaagcctgctgacctgtggagacgtggaggaaaacccaggacca (SEQ ID NO: 55). An E2A peptide may comprise an amino acid sequence comprising QCTNYALLKLAGDVESNPGP (SEQ ID NO: 56) or a sequence having at least 70%, 80%, 90%, 95%, or 99% identity to the amino acid sequence comprising QCTNYALLKLAGDVESNPGP (SEQ ID NO: 56). A GSG-E2A peptide may comprise an amino acid sequence comprising GSGQCTNYALLKLAGDVESNPGP (SEQ ID NO: 57) or a sequence having at least 70%, 80%, 90%, 95%, or 99% identity to the amino acid sequence comprising GSGQCTNYALLKLAGDVESNPGP (SEQ ID NO: 57). An F2A peptide may comprise an amino acid sequence comprising VKQTLNFDLLKLAGDVESNPGP (SEQ ID NO: 58) or a sequence having at least 70%, 80%, 90%, 95%, or 99% identity to the amino acid sequence comprising VKQTLNFDLLKLAGDVESNPGP (SEQ ID NO: 58). A GSG-F2A peptide may comprise an amino acid sequence comprising GSGVKQTLNFDLLKLAGDVESNPGP (SEQ ID NO: 59) or a sequence having at least 70%, 80%, 90%, 95%, or 99% identity to the amino acid sequence comprising GSGVKQTLNFDLLKLAGDVESNPGP (SEQ ID NO: 59). A P2A peptide may comprise an amino acid sequence comprising ATNFSLLKQAGDVEENPGP (SEQ ID NO: 60) or a sequence having at least 70%, 80%, 90%, 95%, or 99% identity to the amino acid sequence comprising ATNFSLLKQAGDVEENPGP (SEQ ID NO: 60). A GSG-P2A peptide may comprise an amino acid sequence comprising GSGATNFSLLKQAGDVEENPGP (SEQ ID NO: 61) or a sequence having at least 70%, 80%, 90%, 95%, or 99% identity to the amino acid sequence comprising GSGATNFSLLKQAGDVEENPGP (SEQ ID NO: 61).

The disclosure provides a vector comprising the CAR of the disclosure. In certain embodiments, the vector is a nanoparticle. Exemplary nanoparticle vectors of the disclosure include, but are not limited to, nucleic acids (e.g. RNA, DNA, synthetic nucleotides, modified nucleotides or any combination thereof), amino acids (L-amino acids, D-amino acids, synthetic amino acids, modified amino acids, or any combination thereof), polymers (e.g. polymersomes), micelles, lipids (e.g. liposomes), organic molecules (e.g. carbon atoms, sheets, fibers, tubes), inorganic molecules (e.g. calcium phosphate or gold) or any combination thereof. A nanoparticle vector may be passively or actively transported across a cell membrane.

Nanoparticle vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methyl-guanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Nanoparticle vectors of the disclosure may comprise an inducible proapoptotic polypeptide comprising (a) a ligand binding region, (b) a linker, and (c) a proapoptotic polypeptide, wherein the inducible proapoptotic polypeptide does not comprise a non-human sequence. In certain embodiments, the non-human sequence comprises a restriction site. In certain embodiments, the ligand binding region may be a multimeric ligand binding region. Inducible proapoptotic polypeptides of the disclosure may also be referred to as an "iC9 safety switch". In certain embodiments, nanoparticle vectors of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, nanoparticle vectors of the disclosure may comprise an inducible caspase polypeptide comprising (a) a ligand binding region, (b) a linker, and (c) a caspase polypeptide, wherein the inducible proapoptotic polypeptide does not comprise a non-human sequence. In certain embodiments, nanoparticle vectors of the disclosure may comprise an inducible caspase polypeptide comprising (a) a ligand binding region, (b) a linker, and (c) a truncated caspase 9 polypeptide, wherein the inducible proapoptotic polypeptide does not comprise a non-human sequence. In certain embodiments of the inducible proapoptotic polypeptides, inducible caspase polypeptides or truncated caspase 9 polypeptides of the disclosure, the ligand binding region may comprise a FK506 binding protein 12 (FKBP12) polypeptide. In certain embodiments, the amino acid sequence of the ligand binding region that comprise a FK506 binding protein 12 (FKBP12) polypeptide may comprise a modification at position 36 of the sequence. The modification may be a substitution of valine (V) for phenylalanine (F) at position 36 (F36V). In certain embodiments, the FKBP12 polypeptide is encoded by an amino acid sequence comprising GVQVETISPGDGRTFPKRGQTCVVHYTGMLEDGKKVDSSRDRNKPFKFMLGKQEVI RGWEEGVAQMSVGQRAKLTISPDYAYGATGHPGIIPPHATLVFDVELLKLE (SEQ ID NO: 45). In certain embodiments, the FKBP12 polypeptide is encoded by a nucleic acid sequence comprising GGGGTCCAGGTCGAGACTATTTCACCAGGG- GATGGGCGAACATTTCCAAAAAGG GGCCAGACTTGCGTCGTGCATTACACCGGGATGCTGGAGGACGGGAAGAAAGTG GACAGCTCCAGGGATCGCAACAAGCCCTTCAAGTTCATGCTGGGAAAGCAGGAA GTGATCCGAGGATGGGAGGAAGGCGTGGCACAGATGTCAGTCGGCCAGCGGGCC AAACTGACCATTAGCCCTGACTACGCTTATGGAGCAACAGGCCACCCAGGGATC ATTCCCCCTCATGCCACCCTGGTCTTCGAT GTGGAACTGCTGAAGCTGGAG (SEQ ID NO: 46). In certain embodiments, the induction agent specific for the ligand binding region may comprise a FK506 binding protein 12 (FKBP12) polypeptide having a substitution of valine (V) for phenylalanine (F) at position 36 (F36V) comprises AP20187 and/or AP1903, both synthetic drugs.

In certain embodiments of the inducible proapoptotic polypeptides, inducible caspase polypeptides or truncated caspase 9 polypeptides of the disclosure, the linker region is encoded by an amino acid comprising GGGGS (SEQ ID NO: 47) or a nucleic acid sequence comprising GGAGGAGGAGGATCC (SEQ ID NO: 48). In certain embodiments, the nucleic acid sequence encoding the linker does not comprise a restriction site.

In certain embodiments of the truncated caspase 9 polypeptides of the disclosure, the truncated caspase 9 polypeptide is encoded by an amino acid sequence that does not comprise an arginine (R) at position 87 of the sequence. Alternatively, or in addition, in certain embodiments of the inducible proapoptotic polypeptides, inducible caspase polypeptides or truncated caspase 9 polypeptides of the disclosure, the truncated caspase 9 polypeptide is encoded by an amino acid sequence that does not comprise an alanine (A) at position 282 the sequence. In certain embodiments of the inducible proapoptotic polypeptides, inducible caspase polypeptides or truncated caspase 9 polypeptides of the disclosure, the truncated caspase 9 polypeptide is encoded by an amino acid comprising GFGDVGALESLRGNADLAYISLMEPCGHCLIINNVNFCRESGLRTRTGSNIDCEKLRR RFSSLHFMVEVKGDLTAKKMVLALLELAQQDHGALDCCVVVILSHGCQASHLQFPG AVYGTDGCPVS-VEKIVNIFNGTSCPSLGGKPKLFFIQACGGEQKDHGFEVASTSPEDE SPGSNPEPDATPFQEGLRTFDQLDAISSLPTPSDIFVSYSTFPGFVSWRDPKSGSWYVE TLDDIFEQWAHSEDLQSLLLRVA-NAVSVKGIYKQMPGCNFLRKKLFFKTS (SEQ ID NO: 49) or a nucleic acid sequence comprising TTTGGGGACGTGGGGGCCCTGGAGTCTCTGCGAGGAAATGCCGATCTGGCTTACA TCCTGAGCATGGAACCCTGCGGCCACTGTCTGATCATTAACAATGTGAACTTCTG CAGAGAAAGCGGACTGCGAACACGGACTGGCTCCAATATTGACTGTGAAGCT GCGGAGAAGGTTCTCTAGTCTGCACTTTATGGTCGAAGTGAAAGGGGATCTGACC GCCAAGAAAATGGTGCTGGCCCTGCTGGAGCTGGCTCAGCAGGACCATGGAGCT CTGGATTGCTGCGTGGTCGTGATCCTGTCCCACGGGTGCCAGGCTTCTCATCTGC AGTTCCCCGGAGCAGTGTACGGAACAGACGGCTGTCCTGTCAGCGTGGAGAAGA TCGTCAACATCTTCAACGGCACTTCTTGCCCTAGTCTGGGGGGAAAGCCAAAACT GTTCTTTATCCAGGCCTGTGGCGGGGAACAGAAAGATCACGGCTTCGAGGTGGC CAGCACCAGCCCTGAGGACGAATCACCAGGGAGCAACCCTGAACCAGATGCAAC TCCATTCCAGGAGGGACTGAGGACCTTTGACCAGCTGGATGCTATCTCAAGCCTG CCCACTCCTAGTGACATTTTCGTGTCTTACAGTACCTTCCCAGGCTTTGTCTCATG GCGCGATCCCAAGTCAGGGAGCTGGTACGTGGAGACACTGGACGACATCTTTGA ACAGTGGGCCCATTCAGAGGACCTGCAGAGCCTGCTGCTGCGAGTGGCAAACGC TGTCTCTGTGAAGGGCATCTACAAACAGATGCCCGGGTGCTTCAATTTTCTGAGA AAGAAACTGTTCTTTAAGACTTCC (SEQ ID NO: 50).

In certain embodiments of the inducible proapoptotic polypeptides, wherein the polypeptide comprises a truncated caspase 9 polypeptide, the inducible proapoptotic polypeptide is encoded by an amino acid sequence comprising GVQVETISPGDGRTFPKRGQTCVVHYTGMLEDGKKVDSSRDRNKPFKFMLGKQEVI RGWEEGVAQMSVGQRAKLTISPDYAYGATGHPGIIPPHATLVFDVELLKLEGGGGGS GFGDVGALESLRGNADLAYISLMEPCGHCLIINNVNFCRESGLRTRTGSNIDCEKLRR RFSSLHFMVEVKGDLTAKKMVLALLELAQQDHGALDCCVVVILSHGCQASHLQFPG AVYGTDGCPVS-VEKIVNIFNGTSCPSLGGKPKLFFIQACGGEQKDHGFEVASTSPEDE SPGSNPEPDATPFQEGLRTFDQLDAISSLPTPSDIFVSYSTFPGFVSWRDPKSGSWYVE TLDDIFEQWAHSEDLQSLLLRVA-NAVSVKGIYKQMPGCNFLRKKLFFKTS (SEQ ID NO: 51) or the nucleic acid sequence comprising GGGGTCCAGGTCGAGACTATTTCACCAGGGGATGGGCGAACATTTCCAAAAAGG GGCCAGACTTGCGTCGTGCATTACACCGGGATGCTGGAGGACGGGAAGAAAGTG GACAGCTCCAGGGATCGCAACAAGCCCTTCAAGTTCATGCTGGGAAAGCAGGAA GTGATCCGAGGATGGGAGGAAGGCGTGGCACAGATGTCAGTCGGCCAGCGGGCC AAACTGACCATTAGCCCTGACTACGCTTATGGAGCAACAGGCCACCCAGGGATC ATTCCCCCTCATGCCACCCTGGTCTTCGATGTGGAACTGCTGAAGCTGGAGGGAG GAGGAGGATCCGAATTTGGGGACGTGGGGGCCCTGGAGTCTCTGCGAGGAAATG CCGATCTGGCTTACATCCTGAGCATGGAACCCTGCGGCCACTGTCTGATCATTAA CAATGTGAACTTCTGCAGAGAAAGCGGACTGCGAACACGGACTGGCTCCAATAT TGACTGTGAGAAGCTGCGGAGAAGGTTCTCTAGTCTGCACTTTATGGTCGAAGTG AAAGGGGATCTGACCGCCAAGAAAATGGTGCTGGCCCTGCTGGAGCTGGCTCAG CAGGACCATGGAGCTCTGGATTGCTGCGTGGTCGTGATCCTGTCCCACGGGTGCC AGGCTTCTCATCTGCAGTTCCCCGGAGCAGTGTACGGAACAGACGGCTGTCCTGT CAGCGTGGAGAAGATCGTCAACATCTTCAACGGCACTTCTTGCCCTAGTCTGGGG GGAAAGCCAAAACTGTTCTTTATCCAGGCCTGTGGCGGGGAACAGAAAGATCAC GGCTTCGAGGTGGCCAGCACCAGCCCTGAGGACGAATCACCAGGGAGCAACCCT GAACCAGATGCAACTCCATTCCAGGAGGGACTGAGGACCTTTGACCAGCTGGAT GCTATCTCAAGCCTGCCCACTCCTAGTGACATTTTCGTGTCTTACAGTACCTTCCC AGGCTTTGTCTCATGGCGCGATCCCAAGTCAGG- GAGCTGGTACGTGGAGACACT GGACGACATCTTTGAACAGTGGGCCCAT-TCAGAGGACCTGCAGAGCCTGCTGCT GCGAGTGGCAAACGCTGTCTCTGTGAAGGGCATC-TACAAACAGATGCCCGGGTG CTTCAATTTTCT-GAGAAAGAAACTGTTCTTTAAGACTTCC (SEQ ID NO: 52).

Nanoparticle vectors of the disclosure may comprise at least one self-cleaving peptide. In some embodiments, the nanoparticle vector may comprise at least one self-cleaving peptide and wherein a self-cleaving peptide is located between a CAR and the nanoparticle. In some embodiments, the nanoparticle vector may comprise at least one self-cleaving peptide and wherein a first self-cleaving peptide is located upstream of a CAR and a second self-cleaving peptide is located downstream of a CAR. In some embodiments, the nanoparticle vector may comprise at least one self-cleaving peptide and wherein a first self-cleaving peptide is located between a CAR and the nanoparticle and a second self-cleaving peptide is located downstream of the CAR. In some embodiments, the nanoparticle vector may comprise at least one self-cleaving peptide and wherein a first self-cleaving peptide is located between a CAR and the nanoparticle and a second self-cleaving peptide is located downstream of the CAR, for example, between the CAR and a selection gene. Nanoparticle vectors of the disclosure may comprise at least one self-cleaving peptide(s) located, for example, between one or more of a protein scaffold, Centyrin or CARTyrin of the disclosure and an inducible proapoptotic polypeptide of the disclosure. Nanoparticle vectors of the disclosure may comprise at least two self-cleaving peptide(s), a first self-cleaving peptide located, for example, upstream or immediately upstream of an inducible proapoptotic polypeptide of the disclosure and a second first self-cleaving peptide located, for example, downstream or immediately upstream of an inducible proapoptotic polypeptide of the disclosure. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 53) or a sequence having at least 70%, 80%, 90%, 95%, or 99% identity to the amino acid sequence comprising EGRGSLLTCGDVEENPGP (SEQ ID NO: 53). A GSG-T2A peptide may comprise an amino acid sequence comprising GSGEGRGSLLTCGDVEENPGP (SEQ ID NO: 54) or a sequence having at least 70%, 80%, 90%, 95%, or 99% identity to the amino acid sequence comprising GSGEGRGSLLTCGDVEENPGP (SEQ ID NO: 54). A GSG-T2A peptide may comprise a nucleic acid sequence comprising ggatctggagagggaaggggaagcctgctgacctgtggagacgtggaggaaaacccaggacca (SEQ ID NO: 55). An E2A peptide may comprise an amino acid sequence comprising QCTNYALLKLAGDVESNPGP (SEQ ID NO: 56) or a sequence having at least 70%, 80%, 90%, 95%, or 99% identity to the amino acid sequence comprising QCTNYALLKLAGDVESNPGP (SEQ ID NO: 56). A GSG-E2A peptide may comprise an amino acid sequence comprising GSGQCTNYALLKLAGDVESNPGP (SEQ ID NO: 57) or a sequence having at least 70%, 80%, 90%, 95%, or 99% identity to the amino acid sequence comprising GSGQCTNYALLKLAGDVESNPGP (SEQ ID NO: 57). An F2A peptide may comprise an amino acid sequence comprising VKQTLNFDLLKLAGDVESNPGP (SEQ ID NO: 58) or a sequence having at least 70%, 80%, 90%, 95%, or 99% identity to the amino acid sequence comprising VKQTLNFDLLKLAGDVESNPGP (SEQ ID NO: 58). A GSG-F2A peptide may comprise an amino acid sequence comprising GSGVKQTLNFDLLKLAGDVESNPGP (SEQ ID NO: 59) or a sequence having at least 70%, 80%, 90%, 95%, or 99% identity to the amino acid sequence comprising GSGVKQTLNFDLLKLAGDVESNPGP (SEQ ID NO: 59). A P2A peptide may comprise an amino acid sequence comprising ATNFSLLKQAGDVEENPGP (SEQ ID NO: 60) or a sequence having at least 70%, 80%, 90%, 95%, or 99% identity to the amino acid sequence comprising ATNFSLLKQAGDVEENPGP (SEQ ID NO: 60). A GSG-P2A peptide may comprise an amino acid sequence comprising GSGATNFSLLKQAGDVEENPGP (SEQ ID NO: 61) or a sequence having at least 70%, 80%, 90%, 95%, or 99% identity to the amino acid sequence comprising GSGATNFSLLKQAGDVEENPGP (SEQ ID NO: 61).

The disclosure provides a composition comprising a vector of the disclosure.

CAR-expressing Cells

The disclosure provides a cell comprising a CAR of the disclosure. The disclosure provides a cell comprising a transposon of the disclosure. In certain embodiments, the cell comprising a CAR, a transposon, or a vector of the disclosure may express a CAR on the cell surface. The cell may be any type of cell.

In certain embodiments of the disclosure, the cell is an immune cell. The immune cell may be a T-cell, a Natural Killer (NK) cell, a Natural Killer (NK)-like cell (e.g. a Cytokine Induced Killer (CIK) cell), a hematopoeitic progenitor cell, a peripheral blood (PB) derived T cell or an umbilical cord blood (UCB) derived T-cell.

In certain embodiments of the disclosure, the immune cell is a T-cell. The T cell may be a helper T cell, a helper type 1 T cell, a helper type 2 T cell, a helper 17 T cell, a regulatory T cell, a natural regulatory T cell, or an induced regulatory T cell. The T cell may be CD4+.

In certain embodiments of the disclosure, the cell is an artificial ligand presenting cell, which, optionally, may be used to stimulate and expand a modified immune cell or T cell of the disclosure.

In certain embodiments of the disclosure, the cell is tumor cell, which, optionally, may be used as an artificial or modified ligand presenting cell.

Modified cells of the disclosure that may be used for adoptive therapy may be autologous or allogeneic.

Methods of Making CAR-Expressing Cells

The disclosure provides a method for expressing a chimeric ligand/antigen receptor (CLR/CAR) on the surface of a cell, comprising: (a) obtaining a cell population; (b) contacting the cell population to a composition comprising a CAR of the disclosure or a sequence encoding the CAR, under conditions sufficient to transfer the CAR across a cell membrane of at least one cell in the cell population, thereby generating a modified cell population; (c) culturing the modified cell population under conditions suitable for integration of the transposon; and (d) expanding and/or selecting at least one cell from the modified cell population that express the CAR on the cell surface.

In certain embodiments of this method of expressing a CAR, the cell population may comprise leukocytes and/or CD4+ and CD8+ leukocytes. The cell population may comprise CD4+ and CD8+ leukocytes in an optimized ratio. The optimized ratio of CD4+ to CD8+ leukocytes does not naturally occur in vivo. The cell population may comprise a tumor cell.

In certain embodiments of this method of expressing a CAR, a transposon or vector comprises the CAR or the sequence encoding the CAR.

In certain embodiments of this method of expressing a CAR, the conditions sufficient to transfer the sequence encoding the CAR across a cell membrane of at least one cell in the cell population comprise nucleofection.

In certain embodiments of this method of expressing a CAR, wherein the conditions sufficient to transfer the sequence encoding the CAR across a cell membrane of at least one cell in the cell population comprise at least one of an application of one or more pulses of electricity at a specified voltage, a buffer, and one or more supplemental factor(s). In certain embodiments, the buffer may comprise PBS, HBSS, OptiMEM, BTXpress, Amaxa Nucleofector, Human T cell nucleofection buffer or any combination thereof. In certain embodiments, the one or more supplemental factor(s) may comprise (a) a recombinant human cytokine, a chemokine, an interleukin or any combination thereof; (b) a salt, a mineral, a metabolite or any combination thereof; (c) a cell medium; (d) an inhibitor of cellular DNA sensing, metabolism, differentiation, signal transduction, one or more apoptotic pathway(s) or combinations thereof; and (e) a reagent that modifies or stabilizes one or more nucleic acids. The recombinant human cytokine, the chemokine, the interleukin or any combination thereof may comprise IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L or any combination thereof. The salt, the mineral, the metabolite or any combination thereof may comprise HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, anti-biotics, pH adjusters, Earle's Salts, 2-Mercaptoethanol, Human transferrin, Recombinant human insulin, Human serum albumin, Nucleofector PLUS Supplement, KCL, MgCl2, Na2HPO4, NAH2PO4, Sodium lactobionate, Manitol, Sodium succinate, Sodium Chloride, ClNa, Glucose, Ca(N03)2, Tris/HCl, K2HPO4, KH2PO4, Polyethylenimine, Poly-ethylene-glycol, Poloxamer 188, Poloxamer 181, Poloxamer 407, Poly-vinylpyrrolidone, Pop313, Crown-5, or any combination thereof. The cell medium may comprise PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium or any combination thereof. The inhibitor of cellular DNA sensing, metabolism, differentiation, signal transduction, one or more apoptotic pathway(s) or combinations thereof comprise inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspasel, Pro-IL1B, PI3K, Akt, Wnt3A, inhibitors of glycogen synthase kinase-3β (GSK-3 β) (e.g. TWS119), Bafilomycin, Chloroquine, Quinacrine, AC-YVAD-CMK, Z-VAD-FMK, Z-IETD-FMK or any combination thereof. The reagent that modifies or stabilizes one or more nucleic acids comprises a pH modifier, a DNA-binding protein, a lipid, a phospholipid, CaPO4, a net neutral charge DNA binding peptide with or without a NLS sequence, a TREX1 enzyme or any combination thereof.

In certain embodiments of this method of expressing a CAR, the conditions suitable for integration of the CAR or a sequence encoding the CAR of the disclosure comprise at least one of a buffer and one or more supplemental factor(s). In certain embodiments, a transposon or vector of the disclosure comprise the CAR or a sequence encoding the CAR of the disclosure. In certain embodiments, the buffer may comprise PBS, HBSS, OptiMEM, BTXpress, Amaxa Nucleofector, Human T cell nucleofection buffer or any combination thereof. In certain embodiments, the one or more supplemental factor(s) may comprise (a) a recombinant human cytokine, a chemokine, an interleukin or any combination thereof; (b) a salt, a mineral, a metabolite or any combination thereof; (c) a cell medium; (d) an inhibitor of cellular DNA sensing, metabolism, differentiation, signal transduction, one or more apoptotic pathway(s) or combinations thereof; and (e) a reagent that modifies or stabilizes one or more nucleic acids. The recombinant human cytokine, the chemokine, the interleukin or any combination thereof may comprise IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSFI1/RANK L or any combination thereof. The salt, the mineral, the metabolite or any combination thereof may comprise HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, anti-biotics, pH adjusters, Earle's Salts, 2-Mercaptoethanol, Human transferrin, Recombinant human insulin, Human serum albumin, Nucleofector PLUS Supplement, KCL, MgCl2, Na2HPO4, NAH2PO4, Sodium lactobionate, Manitol, Sodium succinate, Sodium Chloride, ClNa, Glucose, Ca(N03)2, Tris/HCl, K2HPO4, KH2PO4, Polyethylenimine, Poly-ethylene-glycol, Poloxamer 188, Poloxamer 181, Poloxamer 407, Poly-vinylpyrrolidone, Pop313, Crown-5, or any combination thereof. The cell medium may comprise PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium or any combination thereof. The inhibitor of cellular DNA sensing, metabolism, differentiation, signal transduction, one or more apoptotic pathway(s) or combinations thereof comprise inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspasel, Pro-IL1B, PI3K, Akt, Wnt3A, inhibitors of glycogen synthase kinase-3β (GSK-3 β) (e.g. TWS119), Bafilomycin, Chloroquine, Quinacrine, AC-YVAD-CMK, Z-VAD-FMK, Z-IETD-FMK or any combination thereof. The reagent that modifies or stabilizes one or more nucleic acids comprises a pH modifier, a DNA-binding protein, a lipid, a phospholipid, CaPO4, a net neutral charge DNA binding peptide with or without a NLS sequence, a TREX1 enzyme or any combination thereof.

In certain embodiments of this method of expressing a CAR, the expansion and selection steps occur sequentially. The expansion may occur prior to selection. The expansion may occur following selection, and, optionally, a further (i.e. second) selection may occur following expansion.

In certain embodiments of this method of expressing a CAR, the expansion and selection steps may occur simultaneously.

In certain embodiments of this method of expressing a CAR, the expansion may comprise contacting at least one cell of the modified cell population with a ligand to stimulate the at least one cell through the CAR, thereby generating an expanded cell population. The ligand may be presented on the surface of a substrate. The substrate may have any form, including, but not limited to a surface, a well, a bead or a plurality thereof, and a matrix. The substrate may further comprise a paramagnetic or magnetic component. In certain embodiments of this method of expressing a CAR, the ligand may be presented on the surface of a substrate, wherein the substrate is a magnetic bead, and wherein a magnet may be used to remove or separate the magnetic beads from the modified and expanded cell population. The ligand may be presented on the surface of a cell or an artificial ligand presenting cell. Artificial ligand presenting cells of the disclosure may include, but are not limited to, tumor cells and stem cells.

In certain embodiments of this method of expressing a CAR, wherein the transposon or vector comprises a selection gene and wherein the selection step comprises contacting at least one cell of the modified cell population with a compound to which the selection gene confers resistance, thereby identifying a cell expressing the selection gene as surviving the selection and identifying a cell failing to express the selection gene as failing to survive the selection step.

In certain embodiments of this method of expressing a CAR, the expansion and/or selection steps may proceed for a period of 10 to 14 days, inclusive of the endpoints.

The disclosure provides a composition comprising the modified, expanded and selected cell population of the methods of the disclosure.

Hematopoietic Stem Cells

Compositions of the disclosure may comprise a plurality of hematopoietic stem cells (HSCs) for transplantation following the selective removal of native HSCs from a subject.

Hematopoietic stem cells (HSCs) are multipotent, self-renewing progenitor cells. All differentiated blood cells from the lymphoid and myeloid lineages arise from HSCs. HSCs can be found in adult bone marrow, peripheral blood, and umbilical cord blood.

Often HSC transplants, in the form of bone marrow transplants fail because remnants of the subject's immune system attack the transplanted cells or create conditions that are not conducive to the survival of the transplanted cells. Prior to the development of the compositions and methods of the disclosure, the elimination of HSCs prior to a bone marrow transplant was either ineffective or caused harm to cell populations other than the intended HSCs. The compositions and methods of the disclosure provide a method for selectively elimination of HSCs that are damaged, malfunctioning, or carry genetic defects that cause disease by targeting these HSCs with immune cells expressing chimeric ligand receptors (CARs) that specifically target HSC surface ligands. Compositions comprising the CAR-expressing immune cells may be eliminated once they have performed their function, either by pre-irradiating the immune cells or by further modifying these cells to contain an inducible proapoptotic polypeptide that, upon administration of an induction agent, initiates apoptosis of only the exogenous CAR-expressing immune cells that contain the inducible proapoptotic polypeptide (otherwise referred to as a "safety switch").

The compositions and methods of the disclosure further provide for the transplantation of a plurality of HSCs. Preferably, the transplanted HSCs of the disclosure are genetically modified.

HSCs of the disclosure may be modified by a composition comprising a DNA localization domain and an effector domain. In certain embodiments, the DNA localization domain may comprise a DNA binding domain of Cas9, an inactivated Cas9, a short Cas9, a short and inactivated Cas9, a TALEN or a Zinc-finger protein. In certain embodiments, the effector comprises an endonuclease. Preferably, the endonuclease is a type IIS endonuclease. In certain embodiments, the type IIS endonuclease is one or more of AciI, MnlI, AlwI, BbvI, BccI, BceAI, BsmAI, BsmFI, BspCNI, BsrI, BtsCI, HgaI, HphI, HpyAV, MboII, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. For more detail regarding genomic editing tools, see PCT/US2016/037922, the contents of which are incorporated by reference herein in their entirety). Compositions comprising a DNA localization domain and an effector domain may be contained in a transposon. Compositions comprising a DNA localization domain and an effector domain, including those contained in a vector, may be further contained in a vector for expression and/or for delivery to a cell.

HSCs of the disclosure may be modified to remove a genetic or epigenetic marker of a disease or disorder.

HSCs of the disclosure may be modified to express or overexpress a nucleic acid or protein or to secrete a molecule, peptide, protein, or compound to treat a disease or disorder of the disclosure.

HSCs of the disclosure may be modified to express or overexpress a nucleic acid or protein or to secrete a molecule, peptide, protein, or compound to modify an immune response of the disclosure.

HSCs of the disclosure may be modified to express or overexpress a cell surface ligand to modify an activity of a CAR-expressing immune cell of the disclosure. For example, transplanted HSCs may express a ligand, which upon binding to a CAR-expressing immune cell of the disclosure, deactivates the immune cell to prevent any residual CAR-expressing immune cell from selectively eliminating the transplanted HSC cell.

Nucleic Acid Molecules

Nucleic acid molecules of the disclosure encoding protein scaffolds can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one protein scaffold; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold as described herein and/or as known in the art. Of course, the genetic code is well known in the art. Thus, it would be routine for one skilled in the art to generate such degenerate nucleic acid variants that code for specific protein scaffolds of the present invention. See, e.g., Ausubel, et al., supra, and such nucleic acid variants are included in the present invention.

As indicated herein, nucleic acid molecules of the disclosure which comprise a nucleic acid encoding a protein scaffold can include, but are not limited to, those encoding the amino acid sequence of a protein scaffold fragment, by itself, the coding sequence for the entire protein scaffold or a portion thereof; the coding sequence for a protein scaffold, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold can be fused to a marker sequence, such as a sequence encoding a peptide that facilitates purification of the fused protein scaffold comprising a protein scaffold fragment or portion.

Polynucleotides Selectively Hybridizing to a Polynucleotide as Described Herein

The disclosure provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of a protein scaffold encoded by the polynucleotides described herein. The polynucleotides of this invention embrace nucleic acid sequences that can be employed for selective hybridization to a polynucleotide encoding a protein scaffold of the present invention. See, e.g., Ausubel, supra; Colligan, supra, each entirely incorporated herein by reference.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the disclosure can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid of the disclosure. A nucleic acid sequence of the disclosure, for example, a cDNA or a genomic sequence encoding a protein scaffold of the disclosure, can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some embodiments, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Vectors and Host Cells

The disclosure also relates to vectors that include isolated nucleic acid molecules of the disclosure, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

For example, the PB-EF1a vector may be used. The vector comprises the following nucleotide sequence:

(SEQ ID NO: 62)
tgtacatagattaaccctagaaagataatcatattgtgacgtacgttaaa gataatcatgcgtaaaattgacgcatgtgttttatcggtctgtatatcga ggtttatttattaatttgaatagatattaagttttattatatttacactt acatactaataataaattcaacaaacaatttatttatgtttatttattta ttaaaaaaaacaaaaactcaaaatttcttctataaagtaacaaaacttt tatcgaatacctgcagcccgggggatgcagagggacagccccccccaaa gcccccagggatgtaattacgtccctcccccgctaggggcagcagcgag ccgcccggggctccgctccggtccggcgctccccccgcatcccgagccg gcagcgtgcggggacagcccgggcacggggaaggtggcacgggatcgctt tcctctgaacgcttctcgctgctctttgagcctgcagacacctgggggga tacggggaaaagttgactgtgcctttcgatcgaaccatggacagttagct ttgcaaagatggataaagttttaaacagagaggaatctttgcagctaatg gaccttctaggtcttgaaaggagtgggaattggctccggtgcccgtcagt gggcagagcgcacatcgcccacagtccccgagaagttgggggagggtc ggcaattgaaccggtgcctagagaaggtggcgcggggtaaactgggaaag tgatgtcgtgtactggctccgccttttttcccgagggtggggagaaccgt atataagtgcagtagtcgccgtgaacgttcttttttcgcaacgggtttgcc gccagaacacaggtaagtgccgtgtgtggttcccgcgggcctggcctctt tacgggttatggcccttgcgtgccttgaattacttccacctggctgcagt acgtgattcttgatcccgagcttcgggttggaagtgggtgggagagttcg aggccttgcgcttaaggagccccttcgcctcgtgcttgagttgaggcctg gcctgggcgctggggccgccgcgtgcgaatctggtggcaccttcgcgcct gtctcgctgctttcgataagtctctagccatttaaaatttttgatgacct gctgcgacgcttttttttctggcaagatagtcttgtaaatgcgggccaaga tctgcacactggtatttcggttttttggggccgcgggcggcgacggggccc gtgcgtcccagcgcacatgttcggcgaggcggggcctgcgagcgcggcca ccgagaatcggacgggggtagtctcaagctggccggcctgctctggtgcc tggcctcgcgccgccgtgtatcgccccgccctgggcggcaaggctggccc

```
ggtcggcaccagttgcgtgagcggaaagatggccgcttcccggccctgct
gcagggagctcaaaatggaggacgcggcgctcggagagcgggcgggtga
gtcacccacacaaaggaaaagggcctttccgtcctcagccgtcgcttcat
gtgactccacggagtaccgggcgccgtccaggcacctcgattagttctcg
agcttttggagtacgtcgtctttaggttgggggagggttttatgcgat
ggagtttccccacactgagtgggtggagactgaagttaggccagcttggc
acttgatgtaattctccttggaatttgccttttttgagtttggatcttgg
ttcattctcaagcctcagacagtggttcaaagttttttttcttccatttca
ggtgtcgtgagaattctaatacgactcactatagggtgtgctgtctcatc
attttggcaaagattggccaccaagcttgtcctgcaggagggtcgacgcc
tctagacgggcggccgctccggatccacgggtaccgatcacatatgcctt
taattaaacactagttctatagtgtcacctaaattcccttagtgagggt
taatggccgtaggccgccagaattgggtccagacatgataagatacattg
atgagtttggacaaaccacaactagaatgcagtgaaaaaatgctttatt
tgtgaaatttgtgatgctattgctttatttgtaaccattataagctgcaa
taaacaagttaacaacaacaattgcattcattttatgtttcaggttcagg
gggaggtgtgggaggttttttcggactctaggacctgcgcatgcgcttgg
cgtaatcatggtcatagctgtttcctgttttcccgtatccccaggtg
tctgcaggctcaaagagcagcgagaagcgttcagaggaaagcgatcccgt
gccaccttcccgtgccgggctgtccccgcacgctgccggctcggggat
gcgggggagcgccggaccggagcggagcccgggcggctcgctgctgcc
ccctagcggggagggacgtaattacatccctgggggctttgggggggggg
ctgtccctctcaccgcggtggagctccagcttttgttcgaattgggccc
cccctcgagggtatcgatgatatctataacaagaaaatatatatataata
agttatcacgtaagtagaacatgaaataacaatataattatcgtatgagt
taaatcttaaaagtcacgtaaaagataatcatgcgtcattttgactcacg
cggtcgttatagttcaaaatcagtgacacttaccgcattgacaagcacgc
ctcacgggagctccaagcggcgactgagatgtcctaaatgcacagcgacg
gattcgcgctatttagaaagagagagcaatatttcaagaatgcatgcgtc
aattttacgcagactatctttctagggttaatctagctagccttaagggc
gcctattgcgttgcgctcactgcccgctttccagtcgggaaacctgtcgt
gccagctgcattaatgaatcggccaacgcgcggggagaggcggtttgcgt
attgggcgctcttccgcttcctcgctcactgactcgctgcgctcggtcgt
tcggctgcggcgagcggtatcagctcactcaaaggcggtaatacggttat
ccacagaatcaggggataacgcaggaaagaacatgaccaaaatcccttaa
cgtgagttttcgttccactgagcgtcagacccgtagaaagatcaaagg
atcttcttgagatccttttttttctgcgcgtaatctgctgcttgcaaacaa
aaaaccaccgctaccagcggtggtttgtttgccggatcaagagctacca
actcttttccgaaggtaactggcttcagcagagcgcagataccaaatac
tgttcttctagtgtagccgtagttaggccaccacttcaagaactctgtag
caccgcctacatacctcgctctgctaatcctgttaccagtggctgctgcc agtggcgataagtcgtgtcttaccgggttggactcaagacgatagttacc
ggataaggcgcagcggtcgggctgaacgggggttcgtgcacacagccca
gcttggagcgaacgacctacaccgaactgagatacctacagcgtgagcta
tgagaaagcgccacgcttcccgaagggagaaaggcggacaggtatccggt
aagcggcagggtcggaacaggagagcgcacgagggagcttccaggggaa
acgcctggtatctttatagtcctgtcgggtttcgccacctctgacttgag
cgtcgattttttgtgatgctcgtcaggggcggagcctatggaaaaacgc
cagcaacgcggcctttttacggttcctggccttttgctggccttttgctc
acatgagattatcaaaaaggatcttcacctagatcctttaaattaaaaa
tgaagttttaaatcaatctaaagtatatatgagtaaacttggtctgacag
tcagaagaactcgtcaagaaggcgatagaaggcgatgcgctgcgaatcgg
gagcggcgataccgtaaagcacgaggaagcggtcagcccattcgccgcca
agctcttcagcaatatcacgggtagccaacgctatgtcctgatagcggtc
cgccacacccagccggccacagtcgatgaatccagaaaagcggccatttt
ccaccatgatattcggcaagcaggcatcgccatgggtcacgacgagatcc
tcgccgtcgggcatgctcgccttgagcctggcgaacagttcggctggcgc
gagcccctgatgctcttcgtccagatcatcctgatcgacaagaccggctt
ccatccgagtacgtgctcgctcgatgcgatgtttcgcttggtggtcgaat
gggcaggtagccggatcaagcgtatgcagccgccgcattgcatcagccat
gatggatactttctcggcaggagcaaggtgagatgacaggagatcctgcc
ccggcacttcgcccaatagcagccagtcccttcccgcttcagtgacaacg
tcgagcacagctgcgcaaggaacgcccgtcgtggccagccacgatagccg
cgctgcctcgtcttgcagttcattcagggcaccggacaggtcggtcttga
caaaaagaaccgggcgcccctgcgctgacagccggaacacggcggcatca
gagcagccgattgtctgttgtgcccagtcatagccgaatagcctctccac
ccaagcggccggagaacctgcgtgcaatccatcttgttcaatcataatat
tattgaagcatttatcagggttcgtctcgtcccggtctcctcccaatgca
tgtcaatattggccattagccatattattcattggttatatagcataaat
caatattggctattggccattgcatacgttgtatctatatcataata.
```

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one protein scaffold of the disclosure can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the disclosure. Alternatively, nucleic acids of the disclosure can be expressed in a host cell by turning on (by manipulation) in a host cell that contains endogenous DNA encoding a protein scaffold of the disclosure. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of a Protein Scaffold

A protein scaffold can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, N.Y., N.Y., (1997-2001), e.g., Chapters 1, 4, 6, 8, 9, 10, each entirely incorporated herein by reference.

Protein scaffolds of the disclosure include naturally purified products, products of chemical synthetic procedures, and products produced by recombinant techniques from a prokaryotic or eukaryotic host, including, for example, *E. coli*, yeast, higher plant, insect and mammalian cells. Depending upon the host employed in a recombinant production procedure, the protein scaffold of the disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Amino Acid Codes

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the disclosure can include one or more amino acid substitutions, deletions or additions, either from natural mutations or human manipulation, as specified herein. Amino acids in a protein scaffold of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

As those of skill will appreciate, the invention includes at least one biologically active protein scaffold of the disclosure. Biologically active protein scaffolds have a specific activity at least 20%, 30%, or 40%, and, preferably, at least 50%, 60%, or 70%, and, most preferably, at least 80%, 90%, or 95%-99% or more of the specific activity of the native (non-synthetic), endogenous or related and known protein scaffold. Methods of assaying and quantifying measures of enzymatic activity and substrate specificity are well known to those of skill in the art.

In another aspect, the disclosure relates to protein scaffolds and fragments, as described herein, which are modified by the covalent attachment of an organic moiety. Such modification can produce a protein scaffold fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified protein scaffolds and fragments of the disclosure can comprise one or more organic moieties that are covalently bonded, directly or indirectly, to the antibody. Each organic moiety that is bonded to a protein scaffold or fragment of the disclosure can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, a protein scaffold modified by the covalent attachment of polylysine is encompassed by the disclosure. Hydrophilic polymers suitable for modifying protein scaffolds of the disclosure can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the protein scaffold of the disclosure has a molecular weight of about 800 to about 150,000 Daltons as a separate molecular entity. For example, PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying protein scaffolds of the disclosure can be saturated or can contain one or more units of unsaturation. Fatty acids that are suitable for modifying protein scaffolds of the disclosure include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-Δ9-octadecanoate (C18, oleate), all cis-Δ5,8,11,14-eicosatetraenoate (C20, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably, one to about six, carbon atoms.

The modified protein scaffolds and fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —(CH2)3—, —NH—(CH2)6—NH—, —(CH2)2—NH— and —CH2—O—CH2—CH2—O—CH2—CH2O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified protein scaffolds of the disclosure can be produced by reacting a protein scaffold or fragment with a modifying agent. For example, the organic moieties can be bonded to the protein scaffold in a non-site specific manner by employing an amine-reactive modifying agent, for example, an NHS ester of PEG. Modified protein scaffolds and fragments comprising an organic moiety that is bonded to specific sites of a protein scaffold of the disclosure can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

T Cell Isolation from a Leukapheresis Product

A leukapheresis product or blood may be collected from a subject at clinical site using a closed system and standard methods (e.g., a COBE Spectra Apheresis System). Preferably, the product is collected according to standard hospital or institutional Leukapheresis procedures in standard Leukapheresis collection bags. For example, in preferred embodiments of the methods of the disclosure, no additional anticoagulants or blood additives (heparin, etc.) are included beyond those normally used during leukapheresis.

Alternatively, white blood cells (WBC)/Peripheral Blood Mononuclear Cells (PBMC) (using Biosafe Sepax 2 (Closed/Automated)) or T cells (using CliniMACS® Prodigy (Closed/Automated)) may be isolated directly from whole blood. However, in certain subjects (e.g. those diagnosed and/or treated for cancer), the WBC/PBMC yield may be significantly lower when isolated from whole blood than when isolated by leukapheresis.

Either the leukapheresis procedure and/or the direct cell isolation procedure may be used for any subject of the disclosure.

The leukapheresis product, blood, WBC/PBMC composition and/or T-cell composition should be packed in insulated containers and should be kept at controlled room temperature (+19° C. to +25° C.) according to standard hospital of institutional blood collection procedures approved for use with the clinical protocol. The leukapheresis product, blood, WBC/PBMC composition and/or T-cell composition should not be refrigerated.

The cell concentration leukapheresis product, blood, WBC/PBMC composition and/or T-cell composition should not exceed $0.2 \times 10^9$ cells per mL during transportation. Intense mixing of the leukapheresis product, blood, WBC/PBMC composition and/or T-cell composition should be avoided.

If the leukapheresis product, blood, WBC/PBMC composition and/or T-cell composition has to be stored, e.g. overnight, it should be kept at controlled room temperature (same as above). During storage, the concentration of the leukapheresis product, blood, WBC/PBMC composition and/or T-cell composition should never exceed $0.2 \times 10^9$ cell per mL.

Preferably, cells of the leukapheresis product, blood, WBC/PBMC composition and/or T-cell composition should be stored in autologous plasma. In certain embodiments, if the cell concentration of the leukapheresis product, blood, WBC/PBMC composition and/or T-cell composition is higher than $0.2 \times 10^9$ cell per mL, the product should be diluted with autologous plasma.

Preferably, the leukapheresis product, blood, WBC/PBMC composition and/or T-cell composition should not be older than 24 hours when starting the labeling and separation procedure. The leukapheresis product, blood, WBC/PBMC composition and/or T-cell composition may be processed and/or prepared for cell labeling using a closed and/or automated system (e.g., CliniMACS Prodigy).

An automated system may perform additional buffy coat isolation, possibly by ficolation, and/or washing of the cellular product (e.g., the leukapheresis product, blood, WBC/PBMC composition and/or T cell composition).

A closed and/or automated system may be used to prepare and label cells for T-Cell isolation (from, for example, the leukapheresis product, blood, WBC/PBMC composition and/or T cell composition).

Although WBC/PBMCs may be nucleofected directly (which is easier and saves additional steps), the methods of the disclosure may include first isolating T cells prior to nucleofection. The easier strategy of directly nucleofecting PBMC requires selective expansion of CAR+cells that is mediated via CAR signaling, which by itself is proving to be an inferior expansion method that directly reduces the in vivo efficiency of the product by rendering T cells functionally exhausted. The product may be a heterogeneous composition of CAR+cells including T cells, NK cells, NKT cells, monocytes, or any combination thereof, which increases the variability in product from patient to patient and makes dosing and CRS management more difficult. Since T cells are thought to be the primary effectors in tumor suppression and killing, T cell isolation for the manufacture of an autologous product may result in significant benefits over the other more heterogeneous composition.

T cells may be isolated directly, by enrichment of labeled cells or depletion of labeled cells in a one-way labeling procedure or, indirectly, in a two-step labeling procedure. According to certain enrichment strategies of the disclosure, T cells may be collected in a Cell Collection Bag and the non-labeled cells (non-target cells) in a Negative Fraction Bag. In contrast to an enrichment strategy of the disclosure, the non-labeled cells (target cells) are collected in a Cell Collection Bag and the labeled cells (non-target cells) are collected in a Negative Fraction Bag or in the Non-Target Cell Bag, respectively. Selection reagents may include, but are not limited to, antibody-coated beads. Antibody-coated beads may either be removed prior to a modification and/or an expansion step, or, retained on the cells prior to a modification and/or an expansion step. One or more of the following non-limiting examples of cellular markers may be used to isolate T-cells: CD3, CD4, CD8, CD25, anti-biotin, CD1c, CD3/CD19, CD3/CD56, CD14, CD19, CD34, CD45RA, CD56, CD62L, CD133, CD137, CD271, CD304, IFN-gamma, TCR alpha/beta, and/or any combination thereof. Methods for the isolation of T-cells may include one or more reagents that specifically bind and/or detectably-label one or more of the following non-limiting examples of cellular markers may be used to isolate T-cells: CD3, CD4, CD8, CD25, anti-biotin, CD1c, CD3/CD19, CD3/CD56, CD14, CD19, CD34, CD45RA, CD56, CD62L, CD133, CD137, CD271, CD304, IFN-gamma, TCR alpha/beta, and/or any combination thereof. These reagents may or may not be "Good Manufacturing Practices" ("GMP") grade. Reagents may include, but are not limited to, Thermo DynaBeads and Miltenyi CliniMACS products. Methods of isolating T-cells of the disclosure may include multiple iterations of labeling and/or isolation steps. At any point in the methods of isolating T-cells of the disclosure, unwanted cells and/or unwanted cell types may be depleted from a T cell product composition of the disclosure by positively or negatively selecting for the unwanted cells and/or unwanted cell types. A T cell product composition of the disclosure may contain additional cell types that may express CD4, CD8, and/or another T cell marker(s).

Methods of the disclosure for nucleofection of T cells may eliminate the step of T cell isolation by, for example, a process for nucleofection of T cells in a population or composition of WBC/PBMCs that, following nucleofection, includes an isolation step or a selective expansion step via TCR signaling.

Certain cell populations may be depleted by positive or negative selection before or after T cell enrichment and/or sorting. Examples of cell compositions that may be depleted from a cell product composition may include myeloid cells, CD25+ regulatory T cells (T Regs), dendritic cells, macrophages, red blood cells, mast cells, gamma-delta T cells, natural killer (NK) cells, a Natural Killer (NK)-like cell (e.g. a Cytokine Induced Killer (CIK) cell), induced natural killer (iNK) T cells, NK T cells, B cells, or any combination thereof.

T cell product compositions of the disclosure may include CD4+ and CD8+ T-Cells. CD4+ and CD8+ T-Cells may be isolated into separate collection bags during an isolation or selection procedure. CD4+ T cells and CD8+ T cells may be further treated separately, or treated after reconstitution (combination into the same composition) at a particular ratio.

The particular ratio at which CD4+ T cells and CD8+ T cells may be reconstituted may depend upon the type and efficacy of expansion technology used, cell medium, and/or growth conditions utilized for expansion of T-cell product compositions. Examples of possible CD4+: CD8+ ratios include, but are not limited to, 50%:50%, 60%:40%, 40%:60% 75%:25% and 25%:75%.

CD8+ T cells exhibit a potent capacity for tumor cell killing, while CD4+ T cells provide many of the cytokines required to support CD8+ T cell proliferative capacity and function. Because T cells isolated from normal donors are predominantly CD4+, the T-cell product compositions are artificially adjusted in vitro with respect to the CD4+:CD8+ ratio to improve upon the ratio of CD4+ T cells to CD8+ T cells that would otherwise be present in vivo. An optimized ratio may also be used for the ex vivo expansion of the autologous T-cell product composition. In view of the artificially adjusted CD4+:CD8+ ratio of the T-cell product composition, it is important to note that the product compositions of the disclosure may be significantly different and provide significantly greater advantage than any naturally-occurring population of T-cells.

Preferred methods for T cell isolation may include a negative selection strategy for yielding untouched pan T cell, meaning that the resultant T-cell composition includes T-cells that have not been manipulated and that contain a naturally-occurring variety/ratio of T-cells.

Reagents that may be used for positive or negative selection include, but are not limited to, magnetic cell separation beads. Magnetic cell separation beads may or may not be removed or depleted from selected populations of CD4+ T cells, CD8+ T cells, or a mixed population of both CD4+ and CD8+ T cells before performing the next step in a T-cell isolation method of the disclosure.

T cell compositions and T cell product compositions may be prepared for cryopreservation, storage in standard T Cell Culture Medium, and/or genetic modification.

T cell compositions, T cell product compositions, unstimulated T cell compositions, resting T cell compositions or any portion thereof may be cryopreserved using a standard cryopreservation method optimized for storing and recovering human cells with high recovery, viability, phenotype, and/or functional capacity. Commercially-available cryopreservation media and/or protocols may be used. Cryopreservation methods of the disclosure may include a DMSO free cryopreservant (e.g. CryoSOfree™ DMSO-free Cryopreservation Medium) reduce freezing-related toxicity.

T cell compositions, T cell product compositions, unstimulated T cell compositions, resting T cell compositions or any portion thereof may be stored in a culture medium. T cell culture media of the disclosure may be optimized for cell storage, cell genetic modification, cell phenotype and/or cell expansion. T cell culture media of the disclosure may include one or more antibiotics. Because the inclusion of an antibiotic within a cell culture media may decrease transfection efficiency and/or cell yield following genetic modification via nucleofection, the specific antibiotics (or combinations thereof) and their respective concentration(s) may be altered for optimal transfection efficiency and/or cell yield following genetic modification via nucleofection.

T cell culture media of the disclosure may include serum, and, moreover, the serum composition and concentration may be altered for optimal cell outcomes. Human AB serum is preferred over FBS/FCS for culture of T cells because, although contemplated for use in T cell culture media of the disclosure, FBS/FCS may introduce xeno-proteins. Serum may be isolated form the blood of the subject for whom the T-cell composition in culture is intended for administration, thus, a T cell culture medium of the disclosure may comprise autologous serum. Serum-free media or serum-substitute may also be used in T-cell culture media of the disclosure. In certain embodiments of the T-cell culture media and methods of the disclosure, serum-free media or serum-substitute may provide advantages over supplementing the medium with xeno-serum, including, but not limited to, healthier cells that have greater viability, nucleofect with higher efficiency, exhibit greater viability post-nucleofection, display a more desirable cell phenotype, and/or greater/faster expansion upon addition of expansion technologies.

T cell culture media may include a commercially-available cell growth media. Exemplary commercially-available cell growth media include, but are not limited to, PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium, or any combination thereof.

T cell compositions, T cell product compositions, unstimulated T cell compositions, resting T cell compositions or any portion thereof may be prepared for genetic modification. Preparation of T cell compositions, T cell product compositions, unstimulated T cell compositions, resting T cell compositions or any portion thereof for genetic modification may include cell washing and/or resuspension in a desired nucleofection buffer. Cryopreserved T-cell compositions may be thawed and prepared for genetic modification by nucleofection. Cryopreserved cells may be thawed according to standard or known protocols. Thawing and preparation of cryopreserved cells may be optimized to yield cells that have greater viability, nucleofect with higher efficiency, exhibit greater viability post-nucleofection, display a more desirable cell phenotype, and/or greater/faster expansion upon addition of expansion technologies. For example, Grifols Albutein (25% human albumin) may be used in the thawing and/or preparation process.

Genetic Modification T Cells

T cell compositions, T cell product compositions, unstimulated T cell compositions, resting T cell compositions or any portion thereof may be genetically modified using, for example, a nucleofection strategy such as electroporation. The total number of cells to be nucleofected, the total volume of the nucleofection reaction, and the precise timing of the preparation of the sample may be optimized to yield cells that have greater viability, nucleofect with higher efficiency, exhibit greater viability post-nucleofection, display a more desirable cell phenotype, and/or greater/faster expansion upon addition of expansion technologies.

Nucleofection and/or electroporation may be accomplished using, for example, Lonza Amaxa, MaxCyte PulseAgile, Harvard Apparatus BTX, and/or Invitrogen Neon. Non-metal electrode systems, including, but not limited to, plastic polymer electrodes, may be preferred for nucleofection.

Prior to genetic modification by nucleofection, T cell compositions, T cell product compositions, unstimulated T cell compositions, resting T cell compositions or any portion thereof may be resuspended in a nucleofection buffer. Nucleofection buffers of the disclosure include commercially-available nucleofection buffers. Nucleofection buffers of the disclosure may be optimized to yield cells that have greater viability, nucleofect with higher efficiency, exhibit greater viability post-nucleofection, display a more desirable cell phenotype, and/or greater/faster expansion upon addition of expansion technologies. Nucleofection buffers of the disclosure may include, but are not limited to, PBS, HBSS, OptiMEM, BTXpress, Amaxa Nucleofector, Human T cell nucleofection buffer and any combination thereof. Nucleofection buffers of the disclosure may comprise one or more supplemental factors to yield cells that have greater viability, nucleofect with higher efficiency, exhibit greater viability post-nucleofection, display a more desirable cell phenotype, and/or greater/faster expansion upon addition of expansion technologies. Exemplary supplemental factors include, but are not limited to, recombinant human cytokines, chemokines, interleukins and any combination thereof. Exemplary cytokines, chemokines, and interleukins include, but are not limited to, IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L and any combination thereof. Exemplary supplemental factors include, but are not limited to, salts, minerals, metabolites or any combination thereof. Exemplary salts, minerals, and metabolites include, but are not limited to, HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, anti-biotics, pH adjusters, Earle's Salts, 2-Mercaptoethanol, Human transferrin, Recombinant human insulin, Human serum albumin, Nucleofector PLUS Supplement, KCL, MgCl2, Na2HPO4, NAH2PO4, Sodium lactobionate, Manitol, Sodium succinate, Sodium Chloride, ClNa, Glucose, Ca(N03)2, Tris/HCl, K2HPO4, KH2PO4, Polyethylenimine, Poly-ethylene-glycol, Poloxamer 188, Poloxamer 181, Poloxamer 407, Poly-vinylpyrrolidone, Pop313, Crown-5, and any combination thereof. Exemplary supplemental factors include, but are not limited to, media such as PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium and any combination thereof. Exemplary supplemental factors include, but are not limited to, inhibitors of cellular DNA sensing, metabolism, differentiation, signal transduction, the apoptotic pathway and combinations thereof. Exemplary inhibitors include, but are not limited to, inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspase1, Pro-IL1B, P13K, Akt, Wnt3A, inhibitors of glycogen synthase kinase-3β (GSK-3 β) (e.g. TWS119), Bafilomycin, Chloroquine, Quinacrine, AC-YVAD-CMK, Z-VAD-FMK, Z-IETD-FMK and any combination thereof. Exemplary supplemental factors include, but are not limited to, reagents that modify or stabilize one or more nucleic acids in a way to enhance cellular delivery, enhance nuclear delivery or transport, enhance the facilitated transport of nucleic acid into the nucleus, enhance degradation of epichromosomal nucleic acid, and/or decrease DNA-mediated toxicity. Exemplary reagents that modify or stabilize one or more nucleic acids include, but are not limited to, pH modifiers, DNA-binding proteins, lipids, phospholipids, CaPO4, net neutral charge DNA binding peptides with or without NLS sequences, TREX1 enzyme, and any combination thereof.

Transposition reagents, including a transposon and a transposase, may be added to a nucleofection reaction of the disclosure prior to, simultaneously with, or after an addition of cells to a nucleofection buffer (optionally, contained within a nucleofection reaction vial or cuvette). Transposons of the disclosure may comprise plasmid DNA, linearized plasmid DNA, a PCR product, DOGGYBONE™ DNA, an mRNA template, a single or double-stranded DNA, a protein-nucleic acid combination or any combination thereof. Transposons of the disclosure may comprised one or more sequences that encode one or more TTAA site(s), one or more inverted terminal repeat(s) (ITRs), one or more long terminal repeat(s) (LTRs), one or more insulator(s), one or more promotor(s), one or more full-length or truncated gene(s), one or more polyA signal(s), one or more self-cleaving 2A peptide cleavage site(s), one or more internal ribosome entry site(s) (IRES), one or more enhancer(s), one or more regulator(s), one or more replication origin(s), and any combination thereof.

Transposons of the disclosure may comprise one or more sequences that encode one or more full-length or truncated gene(s). Full-length and/or truncated gene(s) introduced by transposons of the disclosure may encode one or more of a signal peptide, a Centyrin, a single chain variable fragment (scFv), a hinge, a transmembrane domain, a costimulatory domain, a chimeric ligand/antigen receptor (CLR/CAR), a chimeric T-cell receptor (CAR-T), a CARTyrin (a CAR-T comprising a Centyrin), a receptor, a ligand, a cytokine, a drug resistance gene, a tumor ligand, an allo or auto ligand, an enzyme, a protein, a peptide, a poly-peptide, a fluorescent protein, a mutein or any combination thereof.

Transposons of the disclosure may be prepared in water, TAE, TBE, PBS, HBSS, media, a supplemental factor of the disclosure or any combination thereof.

Transposons of the disclosure may be designed to optimize clinical safety and/or improve manufacturability. As a non-limiting example, transposons of the disclosure may be designed to optimize clinical safety and/or improve manufacturability by eliminating unnecessary sequences or regions and/or including a non-antibiotic selection marker. Transposons of the disclosure may or may not be GMP grade.

Transposase enzymes of the disclosure may be encoded by one or more sequences of plasmid DNA, mRNA, protein, protein-nucleic acid combination or any combination thereof.

Transposase enzymes of the disclosure may be prepared in water, TAE, TBE, PBS, HBSS, media, a supplemental factor of the disclosure or any combination thereof. Transposase enzymes of the disclosure or the sequences/constructs encoding or delivering them may or may not be GMP grade.

Transposons and transposase enzymes of the disclosure may be delivered to a cell by any means.

Although compositions and methods of the disclosure include delivery of a transposon and/or transposase of the disclosure to a cell by plasmid DNA (pDNA), the use of a plasmid for delivery may allow the transposon and/or transposase to be integrated into the chromosomal DNA of the cell, which may lead to continued transposase expression. Accordingly, transposon and/or transposase enzymes of the disclosure may be delivered to a cell as either mRNA or protein to remove any possibility for chromosomal integration.

Transposons and transposases of the disclosure may be pre-incubated alone or in combination with one another prior to the introduction of the transposon and/or transposase into a nucleofection reaction. The absolute amounts of each of the transposon and the transposase, as well as the relative amounts, e.g., a ratio of transposon to transposase may be optimized.

Following preparation of nucleofection reaction, optionally, in a vial or cuvette, the reaction may be loaded into a nucleofector apparatus and activated for delivery of an electric pulse according to the manufacturer's protocol. Electric pulse conditions used for delivery of a transposon and/or a transposase of the disclosure (or a sequence encoding a transposon and/or a transposase of the disclosure) to a cell may be optimized for yielding cells with enhanced viability, higher nucleofection efficiency, greater viability post-nucleofection, desirable cell phenotype, and/or greater/faster expansion upon addition of expansion technologies. When using Amaxa nucleofector technology, each of the various nucleofection programs for the Amaxa 2B or 4D nucleofector are contemplated.

Following a nucleofection reaction of the disclosure, cells may be gently added to a cell medium. For example, when T cells undergo the nucleofection reaction, the T cells may be added to a T cell medium. Post-nucleofection cell media of the disclosure may comprise any one or more commercially-available media. Post-nucleofection cell media of the disclosure (including post-nucleofection T cell media of the disclosure) may be optimized to yield cells with greater viability, higher nucleofection efficiency, exhibit greater viability post-nucleofection, display a more desirable cell phenotype, and/or greater/faster expansion upon addition of expansion technologies. Post-nucleofection cell media of the disclosure (including post-nucleofection T cell media of the disclosure) may comprise PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium and any combination thereof. Post-nucleofection cell media of the disclosure (including post-nucleofection T cell media of the disclosure) may comprise one or more supplemental factors of the disclosure to enhance viability, nucleofection efficiency, viability post-nucleofection, cell phenotype, and/or greater/faster expansion upon addition of expansion technologies. Exemplary supplemental factors include, but are not limited to, recombinant human cytokines, chemokines, interleukins and any combination thereof. Exemplary cytokines, chemokines, and interleukins include, but are not limited to, IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L and any combination thereof. Exemplary supplemental factors include, but are not limited to, salts, minerals, metabolites or any combination thereof. Exemplary salts, minerals, and metabolites include, but are not limited to, HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, anti-biotics, pH adjusters, Earle's Salts, 2-Mercaptoethanol, Human transferrin, Recombinant human insulin, Human serum albumin, Nucleofector PLUS Supplement, KCL, MgCl2, Na2HPO4, NAH2PO4, Sodium lactobionate, Manitol, Sodium succinate, Sodium Chloride, ClNa, Glucose, Ca(N03)2, Tris/HCl, K2HPO4, KH2PO4, Polyethylenimine, Poly-ethylene-glycol, Poloxamer 188, Poloxamer 181, Poloxamer 407, Poly-vinylpyrrolidone, Pop313, Crown-5, and any combination thereof. Exemplary supplemental factors include, but are not limited to, media such as PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium and any combination thereof. Exemplary supplemental factors include, but are not limited to, inhibitors of cellular DNA sensing, metabolism, differentiation, signal transduction, the apoptotic pathway and combinations thereof. Exemplary inhibitors include, but are not limited to, inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspasel, Pro-IL1B, PI3K, Akt, Wnt3A, inhibitors of glycogen synthase kinase-3β (GSK-3 j) (e.g. TWS119), Bafilomycin, Chloroquine, Quinacrine, AC-YVAD-CMK, Z-VAD-FMK, Z-IETD-FMK and any combination thereof. Exemplary supplemental factors include, but are not limited to, reagents that modify or stabilize one or more nucleic acids in a way to enhance cellular delivery, enhance nuclear delivery or transport, enhance the facilitated transport of nucleic acid into the nucleus, enhance degradation of epi-chromosomal nucleic acid, and/or decrease DNA-mediated toxicity. Exemplary reagents that modify or stabilize one or more nucleic acids include, but are not limited to, pH modifiers, DNA-binding proteins, lipids, phospholipids, CaPO4, net neutral charge DNA binding peptides with or without NLS sequences, TREX1 enzyme, and any combination thereof.

Post-nucleofection cell media of the disclosure (including post-nucleofection T cell media of the disclosure) may be used at room temperature or pre-warmed to, for example to between 32° C. to 37° C., inclusive of the endpoints. Post-nucleofection cell media of the disclosure (including post-nucleofection T cell media of the disclosure) may be pre-warmed to any temperature that maintains or enhances cell viability and/or expression of a transposon or portion thereof of the disclosure.

Post-nucleofection cell media of the disclosure (including post-nucleofection T cell media of the disclosure) may be contained in tissue culture flasks or dishes, G-Rex flasks, Bioreactor or cell culture bags, or any other standard receptacle. Post-nucleofection cell cultures of the disclosure (including post-nucleofection T cell cultures of the disclosure) may be may be kept still, or, alternatively, they may be perturbed (e.g. rocked, swirled, or shaken).

Post-nucleofection cell cultures may comprise genetically-modified cells. Post-nucleofection T cell cultures may comprise genetically-modified T cells. Genetically modified cells of the disclosure may be either rested for a defined period of time or stimulated for expansion by, for example, the addition of a T Cell Expander technology. In certain embodiments, genetically modified cells of the disclosure may be either rested for a defined period of time or immediately stimulated for expansion by, for example, the addition of a T Cell Expander technology. Genetically modified cells of the disclosure may be rested to allow them sufficient time to acclimate, time for transposition to occur, and/or time for positive or negative selection, resulting in cells with enhanced viability, higher nucleofection efficiency, greater viability post-nucleofection, desirable cell phenotype, and/or greater/faster expansion upon addition of expansion technologies. Genetically modified cells of the disclosure may be rested, for example, for 1, 2, 3, 4, 5, 6, 7, 8, 9, 10, 11, 12, 13, 14, 15, 16, 17, 18, 19, 20, 21, 22, 23, 24, or more hours. In certain embodiments, genetically modified cells of the disclosure may be rested, for example, for an overnight. In certain aspects, an overnight is about 12 hours. Genetically modified cells of the disclosure may be rested, for example, for 1, 2, 3, 4, 5, 6, 7, 8, 9, 10, 11, 12, 13, 14 or more days.

Genetically modified cells of the disclosure may be selected following a nucleofection reaction and prior to addition of an expander technology. For optimal selection of genetically-modified cells, the cells may be allowed to rest in a post-nucleofection cell medium for at least 2-14 days to facilitate identification of modified cells (e.g., differentiation of modified from non-modified cells).

As early as 24-hours post-nucleofection, expression of a CAR/CARTyrin and selection marker of the disclosure may be detectable in modified T cells upon successful nucleofection of a transposon of the disclosure. Due to epi-chromosomal expression of the transposon, expression of a selection marker alone may not differentiate modified T cells (those cells in which the transposon has been successfully integrated) from unmodified T cells (those cells in which the transposon was not successfully integrated). When epi-chromosomal expression of the transposon obscures the detection of modified cells by the selection marker, the nucleofected cells (both modified and unmodified cells) may be rested for a period of time (e.g. 2-14 days) to allow the cells to cease expression or lose all epi-chromosomal transposon expression. Following this extended resting period, only modified T cells should remain positive for expression of selection marker. The length of this extended resting period may be optimized for each nucleofection reaction and selection process. When epi-chromosomal expression of the transposon obscures the detection of modified cells by the selection marker, selection may be performed without this extended resting period, however, an additional selection step may be included at a later time point (e.g. either during or after the expansion stage).

Selection of genetically modified cells of the disclosure may be performed by any means. In certain embodiments of the methods of the disclosure, selection of genetically modified cells of the disclosure may be performed by isolating cells expressing a specific selection marker. Selection markers of the disclosure may be encoded by one or more sequences in the transposon. Selection markers of the disclosure may be expressed by the modified cell as a result of successful transposition (i.e., not encoded by one or more sequences in the transposon). In certain embodiments, genetically modified cells of the disclosure contain a selection marker that confers resistance to a target compound of the post-nucleofection cell medium. The target compound may comprise, for example, an antibiotic or a drug that, absent the resistance conferred by the selection marker to the modified cells, would result in cell death. Exemplary selection markers include, but are not limited to, wild type (WT) or mutant forms of one or more of the following genes: neo, DHFR, TYMS, ALDH, MDR1, MGMT, FANCF, RAD51C, GCS, and NKX2.2. Exemplary selection markers include, but are not limited to, a surface-expressed selection marker or surface-expressed tag may be targeted by Ab-coated magnetic bead technology or column selection, respectively. A cleavable tag such as those used in protein purification may be added to a selection marker of the disclosure for efficient column selection, washing, and elution. In certain embodiments, selection markers of the disclosure are not expressed by the modified cells (including modified T cells) naturally and, therefore, may be useful in the physical isolation of modified cells (by, for example, cell sorting techniques). Exemplary selection markers of the disclosure are not expressed by the modified cells (including modified T cells) naturally include, but are not limited to, full-length, mutated, or truncated forms of CD271, CD19 CD52, CD34, RQR8, CD22, CD20, CD33 and any combination thereof.

Genetically modified cells of the disclosure may be selective expanded following a nucleofection reaction. In certain embodiments, modified T cells comprising a CAR/CAR-Tyrin may be selectively expanded by CAR/CARTyrin stimulation. Modified T cells comprising a CAR/CARTyrin may be stimulated by contact with a target-covered reagent (e.g. a tumor line or a normal cell line expressing a target or expander beads covered in a target). Alternatively, modified T cells comprising a CAR/CARTyrin may be stimulated by contact with an irradiated tumor cell, an irradiated allogeneic normal cell, an irradiated autologous PBMC. To minimize contamination of cell product compositions of the disclosure with a target-expressing cell used for stimulation, for example, when the cell product composition may be administered directly to a subject, the stimulation may be performed using expander beads coated with CAR/CARTyrin target protein. Selective expansion of modified T cells comprising a CAR/CARTyrin by CAR/CARTyrin stimulation may be optimized to avoid functionally-exhausting the modified T-cells.

Selected genetically-modified cells of the disclosure may be cryopreserved, rested for a defined period of time, or stimulated for expansion by the addition of a Cell Expander technology. Selected genetically-modified cells of the disclosure may be cryopreserved, rested for a defined period of time, or immediately stimulated for expansion by the addition of a Cell Expander technology. When the selected genetically-modified cells are T cells, the T cells may be stimulated for expansion by the addition of a T-Cell Expander technology. Selected genetically modified cells of the disclosure may be rested, for example, for 1, 2, 3, 4, 5, 6, 7, 8, 9, 10, 11, 12, 13, 14, 15, 16, 17, 18, 19, 20, 21, 22, 23, 24, or more hours. In certain embodiments, selected genetically modified cells of the disclosure may be rested, for example, for an overnight. In certain aspects, an overnight is about 12 hours. Selected genetically modified cells of the disclosure may be rested, for example, for 1, 2, 3, 4, 5, 6, 7, 8, 9, 10, 11, 12, 13, 14 or more days. Selected genetically modified cells of the disclosure may be rested for any period of time resulting in cells with enhanced viability, higher nucleofection efficiency, greater viability post-nucleofection, desirable cell phenotype, and/or greater/faster expansion upon addition of expansion technologies.

Selected genetically-modified cells (including selected genetically-modified T cells of the disclosure) may be cryopreserved using any standard cryopreservation method, which may be optimized for storing and/or recovering human cells with high recovery, viability, phenotype, and/or functional capacity. Cryopreservation methods of the disclosure may include commercially-available cryopreservation media and/or protocols.

A transposition efficiency of selected genetically-modified cells (including selected genetically-modified T cells of the disclosure) may be assessed by any means. For example, prior to the application of an expander technology, expression of the transposon by selected genetically-modified cells (including selected genetically-modified T cells of the disclosure) may be measured by fluorescence-activated cell sorting (FACS). Determination of a transposition efficiency of selected genetically-modified cells (including selected genetically-modified T cells of the disclosure) may include determining a percentage of selected cells expressing the transposon (e.g. a CAR). Alternatively, or in addition, a purity of T cells, a Mean Fluorescence Intensity (MFI) of the transposon expression (e.g. CAR expression), an ability of a CAR (delivered in the transposon) to mediate degranulation and/or killing of a target cell expressing the CAR ligand, and/or a phenotype of selected genetically-modified cells (including selected genetically-modified T cells of the disclosure) may be assessed by any means.

Cell product compositions of the disclosure may be released for administration to a subject upon meeting certain release criteria. Exemplary release criteria may include, but are not limited to, a particular percentage of modified, selected and/or expanded T cells expressing detectable levels of a CAR on the cell surface.

Production of CAR-Expressing T Cells

Genetically-modified cells (including genetically-modified T cells) of the disclosure may be expanded using an expander technology. Expander technologies of the disclosure may comprise a commercially-available expander technology. Exemplary expander technologies of the disclosure include stimulation a genetically-modified T cell of the disclosure via the TCR. While all means for stimulation of a genetically-modified T cell of the disclosure are contemplated, stimulation a genetically-modified T cell of the disclosure via the TCR is a preferred method, yielding a product with a superior level of killing capacity.

To stimulate a genetically-modified T cell of the disclosure via the TCR, Thermo Expander DynaBeads may be used at a 3:1 bead to T cell ratio. If the expander beads are not biodegradable, the beads may be removed from the expander composition. For example, the beads may be removed from the expander composition after about 5 days. To stimulate a genetically-modified T cell of the disclosure via the TCR, a Miltenyi T Cell Activation/Expansion Reagent may be used. To stimulate a genetically-modified T cell of the disclosure via the TCR, StemCell Technologies' ImmunoCult Human CD3/CD28 or CD3/CD28/CD2 T Cell Activator Reagent may be used. This technology may be preferred since the soluble tetrameric antibody complexes would degrade after a period and would not require removal from the process.

Artificial ligand presenting cells (APCs) may be engineered to co-express the target ligand and may be used to stimulate a cell or T-cell of the disclosure through a TCR and/or CAR of the disclosure. Artificial APCs may comprise or may be derived from a tumor cell line (including, for example, the immortalized myelogenous leukemia line K562) and may be engineered to co-express multiple costimulatory molecules or technologies (such as CD28, 4-1BBL, CD64, mbIL-21, mbIL-15, CAR target molecule, etc.). When artificial APCs of the disclosure are combined with costimulatory molecules, conditions may be optimized to prevent the development or emergence of an undesirable phenotype and functional capacity, namely terminally-differentiated effector T cells.

Irradiated PBMCs (auto or allo) may express some target ligands, such as CD19, and may be used to stimulate a cell or T-cell of the disclosure through a TCR and/or CAR of the disclosure. Alternatively, or in addition, irradiated tumor cells may express some target ligands and may be used to stimulate a cell or T-cell of the disclosure through a TCR and/or CAR of the disclosure.

Plate-bound and/or soluble anti-CD3, anti-CD2 and/or anti-CD28 stimulate may be used to stimulate a cell or T-cell of the disclosure through a TCR and/or CAR of the disclosure.

Ligand-coated beads may display target protein and may be used to stimulate a cell or T-cell of the disclosure through a TCR and/or CAR of the disclosure. Alternatively, or in addition, expander beads coated with a CAR/CARTyrin target protein may be used to stimulate a cell or T-cell of the disclosure through a TCR and/or CAR of the disclosure.

Expansion methods drawn to stimulation of a cell or T-cell of the disclosure through the TCR or CAR/CARTyrin and via surface-expressed CD2, CD3, CD28, 4-1BB, and/or other markers on genetically-modified T cells.

An expansion technology may be applied to a cell of the disclosure immediately post-nucleofection until approximately 24 hours post-nucleofection. While various cell media may be used during an expansion procedure, a desirable T Cell Expansion Media of the disclosure may yield cells with, for example, greater viability, cell phenotype, total expansion, or greater capacity for in vivo persistence, engraftment, and/or CAR-mediated killing. Cell media of the disclosure may be optimized to improve/enhance expansion, phenotype, and function of genetically-modified cells of the disclosure. A preferred phenotype of expanded T cells may include a mixture of T stem cell memory, T central, and T effector memory cells. Expander Dynabeads may yield mainly central memory T cells which may lead to superior performance in the clinic.

Exemplary T cell expansion media of the disclosure may include, in part or in total, PBS, HBSS, OptiMEM, DMEM, RPMI 1640, AIM-V, X—VIVO 15, CellGro DC Medium, CTS OpTimizer T Cell Expansion SFM, TexMACS™ Medium, PRIME-XV T Cell Expansion Medium, ImmunoCult-XF T Cell Expansion Medium, or any combination thereof. T cell expansion media of the disclosure may further include one or more supplemental factors. Supplemental factors that may be included in a T cell expansion media of the disclosure enhance viability, cell phenotype, total expansion, or increase capacity for in vivo persistence, engraftment, and/or CAR-mediated killing. Supplemental factors that may be included in a T cell expansion media of the disclosure include, but are not limited to, recombinant human cytokines, chemokines, and/or interleukins such as IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L, or any combination thereof. Supplemental factors that may be included in a T cell expansion media of the disclosure include, but are not limited to, salts, minerals, and/or metabolites such as HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, anti-biotics, pH adjusters, Earle's Salts, 2-Mercaptoethanol, Human transferrin, Recombinant human insulin, Human serum albumin, Nucleofector PLUS Supplement, KCL, MgCl2, Na2HPO4, NAH2PO4, Sodium lactobionate, Manitol, Sodium succinate, Sodium Chloride, *ClNa*, Glucose, Ca(N03)2, Tris/HCl, K2HPO4, KH2PO4, Polyethylenimine, Poly-ethylene-glycol, Poloxamer 188, Poloxamer 181, Poloxamer 407, Polyvinylpyrrolidone, Pop313, Crown-5 or any combination thereof. Supplemental factors that may be included in a T cell expansion media of the disclosure include, but are not limited to, inhibitors of cellular DNA sensing, metabolism, differentiation, signal transduction, and/or the apoptotic pathway such as inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspasel, Pro-IL1B, PI3K, Akt, Wnt3A, inhibitors of glycogen synthase kinase-3β (GSK-3 β) (e.g. TWS119), Bafilomycin, Chloroquine, Quinacrine, AC-YVAD-CMK, Z-VAD-FMK, Z-IETD-FMK, or any combination thereof.

Supplemental factors that may be included in a T cell expansion media of the disclosure include, but are not limited to, reagents that modify or stabilize nucleic acids in a way to enhance cellular delivery, enhance nuclear delivery or transport, enhance the facilitated transport of nucleic acid into the nucleus, enhance degradation of epi-chromosomal nucleic acid, and/or decrease DNA-mediated toxicity, such as pH modifiers, DNA-binding proteins, lipids, phospholipids, CaPO4, net neutral charge DNA binding peptides with or without NLS sequences, TREX1 enzyme, or any combination thereof.

Genetically-modified cells of the disclosure may be selected during the expansion process by the use of selectable drugs or compounds. For example, in certain embodiments, when a transposon of the disclosure may encode a selection marker that confers to genetically-modified cells resistance to a drug added to the culture medium, selection may occur during the expansion process and may require approximately 1-14 days of culture for selection to occur. Examples of drug resistance genes that may be used as selection markers encoded by a transposon of the disclosure, include, but are not limited to, wild type (WT) or mutant forms of the genes neo, DHFR, TYMS, ALDH, MDR1, MGMT, FANCF, RAD51C, GCS, NKX2.2, or any combination thereof. Examples of corresponding drugs or compounds that may be added to the culture medium to which a selection marker may confer resistance include, but are not limited to, G418, Puromycin, Ampicillin, Kanamycin, Methotrexate, Mephalan, Temozolomide, Vincristine, Etoposide, Doxorubicin, Bendamustine, Fludarabine, Aredia (Pamidronate Disodium), Becenum (Carmustine), BiCNU (Carmustine), Bortezomib, Carfilzomib, Carmubris (Carmustine), Carmustine, Clafen (Cyclophosphamide), Cyclophosphamide, Cytoxan (Cyclophosphamide), Daratumumab, Darzalex (Daratumumab), Doxil (Doxorubicin Hydrochloride Liposome), Doxorubicin Hydrochloride Liposome, Dox-SL (Doxorubicin Hydrochloride Liposome), Elotuzumab, Empliciti (Elotuzumab), Evacet (Doxorubicin Hydrochloride Liposome), Farydak (Panobinostat), Ixazomib Citrate, Kyprolis (Carfilzomib), Lenalidomide, LipoDox (Doxorubicin Hydrochloride Liposome), Mozobil (Plerixafor), Neosar (Cyclophosphamide), Ninlaro (Ixazomib Citrate), Pamidronate Disodium, Panobinostat, Plerixafor, Pomalidomide, Pomalyst (Pomalidomide), Revlimid (Lenalidomide), Synovir (Thalidomide), Thalidomide, Thalomid (Thalidomide), Velcade (Bortezomib), Zoledronic Acid, Zometa (Zoledronic Acid), or any combination thereof.

A T-Cell Expansion process of the disclosure may occur in a cell culture bag in a WAVE Bioreactor, a G-Rex flask, or in any other suitable container and/or reactor.

A cell or T-cell culture of the disclosure may be kept steady, rocked, swirled, or shaken.

A cell or T-cell expansion process of the disclosure may optimize certain conditions, including, but not limited to culture duration, cell concentration, schedule for T cell medium addition/removal, cell size, total cell number, cell phenotype, purity of cell population, percentage of genetically-modified cells in growing cell population, use and composition of supplements, the addition/removal of expander technologies, or any combination thereof.

A cell or T-cell expansion process of the disclosure may continue until a predefined endpoint prior to formulation of the resultant expanded cell population. For example, a cell or T-cell expansion process of the disclosure may continue for a predetermined amount of time: at least, 2, 4, 6, 8, 10, 12, 14, 16, 18, 20, 22, 24 hours; at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days; at least 1, 2, 3, 4, 5, 6, 7, 8, 9, 10, 11, 12 weeks; at least 1, 2, 3, 4, 5, 6, months, or at least 1 year. A cell or T-cell expansion process of the disclosure may continue until the resultant culture reaches a predetermined overall cell density: 1, 10, 100, 1000, 104, 105, 106, 107, 108, 109, 1010 cells per volume (µl, ml, L) or any density in between. A cell or T-cell expansion process of the disclosure may continue until the genetically-modified cells of a resultant culture demonstrate a predetermined level of expression of a transposon of the disclosure: 1%, 10%, 20%, 30%, 40%, 50%, 60%, 70%, 80%, 90%, or 100% or any percentage in between of a threshold level of expression (a minimum, maximum or mean level of expression indicating the resultant genetically-modified cells are clinically-efficacious). A cell or T-cell expansion process of the disclosure may continue until the proportion of genetically-modified cells of a resultant culture to the proportion of unmodified cells reaches a predetermined threshold: at least 1:10, 1:9, 1:8, 1:7, 1:6, 1:5, 1:4, 1:3, 1:2, 1:1, 2:1, 2:1, 4:1, 5:1, 6:1,7:1, 8:1, 9:1 10:1 or any ratio in between.

Quality Control Analysis of CAR-Expressing T Cells Prior to Administration

A percentage of genetically-modified cells may be assessed during or after an expansion process of the disclosure. Cellular expression of a transposon by a genetically-modified cell of the disclosure may be measured by fluorescence-activated cell sorting (FACS). For example, FACS may be used to determine a percentage of cells or T cells expressing a CAR of the disclosure. Alternatively, or in addition, a purity of genetically-modified cells or T cells, the Mean Fluorescence Intensity (MFI) of a CAR expressed by a genetically-modified cell or T cell of the disclosure, an ability of the CAR to mediate degranulation and/or killing of a target cell expressing the CAR ligand, and/or a phenotype of CAR+ T cells may be assessed.

Compositions of the disclosure intended for administration to a subject may be required to meet one or more "release criteria" that indicate that the composition is safe and efficacious for formulation as a pharmaceutical product and/or administration to a subject. Release criteria may include a requirement that a composition of the disclosure (e.g. a T-cell product of the disclosure) comprises a particular percentage of T cells expressing detectable levels of a CAR of the disclosure on their cell surface.

The expansion process should be continued until a specific criterion has been met (e.g. achieving a certain total number of cells, achieving a particular population of memory cells, achieving a population of a specific size).

Certain criterion signal a point at which the expansion process should end. For example, cells should be formulated, reactivated, or cryopreserved once they reach a cell size of 300fL (otherwise, cells reaching a size above this threshold may start to die). Cryopreservation immediately once a population of cells reaches an average cell size of less than 300 fL may yield better cell recovery upon thawing and culture because the cells haven't yet reached a fully quiescent state prior to cryopreservation (a fully quiescent size is approximately 180 fL). Prior to expansion, T cells of the disclosure may have a cell size of about 180 fL, but may more than quadruple their cell size to approximately 900 fL at 3 days post-expansion. Over the next 6-12 days, the population of T-cells will slowly decrease cell size to full quiescence at 180 fL.

A process for preparing a cell population for formulation may include, but is not limited to the steps of, concentrating the cells of the cell population, washing the cells, and/or further selection of the cells via drug resistance or magnetic bead sorting against a particular surface-expressed marker. A process for preparing a cell population for formulation may further include sorting step to ensure the safety and purity of the final product. For example, if a tumor cell from a patient has been used to stimulate a genetically-modified T-cell of the disclosure or that have been genetically-modified in order to stimulate a genetically-modified T-cell of the disclosure that is being prepared for formulation, it is critical that no tumor cells from the patient are included in the final product.

Administration and Preservation of CAR-Expressing Cells

A pharmaceutical formulation of the disclosure may be distributed into bags for infusion, cryopreservation, and/or storage.

A pharmaceutical formulation of the disclosure may be cryopreserved using a standard protocol and, optionally, an infusible cryopreservation medium. For example, a DMSO free cryopreservant (e.g. CryoSOfree™ DMSO-free Cryopreservation Medium) may be used to reduce freezing-related toxicity. A cryopreserved pharmaceutical formulation of the disclosure may be stored for infusion to a patient at a later date. An effective treatment may require multiple administrations of a pharmaceutical formulation of the disclosure and, therefore, pharmaceutical formulations may be packaged in pre-aliquoted "doses" that may be stored frozen but separated for thawing of individual doses.

A pharmaceutical formulation of the disclosure may be stored at room temperature. An effective treatment may require multiple administrations of a pharmaceutical formulation of the disclosure and, therefore, pharmaceutical formulations may be packaged in pre-aliquoted "doses" that may be stored together but separated for administration of individual doses.

A pharmaceutical formulation of the disclosure may be archived for subsequent re-expansion and/or selection for generation of additional doses to the same patient in the case of an allogenic therapy who may need an administration at a future date following, for example, a remission and relapse of a condition.

Infusion of Modified Cells as Adoptive Cell Therapy

The disclosure provides modified immune cells and HSCs for administration to a subject in need thereof. Modified cells of the disclosure may be formulated for storage at any temperature including room temperature and body temperature. Modified cells of the disclosure may be formulated for cryopreservation and subsequent thawing. Modified cells of the disclosure may be formulated in a pharmaceutically acceptable carrier for direct administration to a subject from sterile packaging. Modified cells of the disclosure may be formulated in a pharmaceutically acceptable carrier with an indicator of cell viability and/or CAR/CARTyrin expression level to ensure a minimal level of cell function and CAR/CARTyrin expression. Modified cells of the disclosure may be formulated in a pharmaceutically acceptable carrier at a prescribed density with one or more reagents to inhibit further expansion and/or prevent cell death.

EXAMPLES

Example 1: Expression and Function of PiggyBac Integrated iC9 Safety Switch into Human Pan T-Cells Human pan T-cells were nucleofected using an Amaxa 4D nucleofector with one of four piggyBac transposons. Modified T cells receiving the "mock" condition were nucleofected with an empty piggyBac transposon. Modified T cells received either a piggyBac transposase containing a therapeutic agent alone (a sequence encoding a CARTyrin) or a piggyBac transposase containing an integrated iC9 sequence and a therapeutic agent (a sequence encoding a CARTyrin).

FIG. 1 provides a schematic diagram of the iC9 safety switch, which contains a ligand binding region, a linker, and a truncated caspase 9 polypeptide. Specifically, the iC9 polypeptide contains a ligand binding region comprising a FK506 binding protein 12 (FKBP12) polypeptide including a substitution of valine (V) for phenylalanine (F) at position 36 (F36V). The FKBP12 polypeptide of the iC9 polypeptide is encoded by an amino acid sequence comprising GVQVETISPGDGRTFPKRGQTCVVHYTGMLEDGK-KVDSSRDRNKPFKFMLGKQEVI RGWEEGVAQMSVGQRAKLTISPDYAYGATGHPGIIP-PHATLVFDVELLKLE (SEQ ID NO: 45). The FKBP12 polypeptide of the iC9 polypeptide is encoded by a nucleic acid sequence comprising GGGGTCCAGGTCGAGACT-ATTTCACCAGGGGATGGGCGAACATTTC-CAAAAAGG GGCCAGACTTGCGTCGTGATTA-CACCGGGATGCTGGAGGACGGGAAGAAAGTG GACAGCTCCAGGGATCGCAACAAGCCCTT-CAAGTTCATGCTGGGAAAGCAGGAA GTGATCCGAGGATGGGAGGAAGGCGTGGCACA-GATGTCAGTCGGCCAGCGGGCC AAACTGACCATT-AGCCCTGACTACGCTTATGGAGCAACAGGC-CACCCAGGGATC ATTCCCCCTCATGCCACCCTGGTCTTCGAT GTG-GAACTGCTGAAGCTGGAG (SEQ ID NO: 46). The linker region of the iC9 polypeptide is encoded by an amino acid comprising GGGGS (SEQ ID NO: 47) and a nucleic acid sequence comprising GGAGGAGGAGGATCC (SEQ ID NO: 48). The nucleic acid sequence encoding the linker region of the iC9 polypeptide is encoded by an amino acid comprising GFGDVGALESLRGNADLAYIS-LMEPCGHCLIINNVNFCRESGLRTRTGSNIDCEKLRR RFSSLHFMVEVKGDLTAKKMVLALLE-LAQQDHGALDCCVVVILSHGCQASHLQFPG AVYGTDGCPVS-VEKIVNIFNGTSCPSLGGKPKLFFIQACGGEQKD-HGFEVASTSPEDE SPGSNPEPDATPFQEGLRTFDQL-DAISSLPTPSDIFVSYSTFPGFVSWRDPKSGSWYVE TLDDIFEQWAHSEDLQSLLLRVA-NAVSVKGIYKQMPGCNFLRKKLFFKTS (SEQ ID NO: 49). The nucleic acid sequence encoding the linker region of the iC9 polypeptide is encoded by a nucleic acid sequence comprising TTTGGGGACGTGGGGGCCCTG-GAGTCTCTGCGAGGAAATGCCGATCTGGCTTACA TCCTGAGCATGGAACCCTGCGGCCACTGTCTGAT-CATTAACAATGTGAACTTCTG CAGAGAAAGCGGACTGCGAACACGGACTGGCTC-CAATATTGACTGTGAGAAGCT GCG-GAGAAGGTTCTCTAGTCTGCACTT-TATGGTCGAAGTGAAAGGGGATCTGACC GCCAAGAAAATGGTGCTGGCCCTGCTG-GAGCTGGCTCAGCAGGACCATGGAGCT CTGGAT-TGCTGCGTGGTCGTGATCCTGTCC-CACGGGTGCCAGGCTTCTCATCTGC AGTTCCCCGGAGCAGTGTACGGAACA-GACGGCTGTCCTGTCAGCGTGGAGAAGA TCGT-CAACATCTT-CAACGGCACTTCTTGCCCTAGTCTGGGGGGAAAGC-CAAAACT GTTCTTTATCCAGGCCTGTGGCGGGGAACAGAAA-GATCACGGCTTCGAGGTGGC CAGCACCAGCCCT-GAGGACGAATCACCAGGGAGCAACCCTGAACCA-GATGCAAC TCCATTCCAGGAGGGACT-GAGGACCTTTGACCAGCTGGATGCTATCT-CAAGCCTG CCCACTCCTAGTGACATTTTCGTGTCT-TACAGTACCTTCCCAGGCTTTGTCTCATG GCGCGATCCCAAGTCAGGGAGCTGGTACGTGGA-GACACTGGACGACATCTTTGA ACAGTGGGCC-CATTCAGAGGACCTGCAGAGCC-TGCTGCTGCGAGTGGCAAACGC TGTCTCTGT-GAAGGGCATCTACAAACAGATGCCCGGGTGCTT-CAATTTTCTGAGA AAGAAACTGTTCTTTAA-GACTTCC (SEQ ID NO: 50).

To test the iC9 safety switch, each of the four modified T cells were incubated for 24 hours with 0, 0.1 nM, 1 nM, 10 nM, 100 nM or 1000 nM AP1903 (an induction agent for AP1903). Viability was assessed by flow cytometry using 7-aminoactinomycin D (7-AAD), a fluorescent intercalator, as a marker for cells undergoing apoptosis.

Figures 2A, 2B:
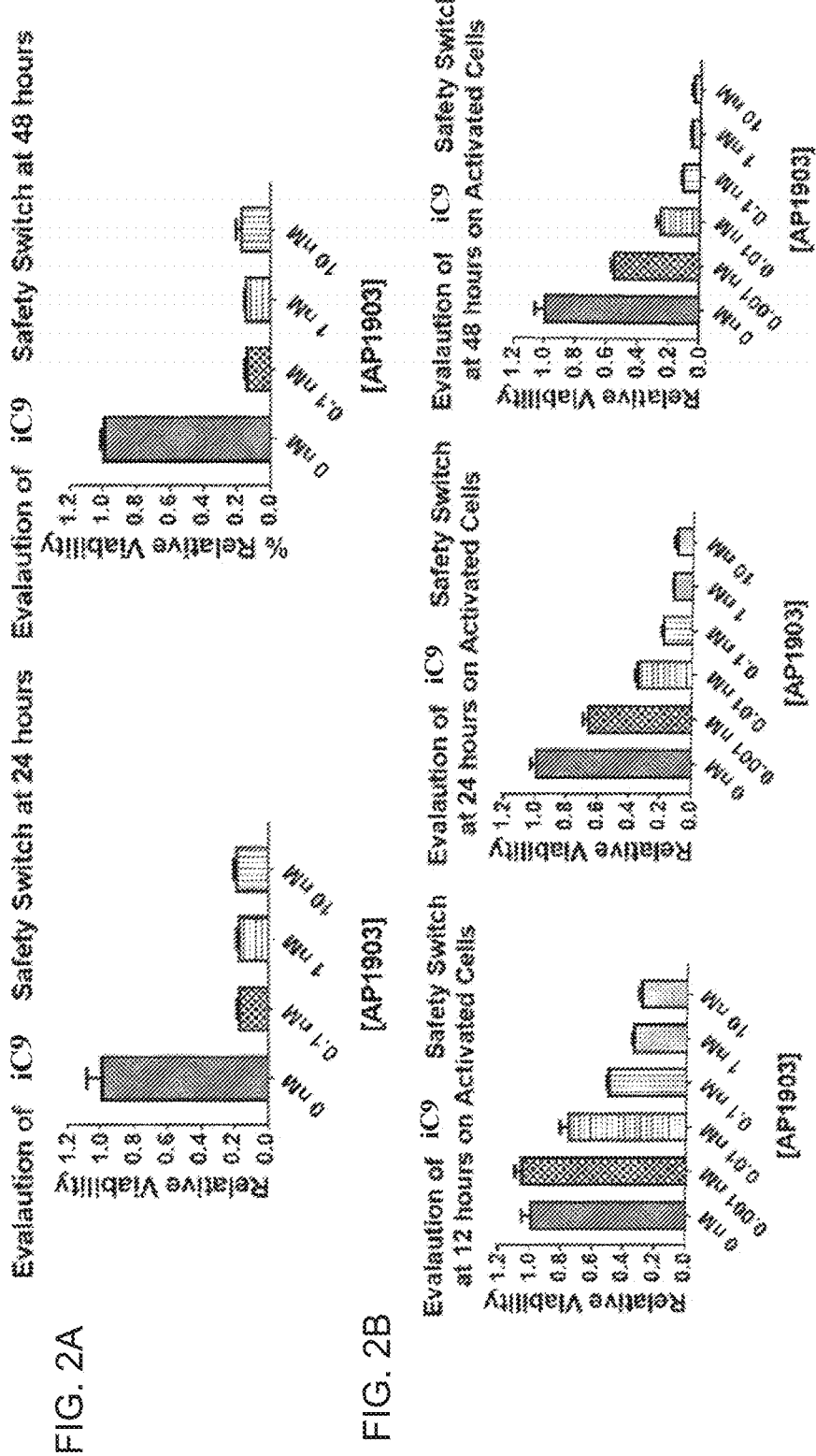
FIGS. 2A-2B is a series of graphs depicting results of evaluating the in vitro efficacy of an inducible proapoptotic polypeptide (iC9 safety switch) of the disclosure using the exemplary induction agent AP1903. Cells expressing a CARTyrin of the disclosure were A) thawed and rested overnight or B) activated using ImmunoCult™ Human CD3/CD28/CD2 T cell Activator reagent for 5 days were treated with AP1903 for the indicated length of time and concentrations. All data points were collected in triplicate and relative viability determined by dividing the number of live cells in the treatment group by the average number of live cells in the no treatment group per 1,500 bead events collected. Greater than 80% of the non-activated CARTyrin-expressing cells were eliminated from the culture at 24 hours across all dose levels tested (FIG. 1). There was no observable difference between the 24 hour and 48 hour time point in the non-activated cells. In the activated CARTyrin-expressing cells however, both a dose response as well as temporal response were observed. At 12 hours post AP1903 administration, >65% of the cells were killed by concentrations as low as 1 nM. The data demonstrate that the iC9 safety switch was both functionally expressed and effective in the CARTyrin-expressing cells. The AP1903/iC9 system was more effective when used against activated cells when compared to the non-activated cells. Expression of the CARTyrin is be increased upon activation of the cells, and provided the vector design; the expression of iC9 could also increase. Therefore, an activated cell may express higher levels of iC9 making it more sensitive to AP1903. In many embodiments, the activated cells will be the target if and when employing the safety switch. These data confirm that the activated cells are indeed more sensitive to AP1903 with >95% of the cells killed at 48 hours.

Cell viability was assessed at day 12 (see FIG. 2). The data demonstrate a shift of cell populations from the lower right to the upper left quadrants with increasing concentration of the induction agent in cells containing the iC9 construct; however, this effect is not observed in cells lacking the iC9 construct (those receiving only the CAR-Tyrin), in which cells are evenly distributed among these two areas regardless of the concentration of the induction agent. Moreover, cell viability was assessed at day 19 (see FIG. 3). The data reveal the same trend as shown in FIG. 2 (day 12 post-nucleofection); however, the population shift to the upper left quadrant is more pronounced at this later time point (day 19 post-nucleofection).

Figure 3:
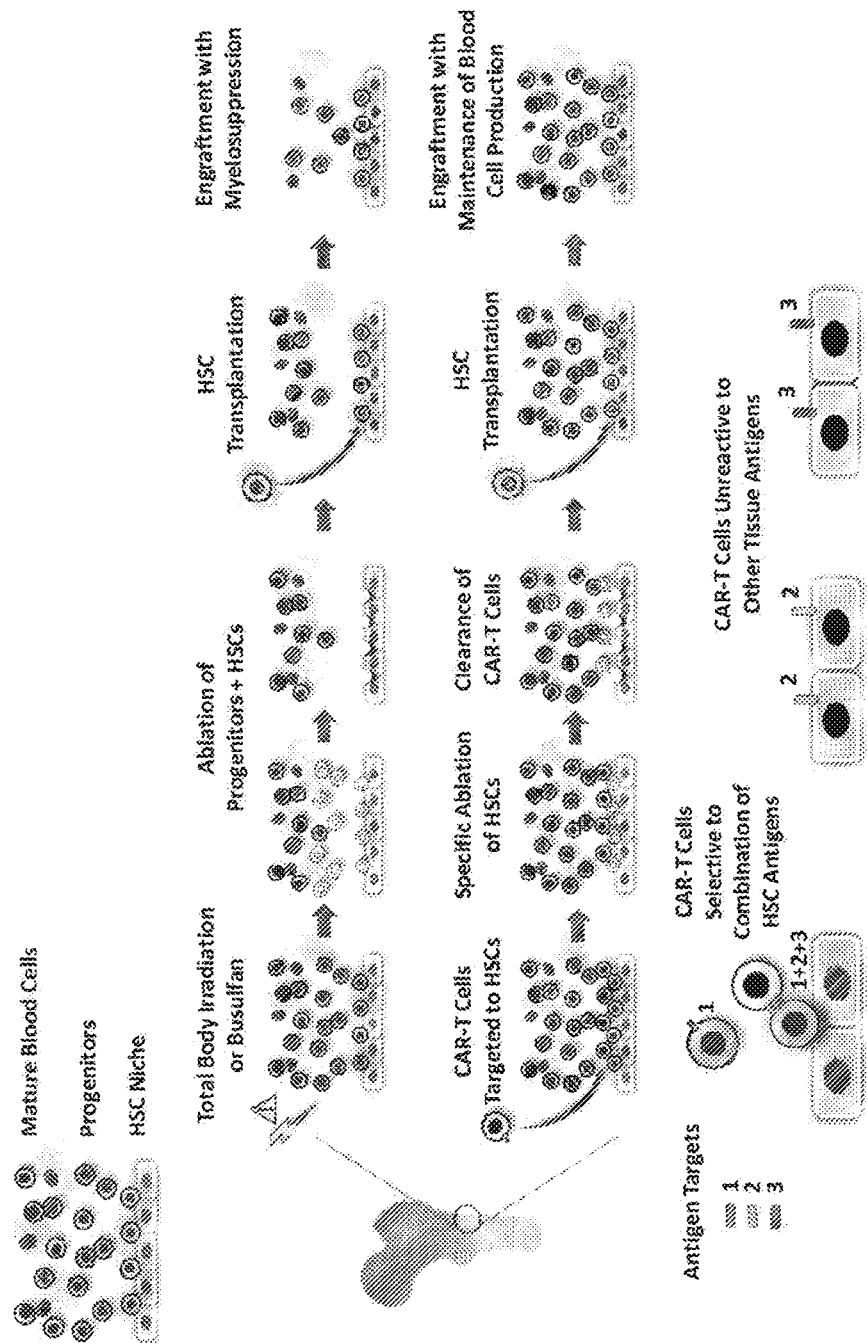
FIG. 3 is a schematic diagram contrasting the traditional method of ablation of HSCs prior to transplant using genotoxic agents such as whole body irradiation or busulfan (top sequence) with the methods of the disclosure (bottom sequence). As shown in this figure, the compositions and methods of the disclosure produce a non-genotoxic method of achieving superior engraftment of HSCs upon transplantation that are functional and maintain healthy levels of blood cell production.
Figure 4:
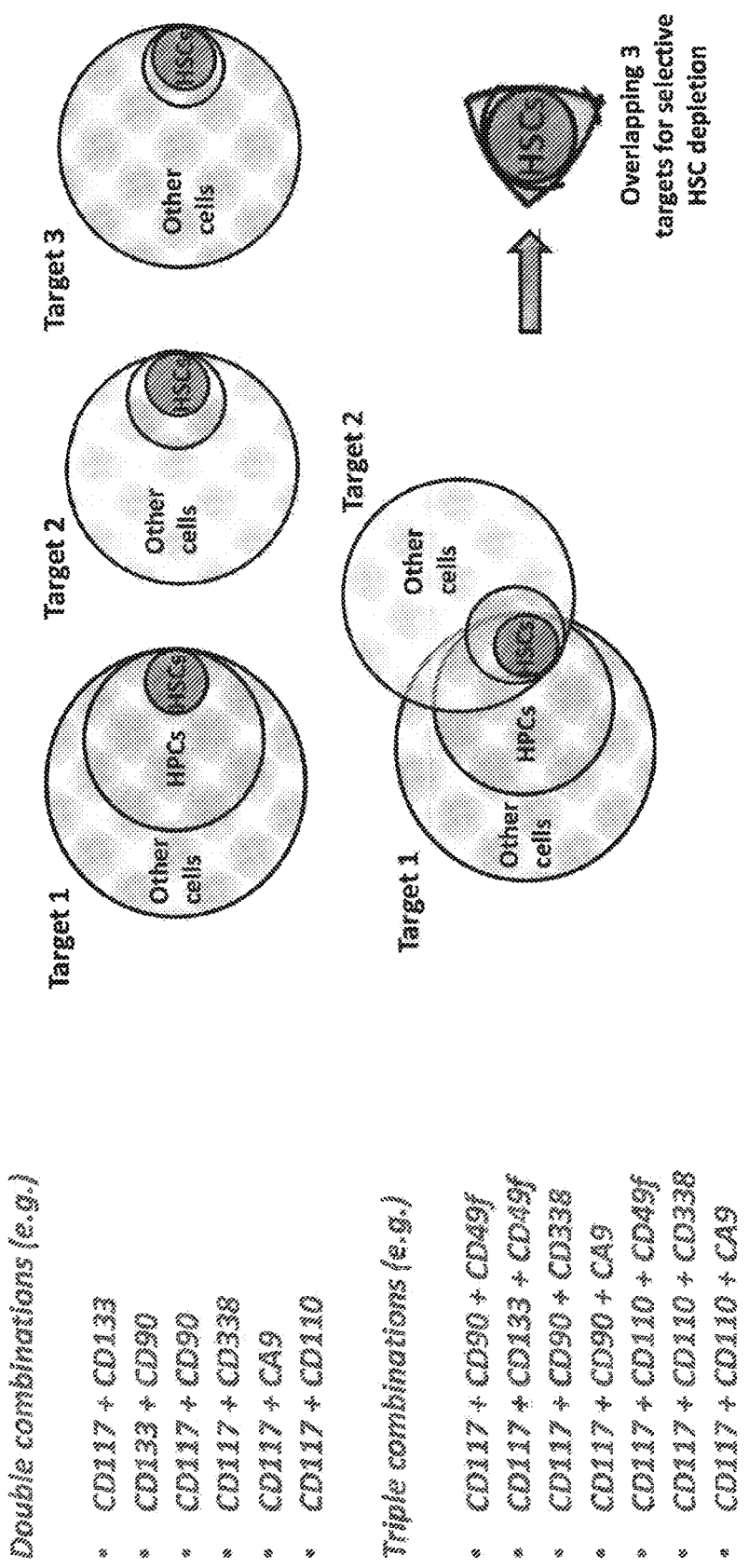
FIG. 4 is a schematic diagram depicting possible surface HSC marker combinations for autologous or allogeneic CAR tandem targeting to minimize depletion of non-HSCs including hematopoietic progenitor cells (HPCs).

A quantification of the aggregated results was performed and is provided in FIG. 4, showing the significant impact of the iC9 safety switch on the percent cell viability as a function of the concentration of the induction agent (AP1903) of the iC9 switch for each modified cell type at either day 12 (FIG. 2 and left graph) or day 19 (FIG. 3 and right graph). The presence of the iC9 safety switch induces apoptosis in a significant majority of cells by day 12 and the effect is even more dramatic by day 19.

The results of this study show that the iC9 safety switch is extremely effective at eliminating active cells upon contact with an induction agent (e.g. AP1903) because AP1903 induces apoptosis at even the lowest concentrations of the study (0.1 nM). Furthermore, the iC9 safety switch may be functionally expressed as part of a tricistronic vector.

Example 2: Depletion of Hematopoietic Cells by CAR-T Cells Targeting c-Kit (CD117) and Prominin-1 (CD133)

Figure 5A:
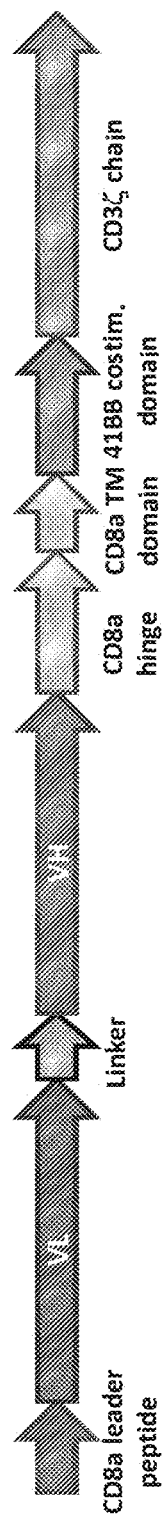
FIG. 5A is a schematic diagram depicting CAR constructs having ScFv sequences directed against c-kit or CD133 expressing cells. The CAR constructs depict an exemplary CAR sequence coupled to exemplary signaling domains as encoded by the mRNA used to produce CAR-T cells.

An experimental study was performed to demonstrate the ability of human CAR-T cells to be specifically activated and deplete hematopoietic cells bearing human c-kit (CD117) or prominin-1 (CD133), markers known to be antigenically expressed on the surface of HSCs. To select lead candidates from a panel of CAR constructs, CD3/CD28-stimulated pan T cells isolated from human peripheral blood were first electroporated with mRNA encoding each of the CAR candidates directed against either c-kit or CD133 (FIG. 5). The level of CAR surface expression was determined in transfected T cells by flow cytometry (FIG. 6A). In vitro functional assays were then performed by co-culturing mRNA-transfected CAR-T cells with mouse or human cell lines (EML-C1 and TF-1), expressing either c-kit or CD133, as well as human primary BM cells. Lead anti-c-kit and anti-CD133 CAR candidates were identified from their level of expression at the surface as well as specific activation of the CAR-T cells through degranulation according to CD107a expression (FIGS. 6B and C). Further, co-culture of the CAR-T cells with human bone marrow over 2 days to assess CAR-T killing capacity was followed by flow cytometric analysis of CD34, CD117 and CD133 cell surface antigens and plating the cells in methylcellulose cultures supplemented with human growth factors (Metho- Cult™, H4434) for the generation of hematopoietic colonies (CFUs) over 12 days. A reduction in the proportion of CD34+/CD117+ cells were seen following culture with 3 of 6 anti-c-kit CAR-T cell candidates while a decrease CD34+/CD133+ cells was observed for 3 of 7 anti-CD133 CAR-T candidates (FIG. 6D). The CFU functional assay showed effective depletion of the hematopoietic progenitors in the bone marrow by 7 of the 8 anti-c-kit CAR-T cell candidates (FIG. 6E). These data therefore support our novel approach towards minimally-toxic transplant regimens for depletion of endogenous HSCs in the BM and to allow for their replacement with engrafted allogeneic or gene-corrected stem cells.

Figure 7:
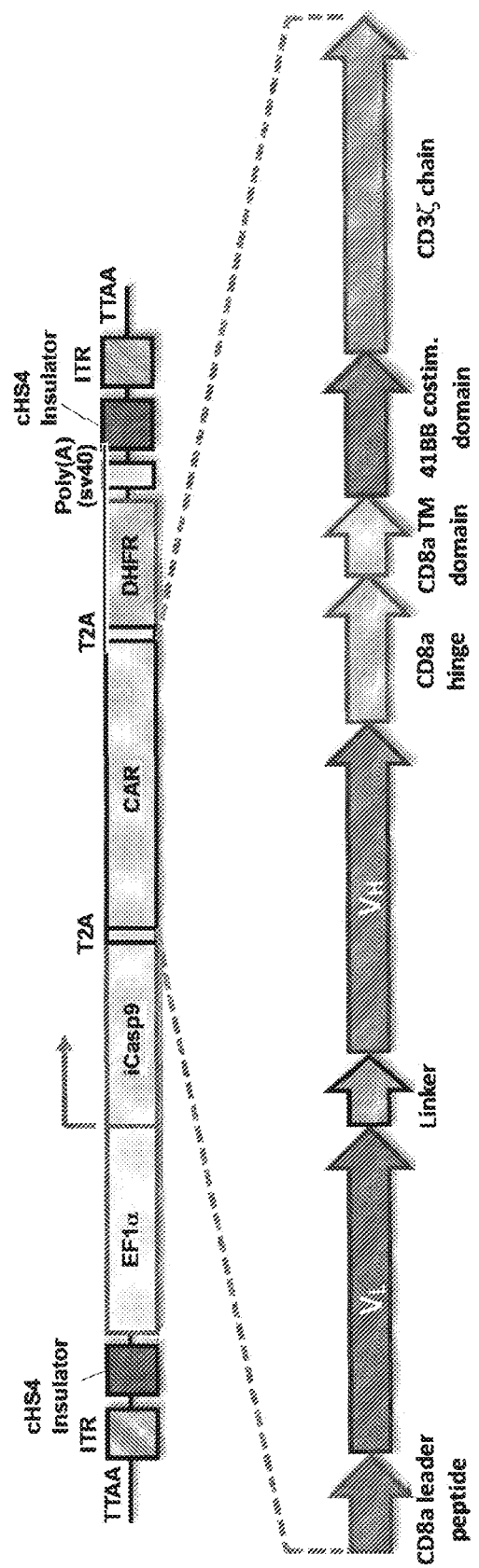
FIG. 7 is a schematic diagram depicting the piggyBac (PB) transposon vector for targeting HSCs. The elongation factor-1 alpha (EF1u) is used as a constitutive promoter to drive the tris-cistronic cassette consisting of the inducible truncated caspase 9 (iCasp9), the chimeric antigen receptor (CAR) and the dihydrofolate reductase resistance (DHFR) genes. The CAR region comprises of variable regions (VL and VH ScFv sequences) from anti-human c-kit and CD133 IgG coupled to the signaling domains consisting of the CD8a leader peptide, CD8a hinge, CD8a transmembrane (TM) domain, 41BB costimulatory domain and the CD3 zeta chain. The SV40 polyA signal and the 250 bp cHS4 chromatin insulator are indicated. During transposition, the co-delivered PB transposase recognizes the transposon-specific inverted terminal repeat sequence (ITR) located on both ends of the transposon vector and efficiently moves the contents from the original sites in the delivered DNA plasmid and efficiently integrates them into TTAA chromosomal sites.
Figure 8A:
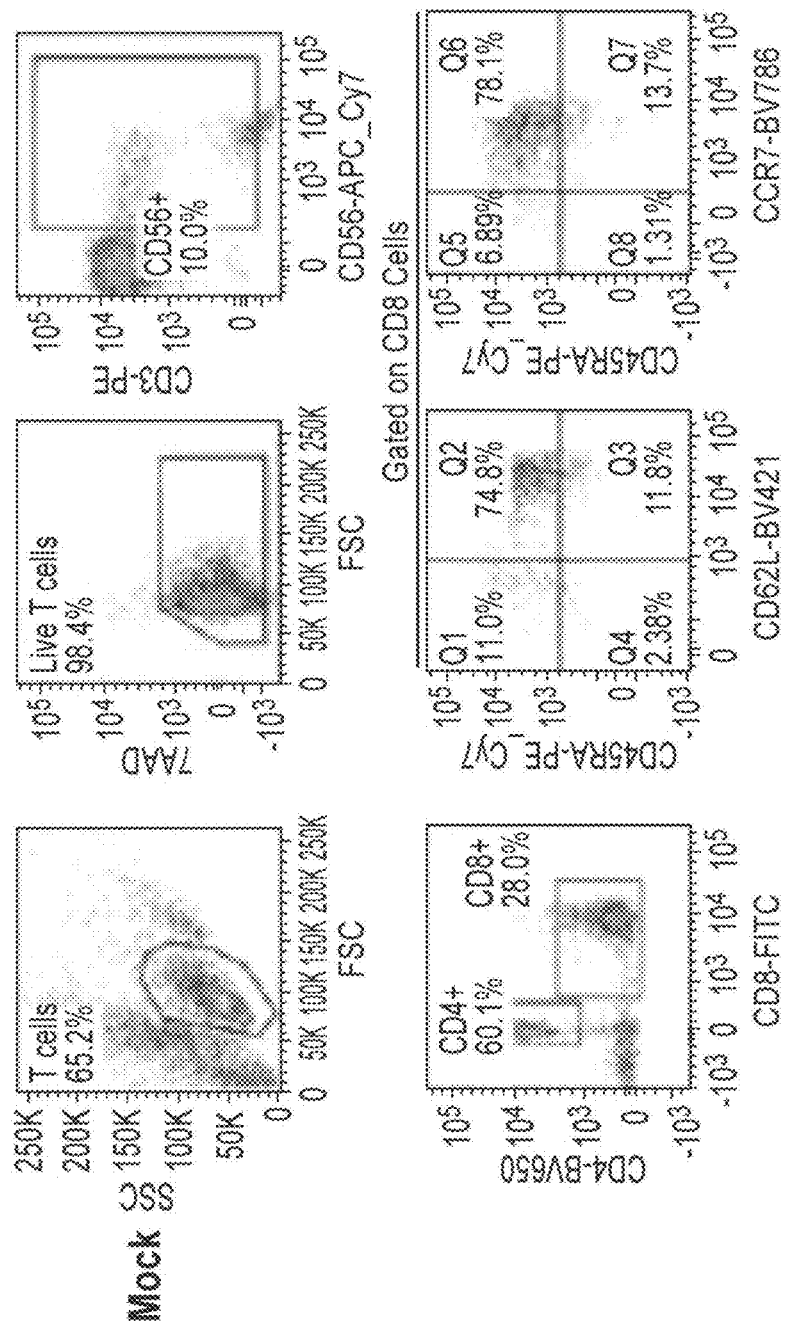
FIG. 8A is a series of plots depicting a flow cytometric analysis ofpiggyBac (PB) transposed anti-CD117 or anti-CD133 CAR-T cells. Human peripheral blood T-cells were previously electroporated with PB transposon pDNA (FIG. 7) together with mRNA encoding the super piggyBac (SPB) transposase. Phenotypic analysis was performed using antibodies directed against CD3, CD4, CD8, CD56, CD45RA, CD62L, CCR7, CD45RO, PD1, Tim3, Lag3, CD184/CXCR4, CD25, CD127 and CD28.
Figure 8A:
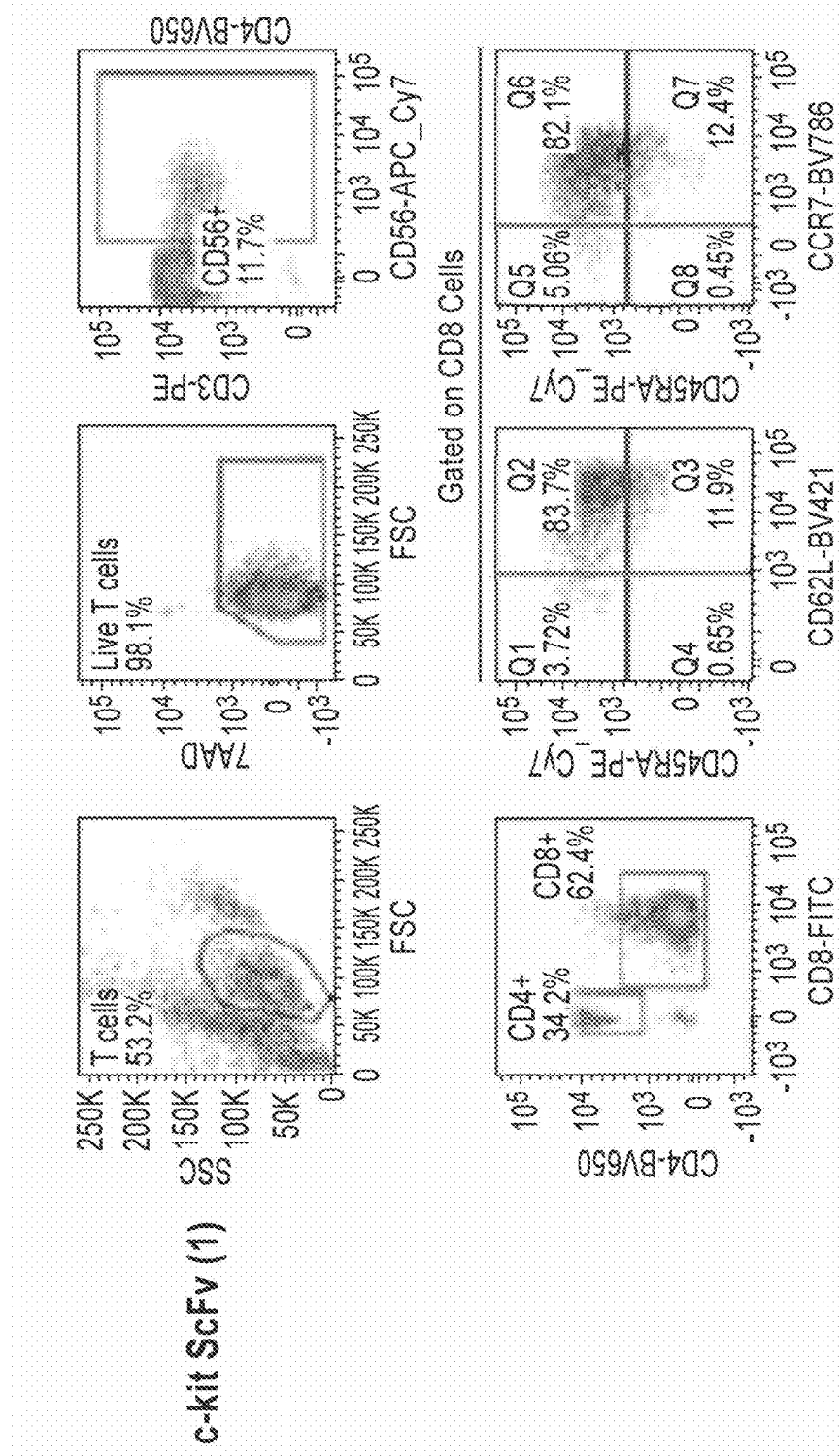
Figure 8A:
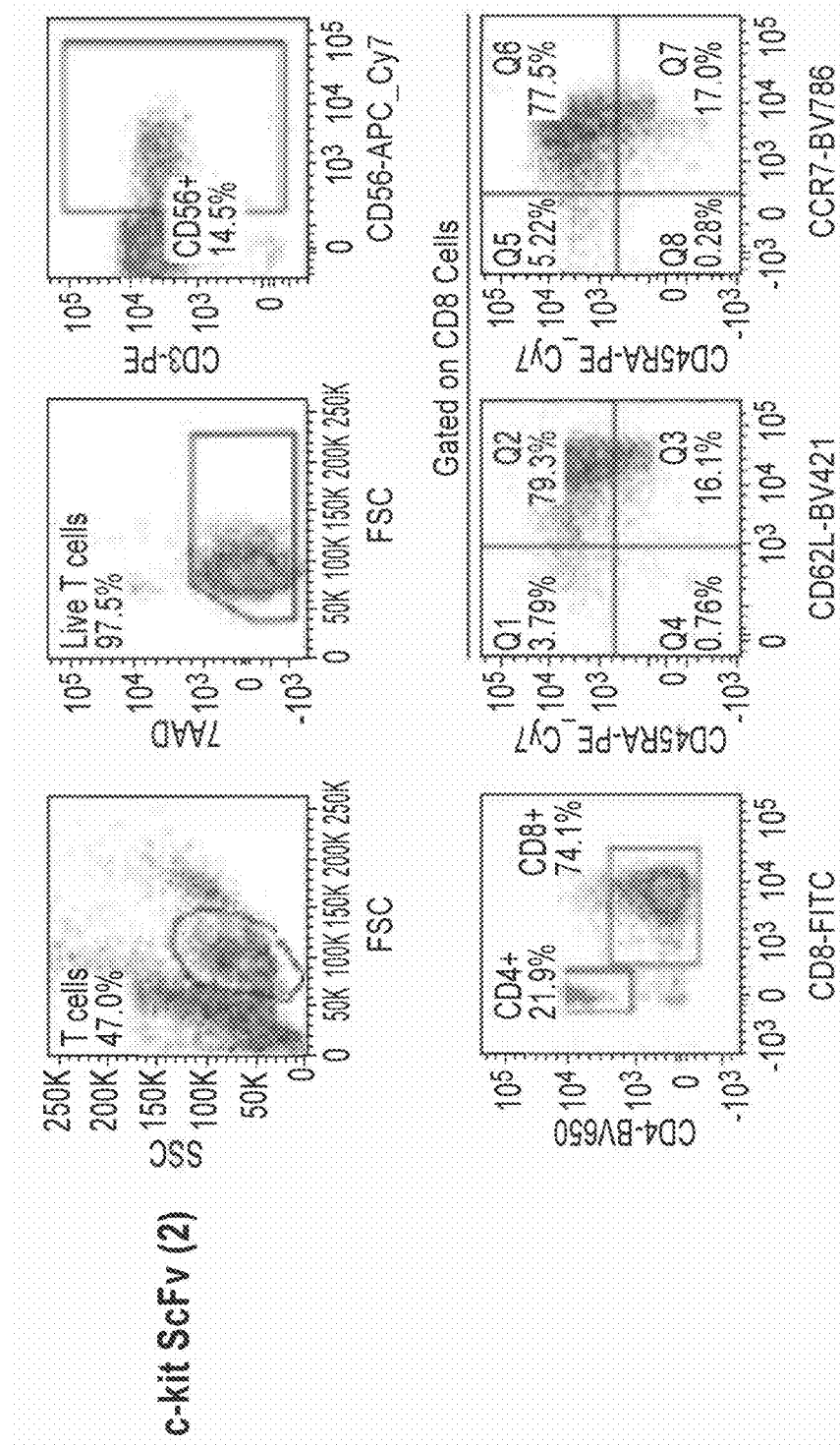
Figure 8A:
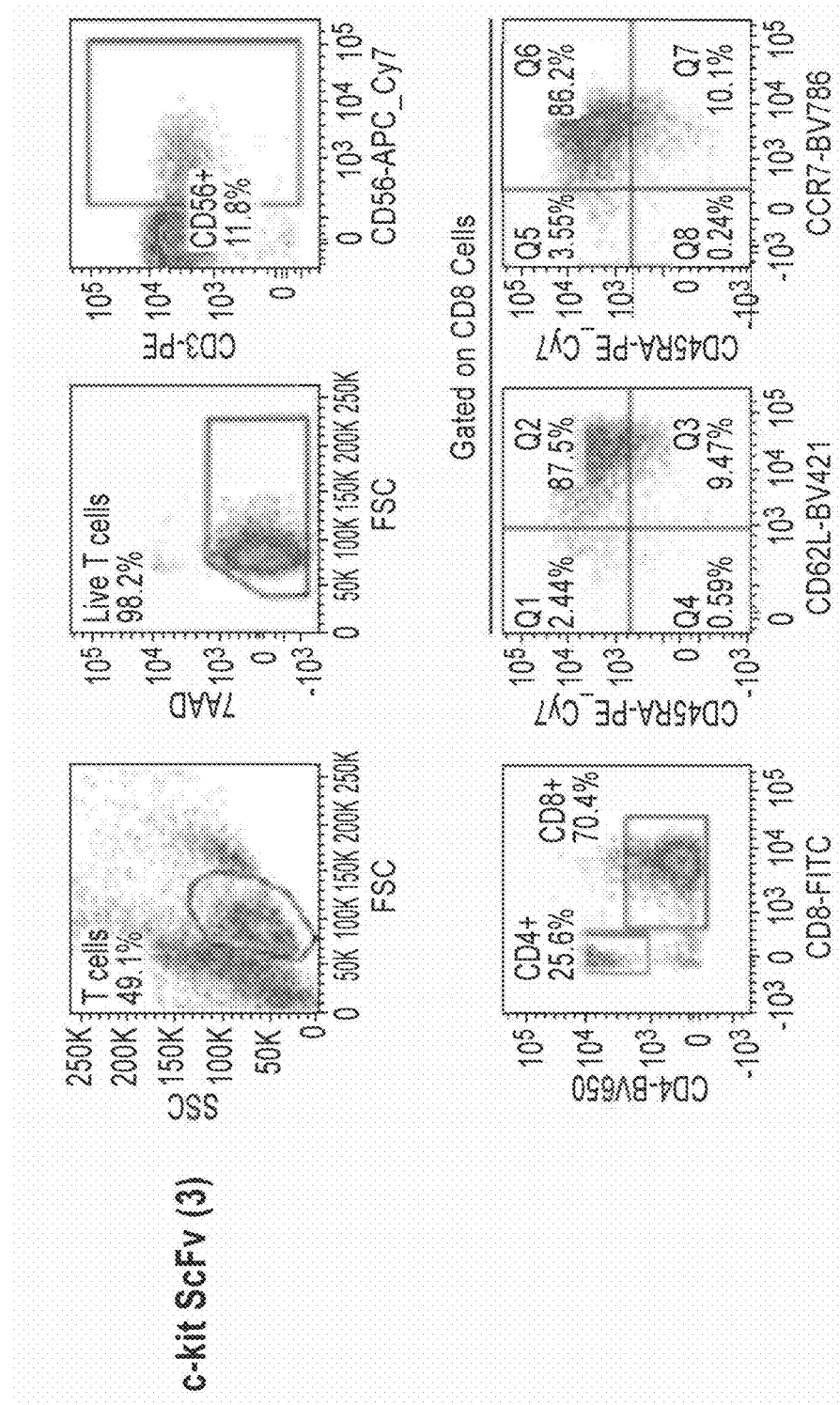
Figure 8A:
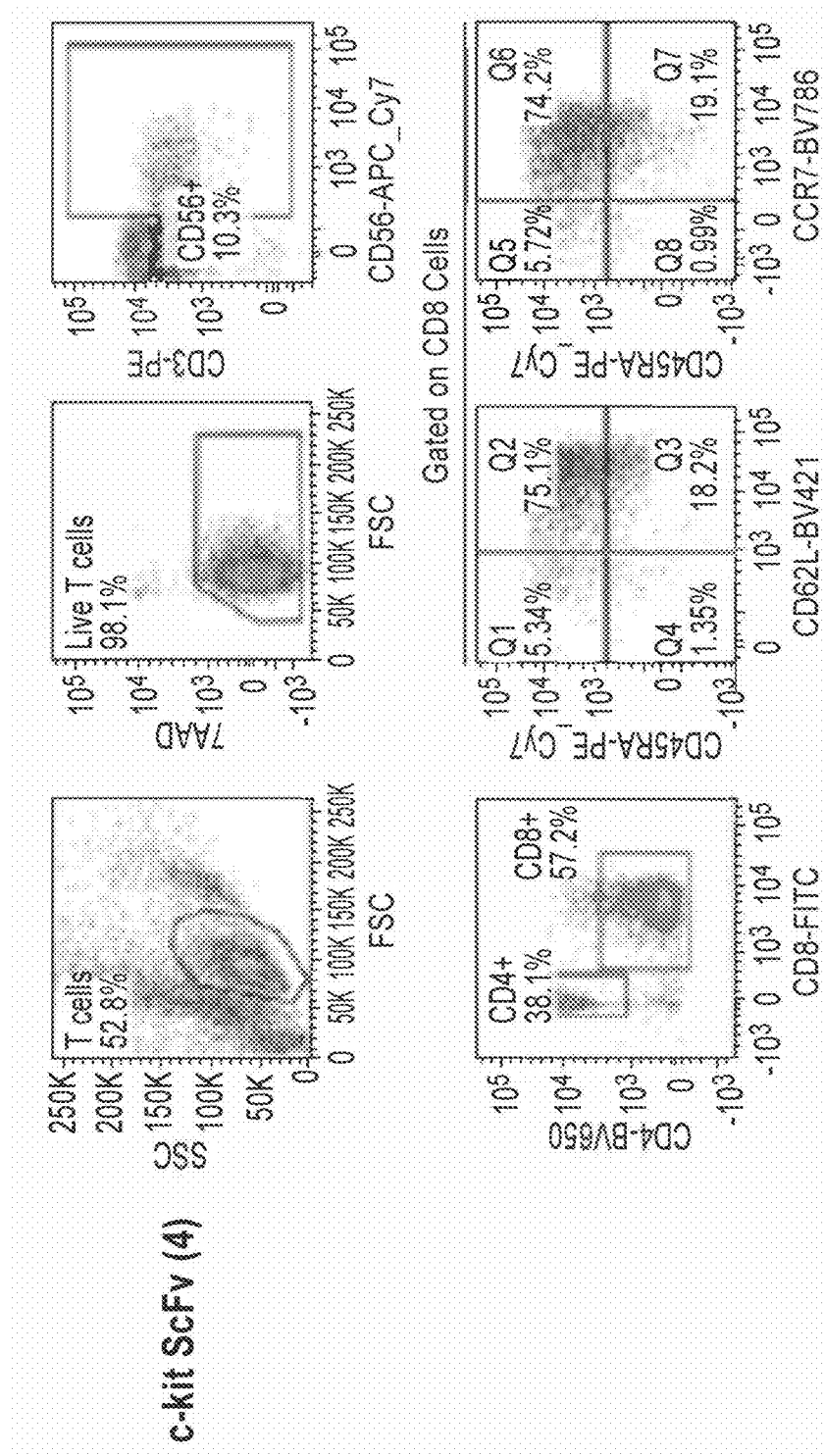
Figure 8A:
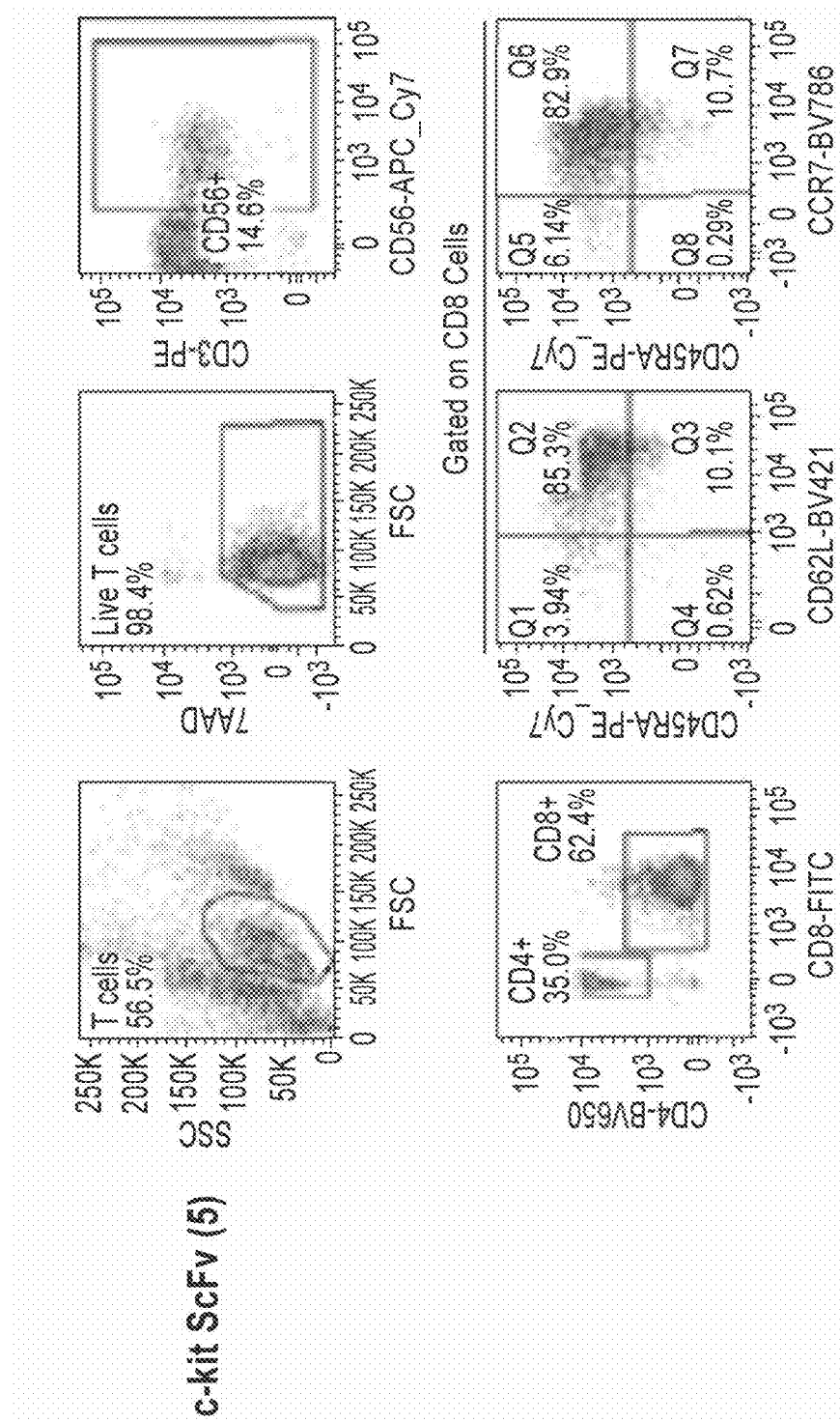
Figure 8A:
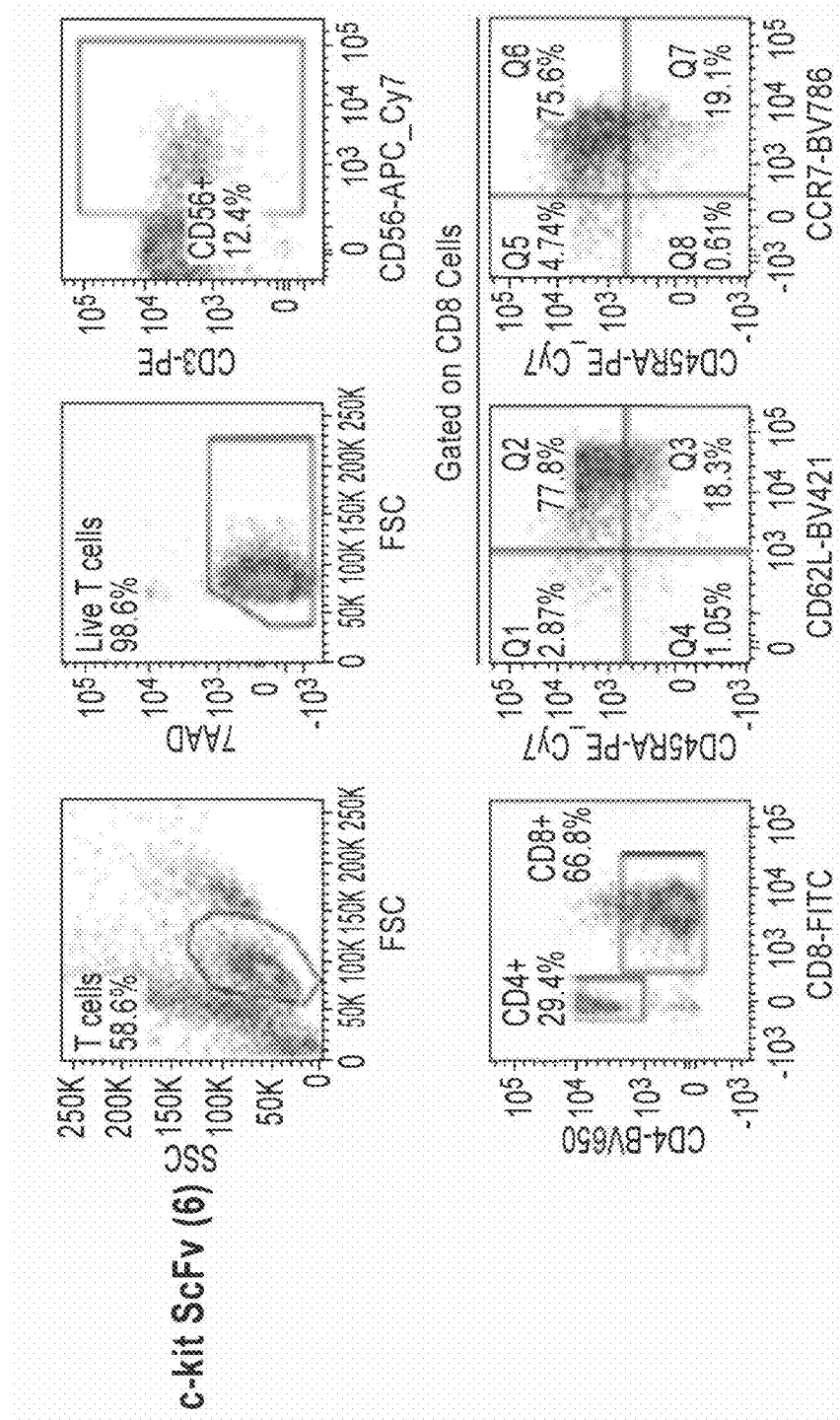
Figure 8B:
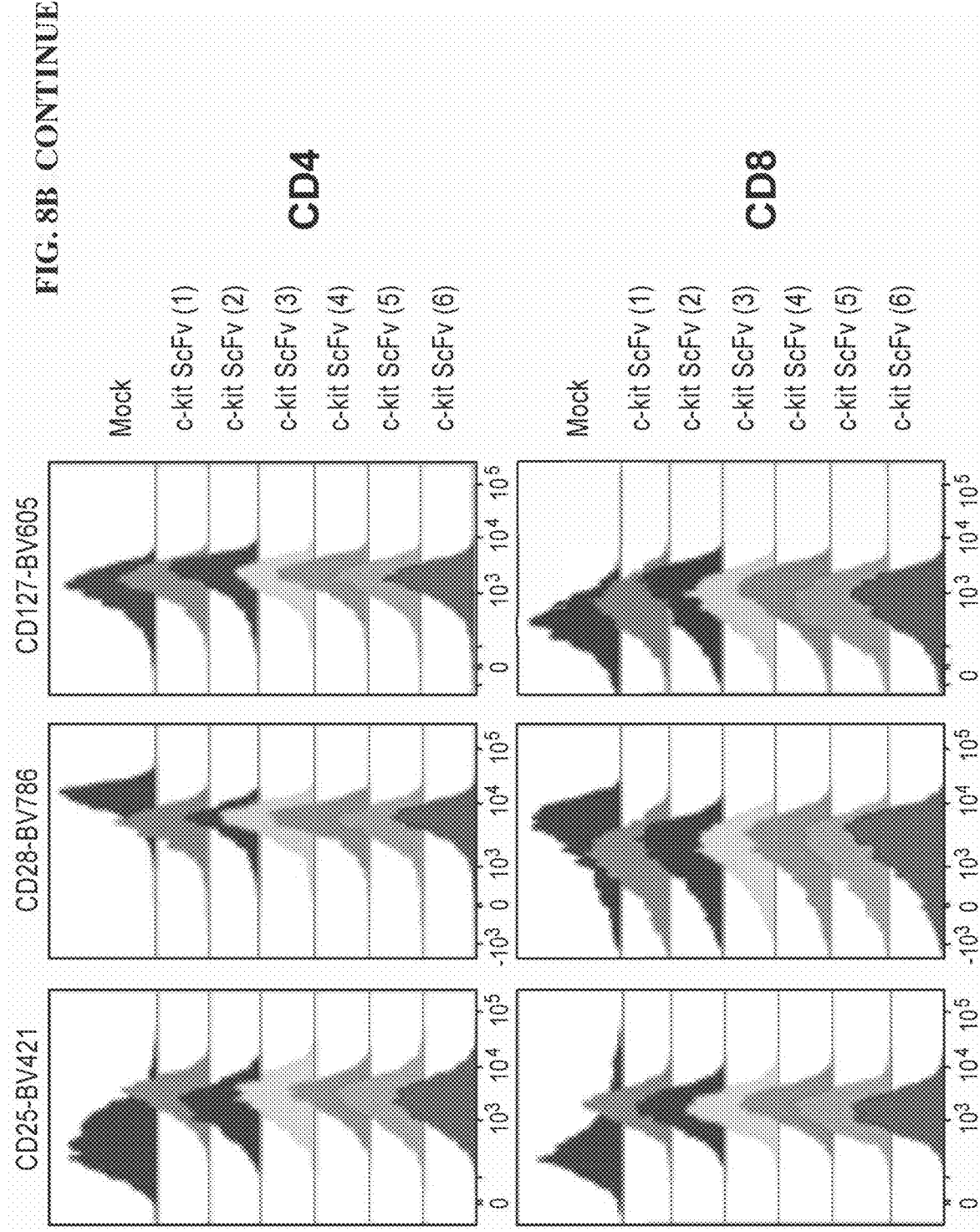
FIG. 8B is a series of graphs depicting the proportion of CD4—and CD8-positive T cells present under each of the conditions shown in FIG. 8A.
Figure 8C:
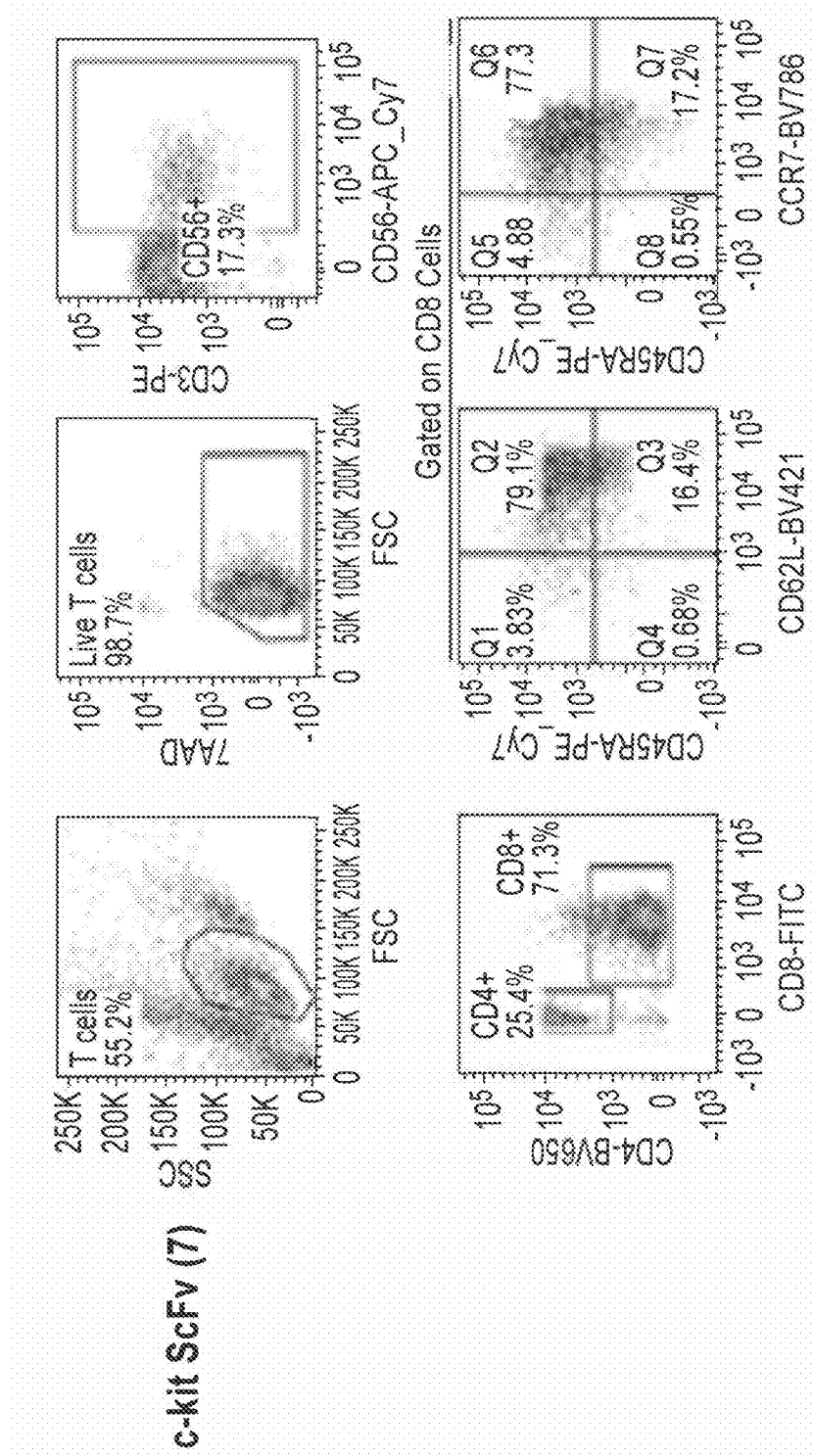
FIG. 8C is a series of plots depicting a flow cytometric analysis ofpiggyBac (PB) transposed anti-CD117 or anti-CD133 CAR-T cells. Human peripheral blood T-cells were previously electroporated with PB transposon pDNA (FIG. 7) together with mRNA encoding the super piggyBac (SPB) transposase. Phenotypic analysis was performed using antibodies directed against CD3, CD4, CD8, CD56, CD45RA, CD62L, CCR7, CD45RO, PD1, Tim3, Lag3, CD184/CXCR4, CD25, CD127 and CD28.
Figure 8C:
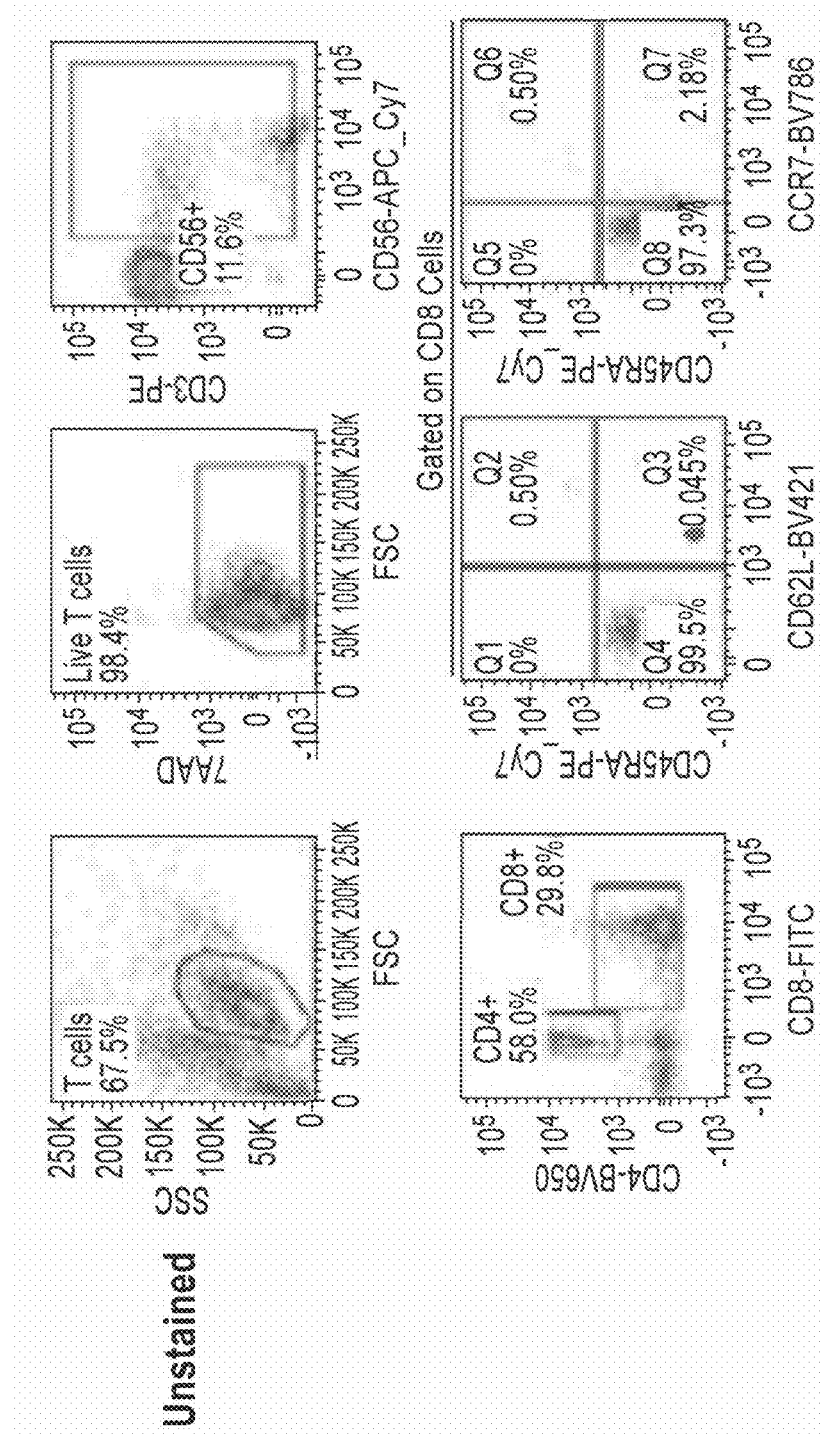
Figure 8D:
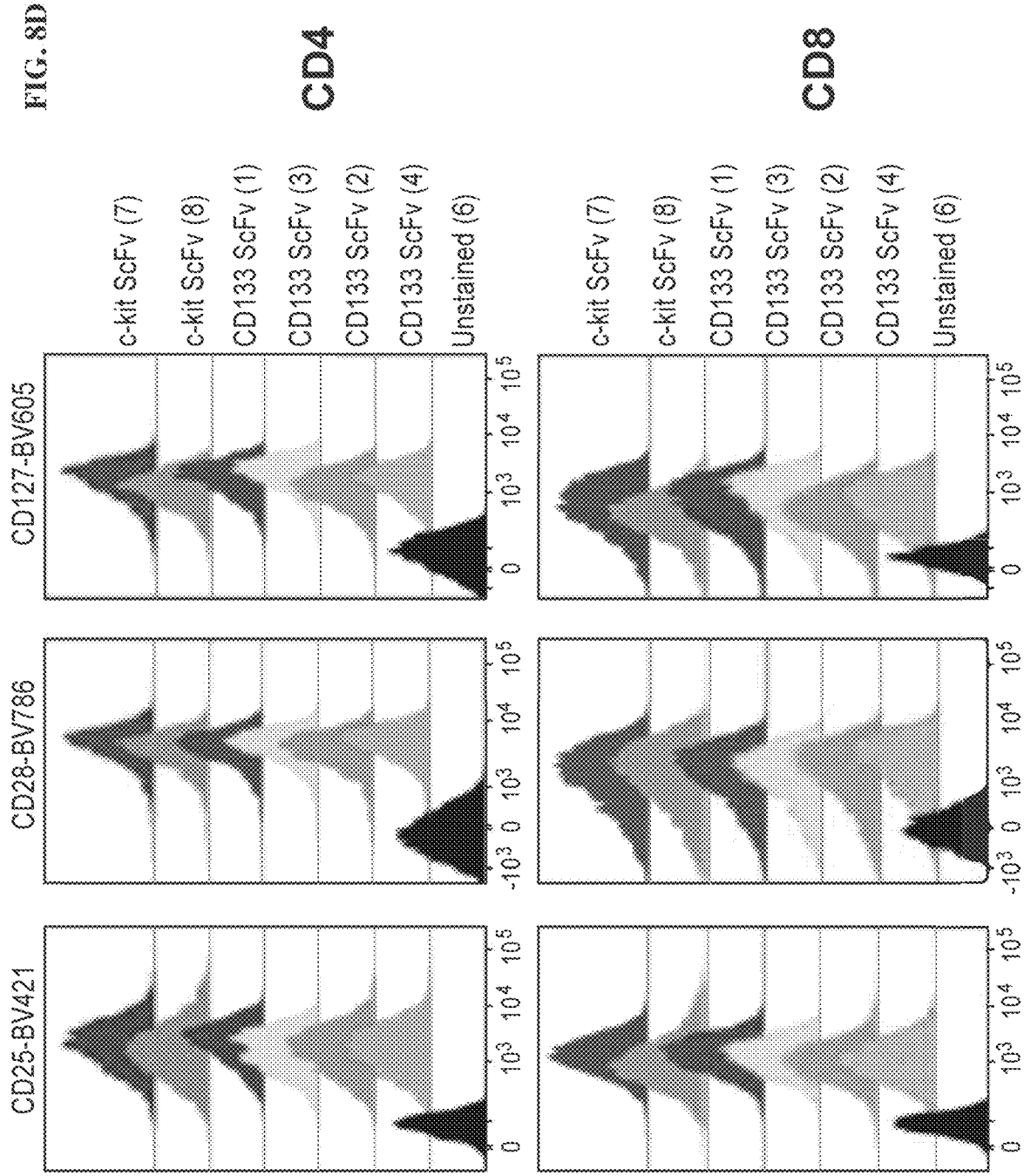
FIG. 8D is a series of graphs depicting the proportion of CD4—and CD8-positive T cells present under each of the conditions shown in FIG. 8C.

The same CAR cassettes directed against either c-kit or CD133 (FIG. 5) are inserted in the tricistronic piggyBac transposon vector (FIG. 7) together with the DHFR gene, that is used for selection of transposed T-cells following ex vivo treatment with methotrexate, and the iC9 gene that allows the clearance of CAR-T cells in vivo following administration of e.g. AP1903 and prior to the transplant of donor HSCs.

The piggyBac transposons (FIG. 7) encoding each of the selected CAR candidates directed against either c-kit or CD133 (FIG. 5) were introduced into isolated pan T cells from human peripheral blood via electroporation of the respective pDNA together with mRNA encoding the super piggyBac (SPB) transposase. Harvested cells were then phenotyped via flow cytometry for cell surface antigens using antibodies directed against CD3, CD4, CD8, CD56, CD45RA, CD62L, CCR7, CD45RO, PD1, Tim3, Lag3, CD184/CXCR4, CD25, CD127 and CD28 (FIG. 8). This analysis showed that the majority of the CD8+ T cells were of the stem cell memory (SCM) phenotype according to CD45RA and CD62L co-expression (68.7-88.7%). Most CD8+ T cells also expressed CXCR4 (73.1-93.6%), the receptor for the chemokine CXCL12/SDF-1 that is known to mediate homing of cells to the bone marrow.

In vitro functional assays were then performed to assess CAR-T killing capacity by co-culturing the above piggyBac transposed CAR-T cells with human bone marrow (HuBM) cells or monkey (rhesus macaque) bone marrow (MoBM) cells over 2 days and plating the cells in methylcellulose cultures supplemented with human growth factors (Metho-Cult™, H4434) for the generation of hematopoietic colonies (CFUs) over 12 days. The CFU functional assay showed effective depletion of the human hematopoietic progenitors in the bone marrow by 3 of the 8 anti-c-kit CAR-T cell candidates (FIG. 9A) while depletion of monkey bone marrow progenitors was observed for 4 of the 8 anti-c-kit CAR-T cell candidates (FIG. 9B).

Figure 10A:
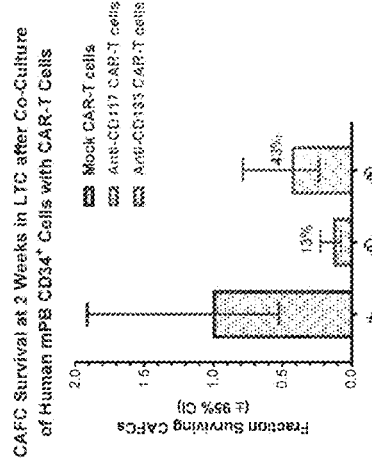
FIGS. 10A-10D is a pair of graphs showing the depletion of cobblestone area forming cells (CAFCs) by anti-c-kit and anti-CD133 CAR-T cells. Human mPB CD34+ cells were co-cultured for 24 hours with either anti-c-kit CAR-T cells (effector to target cell ratio of 3:1) encoding c-kit ScFv (2) or anti-CD133 CAR-T cells encoding CD133 ScFv (3) (FIG. 5). The co-cultures were then treated for a further 24 hours with 10 nM AP1903 for removal of CAR-T cells attributed to co-expression of iC9 in the piggyBac transposon (FIG. 1) and the cells plated on pre-established and irradiated (30 Gy) MS-5 bone marrow stromal cell layers in 96-well plates in serial dilutions in MyeloCult medium (Stem Cell Technologies) supplemented with $10^{-6}$ M hydrocortisone. Wells that were either positive or negative for the formation of CAFCs were enumerated at 2 and 5 weeks in LTC and the CAFC frequency and number was determined by limiting dilution analysis using L-Calc software (Stem Cell Technologies).
Figure 10B:
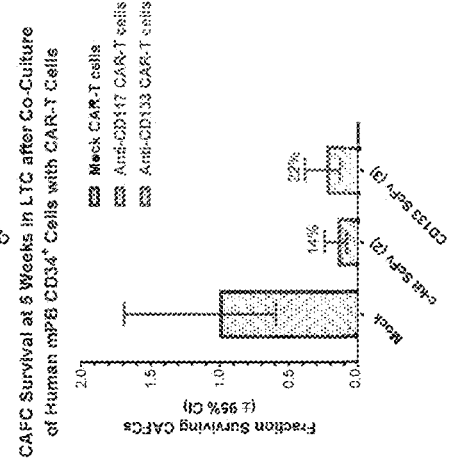
Figure 10C:
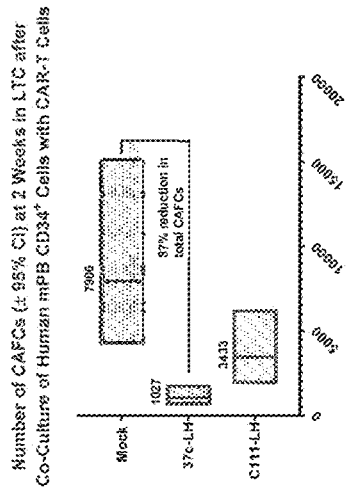
Figure 10D:
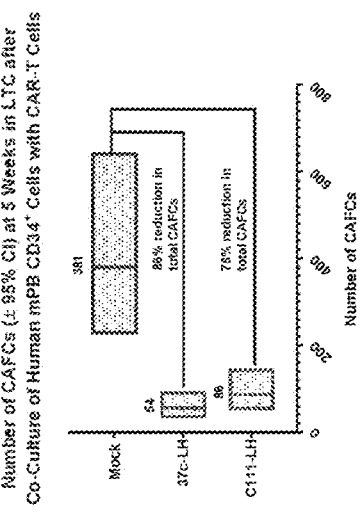
Figure 11A:
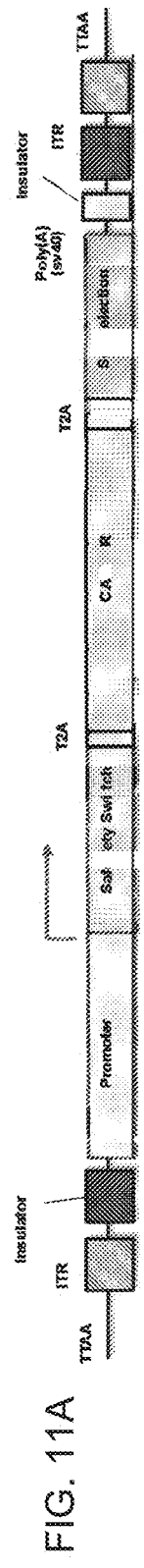
FIGS. 11A-11B are a series of diagrams depicting an exemplary PB vector construct and manufacturing process.
Figure 11B:
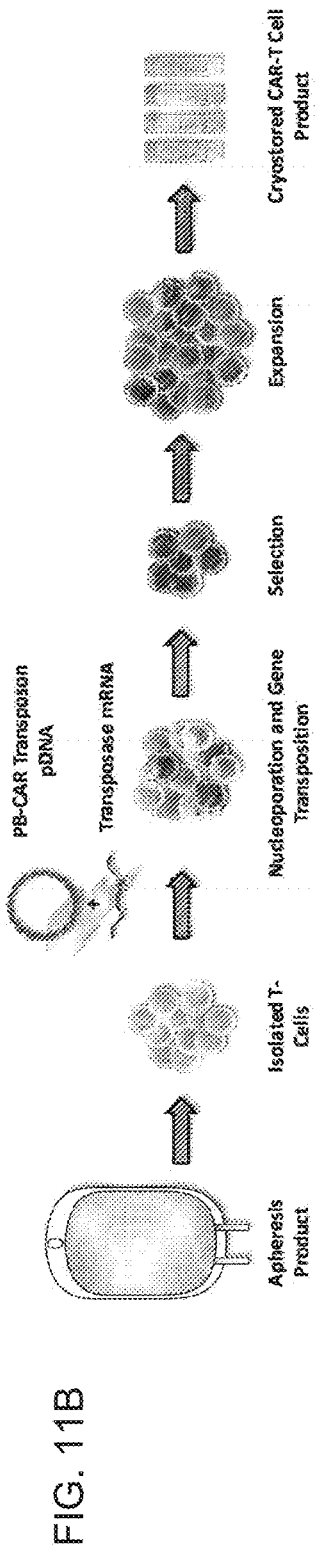
Figure 14:
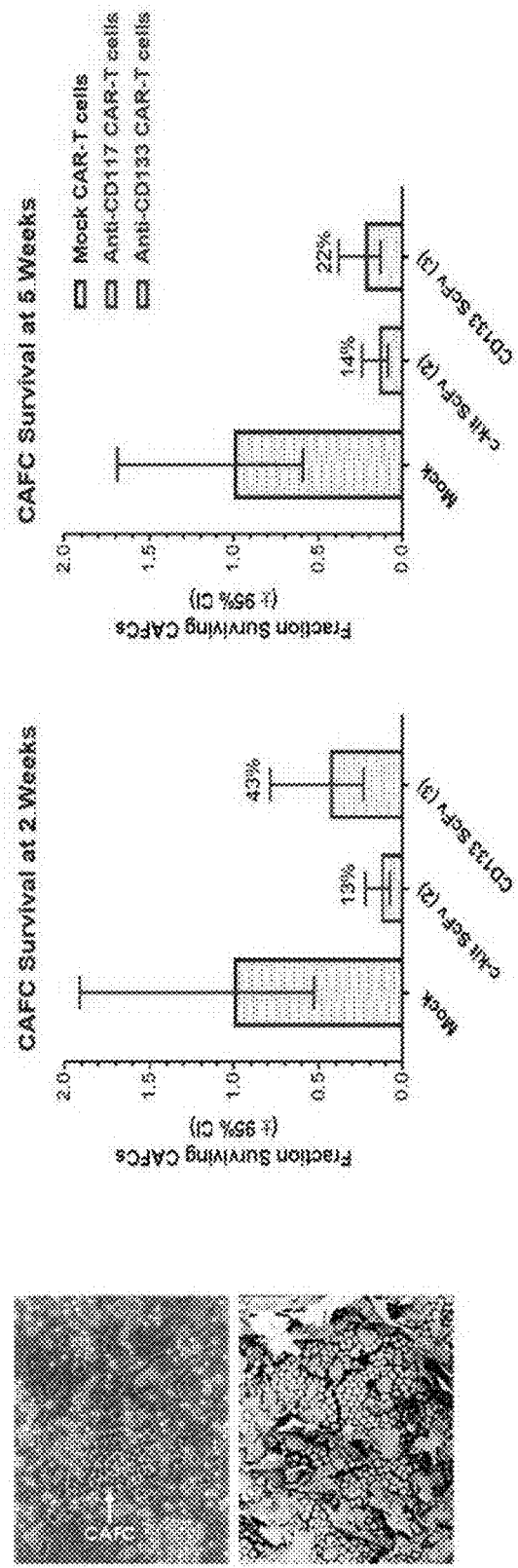
FIG. 14 is a pair of graphs and corresponding photographs depicting an exemplary activity of anti-CD117 or -CD133 CAR-T cells Against Long-Term Cobblestone Area Forming Cells (CAFCs): Following co-culture of the CAR-T cells with human mobilized peripheral blood CD34+ cells for 2 days (effector to target cell ratio of 3:1), the cells were plated on MS-5 stromal cells over serial dilutions for the generation of CAFCs over 2 months. At 5 weeks post-plating, both CAR-T cells significantly reduce the frequency of CAFCs suggesting these CAR-T cells successfully target very primitive cells

Further studies on selected piggyBac transposed CAR-T cells directed against c-kit or CD133 was performed following their co-culture with CD34+ cells isolated from G-CSF mobilized peripheral blood (mPB) cells and subsequently treated with AP1903 for removal of CAR-T cells attributed to iC9 in the piggyBac vector (FIG. 1) prior to culture on irradiated MS-5 bone marrow stromal cells over serial dilutions. These long-term cultures (LTCs) were evaluated for the presence or absence of cobblestone-area forming cells (CAFCs) that assesses the formation of hematopoietic cell subsets of increasing primitiveness with time in culture. At 2 and 5 weeks after plating, the CAFC frequency and number with 95% confidence intervals (95% CI) was determined by limiting dilution analysis using L-Calc software (Stem Cell Technologies). The previous co-culture of the CD34+ cells with anti-c-kit CAR-T cells had the effect of significantly depleting the number of CAFCs forming at 2 weeks in LTC (FIG. 10A) with a surviving fraction of 13% (FIG. 10B) while co-culture with anti-CD133 CAR-Ts had a more moderate depletion of CAFCs to 43% survival. Evaluation of CAFC frequencies at the later time-point of 5 weeks also showed similar level of depletion from anti-c-kit CAR-T cells at 14% survival while this CAFC subset showed higher depletion from anti-CD133 CAR-T cells (22% survival) as compared to CAFCs developing earlier at 2 week (FIGS. 10C and 10 D). The more selective depletion of primitive hematopoietic cells with long-term growth potential by anti-CD133 CAR-Ts provides the basis for improved clinical outcome in patients receiving a subsequent HSC transplant by allowing permanent engraftment from primitive HSCs while sparing committed HPCs that allows more rapid and transient hematological recovery post-transplant (FIG. 3).

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A method of eliminating at least one target hematopoietic stem cell (HSC) in a subject, comprising administering to the subject an effective amount of a composition comprising a plurality of T-cells that express at least one chimeric ligand receptor (CLR) that specifically binds to c-KIT, wherein the specific binding of the at least one CLR to c-KIT activates the T-cell, wherein the activated T-cell induces death of the at least one target HSC, and wherein the at least one CLR comprises:
 (a) an ectodomain comprising
  i) a signal peptide comprising a human CD8α signal peptide;
  ii) a scFv comprising the amino acid sequence of SEQ ID NO: 73; and
  iii) a hinge domain comprising a human CD8α hinge domain;
 (b) a transmembrane domain comprising a human CD8α transmembrane domain;
 (c) a co-stimulatory domain comprising a human 4-1BB costimulatory domain; and
 (d) a endodomain comprising a human CD3ζ endodomain.

2. The method of claim 1, further comprising eliminating the plurality of T-cells following the death of the at least one target cell.

3. The method of claim 2, further comprising administering to the subject an effective amount of a composition comprising a plurality of therapeutic hematopoietic stem cells (HSCs) after eliminating the plurality of T-cells.

4. The method of claim 1, wherein the plurality of T-cells in the composition comprises resting CAR-T-cells, activated CAR-T cells, or a combination thereof.

5. The method of claim 1, wherein the composition comprises a plurality of allogeneic T-cells.

6. The method of claim 1, wherein the composition comprises a plurality of autologous T-cells.

7. The method of claim 1, further comprising administering to the subject an effective amount of a preconditioning composition to enhance engraftment of the composition comprising the plurality of T-cells.

8. The method of claim 7, wherein the preconditioning composition suppresses the immune system of the subject.

9. The method of claim 1, wherein the subject has or is at risk of developing an immune system disease or disorder, is immunocompromised, has an autoimmune disease or disorder, has an inflammatory disease or disorder, or any combination thereof.

10. The method of claim 1, wherein the subject has a genetic or epigenetic marker for a disease or disorder that manifests in a blood cell, an immune cell circulating in the blood, a bone marrow cell or a precursor cell thereof.

11. The method of claim 1, wherein the subject has an anemia, a clotting disorder or a hemorrhagic condition.

12. The method of claim 1, wherein the subject has cancer.

13. The method of claim 12, wherein the cancer is a lymphoma, a leukemia, a myeloma or a malignant immunoproliferative disease.

14. The method of claim 1, wherein i) the signal peptide comprises the amino acid sequence of SEQ ID NO: 31.

15. The method of claim 1, wherein iii) a hinge domain comprises the amino acid sequence of SEQ ID NO: 40.

16. The method of claim 1, wherein (b) the transmembrane domain comprises the amino acid of SEQ ID NO: 33.

17. The method of claim 1, wherein (c) the first costimulatory domain comprises the amino acid of SEQ ID NO: 38.

18. The method of claim 1, wherein (d) the endodomain comprises the amino acid sequence of SEQ ID NO: 36.

19. The method of claim 1, wherein
 (a) the ectodomain comprises
  i) a signal peptide comprising the amino acid sequence of SEQ ID NO: 31;
  ii) an scFv comprising the amino acid sequence of SEQ ID NO: 73;
  iii) a hinge domain comprising the amino acid sequence of SEQ ID NO: 40;
 (b) the transmembrane domain comprises the amino acid of SEQ ID NO: 33;
 (c) the first costimulatory domain comprises the amino acid of SEQ ID NO: 38; and
 (d) the endodomain comprises the amino acid sequence of SEQ ID NO: 36.

* * * * *

SEQUENCE LISTING

```
<160> NUMBER OF SEQ ID NOS: 88

<210> SEQ ID NO 1
<211> LENGTH: 594
<212> TYPE: PRT
<213> ORGANISM: Homo sapiens

<400> SEQUENCE: 1

Met Gly Ser Ser Leu Asp Asp Glu His Ile Leu Ser Ala Leu Leu Gln
```

-continued

```
1               5                   10                  15
Ser Asp Asp Glu Leu Val Gly Glu Asp Ser Asp Ser Glu Ile Ser Asp
                20                  25                  30
His Val Ser Glu Asp Val Gln Ser Asp Thr Glu Glu Ala Phe Ile
            35                  40                  45
Asp Glu Val His Glu Val Gln Pro Thr Ser Ser Gly Ser Glu Ile Leu
        50                  55                  60
Asp Glu Gln Asn Val Ile Glu Gln Pro Gly Ser Ser Leu Ala Ser Asn
65                  70                  75                  80
Arg Ile Leu Thr Leu Pro Gln Arg Thr Ile Arg Gly Lys Asn Lys His
                85                  90                  95
Cys Trp Ser Thr Ser Lys Ser Thr Arg Arg Ser Arg Val Ser Ala Leu
                100                 105                 110
Asn Ile Val Arg Ser Gln Arg Gly Pro Thr Arg Met Cys Arg Asn Ile
            115                 120                 125
Tyr Asp Pro Leu Leu Cys Phe Lys Leu Phe Phe Thr Asp Glu Ile Ile
        130                 135                 140
Ser Glu Ile Val Lys Trp Thr Asn Ala Glu Ile Ser Leu Lys Arg Arg
145                 150                 155                 160
Glu Ser Met Thr Gly Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
            180                 185                 190
His Met Ser Thr Asp Asp Leu Phe Asp Arg Ser Leu Ser Met Val Tyr
        195                 200                 205
Val Ser Val Met Ser Arg Asp Arg Phe Asp Phe Leu Ile Arg Cys Leu
210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Met Tyr Ile Pro Asn Lys Pro
        275                 280                 285
Ser Lys Tyr Gly Ile Lys Ile Leu Met Met Cys Asp Ser Gly Tyr Lys
        290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Arg Ser Asn Lys Arg Glu Ile Pro Glu Val Leu Lys Asn
        370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
```

```
Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 2
<211> LENGTH: 594
<212> TYPE: PRT
<213> ORGANISM: Homo sapiens

<400> SEQUENCE: 2

Met Gly Ser Ser Leu Asp Glu His Ile Leu Ser Ala Leu Leu Gln
1               5                   10                  15

Ser Asp Asp Glu Leu Val Gly Glu Asp Ser Asp Ser Glu Val Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
            130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
            165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205
```

Val Ser Val Met Ser Arg Asp Arg Phe Asp Phe Leu Ile Arg Cys Leu
            210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 3
<211> LENGTH: 1368
<212> TYPE: PRT

```
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Asp Lys Lys Tyr Ser Ile Gly Leu Ala Ile Gly Thr Asn Ser Val
 1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380
```

```
Gly Thr Glu Glu Leu Leu Val Lys Leu Asn Arg Gly Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800
```

```
Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
```

```
                    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 4
<211> LENGTH: 1053
<212> TYPE: PRT
<213> ORGANISM: Homo sapiens

<400> SEQUENCE: 4

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205
```

```
Arg Thr Tyr Tyr Glu Gly Pro Gly Glu Gly Ser Pro Phe Gly Trp Lys
    210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
                260                 265                 270
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
    450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
                500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
    530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Ala Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
    610                 615                 620
Tyr Leu Leu Glu Glu Arg Asp Ile Asn Arg Phe Ser Val Gln Lys Asp
```

-continued

```
625                 630                 635                 640
    Phe Ile Asn Arg Asn Leu Val Asp Thr Arg Tyr Ala Thr Arg Gly Leu
                    645                 650                 655
    Met Asn Leu Leu Arg Ser Tyr Phe Arg Val Asn Asn Leu Asp Val Lys
                    660                 665                 670
    Val Lys Ser Ile Asn Gly Gly Phe Thr Ser Phe Leu Arg Arg Lys Trp
                    675                 680                 685
    Lys Phe Lys Lys Glu Arg Asn Lys Gly Tyr Lys His His Ala Glu Asp
                    690                 695                 700
    Ala Leu Ile Ile Ala Asn Ala Asp Phe Ile Phe Lys Glu Trp Lys Lys
    705                 710                 715                 720
    Leu Asp Lys Ala Lys Lys Val Met Glu Asn Gln Met Phe Glu Glu Lys
                        725                 730                 735
    Gln Ala Glu Ser Met Pro Glu Ile Glu Thr Glu Gln Glu Tyr Lys Glu
                        740                 745                 750
    Ile Phe Ile Thr Pro His Gln Ile Lys His Ile Lys Asp Phe Lys Asp
                        755                 760                 765
    Tyr Lys Tyr Ser His Arg Val Asp Lys Lys Pro Asn Arg Glu Leu Ile
                    770                 775                 780
    Asn Asp Thr Leu Tyr Ser Thr Arg Lys Asp Asp Lys Gly Asn Thr Leu
    785                 790                 795                 800
    Ile Val Asn Asn Leu Asn Gly Leu Tyr Asp Lys Asp Asn Asp Lys Leu
                        805                 810                 815
    Lys Lys Leu Ile Asn Lys Ser Pro Glu Lys Leu Leu Met Tyr His His
                    820                 825                 830
    Asp Pro Gln Thr Tyr Gln Lys Leu Lys Leu Ile Met Glu Gln Tyr Gly
                    835                 840                 845
    Asp Glu Lys Asn Pro Leu Tyr Lys Tyr Tyr Glu Glu Thr Gly Asn Tyr
                    850                 855                 860
    Leu Thr Lys Tyr Ser Lys Lys Asp Asn Gly Pro Val Ile Lys Lys Ile
    865                 870                 875                 880
    Lys Tyr Tyr Gly Asn Lys Leu Asn Ala His Leu Asp Ile Thr Asp Asp
                        885                 890                 895
    Tyr Pro Asn Ser Arg Asn Lys Val Val Lys Leu Ser Leu Lys Pro Tyr
                    900                 905                 910
    Arg Phe Asp Val Tyr Leu Asp Asn Gly Val Tyr Lys Phe Val Thr Val
                    915                 920                 925
    Lys Asn Leu Asp Val Ile Lys Lys Glu Asn Tyr Tyr Glu Val Asn Ser
                    930                 935                 940
    Lys Cys Tyr Glu Glu Ala Lys Lys Leu Lys Lys Ile Ser Asn Gln Ala
    945                 950                 955                 960
    Glu Phe Ile Ala Ser Phe Tyr Asn Asn Asp Leu Ile Lys Ile Asn Gly
                        965                 970                 975
    Glu Leu Tyr Arg Val Ile Gly Val Asn Asn Asp Leu Leu Asn Arg Ile
                        980                 985                 990
    Glu Val Asn Met Ile Asp Ile Thr Tyr Arg Glu Tyr Leu Glu Asn Met
                    995                 1000                1005
    Asn Asp Lys Arg Pro Pro Arg Ile Ile Lys Thr Ile Ala Ser Lys
                    1010                1015                1020
    Thr Gln Ser Ile Lys Lys Tyr Ser Thr Asp Ile Leu Gly Asn Leu
                    1025                1030                1035
    Tyr Glu Val Lys Ser Lys Lys His Pro Gln Ile Ile Lys Lys Gly
                    1040                1045                1050
```

```
<210> SEQ ID NO 5
<211> LENGTH: 433
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1               5                   10                  15

His Ala Ala Arg Pro Glu Gly Ile Cys Arg Asn Arg Val Thr Asn Asn
            20                  25                  30

Val Lys Asp Val Thr Lys Leu Val Ala Asn Leu Pro Lys Asp Tyr Met
        35                  40                  45

Ile Thr Leu Lys Tyr Val Pro Gly Met Asp Val Leu Pro Ser His Cys
    50                  55                  60

Trp Ile Ser Glu Met Val Val Gln Leu Ser Asp Ser Leu Thr Asp Leu
65                  70                  75                  80

Leu Asp Lys Phe Ser Asn Ile Ser Glu Gly Leu Ser Asn Tyr Ser Ile
                85                  90                  95

Ile Asp Lys Leu Val Asn Ile Val Asp Asp Leu Val Glu Cys Val Lys
            100                 105                 110

Glu Asn Ser Ser Lys Asp Leu Lys Lys Ser Phe Lys Ser Pro Glu Pro
        115                 120                 125

Arg Leu Phe Thr Pro Glu Glu Phe Phe Arg Ile Phe Asn Arg Ser Ile
    130                 135                 140

Asp Ala Phe Lys Asp Phe Val Val Ala Ser Glu Thr Ser Asp Cys Val
145                 150                 155                 160

Val Ser Ser Thr Leu Ser Pro Glu Lys Asp Ser Arg Val Ser Val Thr
                165                 170                 175

Lys Pro Phe Met Leu Pro Pro Val Ala Ala Ser Ser Leu Arg Asn Asp
            180                 185                 190

Ser Ser Ser Ser Asn Arg Lys Ala Lys Asn Pro Pro Gly Asp Ser Ser
        195                 200                 205

Leu His Thr Thr Thr Pro Ala Pro Arg Pro Pro Thr Pro Ala Pro Thr
    210                 215                 220

Ile Ala Ser Gln Pro Leu Ser Leu Arg Pro Glu Ala Cys Arg Pro Ala
225                 230                 235                 240

Ala Gly Gly Ala Val His Thr Arg Gly Leu Asp Phe Ala Cys Asp Ile
                245                 250                 255

Tyr Ile Trp Ala Pro Leu Ala Gly Thr Cys Gly Val Leu Leu Leu Ser
            260                 265                 270

Leu Val Ile Thr Leu Tyr Cys Lys Arg Gly Arg Lys Lys Leu Leu Tyr
        275                 280                 285

Ile Phe Lys Gln Pro Phe Met Arg Pro Val Gln Thr Thr Gln Glu Glu
    290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Lys Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
```

```
            370                 375                 380
Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 6
<211> LENGTH: 405
<212> TYPE: PRT
<213> ORGANISM: Homo sapiens

<400> SEQUENCE: 6

Met Ala Leu Pro Val Thr Ala Leu Leu Leu Pro Leu Ala Leu Leu Leu
1               5                   10                  15

His Ala Ala Arg Pro Glu Gly Ile Cys Arg Asn Arg Val Thr Asn Asn
                20                  25                  30

Val Lys Asp Val Thr Lys Leu Val Ala Asn Leu Pro Lys Asp Tyr Met
            35                  40                  45

Ile Thr Leu Lys Tyr Val Pro Gly Met Asp Val Leu Pro Ser His Cys
50                  55                  60

Trp Ile Ser Glu Met Val Val Gln Leu Ser Asp Ser Leu Thr Asp Leu
65                  70                  75                  80

Leu Asp Lys Phe Ser Asn Ile Ser Glu Gly Leu Ser Asn Tyr Ser Ile
                85                  90                  95

Ile Asp Lys Leu Val Asn Ile Val Asp Asp Leu Val Glu Cys Val Lys
            100                 105                 110

Glu Asn Ser Ser Lys Asp Leu Lys Lys Ser Phe Lys Ser Pro Glu Pro
        115                 120                 125

Arg Leu Phe Thr Pro Glu Glu Phe Phe Arg Ile Phe Asn Arg Ser Ile
    130                 135                 140

Asp Ala Phe Lys Asp Phe Val Val Ala Ser Glu Thr Ser Asp Cys Val
145                 150                 155                 160

Val Ser Ser Thr Leu Ser Pro Glu Lys Gly Lys Ala Lys Asn Pro Pro
                165                 170                 175

Gly Asp Ser Ser Leu His Thr Thr Thr Pro Ala Pro Arg Pro Pro Thr
            180                 185                 190

Pro Ala Pro Thr Ile Ala Ser Gln Pro Leu Ser Leu Arg Pro Glu Ala
        195                 200                 205

Cys Arg Pro Ala Ala Gly Gly Ala Val His Thr Arg Gly Leu Asp Phe
    210                 215                 220

Ala Cys Asp Ile Tyr Ile Trp Ala Pro Leu Ala Gly Thr Cys Gly Val
225                 230                 235                 240

Leu Leu Leu Ser Leu Val Ile Thr Leu Tyr Cys Lys Arg Gly Arg Lys
                245                 250                 255

Lys Leu Leu Tyr Ile Phe Lys Gln Pro Phe Met Arg Pro Val Gln Thr
            260                 265                 270

Thr Gln Glu Glu Asp Gly Cys Ser Cys Arg Phe Pro Glu Glu Glu Glu
        275                 280                 285

Gly Gly Cys Glu Leu Arg Val Lys Phe Ser Arg Ser Ala Asp Ala Pro
    290                 295                 300

Ala Tyr Lys Gln Gly Gln Asn Gln Leu Tyr Asn Glu Leu Asn Leu Gly
```

```
                    305                 310                 315                 320
Arg Arg Glu Glu Tyr Asp Val Leu Asp Lys Arg Arg Gly Arg Asp Pro
                325                 330                 335

Glu Met Gly Gly Lys Pro Arg Arg Lys Asn Pro Gln Glu Gly Leu Tyr
                340                 345                 350

Asn Glu Leu Gln Lys Asp Lys Met Ala Glu Ala Tyr Ser Glu Ile Gly
                355                 360                 365

Met Lys Gly Glu Arg Arg Arg Gly Lys Gly His Asp Gly Leu Tyr Gln
                370                 375                 380

Gly Leu Ser Thr Ala Thr Lys Asp Thr Tyr Asp Ala Leu His Met Gln
385                 390                 395                 400

Ala Leu Pro Pro Arg
                405

<210> SEQ ID NO 7
<211> LENGTH: 492
<212> TYPE: PRT
<213> ORGANISM: Homo sapiens

<400> SEQUENCE: 7

Met Ala Leu Pro Val Thr Ala Leu Leu Leu Pro Leu Ala Leu Leu Leu
1               5                   10                  15

His Ala Ala Arg Pro Met Ala Gln Val Gln Leu Val Glu Ser Trp Gly
                20                  25                  30

Gly Val Ala Gln Pro Gly Arg Ser Leu Arg Leu Ser Cys Ala Ala Ser
            35                  40                  45

Gly Phe Thr Phe Ser Ser Phe Ala Met His Trp Val Arg Gln Ala Pro
        50                  55                  60

Gly Lys Gly Leu Glu Trp Val Ala Val Thr Ser Tyr Asp Gly Ser Asn
65                  70                  75                  80

Glu Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
                100                 105                 110

Asp Thr Ala Val Tyr Tyr Cys Ala Lys Ala Met Val Arg Gly Val Thr
            115                 120                 125

Phe Gly Asp Leu Asp Tyr Trp Gly Gln Gly Thr Leu Val Thr Val Ser
        130                 135                 140

Ser Gly Gly Gly Gly Ser Gly Gly Gly Ser Gly Gly Gly Gly Ser
145                 150                 155                 160

Ser Glu Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Glu Gln Ala Pro Val Leu Val Ile Tyr Gly
        195                 200                 205

Glu Asn Ser Arg Pro Ser Gly Ile Pro Asp Arg Phe Ser Gly Ser Ser
        210                 215                 220

Ser Gly Asn Thr Ala Ser Leu Thr Ile Thr Gly Ala Gln Ala Glu Asp
225                 230                 235                 240

Glu Ala Asp Tyr Tyr Cys Asn Ser Arg Asp Ser Ser Gly Thr His Leu
                245                 250                 255

Arg Val Phe Gly Gly Gly Thr Lys Leu Thr Val Leu Gly Thr Thr Thr
            260                 265                 270
```

Pro Ala Pro Arg Pro Pro Thr Pro Ala Pro Thr Ile Ala Ser Gln Pro
              275                 280                 285

Leu Ser Leu Arg Pro Glu Ala Cys Arg Pro Ala Ala Gly Gly Ala Val
        290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
        370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 8
<211> LENGTH: 491
<212> TYPE: PRT
<213> ORGANISM: Homo sapiens

<400> SEQUENCE: 8

Met Ala Leu Pro Val Thr Ala Leu Leu Leu Pro Leu Ala Leu Leu Leu
1               5                   10                  15

His Ala Ala Arg Pro Met Ala Gln Val Gln Leu Val Glu Ser Trp Gly
                20                  25                  30

Gly Val Ala Gln Pro Gly Arg Ser Leu Arg Leu Ser Cys Ala Ala Ser
            35                  40                  45

Gly Phe Thr Phe Ser Ser Phe Ala Met His Trp Val Arg Gln Ala Pro
        50                  55                  60

Gly Lys Gly Leu Glu Trp Val Ala Val Thr Ser Tyr Asp Gly Ser Asn
65                  70                  75                  80

Glu Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Lys Ala Met Val Arg Gly Val Thr
        115                 120                 125

Phe Gly Asp Leu Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Ser Glu Leu Thr Gln Asp Pro Ala Val Ser Val Ala Leu Gly Gln Thr
            165                 170                 175

Val Arg Lys Thr Cys Gln Gly Asp Ser Leu Lys Ser Tyr Tyr Ala Ser
            180                 185                 190

Trp Tyr Gln Gln Lys Pro Gly Gln Ala Pro Val Leu Val Ile Tyr Gly
            195                 200                 205

Glu Asn Ser Arg Pro Ser Gly Ile Pro Asp Arg Phe Ser Gly Ser Ser
            210                 215                 220

Ser Gly Asn Thr Ala Ser Leu Thr Ile Thr Gly Ala Gln Ala Glu Asp
225                 230                 235                 240

Glu Ala Asp Tyr Tyr Cys Cys Ser Arg Ala Thr Gly Tyr His Arg
            245                 250                 255

Ile Phe Gly Gly Gly Thr Lys Leu Thr Val Leu Gly Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Gly Gly Cys Glu Leu Arg Val Lys Phe Ser
            370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 9
<211> LENGTH: 491
<212> TYPE: PRT
<213> ORGANISM: Homo sapiens

<400> SEQUENCE: 9

Met Ala Leu Pro Val Thr Ala Leu Leu Leu Pro Leu Ala Leu Leu Leu
1               5                   10                  15

His Ala Ala Arg Pro Met Ala Gln Val Lys Leu Gln Glu Ser Gly Gly
            20                  25                  30

Gly Leu Val Gln Pro Gly Gly Ser Leu Arg Leu Ser Cys Ala Ala Ser

```
            35                  40                  45
Gly Phe Thr Phe Asp Ser Tyr Ala Met Ser Trp Val Arg Gln Ala Pro
 50                  55                  60

Gly Lys Gly Leu Glu Trp Val Ser Tyr Ile Thr Ser Ser Ser Ser Thr
 65                  70                  75                  80

Ile Tyr Tyr Val Asp Ser Val Lys Gly Arg Phe Thr Ile Ser Arg Asp
                 85                  90                  95

Asn Ala Lys Asn Ser Leu Tyr Leu Gln Met Asn Ser Leu Arg Asp Glu
            100                 105                 110

Asp Thr Ala Val Tyr Tyr Cys Ala Arg Leu Arg Asn Ser Glu Gly Tyr
        115                 120                 125

Trp Tyr Phe Asp Leu Trp Gly Arg Gly Thr Leu Val Thr Val Ser Ser
    130                 135                 140

Gly Gly Gly Gly Ser Gly Gly Gly Ser Gly Gly Gly Gly Ser Gln
145                 150                 155                 160

Ser Ala Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Phe Ala Ser
            180                 185                 190

Trp Tyr Gln Gln Lys Pro Gly Gln Ala Pro Leu Leu Val Met Tyr Gly
        195                 200                 205

Gln Asn Ile Arg Pro Ser Gly Ile Pro Asp Arg Phe Ser Gly Ser Ser
    210                 215                 220

Ser Gly Asn Ser Ala Ser Leu Thr Ile Thr Gly Ala Gln Ala Glu Asp
225                 230                 235                 240

Glu Ala Asp Tyr Tyr Cys Asn Ser Arg Asp Ser Ser Tyr Asn His Trp
                245                 250                 255

Val Phe Gly Gly Gly Thr Lys Leu Thr Val Leu Gly Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460
```

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 10
<211> LENGTH: 493
<212> TYPE: PRT
<213> ORGANISM: Homo sapiens

<400> SEQUENCE: 10

Met Ala Leu Pro Val Thr Ala Leu Leu Leu Pro Leu Ala Leu Leu Leu
1               5                   10                  15

His Ala Ala Arg Pro Met Ala Gln Val Lys Leu Gln Glu Ser Gly Gly
                20                  25                  30

Gly Leu Val Gln Pro Gly Gly Ser Leu Arg Leu Ser Cys Ala Ala Ser
            35                  40                  45

Gly Phe Thr Phe Asp Ser Tyr Ala Met Ser Trp Val Arg Gln Ala Pro
50                  55                  60

Gly Lys Gly Leu Glu Trp Val Ser Tyr Ile Thr Ser Ser Ser Ser Thr
65                  70                  75                  80

Ile Tyr Tyr Val Asp Ser Val Lys Gly Arg Phe Thr Ile Ser Arg Asp
                85                  90                  95

Asn Ala Lys Asn Ser Leu Tyr Leu Gln Met Asn Ser Leu Arg Asp Glu
                100                 105                 110

Asp Thr Ala Val Tyr Tyr Cys Ala Arg Leu Arg Asn Ser Glu Gly Tyr
            115                 120                 125

Trp Tyr Phe Asp Leu Trp Gly Arg Gly Thr Leu Val Thr Val Ser Ser
130                 135                 140

Gly Gly Gly Gly Ser Gly Gly Gly Ser Gly Gly Gly Gly Ser Gln
145                 150                 155                 160

Ser Val Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Leu Leu Val Met Tyr Gly
195                 200                 205

Glu Asn Ile Arg Pro Ser Gly Ile Pro Asp Arg Phe Ser Gly Ser Thr
            210                 215                 220

Ser Gly Asn Ser Ala Ser Leu Thr Ile Thr Gly Ala Gln Ala Glu Asp
225                 230                 235                 240

Glu Ala Asp Tyr Tyr Cys Asn Ser Arg Asp Ser Ser Gly Asn His Leu
                245                 250                 255

Asn Trp Val Phe Gly Gly Gly Thr Lys Leu Thr Val Leu Gly Thr Thr
            260                 265                 270

Thr Pro Ala Pro Arg Pro Pro Thr Pro Ala Pro Thr Ile Ala Ser Gln
275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln

```
                    340                 345                 350
Pro Phe Met Arg Pro Val Gln Thr Thr Gln Glu Glu Asp Gly Cys Ser
                355                 360                 365

Cys Arg Phe Pro Glu Glu Glu Gly Gly Cys Glu Leu Arg Val Lys
            370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 11
<211> LENGTH: 483
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Ala Glu Leu
            20                  25                  30

Val Arg Pro Gly Ala Ser Val Lys Leu Ser Cys Lys Ala Ser Gly Tyr
        35                  40                  45

Thr Phe Thr Asp Tyr Tyr Ile Asn Trp Val Lys Gln Arg Pro Gly Gln
    50                  55                  60

Gly Leu Glu Trp Ile Ala Arg Ile Tyr Pro Gly Ser Gly Asn Thr Tyr
65                  70                  75                  80

Tyr Asn Glu Lys Phe Lys Gly Lys Ala Thr Leu Thr Ala Glu Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Arg Gly Val Tyr Tyr Phe Asp Tyr Trp Gly
        115                 120                 125

Gln Gly Thr Thr Leu Thr Val Ser Ala Gly Gly Gly Ser Gly Gly
    130                 135                 140

Gly Gly Ser Gly Gly Gly Gly Ser Asp Ile Val Met Thr Gln Ser Gln
145                 150                 155                 160

Lys Phe Met Ser Thr Ser Val Gly Asp Arg Val Ser Val Thr Cys Lys
                165                 170                 175

Ala Ser Gln Asn Val Arg Thr Asn Val Ala Trp Tyr Gln Gln Lys Pro
            180                 185                 190

Gly Gln Ser Pro Lys Ala Leu Ile Tyr Ser Ala Ser Tyr Arg Tyr Ser
        195                 200                 205

Gly Val Pro Asp Arg Phe Thr Gly Ser Gly Ser Gly Thr Asp Phe Thr
    210                 215                 220
```

Leu Thr Ile Ser Asn Val Gln Ser Glu Asp Leu Ala Asp Tyr Phe Cys
225                 230                 235                 240

Gln Gln Tyr Asn Ser Tyr Pro Arg Thr Phe Gly Gly Gly Thr Lys Leu
            245                 250                 255

Glu Ile Lys Arg Thr Thr Thr Pro Ala Pro Arg Pro Pro Thr Pro Ala
        260                 265                 270

Pro Thr Ile Ala Ser Gln Pro Leu Ser Leu Arg Pro Glu Ala Cys Arg
    275                 280                 285

Pro Ala Ala Gly Gly Ala Val His Thr Arg Gly Leu Asp Phe Ala Cys
290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Gly Gly
        355                 360                 365

Cys Glu Leu Arg Val Lys Phe Ser Arg Ser Ala Asp Ala Pro Ala Tyr
370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 12
<211> LENGTH: 483
<212> TYPE: PRT
<213> ORGANISM: Homo sapiens

<400> SEQUENCE: 12

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Phe Met
            20                  25                  30

Ser Thr Ser Val Gly Asp Arg Val Ser Val Thr Cys Lys Ala Ser Gln
        35                  40                  45

Asn Val Arg Thr Asn Val Ala Trp Tyr Gln Gln Lys Pro Gly Gln Ser
    50                  55                  60

Pro Lys Ala Leu Ile Tyr Ser Ala Ser Tyr Arg Tyr Ser Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Asp Tyr Phe Cys Gln Gln Tyr
                100                 105                 110

```
Asn Ser Tyr Pro Arg Thr Phe Gly Gly Gly Thr Lys Leu Glu Ile Lys
            115                 120                 125

Arg Gly Gly Gly Gly Ser Gly Gly Gly Ser Gly Gly Gly Gly Ser
130                 135                 140

Gln Val Gln Leu Lys Gln Ser Gly Ala Glu Leu Val Arg Pro Gly Ala
145                 150                 155                 160

Ser Val Lys Leu Ser Cys Lys Ala Ser Gly Tyr Thr Phe Thr Asp Tyr
                165                 170                 175

Tyr Ile Asn Trp Val Lys Gln Arg Pro Gly Gln Gly Leu Glu Trp Ile
            180                 185                 190

Ala Arg Ile Tyr Pro Gly Ser Gly Asn Thr Tyr Tyr Asn Glu Lys Phe
        195                 200                 205

Lys Gly Lys Ala Thr Leu Thr Ala Glu Lys Ser Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Gly Val Tyr Tyr Phe Asp Tyr Trp Gly Gln Gly Thr Thr Leu
                245                 250                 255

Thr Val Ser Ala Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 13
<211> LENGTH: 483
<212> TYPE: PRT
<213> ORGANISM: Homo sapiens

<400> SEQUENCE: 13
```

-continued

```
Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Ala Glu Leu
            20                  25                  30

Val Arg Pro Gly Ala Ser Val Lys Leu Ser Cys Lys Ala Ser Gly Tyr
        35                  40                  45

Thr Phe Thr Asp Tyr Tyr Ile Asn Trp Val Lys Gln Arg Pro Gly Gln
    50                  55                  60

Gly Leu Glu Trp Ile Ala Arg Ile Tyr Pro Gly Ser Gly Asn Thr Tyr
65                  70                  75                  80

Tyr Asn Glu Lys Phe Lys Gly Lys Ala Thr Leu Thr Ala Glu Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Arg Gly Val Tyr Tyr Phe Asp Tyr Trp Gly
        115                 120                 125

Gln Gly Thr Thr Leu Thr Val Ser Ser Gly Gly Gly Ser Gly Gly
    130                 135                 140

Gly Gly Ser Gly Gly Gly Ser Asp Ile Val Met Thr Gln Ser Gln
145                 150                 155                 160

Lys Phe Met Ser Thr Ser Val Gly Asp Arg Val Ser Val Thr Cys Lys
                165                 170                 175

Ala Ser Gln Asn Val Arg Thr Asn Val Ala Trp Tyr Gln Gln Lys Pro
            180                 185                 190

Gly Gln Ser Pro Lys Ala Leu Ile Tyr Ser Ala Ser Tyr Arg Tyr Ser
        195                 200                 205

Gly Val Pro Asp Arg Phe Thr Gly Ser Gly Ser Gly Thr Asp Phe Thr
    210                 215                 220

Leu Thr Ile Ser Asn Val Gln Ser Glu Asp Leu Ala Asp Tyr Phe Cys
225                 230                 235                 240

Gln Gln Tyr Asn Ser Tyr Pro Arg Thr Phe Gly Gly Gly Thr Lys Leu
                245                 250                 255

Glu Ile Lys Arg Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
```

```
                    420                 425                 430
Leu Gln Lys Asp Lys Met Ala Glu Ala Tyr Ser Glu Ile Gly Met Lys
            435                 440                 445
Gly Glu Arg Arg Gly Lys Gly His Asp Gly Leu Tyr Gln Gly Leu
        450                 455                 460
Ser Thr Ala Thr Lys Asp Thr Tyr Asp Ala Leu His Met Gln Ala Leu
465                 470                 475                 480
Pro Pro Arg

<210> SEQ ID NO 14
<211> LENGTH: 483
<212> TYPE: PRT
<213> ORGANISM: Homo sapiens

<400> SEQUENCE: 14

Met Ala Leu Pro Val Thr Ala Leu Leu Leu Pro Leu Ala Leu Leu Leu
1               5                   10                  15
His Ala Ala Arg Pro Asp Ile Val Met Thr Gln Ser Gln Lys Phe Met
            20                  25                  30
Ser Thr Ser Val Gly Asp Arg Val Ser Val Thr Cys Lys Ala Ser Gln
        35                  40                  45
Asn Val Arg Thr Asn Val Ala Trp Tyr Gln Gln Lys Pro Gly Gln Ser
    50                  55                  60
Pro Lys Ala Leu Ile Tyr Ser Ala Ser Tyr Arg Tyr Ser Gly Val Pro
65                  70                  75                  80
Asp Arg Phe Thr Gly Ser Gly Ser Gly Thr Asp Phe Thr Leu Thr Ile
                85                  90                  95
Ser Asn Val Gln Ser Glu Asp Leu Ala Asp Tyr Phe Cys Gln Gln Tyr
            100                 105                 110
Asn Ser Tyr Pro Arg Thr Phe Gly Gly Gly Thr Lys Leu Glu Ile Lys
        115                 120                 125
Arg Gly Gly Gly Gly Ser Gly Gly Gly Gly Ser Gly Gly Gly Gly Ser
    130                 135                 140
Gln Val Gln Leu Lys Gln Ser Gly Ala Glu Leu Val Arg Pro Gly Ala
145                 150                 155                 160
Ser Val Lys Leu Ser Cys Lys Ala Ser Gly Tyr Thr Phe Thr Asp Tyr
                165                 170                 175
Tyr Ile Asn Trp Val Lys Gln Arg Pro Gly Gln Gly Leu Glu Trp Ile
            180                 185                 190
Ala Arg Ile Tyr Pro Gly Ser Gly Asn Thr Tyr Tyr Asn Glu Lys Phe
        195                 200                 205
Lys Gly Lys Ala Thr Leu Thr Ala Glu Lys Ser Ser Ser Thr Ala Tyr
    210                 215                 220
Met Gln Leu Ser Ser Leu Thr Ser Glu Asp Ser Ala Val Tyr Phe Cys
225                 230                 235                 240
Ala Arg Gly Val Tyr Tyr Phe Asp Tyr Trp Gly Gln Gly Thr Thr Leu
                245                 250                 255
Thr Val Ser Ser Thr Thr Thr Pro Ala Pro Arg Pro Pro Thr Pro Ala
            260                 265                 270
Pro Thr Ile Ala Ser Gln Pro Leu Ser Leu Arg Pro Glu Ala Cys Arg
        275                 280                 285
Pro Ala Ala Gly Gly Ala Val His Thr Arg Gly Leu Asp Phe Ala Cys
    290                 295                 300
Asp Ile Tyr Ile Trp Ala Pro Leu Ala Gly Thr Cys Gly Val Leu Leu
```

```
              305                 310                 315                 320
Leu Ser Leu Val Ile Thr Leu Tyr Cys Lys Arg Gly Arg Lys Lys Leu
                    325                 330                 335

Leu Tyr Ile Phe Lys Gln Pro Phe Met Arg Pro Val Gln Thr Thr Gln
                340                 345                 350

Glu Glu Asp Gly Cys Ser Cys Arg Phe Pro Glu Glu Glu Glu Gly Gly
            355                 360                 365

Cys Glu Leu Arg Val Lys Phe Ser Arg Ser Ala Asp Ala Pro Ala Tyr
        370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg

<210> SEQ ID NO 15
<211> LENGTH: 487
<212> TYPE: PRT
<213> ORGANISM: Homo sapiens

<400> SEQUENCE: 15

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Asn Tyr Leu Met Ser Trp Val Arg Gln Ala Pro Gly Lys
        50                  55                  60

Gly Leu Glu Trp Val Ser Ser Ile Val Pro Ser Gly Gly Phe Thr His
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Leu Gln Thr Gly Ser Trp Arg Val His
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Thr Ser Leu Ser Ala Phe Val Gly Asp Arg
                165                 170                 175

Val Thr Ile Thr Cys Gln Ala Ser Gln Asp Ile Gly Asn Tyr Leu Asn
            180                 185                 190

Trp Tyr Gln Gln Lys Ser Gly Glu Pro Pro Lys Leu Leu Val Tyr Asp
```

```
            195                 200                 205
Ala Ser Phe Leu Lys Lys Gly Val Pro Ser Arg Phe Ser Gly Ser Gly
    210                 215                 220

Ser Gly Thr Gln Tyr Phe Leu Thr Ile Tyr Ser Leu Gln Pro Glu Asp
225                 230                 235                 240

Phe Ala Thr Tyr Phe Cys Gln His Ser Asp Asn Leu Ser Val Thr Phe
                245                 250                 255

Gly Gly Gly Thr Lys Val Glu Val Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro
                485

<210> SEQ ID NO 16
<211> LENGTH: 488
<212> TYPE: PRT
<213> ORGANISM: Homo sapiens

<400> SEQUENCE: 16

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Thr Ser Leu
            20                  25                  30

Ser Ala Phe Val Gly Asp Arg Val Thr Ile Thr Cys Gln Ala Ser Gln
        35                  40                  45

Asp Ile Gly Asn Tyr Leu Asn Trp Tyr Gln Gln Lys Ser Gly Glu Pro
    50                  55                  60

Pro Lys Leu Leu Val Tyr Asp Ala Ser Phe Leu Lys Lys Gly Val Pro
65                  70                  75                  80
```

-continued

```
Ser Arg Phe Ser Gly Ser Gly Ser Gly Thr Gln Tyr Phe Leu Thr Ile
                85                  90                  95

Tyr Ser Leu Gln Pro Glu Asp Phe Ala Thr Tyr Phe Cys Gln His Ser
            100                 105                 110

Asp Asn Leu Ser Val Thr Phe Gly Gly Gly Thr Lys Val Glu Val Lys
            115                 120                 125

Gly Gly Gly Gly Ser Gly Gly Gly Ser Gly Gly Gly Gly Ser Glu
            130                 135                 140

Val Gln Leu Leu Glu Ser Gly Gly Gly Leu Val Gln Pro Gly Gly Ser
145                 150                 155                 160

Leu Arg Leu Ser Cys Ala Ala Ser Gly Phe Thr Phe Ser Asn Tyr Leu
                165                 170                 175

Met Ser Trp Val Arg Gln Ala Pro Gly Lys Gly Leu Glu Trp Val Ser
            180                 185                 190

Ser Ile Val Pro Ser Gly Gly Phe Thr His Tyr Ala Asp Ser Val Lys
            195                 200                 205

Gly Arg Phe Thr Ile Ser Arg Asp Asn Ser Lys Asn Thr Leu Tyr Leu
            210                 215                 220

Gln Met Asn Ser Leu Arg Ala Glu Asp Thr Ala Val Tyr Tyr Cys Ala
225                 230                 235                 240

Arg Leu Gln Thr Gly Ser Trp Arg Val His Ala Phe Asp Ile Trp Gly
                245                 250                 255

Gln Gly Thr Met Val Thr Val Ser Ser Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

-continued

```
<210> SEQ ID NO 17
<211> LENGTH: 488
<212> TYPE: PRT
<213> ORGANISM: Homo sapiens

<400> SEQUENCE: 17

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Leu Met Ser Trp Val Arg Gln Ala Pro Gly Lys
    50                  55                  60

Gly Leu Glu Trp Val Ser Ser Ile Val Pro Ser Gly Gly Phe Thr His
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Leu Gln Thr Gly Ser Trp Arg Val His
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Thr Ser Leu Ser Ala Phe Val Gly Asp Arg
                165                 170                 175

Val Thr Ile Thr Cys Gln Ala Ser Gln Asp Ile Gly Asn Tyr Leu Asn
            180                 185                 190

Trp Tyr Gln Gln Lys Ser Gly Glu Pro Pro Lys Leu Leu Val Tyr Asp
        195                 200                 205

Ala Ser Phe Leu Lys Lys Gly Val Pro Ser Arg Phe Ser Gly Ser Gly
    210                 215                 220

Ser Gly Thr Gln Tyr Phe Leu Thr Ile Tyr Ser Leu Gln Pro Glu Asp
225                 230                 235                 240

Phe Ala Thr Tyr Phe Cys Gln His Ser Asp Ser Leu Ser Val Thr Phe
                245                 250                 255

Gly Gly Gly Thr Lys Val Glu Val Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380
```

```
Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 18
<211> LENGTH: 488
<212> TYPE: PRT
<213> ORGANISM: Homo sapiens

<400> SEQUENCE: 18

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Thr Ser Leu
                20                  25                  30

Ser Ala Phe Val Gly Asp Arg Val Thr Ile Thr Cys Gln Ala Ser Gln
            35                  40                  45

Asp Ile Gly Asn Tyr Leu Asn Trp Tyr Gln Gln Lys Ser Gly Glu Pro
    50                  55                  60

Pro Lys Leu Leu Val Tyr Asp Ala Ser Phe Leu Lys Lys Gly Val Pro
65                  70                  75                  80

Ser Arg Phe Ser Gly Ser Gly Ser Gly Thr Gln Tyr Phe Leu Thr Ile
                85                  90                  95

Tyr Ser Leu Gln Pro Glu Asp Phe Ala Thr Tyr Phe Cys Gln His Ser
                100                 105                 110

Asp Ser Leu Ser Val Thr Phe Gly Gly Gly Thr Lys Val Glu Val Lys
            115                 120                 125

Gly Gly Gly Gly Ser Gly Gly Gly Ser Gly Gly Gly Gly Ser Glu
    130                 135                 140

Val Gln Leu Leu Glu Ser Gly Gly Gly Leu Val Gln Pro Gly Gly Ser
145                 150                 155                 160

Leu Arg Leu Ser Cys Ala Ala Ser Gly Phe Thr Phe Ser Asn Tyr Leu
                165                 170                 175

Met Ser Trp Val Arg Gln Ala Pro Gly Lys Gly Leu Glu Trp Val Ser
                180                 185                 190

Ser Ile Val Pro Ser Gly Gly Phe Thr His Tyr Ala Asp Ser Val Lys
            195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Arg Leu Gln Thr Gly Ser Trp Arg Val His Ala Phe Asp Ile Trp Gly
                245                 250                 255

Gln Gly Thr Met Val Thr Val Ser Ser Thr Thr Thr Pro Ala Pro Arg
                260                 265                 270
```

```
Pro Pro Thr Pro Ala Pro Thr Ile Ala Ser Gln Pro Leu Ser Leu Arg
        275                 280                 285
Pro Glu Ala Cys Arg Pro Ala Ala Gly Gly Ala Val His Thr Arg Gly
        290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
                340                 345                 350
Val Gln Thr Thr Gln Glu Glu Asp Gly Cys Ser Cys Arg Phe Pro Glu
                355                 360                 365
Glu Glu Glu Gly Gly Cys Glu Leu Arg Val Lys Phe Ser Arg Ser Ala
                370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
                420                 425                 430
Gly Leu Tyr Asn Glu Leu Gln Lys Asp Lys Met Ala Glu Ala Tyr Ser
                435                 440                 445
Glu Ile Gly Met Lys Gly Glu Arg Arg Arg Gly Lys Gly His Asp Gly
                450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 19
<211> LENGTH: 525
<212> TYPE: PRT
<213> ORGANISM: Homo sapiens

<400> SEQUENCE: 19

Met Ala Leu Pro Val Thr Ala Leu Leu Leu Pro Leu Ala Leu Leu Leu
1               5                   10                  15
His Ala Ala Arg Pro Gly Pro Gly Gly Arg Ala Arg His Cys Ser Leu
                20                  25                  30
Pro Val Ser Ser Asn His Val Cys Ile Ser Arg Gly Glu Gly His His
                35                  40                  45
Ile Leu Gln Cys Gln Leu Lys Cys Lys Leu Tyr Val Leu Val Pro Ala
        50                  55                  60
Glu Pro Gly Ser Ser Pro Lys Pro Trp Ile Tyr Arg Thr Ser Asn Leu
65              70                  75                  80
Ala Ser Gly Val Pro Ala Arg Phe Ser Gly Ser Gly Ser Gly Thr Ser
                85                  90                  95
Tyr Ser Leu Thr Ile Ser Ser Met Glu Ala Glu Asp Ala Ala Thr Tyr
                100                 105                 110
Tyr Cys Gln Gln Tyr His Ser Tyr Pro Pro Thr Phe Gly Ala Gly Thr
                115                 120                 125
Lys Leu Glu Leu Lys Ser Ser Gly Gly Gly Ser Gly Gly Gly Gly
                130                 135                 140
Gly Gly Ser Ser Arg Ser Ser Leu Glu Val Lys Leu Val Glu Ser Gly
```

```
            145                 150                 155                 160
    Pro Glu Leu Lys Lys Pro Gly Glu Thr Val Lys Ile Ser Cys Lys Ala
                        165                 170                 175

Ser Gly Tyr Thr Phe Thr Asp Tyr Ser Met His Trp Val Asn Gln Ala
                        180                 185                 190

Pro Gly Lys Gly Leu Lys Trp Met Gly Trp Ile Asn Thr Glu Thr Gly
                        195                 200                 205

Glu Pro Ser Tyr Ala Asp Asp Phe Lys Gly Arg Phe Ala Phe Ser Leu
    210                 215                 220

Glu Thr Ser Ala Ser Thr Ala Tyr Leu Gln Ile Asn Asn Leu Lys Asn
    225                 230                 235                 240

Glu Asp Thr Ala Thr Tyr Phe Cys Ala Thr Asp Tyr Gly Asp Tyr Phe
                        245                 250                 255

Asp Tyr Trp Gly Gln Gly Thr Thr Leu Thr Val Ser Ser Ala Lys Thr
                        260                 265                 270

Thr Pro Pro Ser Val Thr Ser Gly Gln Ala Gly Gln His His His His
                        275                 280                 285

His His Gly Ala Tyr Pro Tyr Asp Val Pro Asp Tyr Ala Ser Thr Thr
                290                 295                 300

Thr Pro Ala Pro Arg Pro Pro Thr Pro Ala Pro Thr Ile Ala Ser Gln
    305                 310                 315                 320

Pro Leu Ser Leu Arg Pro Glu Ala Cys Arg Pro Ala Ala Gly Gly Ala
                        325                 330                 335

Val His Thr Arg Gly Leu Asp Phe Ala Cys Asp Ile Tyr Ile Trp Ala
                        340                 345                 350

Pro Leu Ala Gly Thr Cys Gly Val Leu Leu Leu Ser Leu Val Ile Thr
                        355                 360                 365

Leu Tyr Cys Lys Arg Gly Arg Lys Lys Leu Leu Tyr Ile Phe Lys Gln
                        370                 375                 380

Pro Phe Met Arg Pro Val Gln Thr Thr Gln Glu Glu Asp Gly Cys Ser
    385                 390                 395                 400

Cys Arg Phe Pro Glu Glu Glu Glu Gly Gly Cys Glu Leu Arg Val Lys
                        405                 410                 415

Phe Ser Arg Ser Ala Asp Ala Pro Ala Tyr Lys Gln Gly Gln Asn Gln
                        420                 425                 430

Leu Tyr Asn Glu Leu Asn Leu Gly Arg Arg Glu Glu Tyr Asp Val Leu
                        435                 440                 445

Asp Lys Arg Arg Gly Arg Asp Pro Glu Met Gly Gly Lys Pro Arg Arg
    450                 455                 460

Lys Asn Pro Gln Glu Gly Leu Tyr Asn Glu Leu Gln Lys Asp Lys Met
    465                 470                 475                 480

Ala Glu Ala Tyr Ser Glu Ile Gly Met Lys Gly Glu Arg Arg Arg Gly
                        485                 490                 495

Lys Gly His Asp Gly Leu Tyr Gln Gly Leu Ser Thr Ala Thr Lys Asp
                        500                 505                 510

Thr Tyr Asp Ala Leu His Met Gln Ala Leu Pro Pro Arg
                        515                 520                 525

<210> SEQ ID NO 20
<211> LENGTH: 482
<212> TYPE: PRT
<213> ORGANISM: Homo sapiens

<400> SEQUENCE: 20
```

-continued

```
Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asp Tyr Ser Met His Trp Val Asn Gln Ala Pro Gly Lys
    50                  55                  60

Gly Leu Lys Trp Met Gly Trp Ile Asn Thr Thr Gly Glu Pro Ser
65                  70                  75                  80

Tyr Ala Asp Asp Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Thr Asp Tyr Gly Asp Tyr Phe Asp Tyr Trp
        115                 120                 125

Gly Gln Gly Thr Thr Leu Thr Val Ser Ser Gly Gly Gly Gly Ser Gly
    130                 135                 140

Gly Gly Ser Gly Gly Gly Ser Asp Ile Val Leu Ser Gln Ser
145                 150                 155                 160

Pro Ala Ile Met Ser Ala Ser Pro Gly Glu Lys Val Thr Ile Ser Cys
                165                 170                 175

Ser Ala Ser Ser Ser Val Ser Tyr Met Tyr Trp Tyr Gln Gln Lys Pro
            180                 185                 190

Gly Ser Ser Pro Lys Pro Trp Ile Tyr Arg Thr Ser Asn Leu Ala Ser
        195                 200                 205

Gly Val Pro Ala Arg Phe Ser Gly Ser Gly Ser Gly Thr Ser Tyr Ser
    210                 215                 220

Leu Thr Ile Ser Ser Met Glu Ala Glu Asp Ala Ala Thr Tyr Tyr Cys
225                 230                 235                 240

Gln Gln Tyr His Ser Tyr Pro Pro Thr Phe Gly Ala Gly Thr Lys Leu
                245                 250                 255

Glu Leu Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Lys
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
```

```
                  420                 425                 430
Gln Lys Asp Lys Met Ala Glu Ala Tyr Ser Glu Ile Gly Met Lys Gly
                435                 440                 445

Glu Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 21
<211> LENGTH: 486
<212> TYPE: PRT
<213> ORGANISM: Homo sapiens

<400> SEQUENCE: 21

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Pro Glu Leu
                20                  25                  30

Lys Lys Pro Gly Glu Thr Val Lys Ile Ser Cys Lys Ala Ser Gly Tyr
            35                  40                  45

Thr Phe Thr Asp Tyr Ser Met His Trp Val Asn Gln Ala Pro Gly Lys
    50                  55                  60

Gly Leu Lys Trp Met Gly Trp Ile Asn Thr Glu Thr Gly Glu Pro Ser
65              70                  75                  80

Tyr Ala Asp Asp Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Thr Asp Tyr Gly Asp Tyr Phe Asp Tyr Trp
        115                 120                 125

Gly Gln Gly Thr Thr Leu Thr Val Ser Ser Ser Gly Gly Gly Gly
    130                 135                 140

Ser Gly Gly Gly Gly Gly Ser Ser Arg Ser Ser Leu Asp Ile Val
145                 150                 155                 160

Leu Ser Gln Ser Pro Ala Ile Met Ser Ala Ser Pro Gly Glu Lys Val
                165                 170                 175

Thr Ile Ser Cys Ser Ala Ser Ser Val Ser Tyr Met Tyr Trp Tyr
            180                 185                 190

Gln Gln Lys Pro Gly Ser Ser Pro Lys Pro Trp Ile Tyr Arg Thr Ser
        195                 200                 205

Asn Leu Ala Ser Gly Val Pro Ala Arg Phe Ser Gly Ser Gly Ser Gly
    210                 215                 220

Thr Ser Tyr Ser Leu Thr Ile Ser Ser Met Glu Ala Glu Asp Ala Ala
225                 230                 235                 240

Thr Tyr Tyr Cys Gln Gln Tyr His Ser Tyr Pro Pro Thr Phe Gly Ala
                245                 250                 255

Gly Thr Lys Leu Glu Leu Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
```

```
               305                 310                 315                 320
   Val Leu Leu Leu Ser Leu Val Ile Thr Leu Tyr Cys Lys Arg Gly Arg
                   325                 330                 335

Lys Lys Leu Leu Tyr Ile Phe Lys Gln Pro Phe Met Arg Pro Val Gln
                   340                 345                 350

Thr Thr Gln Glu Glu Asp Gly Cys Ser Cys Arg Phe Pro Glu Glu Glu
                   355                 360                 365

Glu Gly Gly Cys Glu Leu Arg Val Lys Phe Ser Arg Ser Ala Asp Ala
               370                 375                 380

Pro Ala Tyr Lys Gln Gly Gln Asn Gln Leu Tyr Asn Glu Leu Asn Leu
   385                 390                 395                 400

Gly Arg Arg Glu Glu Tyr Asp Val Leu Asp Lys Arg Arg Gly Arg Asp
                   405                 410                 415

Pro Glu Met Gly Gly Lys Pro Arg Arg Lys Asn Pro Gln Glu Gly Leu
                   420                 425                 430

Tyr Asn Glu Leu Gln Lys Asp Lys Met Ala Glu Ala Tyr Ser Glu Ile
                   435                 440                 445

Gly Met Lys Gly Glu Arg Arg Arg Gly Lys Gly His Asp Gly Leu Tyr
               450                 455                 460

Gln Gly Leu Ser Thr Ala Thr Lys Asp Thr Tyr Asp Ala Leu His Met
   465                 470                 475                 480

Gln Ala Leu Pro Pro Arg
                   485

<210> SEQ ID NO 22
<211> LENGTH: 482
<212> TYPE: PRT
<213> ORGANISM: Homo sapiens

<400> SEQUENCE: 22

Met Ala Leu Pro Val Thr Ala Leu Leu Leu Pro Leu Ala Leu Leu Leu
   1               5                   10                  15

His Ala Ala Arg Pro Asp Ile Val Leu Ser Gln Ser Pro Ala Ile Met
                   20                  25                  30

Ser Ala Ser Pro Gly Glu Lys Val Thr Ile Ser Cys Ser Ala Ser Ser
                   35                  40                  45

Ser Val Ser Tyr Met Tyr Trp Tyr Gln Gln Lys Pro Gly Ser Ser Pro
               50                  55                  60

Lys Pro Trp Ile Tyr Arg Thr Ser Asn Leu Ala Ser Gly Val Pro Ala
   65                  70                  75                  80

Arg Phe Ser Gly Ser Gly Ser Gly Thr Ser Tyr Ser Leu Thr Ile Ser
                   85                  90                  95

Ser Met Glu Ala Glu Asp Ala Thr Tyr Tyr Cys Gln Gln Tyr His
                   100                 105                 110

Ser Tyr Pro Pro Thr Phe Gly Ala Gly Thr Lys Leu Glu Leu Lys Gly
               115                 120                 125

Gly Gly Gly Ser Gly Gly Gly Gly Ser Gly Gly Gly Gly Ser Glu Val
               130                 135                 140

Lys Leu Val Glu Ser Gly Pro Glu Leu Lys Lys Pro Gly Glu Thr Val
   145                 150                 155                 160

Lys Ile Ser Cys Lys Ala Ser Gly Tyr Thr Phe Thr Asp Tyr Ser Met
                   165                 170                 175

His Trp Val Asn Gln Ala Pro Gly Lys Gly Leu Lys Trp Met Gly Trp
                   180                 185                 190
```

```
Ile Asn Thr Glu Thr Gly Glu Pro Ser Tyr Ala Asp Phe Lys Gly
            195                 200                 205
Arg Phe Ala Phe Ser Leu Glu Thr Ser Ala Ser Thr Ala Tyr Leu Gln
210                 215                 220
Ile Asn Asn Leu Lys Asn Glu Asp Thr Ala Thr Tyr Phe Cys Ala Thr
225                 230                 235                 240
Asp Tyr Gly Asp Tyr Phe Asp Tyr Trp Gly Gln Gly Thr Thr Leu Thr
                245                 250                 255
Val Ser Ser Thr Thr Thr Pro Ala Pro Arg Pro Pro Thr Pro Ala Pro
            260                 265                 270
Thr Ile Ala Ser Gln Pro Leu Ser Leu Arg Pro Glu Ala Cys Arg Pro
            275                 280                 285
Ala Ala Gly Gly Ala Val His Thr Arg Gly Leu Asp Phe Ala Cys Asp
290                 295                 300
Ile Tyr Ile Trp Ala Pro Leu Ala Gly Thr Cys Gly Val Leu Leu Leu
305                 310                 315                 320
Ser Leu Val Ile Thr Leu Tyr Cys Lys Arg Gly Arg Lys Lys Leu Leu
                325                 330                 335
Tyr Ile Phe Lys Gln Pro Phe Met Arg Pro Val Gln Thr Thr Gln Glu
            340                 345                 350
Glu Asp Gly Cys Ser Cys Arg Phe Pro Glu Glu Glu Glu Gly Gly Cys
            355                 360                 365
Glu Leu Arg Val Lys Phe Ser Arg Ser Ala Asp Ala Pro Ala Tyr Lys
            370                 375                 380
Gln Gly Gln Asn Gln Leu Tyr Asn Glu Leu Asn Leu Gly Arg Arg Glu
385                 390                 395                 400
Glu Tyr Asp Val Leu Asp Lys Arg Arg Gly Arg Asp Pro Glu Met Gly
                405                 410                 415
Gly Lys Pro Arg Arg Lys Asn Pro Gln Glu Gly Leu Tyr Asn Glu Leu
            420                 425                 430
Gln Lys Asp Lys Met Ala Glu Ala Tyr Ser Glu Ile Gly Met Lys Gly
            435                 440                 445
Glu Arg Arg Arg Gly Lys Gly His Asp Gly Leu Tyr Gln Gly Leu Ser
450                 455                 460
Thr Ala Thr Lys Asp Thr Tyr Asp Ala Leu His Met Gln Ala Leu Pro
465                 470                 475                 480
Pro Arg

<210> SEQ ID NO 23
<211> LENGTH: 486
<212> TYPE: PRT
<213> ORGANISM: Homo sapiens

<400> SEQUENCE: 23

Met Ala Leu Pro Val Thr Ala Leu Leu Leu Pro Leu Ala Leu Leu Leu
1               5                   10                  15
His Ala Ala Arg Pro Asp Ile Val Leu Ser Gln Ser Pro Ala Ile Met
                20                  25                  30
Ser Ala Ser Pro Gly Glu Lys Val Thr Ile Ser Cys Ser Ala Ser Ser
            35                  40                  45
Ser Val Ser Tyr Met Tyr Trp Tyr Gln Gln Lys Pro Gly Ser Ser Pro
        50                  55                  60
Lys Pro Trp Ile Tyr Arg Thr Ser Asn Leu Ala Ser Gly Val Pro Ala
65                  70                  75                  80
```

```
Arg Phe Ser Gly Ser Gly Ser Gly Thr Ser Tyr Ser Leu Thr Ile Ser
                 85                  90                  95

Ser Met Glu Ala Glu Asp Ala Ala Thr Tyr Tyr Cys Gln Gln Tyr His
            100                 105                 110

Ser Tyr Pro Pro Thr Phe Gly Ala Gly Thr Lys Leu Glu Leu Lys Ser
        115                 120                 125

Ser Gly Gly Gly Gly Ser Gly Gly Gly Gly Gly Ser Ser Arg Ser
    130                 135                 140

Ser Leu Glu Val Lys Leu Val Glu Ser Gly Pro Glu Leu Lys Lys Pro
145                 150                 155                 160

Gly Glu Thr Val Lys Ile Ser Cys Lys Ala Ser Gly Tyr Thr Phe Thr
                165                 170                 175

Asp Tyr Ser Met His Trp Val Asn Gln Ala Pro Gly Lys Gly Leu Lys
            180                 185                 190

Trp Met Gly Trp Ile Asn Thr Glu Thr Gly Glu Pro Ser Tyr Ala Asp
        195                 200                 205

Asp Phe Lys Gly Arg Phe Ala Phe Ser Leu Glu Thr Ser Ala Ser Thr
    210                 215                 220

Ala Tyr Leu Gln Ile Asn Asn Leu Lys Asn Glu Asp Thr Ala Thr Tyr
225                 230                 235                 240

Phe Cys Ala Thr Asp Tyr Gly Asp Tyr Phe Asp Tyr Trp Gly Gln Gly
                245                 250                 255

Thr Thr Leu Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
            485
```

```
<210> SEQ ID NO 24
<211> LENGTH: 482
<212> TYPE: PRT
<213> ORGANISM: Homo sapiens

<400> SEQUENCE: 24

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asp Tyr Ser Met His Trp Val Asn Gln Ala Pro Gly Lys
    50                  55                  60

Gly Leu Lys Trp Met Gly Trp Ile Asn Thr Glu Thr Gly Glu Pro Ser
65                  70                  75                  80

Tyr Ala Asp Asp Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Thr Asp Tyr Gly Asp Tyr Phe Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Ser Asp Ile Val Leu Thr Gln Ser
145                 150                 155                 160

Pro Ala Ile Met Ser Ala Ser Pro Gly Glu Lys Val Thr Ile Ser Cys
                165                 170                 175

Ser Ala Ser Ser Ser Val Ser Tyr Met Tyr Trp Tyr Gln Gln Lys Pro
            180                 185                 190

Gly Gln Pro Pro Arg Leu Leu Ile Tyr Leu Val Ser Asn Leu Glu Ser
        195                 200                 205

Gly Val Pro Ala Arg Phe Ser Gly Ser Gly Ser Gly Thr Asp Phe Thr
    210                 215                 220

Leu Asn Ile His Pro Val Glu Glu Glu Asp Ala Ala Thr Tyr Tyr Cys
225                 230                 235                 240

Gln Gln Tyr His Ser Tyr Pro Pro Thr Phe Gly Ala Gly Thr Lys Leu
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Lys
    370                 375                 380
```

-continued

```
Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
        420                 425                 430

Gln Lys Asp Lys Met Ala Glu Ala Tyr Ser Glu Ile Gly Met Lys Gly
    435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 25
<211> LENGTH: 486
<212> TYPE: PRT
<213> ORGANISM: Homo sapiens

<400> SEQUENCE: 25

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Asp Tyr Ser Met His Trp Val Asn Gln Ala Pro Gly Lys
    50                  55                  60

Gly Leu Lys Trp Met Gly Trp Ile Asn Thr Glu Thr Gly Glu Pro Ser
65                  70                  75                  80

Tyr Ala Asp Asp Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Thr Asp Tyr Gly Asp Tyr Phe Asp Tyr Trp
        115                 120                 125

Gly Gln Gly Thr Thr Leu Thr Val Ser Ser Ser Gly Gly Gly Gly
    130                 135                 140

Ser Gly Gly Gly Gly Gly Ser Ser Arg Ser Ser Leu Asp Ile Val
145                 150                 155                 160

Leu Thr Gln Ser Pro Ala Ile Met Ser Ala Ser Pro Gly Glu Lys Val
                165                 170                 175

Thr Ile Ser Cys Ser Ala Ser Ser Val Ser Tyr Met Tyr Trp Tyr
            180                 185                 190

Gln Gln Lys Pro Gly Gln Pro Pro Arg Leu Leu Ile Tyr Leu Val Ser
        195                 200                 205

Asn Leu Glu Ser Gly Val Pro Ala Arg Phe Ser Gly Ser Gly Ser Gly
    210                 215                 220

Thr Asp Phe Thr Leu Asn Ile His Pro Val Glu Glu Glu Asp Ala Ala
225                 230                 235                 240

Thr Tyr Tyr Cys Gln Gln Tyr His Ser Tyr Pro Pro Thr Phe Gly Ala
                245                 250                 255

Gly Thr Lys Leu Glu Ile Lys Thr Thr Thr Pro Ala Pro Arg Pro Pro
            260                 265                 270
```

```
Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
        370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 26
<211> LENGTH: 482
<212> TYPE: PRT
<213> ORGANISM: Homo sapiens

<400> SEQUENCE: 26

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ile Met
                20                  25                  30

Ser Ala Ser Pro Gly Glu Lys Val Thr Ile Ser Cys Ser Ala Ser Ser
            35                  40                  45

Ser Val Ser Tyr Met Tyr Trp Tyr Gln Gln Lys Pro Gly Gln Pro Pro
        50                  55                  60

Arg Leu Leu Ile Tyr Leu Val Ser Asn Leu Glu Ser Gly Val Pro Ala
65                  70                  75                  80

Arg Phe Ser Gly Ser Gly Ser Gly Thr Asp Phe Thr Leu Asn Ile His
                85                  90                  95

Pro Val Glu Glu Glu Asp Ala Ala Thr Tyr Tyr Cys Gln Gln Tyr His
                100                 105                 110

Ser Tyr Pro Pro Thr Phe Gly Ala Gly Thr Lys Leu Glu Ile Lys Gly
            115                 120                 125

Gly Gly Gly Ser Gly Gly Gly Gly Ser Gly Gly Gly Gly Ser Glu Val
        130                 135                 140

Lys Leu Val Glu Ser Gly Pro Glu Leu Lys Lys Pro Gly Glu Thr Val
145                 150                 155                 160
```

```
Lys Ile Ser Cys Lys Ala Ser Gly Tyr Thr Phe Thr Asp Tyr Ser Met
                165                 170                 175

His Trp Val Asn Gln Ala Pro Gly Lys Gly Leu Lys Trp Met Gly Trp
            180                 185                 190

Ile Asn Thr Glu Thr Gly Glu Pro Ser Tyr Ala Asp Asp Phe Lys Gly
        195                 200                 205

Arg Phe Ala Phe Ser Leu Glu Thr Ser Ala Ser Thr Ala Tyr Leu Gln
    210                 215                 220

Ile Asn Asn Leu Lys Asn Glu Asp Thr Ala Thr Tyr Phe Cys Ala Thr
225                 230                 235                 240

Asp Tyr Gly Asp Tyr Phe Asp Tyr Trp Gly Gln Gly Thr Thr Leu Thr
                245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Lys
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 27
<211> LENGTH: 486
<212> TYPE: PRT
<213> ORGANISM: Homo sapiens

<400> SEQUENCE: 27

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ile Met
            20                  25                  30

Ser Ala Ser Pro Gly Glu Lys Val Thr Ile Ser Cys Ser Ala Ser Ser
        35                  40                  45
```

```
Ser Val Ser Tyr Met Tyr Trp Tyr Gln Gln Lys Pro Gly Gln Pro Pro
 50                  55                  60

Arg Leu Leu Ile Tyr Leu Val Ser Asn Leu Glu Ser Gly Val Pro Ala
 65                  70                  75                  80

Arg Phe Ser Gly Ser Gly Ser Gly Thr Asp Phe Thr Leu Asn Ile His
                 85                  90                  95

Pro Val Glu Glu Glu Asp Ala Ala Thr Tyr Tyr Cys Gln Gln Tyr His
            100                 105                 110

Ser Tyr Pro Pro Thr Phe Gly Ala Gly Thr Lys Leu Glu Ile Lys Ser
        115                 120                 125

Ser Gly Gly Gly Gly Ser Gly Gly Gly Gly Ser Ser Arg Ser
        130                 135                 140

Ser Leu Glu Val Lys Leu Val Glu Ser Gly Pro Glu Leu Lys Lys Pro
145                 150                 155                 160

Gly Glu Thr Val Lys Ile Ser Cys Lys Ala Ser Gly Tyr Thr Phe Thr
                165                 170                 175

Asp Tyr Ser Met His Trp Val Asn Gln Ala Pro Gly Lys Gly Leu Lys
            180                 185                 190

Trp Met Gly Trp Ile Asn Thr Glu Thr Gly Glu Pro Ser Tyr Ala Asp
        195                 200                 205

Asp Phe Lys Gly Arg Phe Ala Phe Ser Leu Glu Thr Ser Ala Ser Thr
210                 215                 220

Ala Tyr Leu Gln Ile Asn Asn Leu Lys Asn Glu Asp Thr Ala Thr Tyr
225                 230                 235                 240

Phe Cys Ala Thr Asp Tyr Gly Asp Tyr Phe Asp Tyr Trp Gly Gln Gly
                245                 250                 255

Thr Thr Leu Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
450                 455                 460
```

-continued

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 28
<211> LENGTH: 1368
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

Xaa Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys 325                 330                 335
Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

```
Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155
```

-continued

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 29
<211> LENGTH: 1053
<212> TYPE: PRT
<213> ORGANISM: Homo sapiens

<400> SEQUENCE: 29

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

```
Asp Gly Glu Val Arg Gly Ser Ile Asn Arg Phe Lys Thr Ser Asp Tyr
            165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
            210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
            245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
            290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
            325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
            370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
            405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
            450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
            530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
            565                 570                 575
```

```
Gln Glu Glu Ala Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Tyr Glu Glu Thr Gly Asn Tyr
                850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Glu Val Asn Ser
                930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr  Tyr Arg Glu Tyr Leu  Glu Asn Met
```

```
                995                 1000                1005
Asn Asp Lys Arg Pro Pro Arg Ile Ile Lys Thr Ile Ala Ser Lys
               1010                 1015                1020

Thr Gln Ser Ile Lys Lys Tyr Ser Thr Asp Ile Leu Gly Asn Leu
               1025                 1030                1035

Tyr Glu Val Lys Ser Lys Lys His Pro Gln Ile Ile Lys Lys Gly
               1040                 1045                1050

<210> SEQ ID NO 30
<211> LENGTH: 1591
<212> TYPE: PRT
<213> ORGANISM: Homo sapiens

<400> SEQUENCE: 30

Met Ala Pro Lys Lys Arg Lys Val Glu Gly Ile Lys Ser Asn Ile
  1               5                  10                  15

Ser Leu Leu Lys Asp Glu Leu Arg Gly Gln Ile Ser His Ile Ser His
                 20                  25                  30

Glu Tyr Leu Ser Leu Ile Asp Leu Ala Phe Asp Ser Lys Gln Asn Arg
                 35                  40                  45

Leu Phe Glu Met Lys Val Leu Glu Leu Val Asn Glu Tyr Gly Phe
 50                  55                  60

Lys Gly Arg His Leu Gly Gly Ser Arg Lys Pro Asp Gly Ile Val Tyr
 65                  70                  75                  80

Ser Thr Thr Leu Glu Asp Asn Phe Gly Ile Ile Val Asp Thr Lys Ala
                 85                  90                  95

Tyr Ser Glu Gly Tyr Ser Leu Pro Ile Ser Gln Ala Asp Glu Met Glu
                100                 105                 110

Arg Tyr Val Arg Glu Asn Ser Asn Arg Asp Glu Glu Val Asn Pro Asn
                115                 120                 125

Lys Trp Trp Glu Asn Phe Ser Glu Glu Val Lys Lys Tyr Tyr Phe Val
130                 135                 140

Phe Ile Ser Gly Ser Phe Lys Gly Lys Phe Glu Glu Gln Leu Arg Arg
145                 150                 155                 160

Leu Ser Met Thr Thr Gly Val Asn Gly Ser Ala Val Asn Val Val Asn
                165                 170                 175

Leu Leu Leu Gly Ala Glu Lys Ile Arg Ser Gly Glu Met Thr Ile Glu
                180                 185                 190

Glu Leu Glu Arg Ala Met Phe Asn Asn Ser Glu Phe Ile Leu Lys Tyr
                195                 200                 205

Gly Gly Gly Gly Ser Asp Lys Lys Tyr Ser Ile Gly Leu Ala Ile Gly
                210                 215                 220

Thr Asn Ser Val Gly Trp Ala Val Ile Thr Asp Glu Tyr Lys Val Pro
225                 230                 235                 240

Ser Lys Lys Phe Lys Val Leu Gly Asn Thr Asp Arg His Ser Ile Lys
                245                 250                 255

Lys Asn Leu Ile Gly Ala Leu Leu Phe Asp Ser Gly Glu Thr Ala Glu
                260                 265                 270

Ala Thr Arg Leu Lys Arg Thr Ala Arg Arg Tyr Thr Arg Arg Lys
                275                 280                 285

Asn Arg Ile Cys Tyr Leu Gln Glu Ile Phe Ser Asn Glu Met Ala Lys
                290                 295                 300

Val Asp Asp Ser Phe Phe His Arg Leu Glu Glu Ser Phe Leu Val Glu
305                 310                 315                 320
```

```
Glu Asp Lys Lys His Glu Arg His Pro Ile Phe Gly Asn Ile Val Asp
                325                 330                 335

Glu Val Ala Tyr His Glu Lys Tyr Pro Thr Ile Tyr His Leu Arg Lys
            340                 345                 350

Lys Leu Val Asp Ser Thr Asp Lys Ala Asp Leu Arg Leu Ile Tyr Leu
            355                 360                 365

Ala Leu Ala His Met Ile Lys Phe Arg Gly His Phe Leu Ile Glu Gly
        370                 375                 380

Asp Leu Asn Pro Asp Asn Ser Asp Val Asp Lys Leu Phe Ile Gln Leu
385                 390                 395                 400

Val Gln Thr Tyr Asn Gln Leu Phe Glu Glu Asn Pro Ile Asn Ala Ser
                405                 410                 415

Gly Val Asp Ala Lys Ala Ile Leu Ser Ala Arg Leu Ser Lys Ser Arg
            420                 425                 430

Arg Leu Glu Asn Leu Ile Ala Gln Leu Pro Gly Glu Lys Lys Asn Gly
        435                 440                 445

Leu Phe Gly Asn Leu Ile Ala Leu Ser Leu Gly Leu Thr Pro Asn Phe
    450                 455                 460

Lys Ser Asn Phe Asp Leu Ala Glu Asp Ala Lys Leu Gln Leu Ser Lys
465                 470                 475                 480

Asp Thr Tyr Asp Asp Asp Leu Asp Asn Leu Leu Ala Gln Ile Gly Asp
                485                 490                 495

Gln Tyr Ala Asp Leu Phe Leu Ala Ala Lys Asn Leu Ser Asp Ala Ile
            500                 505                 510

Leu Leu Ser Asp Ile Leu Arg Val Asn Thr Glu Ile Thr Lys Ala Pro
        515                 520                 525

Leu Ser Ala Ser Met Ile Lys Arg Tyr Asp Glu His His Gln Asp Leu
    530                 535                 540

Thr Leu Leu Lys Ala Leu Val Arg Gln Gln Leu Pro Glu Lys Tyr Lys
545                 550                 555                 560

Glu Ile Phe Phe Asp Gln Ser Lys Asn Gly Tyr Ala Gly Tyr Ile Asp
                565                 570                 575

Gly Gly Ala Ser Gln Glu Glu Phe Tyr Lys Phe Ile Lys Pro Ile Leu
            580                 585                 590

Glu Lys Met Asp Gly Thr Glu Glu Leu Leu Val Lys Leu Asn Arg Glu
        595                 600                 605

Asp Leu Leu Arg Lys Gln Arg Thr Phe Asp Asn Gly Ser Ile Pro His
    610                 615                 620

Gln Ile His Leu Gly Glu Leu His Ala Ile Leu Arg Arg Gln Glu Asp
625                 630                 635                 640

Phe Tyr Pro Phe Leu Lys Asp Asn Arg Glu Lys Ile Glu Lys Ile Leu
                645                 650                 655

Thr Phe Arg Ile Pro Tyr Tyr Val Gly Pro Leu Ala Arg Gly Asn Ser
            660                 665                 670

Arg Phe Ala Trp Met Thr Arg Lys Ser Glu Glu Thr Ile Thr Pro Trp
        675                 680                 685

Asn Phe Glu Glu Val Val Asp Lys Gly Ala Ser Ala Gln Ser Phe Ile
    690                 695                 700

Glu Arg Met Thr Asn Phe Asp Lys Asn Leu Pro Asn Glu Lys Val Leu
705                 710                 715                 720

Pro Lys His Ser Leu Leu Tyr Glu Tyr Phe Thr Val Tyr Asn Glu Leu
                725                 730                 735

Thr Lys Val Lys Tyr Val Thr Glu Gly Met Arg Lys Pro Ala Phe Leu
```

```
              740                 745                 750
Ser Gly Glu Gln Lys Lys Ala Ile Val Asp Leu Leu Phe Lys Thr Asn
            755                 760                 765

Arg Lys Val Thr Val Lys Gln Leu Lys Glu Asp Tyr Phe Lys Lys Ile
        770                 775                 780

Glu Cys Phe Asp Ser Val Glu Ile Ser Gly Val Glu Asp Arg Phe Asn
785                 790                 795                 800

Ala Ser Leu Gly Thr Tyr His Asp Leu Leu Lys Ile Ile Lys Asp Lys
                805                 810                 815

Asp Phe Leu Asp Asn Glu Glu Asn Glu Asp Ile Leu Glu Asp Ile Val
            820                 825                 830

Leu Thr Leu Thr Leu Phe Glu Asp Arg Glu Met Ile Glu Glu Arg Leu
        835                 840                 845

Lys Thr Tyr Ala His Leu Phe Asp Asp Lys Val Met Lys Gln Leu Lys
    850                 855                 860

Arg Arg Arg Tyr Thr Gly Trp Gly Arg Leu Ser Arg Lys Leu Ile Asn
865                 870                 875                 880

Gly Ile Arg Asp Lys Gln Ser Gly Lys Thr Ile Leu Asp Phe Leu Lys
                885                 890                 895

Ser Asp Gly Phe Ala Asn Arg Asn Phe Met Gln Leu Ile His Asp Asp
            900                 905                 910

Ser Leu Thr Phe Lys Glu Asp Ile Gln Lys Ala Gln Val Ser Gly Gln
        915                 920                 925

Gly Asp Ser Leu His Glu His Ile Ala Asn Leu Ala Gly Ser Pro Ala
    930                 935                 940

Ile Lys Lys Gly Ile Leu Gln Thr Val Lys Val Val Asp Glu Leu Val
945                 950                 955                 960

Lys Val Met Gly Arg His Lys Pro Glu Asn Ile Val Ile Glu Met Ala
                965                 970                 975

Arg Glu Asn Gln Thr Thr Gln Lys Gly Gln Lys Asn Ser Arg Glu Arg
            980                 985                 990

Met Lys Arg Ile Glu Glu Gly Ile Lys Glu Leu Gly Ser Gln Ile Leu
        995                 1000                1005

Lys Glu His Pro Val Glu Asn Thr Gln Leu Gln Asn Glu Lys Leu
    1010                1015                1020

Tyr Leu Tyr Tyr Leu Gln Asn Gly Arg Asp Met Tyr Val Asp Gln
    1025                1030                1035

Glu Leu Asp Ile Asn Arg Leu Ser Asp Tyr Asp Val Asp Ala Ile
    1040                1045                1050

Val Pro Gln Ser Phe Leu Lys Asp Asp Ser Ile Asp Asn Lys Val
    1055                1060                1065

Leu Thr Arg Ser Asp Lys Asn Arg Gly Lys Ser Asp Asn Val Pro
    1070                1075                1080

Ser Glu Glu Val Val Lys Lys Met Lys Asn Tyr Trp Arg Gln Leu
    1085                1090                1095

Leu Asn Ala Lys Leu Ile Thr Gln Arg Lys Phe Asp Asn Leu Thr
    1100                1105                1110

Lys Ala Glu Arg Gly Gly Leu Ser Glu Leu Asp Lys Ala Gly Phe
    1115                1120                1125

Ile Lys Arg Gln Leu Val Glu Thr Arg Gln Ile Thr Lys His Val
    1130                1135                1140

Ala Gln Ile Leu Asp Ser Arg Met Asn Thr Lys Tyr Asp Glu Asn
    1145                1150                1155
```

-continued

```
Asp Lys Leu Ile Arg Glu Val Lys Val Ile Thr Leu Lys Ser Lys
    1160                1165                1170

Leu Val Ser Asp Phe Arg Lys Asp Phe Gln Phe Tyr Lys Val Arg
    1175                1180                1185

Glu Ile Asn Asn Tyr His His Ala His Asp Ala Tyr Leu Asn Ala
    1190                1195                1200

Val Val Gly Thr Ala Leu Ile Lys Lys Tyr Pro Lys Leu Glu Ser
    1205                1210                1215

Glu Phe Val Tyr Gly Asp Tyr Lys Val Tyr Asp Val Arg Lys Met
    1220                1225                1230

Ile Ala Lys Ser Glu Gln Glu Ile Gly Lys Ala Thr Ala Lys Tyr
    1235                1240                1245

Phe Phe Tyr Ser Asn Ile Met Asn Phe Phe Lys Thr Glu Ile Thr
    1250                1255                1260

Leu Ala Asn Gly Glu Ile Arg Lys Arg Pro Leu Ile Glu Thr Asn
    1265                1270                1275

Gly Glu Thr Gly Glu Ile Val Trp Asp Lys Gly Arg Asp Phe Ala
    1280                1285                1290

Thr Val Arg Lys Val Leu Ser Met Pro Gln Val Asn Ile Val Lys
    1295                1300                1305

Lys Thr Glu Val Gln Thr Gly Gly Phe Ser Lys Glu Ser Ile Leu
    1310                1315                1320

Pro Lys Arg Asn Ser Asp Lys Leu Ile Ala Arg Lys Lys Asp Trp
    1325                1330                1335

Asp Pro Lys Lys Tyr Gly Gly Phe Asp Ser Pro Thr Val Ala Tyr
    1340                1345                1350

Ser Val Leu Val Val Ala Lys Val Glu Lys Gly Lys Ser Lys Lys
    1355                1360                1365

Leu Lys Ser Val Lys Glu Leu Leu Gly Ile Thr Ile Met Glu Arg
    1370                1375                1380

Ser Ser Phe Glu Lys Asn Pro Ile Asp Phe Leu Glu Ala Lys Gly
    1385                1390                1395

Tyr Lys Glu Val Lys Lys Asp Leu Ile Ile Lys Leu Pro Lys Tyr
    1400                1405                1410

Ser Leu Phe Glu Leu Glu Asn Gly Arg Lys Arg Met Leu Ala Ser
    1415                1420                1425

Ala Gly Glu Leu Gln Lys Gly Asn Glu Leu Ala Leu Pro Ser Lys
    1430                1435                1440

Tyr Val Asn Phe Leu Tyr Leu Ala Ser His Tyr Glu Lys Leu Lys
    1445                1450                1455

Gly Ser Pro Glu Asp Asn Glu Gln Lys Gln Leu Phe Val Glu Gln
    1460                1465                1470

His Lys His Tyr Leu Asp Glu Ile Ile Glu Gln Ile Ser Glu Phe
    1475                1480                1485

Ser Lys Arg Val Ile Leu Ala Asp Ala Asn Leu Asp Lys Val Leu
    1490                1495                1500

Ser Ala Tyr Asn Lys His Arg Asp Lys Pro Ile Arg Glu Gln Ala
    1505                1510                1515

Glu Asn Ile Ile His Leu Phe Thr Leu Thr Asn Leu Gly Ala Pro
    1520                1525                1530

Ala Ala Phe Lys Tyr Phe Asp Thr Thr Ile Asp Arg Lys Arg Tyr
    1535                1540                1545
```

```
Thr Ser Thr Lys Glu Val Leu Asp Ala Thr Leu Ile His Gln Ser
    1550                1555                1560

Ile Thr Gly Leu Tyr Glu Thr Arg Ile Asp Leu Ser Gln Leu Gly
    1565                1570                1575

Gly Asp Gly Ser Pro Lys Lys Lys Arg Lys Val Ser Ser
    1580                1585                1590

<210> SEQ ID NO 31
<211> LENGTH: 21
<212> TYPE: PRT
<213> ORGANISM: Homo sapiens

<400> SEQUENCE: 31

Met Ala Leu Pro Val Thr Ala Leu Leu Leu Pro Leu Ala Leu Leu
1               5                   10                  15

His Ala Ala Arg Pro
                20

<210> SEQ ID NO 32
<211> LENGTH: 63
<212> TYPE: DNA
<213> ORGANISM: Homo sapiens

<400> SEQUENCE: 32
atggcactgc cagtcaccgc cctgctgctg cctctggctc tgctgctgca cgcagctaga    60
cca                                                                  63

<210> SEQ ID NO 33
<211> LENGTH: 24
<212> TYPE: PRT
<213> ORGANISM: Homo sapiens

<400> SEQUENCE: 33

Ile Tyr Ile Trp Ala Pro Leu Ala Gly Thr Cys Gly Val Leu Leu
1               5                   10                  15

Ser Leu Val Ile Thr Leu Tyr Cys
                20

<210> SEQ ID NO 34
<211> LENGTH: 199
<212> TYPE: PRT
<213> ORGANISM: Homo sapiens

<400> SEQUENCE: 34

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
                20                  25                  30

Phe Asp Ser Lys Gln Asn Arg Leu Phe Glu Met Lys Val Leu Glu Leu
        35                  40                  45

Leu Val Asn Glu Tyr Gly Phe Lys Gly Arg His Leu Gly Gly Ser Arg
    50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
                100                 105                 110

Asp Glu Glu Val Asn Pro Asn Lys Trp Trp Glu Asn Phe Ser Glu Glu
```

-continued

```
            115                 120                 125
Val Lys Lys Tyr Tyr Phe Val Phe Ile Ser Gly Ser Phe Lys Gly Lys
    130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Glu Leu Glu Arg Ala Met Phe Asn Asn
            180                 185                 190

Ser Glu Phe Ile Leu Lys Tyr
        195

<210> SEQ ID NO 35
<211> LENGTH: 72
<212> TYPE: DNA
<213> ORGANISM: Homo sapiens

<400> SEQUENCE: 35
atctacattt gggcaccact ggccgggacc tgtggagtgc tgctgctgag cctggtcatc      60
acactgtact gc                                                         72

<210> SEQ ID NO 36
<211> LENGTH: 112
<212> TYPE: PRT
<213> ORGANISM: Homo sapiens

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 336
<212> TYPE: DNA
<213> ORGANISM: Homo sapiens

<400> SEQUENCE: 37
cgcgtgaagt ttagtcgatc agcagatgcc ccagcttaca acagggacag gaaccagctg      60
tataacgagc tgaatctggg ccgccgagag gaatatgacg tgctggataa gcggagagga     120
cgcgaccccg aaatggggag caagcccagg cgcaaaaacc ctcaggaagg cctgtataac     180
gagctgcaga aggacaaaat ggcagaagcc tattctgaga tcggcatgaa gggggagcga     240
cggagaggca agggcacga tgggctgtac cagggactga gcaccgccac aaaggacacc     300
tatgatgctc tgcatatgca ggcactgcct ccaagg                               336
```

```
<210> SEQ ID NO 38
<211> LENGTH: 42
<212> TYPE: PRT
<213> ORGANISM: Homo sapiens

<400> SEQUENCE: 38

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 39
<211> LENGTH: 126
<212> TYPE: DNA
<213> ORGANISM: Homo sapiens

<400> SEQUENCE: 39
aagagaggca ggaagaaact gctgtatatt ttcaaacagc ccttcatgcg ccccgtgcag      60
actacccagg aggaagacgg gtgctcctgt cgattccctg aggaagagga aggcgggtgt     120
gagctg                                                                126

<210> SEQ ID NO 40
<211> LENGTH: 44
<212> TYPE: PRT
<213> ORGANISM: Homo sapiens

<400> SEQUENCE: 40

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys
        35                  40

<210> SEQ ID NO 41
<211> LENGTH: 135
<212> TYPE: DNA
<213> ORGANISM: Homo sapiens

<400> SEQUENCE: 41
actaccacac cagcacctag accaccaact ccagctccaa ccatcgcgag tcagcccctg      60
agtctgagac ctgaggcctg caggccagct gcaggaggag ctgtgcacac caggggcctg     120
gacttcgcct gcgac                                                      135

<210> SEQ ID NO 42
<211> LENGTH: 89
<212> TYPE: PRT
<213> ORGANISM: Homo sapiens

<400> SEQUENCE: 42

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
```

```
                    50                  55                  60
Thr Glu Tyr Thr Val Ser Ile Tyr Gly Val Lys Gly His Arg Ser
 65                  70                  75                  80

Asn Pro Leu Ser Ala Glu Phe Thr Thr
                 85

<210> SEQ ID NO 43
<211> LENGTH: 90
<212> TYPE: PRT
<213> ORGANISM: Homo sapiens

<400> SEQUENCE: 43

Met Leu Pro Ala Pro Lys Asn Leu Val Val Ser Glu Val Thr Glu Asp
  1               5                  10                  15

Ser Leu Arg Leu Ser Trp Thr Ala Pro Asp Ala Ala Phe Asp Ser Phe
                 20                  25                  30

Leu Ile Gln Tyr Gln Glu Ser Glu Lys Val Gly Glu Ala Ile Asn Leu
             35                  40                  45

Thr Val Pro Gly Ser Glu Arg Ser Tyr Asp Leu Thr Gly Leu Lys Pro
         50                  55                  60

Gly Thr Glu Tyr Thr Val Ser Ile Tyr Gly Val Lys Gly Gly His Arg
 65                  70                  75                  80

Ser Asn Pro Leu Ser Ala Glu Phe Thr Thr
                 85                  90

<210> SEQ ID NO 44
<211> LENGTH: 270
<212> TYPE: DNA
<213> ORGANISM: Homo sapiens

<400> SEQUENCE: 44
atgctgcctg caccaaagaa cctggtggtg tctcatgtga cagaggatag tgccagactg     60
tcatggactc tcccgacgc agccttcgat agtttatca tcgtgtaccg ggagaacatc     120
gaaaccggcg aggccattgt cctgacagtg ccagggtccg aacgctctta tgacctgaca     180
gatctgaagc ccggaactga gtactatgtg cagatcgccg gcgtcaaagg aggcaatatc     240
agcttccctc tgtccgcaat cttcaccaca                                      270

<210> SEQ ID NO 45
<211> LENGTH: 107
<212> TYPE: PRT
<213> ORGANISM: Homo sapiens

<400> SEQUENCE: 45

Gly Val Gln Val Glu Thr Ile Ser Pro Gly Asp Gly Arg Thr Phe Pro
  1               5                  10                  15

Lys Arg Gly Gln Thr Cys Val Val His Tyr Thr Gly Met Leu Glu Asp
                 20                  25                  30

Gly Lys Lys Val Asp Ser Ser Arg Asp Arg Asn Lys Pro Phe Lys Phe
             35                  40                  45

Met Leu Gly Lys Gln Glu Val Ile Arg Gly Trp Glu Glu Gly Val Ala
         50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu
```

100          105

<210> SEQ ID NO 46
<211> LENGTH: 321
<212> TYPE: DNA
<213> ORGANISM: Homo sapiens

<400> SEQUENCE: 46

```
ggggtccagg tcgagactat ttcaccaggg gatgggcgaa catttccaaa aaggggccag      60
acttgcgtcg tgcattacac cgggatgctg gaggacggga agaaagtgga cagctccagg     120
gatcgcaaca agcccttcaa gttcatgctg ggaaagcagg aagtgatccg aggatgggag     180
gaaggcgtgg cacagatgtc agtcggccag cgggccaaac tgaccattag ccctgactac     240
gcttatggag caacaggcca cccagggatc attccccctc atgccaccct ggtcttcgat     300
gtggaactgc tgaagctgga g                                               321
```

<210> SEQ ID NO 47
<211> LENGTH: 5
<212> TYPE: PRT
<213> ORGANISM: Homo sapiens

<400> SEQUENCE: 47

Gly Gly Gly Gly Ser
1               5

<210> SEQ ID NO 48
<211> LENGTH: 15
<212> TYPE: DNA
<213> ORGANISM: Homo sapiens

<400> SEQUENCE: 48
ggaggaggag gatcc                                                       15

<210> SEQ ID NO 49
<211> LENGTH: 281
<212> TYPE: PRT
<213> ORGANISM: Homo sapiens

<400> SEQUENCE: 49

Gly Phe Gly Asp Val Gly Ala Leu Glu Ser Leu Arg Gly Asn Ala Asp
1               5                   10                  15

Leu Ala Tyr Ile Ser Leu Met Glu Pro Cys Gly His Cys Leu Ile Ile
                20                  25                  30

Asn Asn Val Asn Phe Cys Arg Glu Ser Gly Leu Arg Thr Arg Thr Gly
            35                  40                  45

Ser Asn Ile Asp Cys Glu Lys Leu Arg Arg Arg Phe Ser Ser Leu His
        50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His

```
                145                 150                 155                 160
Gly Phe Glu Val Ala Ser Thr Ser Pro Glu Asp Glu Ser Pro Gly Ser
                    165                 170                 175

Asn Pro Glu Pro Asp Ala Thr Pro Phe Gln Glu Gly Leu Arg Thr Phe
                180                 185                 190

Asp Gln Leu Asp Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
        210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Asn Phe Leu
                260                 265                 270

Arg Lys Lys Leu Phe Phe Lys Thr Ser
                275                 280

<210> SEQ ID NO 50
<211> LENGTH: 843
<212> TYPE: DNA
<213> ORGANISM: Homo sapiens

<400> SEQUENCE: 50 tttgggacg tgggggccct ggagtctctg cgaggaaatg ccgatctggc ttacatcctg      60
agcatggaac cctgcggcca ctgtctgatc attaacaatg tgaacttctg cagagaaagc     120
ggactgcgaa cacggactgg ctccaatatt gactgtgaga agctgcggag aaggttctct     180
agtctgcact ttatggtcga agtgaaaggg atctgaccg ccaagaaaat ggtgctggcc      240
ctgctggagc tggctcagca ggaccatgga gctctggatt gctgcgtggt cgtgatcctg     300
tcccacgggt gccaggcttc tcatctgcag ttccccggag cagtgtacgg aacagacggc     360
tgtcctgtca gcgtggagaa gatcgtcaac atcttcaacg gcacttcttg ccctagtctg     420
ggggaaagc caaaactgtt ctttatccag gcctgtggcg ggaacagaa agatcacggc       480
ttcgaggtgg ccagcaccag ccctgaggac gaatcaccag ggagcaaccc tgaaccagat     540
gcaactccat tccaggaggg actgaggacc tttgaccagc tggatgctat ctcaagcctg     600
cccactccta gtgacatttt cgtgtcttac agtaccttcc caggctttgt ctcatggcgc     660
gatcccaagt cagggagctg gtacgtggag acactggacg acatctttga acagtgggcc     720
cattcagagg acctgcagag cctgctgctg cgagtggcaa acgctgtctc tgtgaagggc     780
atctacaaac agatgcccgg gtgcttcaat tttctgagaa agaaactgtt ctttaagact     840
tcc                                                                    843

<210> SEQ ID NO 51
<211> LENGTH: 394
<212> TYPE: PRT
<213> ORGANISM: Homo sapiens

<400> SEQUENCE: 51

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
```

```
            35                  40                  45
Met Leu Gly Lys Gln Glu Val Ile Arg Gly Trp Glu Gly Val Ala
 50                  55                  60
Gln Met Ser Val Gly Gln Arg Ala Lys Leu Thr Ile Ser Pro Asp Tyr
 65                  70                  75                  80
Ala Tyr Gly Ala Thr Gly His Pro Gly Ile Pro Pro His Ala Thr
                 85                  90                  95
Leu Val Phe Asp Val Glu Leu Leu Lys Leu Glu Gly Gly Gly Gly
                100                 105                 110
Ser Gly Phe Gly Asp Val Gly Ala Leu Glu Ser Leu Arg Gly Asn Ala
                115                 120                 125
Asp Leu Ala Tyr Ile Ser Leu Met Glu Pro Cys Gly His Cys Leu Ile
130                 135                 140
Ile Asn Asn Val Asn Phe Cys Arg Glu Ser Gly Leu Arg Thr Arg Thr
145                 150                 155                 160
Gly Ser Asn Ile Asp Cys Glu Lys Leu Arg Arg Arg Phe Ser Ser Leu
                165                 170                 175
His Phe Met Val Glu Val Lys Gly Asp Leu Thr Ala Lys Lys Met Val
                180                 185                 190
Leu Ala Leu Leu Glu Leu Ala Gln Gln Asp His Gly Ala Leu Asp Cys
                195                 200                 205
Cys Val Val Ile Leu Ser His Gly Cys Gln Ala Ser His Leu Gln
210                 215                 220
Phe Pro Gly Ala Val Tyr Gly Thr Asp Gly Cys Pro Val Ser Val Glu
225                 230                 235                 240
Lys Ile Val Asn Ile Phe Asn Gly Thr Ser Cys Pro Ser Leu Gly Gly
                245                 250                 255
Lys Pro Lys Leu Phe Phe Ile Gln Ala Cys Gly Gly Glu Gln Lys Asp
                260                 265                 270
His Gly Phe Glu Val Ala Ser Thr Ser Pro Glu Asp Glu Ser Pro Gly
                275                 280                 285
Ser Asn Pro Glu Pro Asp Ala Thr Pro Phe Gln Glu Gly Leu Arg Thr
                290                 295                 300
Phe Asp Gln Leu Asp Ala Ile Ser Ser Leu Pro Thr Pro Ser Asp Ile
305                 310                 315                 320
Phe Val Ser Tyr Ser Thr Phe Pro Gly Phe Val Ser Trp Arg Asp Pro
                325                 330                 335
Lys Ser Gly Ser Trp Tyr Val Glu Thr Leu Asp Asp Ile Phe Glu Gln
                340                 345                 350
Trp Ala His Ser Glu Asp Leu Gln Ser Leu Leu Leu Arg Val Ala Asn
                355                 360                 365
Ala Val Ser Val Lys Gly Ile Tyr Lys Gln Met Pro Gly Cys Asn Phe
                370                 375                 380
Leu Arg Lys Lys Leu Phe Phe Lys Thr Ser
385                 390
```

<210> SEQ ID NO 52
<211> LENGTH: 1182
<212> TYPE: DNA
<213> ORGANISM: Homo sapiens

<400> SEQUENCE: 52
ggggtccagg tcgagactat tcaccaggg gatgggcgaa catttccaaa aagggggccag      60 acttgcgtcg tgcattacac cgggatgctg gaggacggga agaaagtgga cagctccagg     120

```
gatcgcaaca agcccttcaa gttcatgctg ggaaagcagg aagtgatccg aggatgggag      180
gaaggcgtgg cacagatgtc agtcggccag cgggccaaac tgaccattag ccctgactac      240
gcttatggag caacaggcca cccagggatc attccccctc atgccaccct ggtcttcgat      300
gtggaactgc tgaagctgga gggaggagga ggatccgaat tggggacgt ggggccctg        360 gagtctctgc gaggaaatgc cgatctggct tacatcctga gcatggaacc ctgcggccac      420
tgtctgatca ttaacaatgt gaacttctgc agagaaagcg gactgcgaac acggactggc      480
tccaatattg actgtgagaa gctgcggaga aggttctcta gtctgcactt tatggtcgaa      540
gtgaaagggg atctgaccgc caagaaaatg gtgctggccc tgctggagct ggctcagcag      600
gaccatggag ctctggattg ctgcgtggtc gtgatcctgt cccacggtg ccaggcttct       660 catctgcagt tccccggagc agtgtacgga acagacggct gtcctgtcag cgtggagaag      720
atcgtcaaca tcttcaacgg cacttcttgc cctagtctgg ggggaaagcc aaaactgttc      780
tttatccagg cctgtggcgg ggaacagaaa gatcacggct cgaggtggc cagcaccagc       840 cctgaggacg aatcaccagg gagcaaccct gaaccagatg caactccatt ccaggaggga      900
ctgaggacct tgaccagct ggatgctatc tcaagcctgc ccactcctag tgacattttc       960
gtgtcttaca gtaccttccc aggctttgtc tcatggcgcg atcccaagtc agggagctgg     1020
tacgtggaga cactggacga catctttgaa cagtgggccc attcagagga cctgcagagc     1080
ctgctgctgc gagtggcaaa cgctgtctct gtgaagggca tctacaaaca gatgcccggg     1140
tgcttcaatt ttctgagaaa gaaactgttc tttaagactt cc                       1182
```

```
<210> SEQ ID NO 53
<211> LENGTH: 18
<212> TYPE: PRT
<213> ORGANISM: Homo sapiens

<400> SEQUENCE: 53

Glu Gly Arg Gly Ser Leu Leu Thr Cys Gly Asp Val Glu Glu Asn Pro
1               5                   10                  15

Gly Pro

<210> SEQ ID NO 54
<211> LENGTH: 21
<212> TYPE: PRT
<213> ORGANISM: Homo sapiens

<400> SEQUENCE: 54

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 55
<211> LENGTH: 63
<212> TYPE: DNA
<213> ORGANISM: Homo sapiens

<400> SEQUENCE: 55
ggatctggag agggaagggg aagcctgctg acctgtggag acgtggagga aacccagga       60 cca                                                                   63

<210> SEQ ID NO 56
<211> LENGTH: 20
```

```
<212> TYPE: PRT
<213> ORGANISM: Homo sapiens

<400> SEQUENCE: 56

Gln Cys Thr Asn Tyr Ala Leu Leu Lys Leu Ala Gly Asp Val Glu Ser
1               5                   10                  15

Asn Pro Gly Pro
            20

<210> SEQ ID NO 57
<211> LENGTH: 23
<212> TYPE: PRT
<213> ORGANISM: Homo sapiens

<400> SEQUENCE: 57

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 58
<211> LENGTH: 22
<212> TYPE: PRT
<213> ORGANISM: Homo sapiens

<400> SEQUENCE: 58

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 59
<211> LENGTH: 25
<212> TYPE: PRT
<213> ORGANISM: Homo sapiens

<400> SEQUENCE: 59

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 60
<211> LENGTH: 19
<212> TYPE: PRT
<213> ORGANISM: Homo sapiens

<400> SEQUENCE: 60

Ala Thr Asn Phe Ser Leu Leu Lys Gln Ala Gly Asp Val Glu Glu Asn
1               5                   10                  15

Pro Gly Pro

<210> SEQ ID NO 61
<211> LENGTH: 22
<212> TYPE: PRT
<213> ORGANISM: Homo sapiens

<400> SEQUENCE: 61

Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 62
<211> LENGTH: 4897
<212> TYPE: DNA
<213> ORGANISM: Homo sapiens

<400> SEQUENCE: 62

| | | | | | |
|---|---|---|---|---|---|
| tgtacataga | ttaaccctag | aaagataatc | atattgtgac | gtacgttaaa | gataatcatg | 60 |
| cgtaaaattg | acgcatgtgt | tttatcggtc | tgtatatcga | ggtttattta | ttaatttgaa | 120 |
| tagatattaa | gttttattat | atttacactt | acatactaat | aataaattca | acaaacaatt | 180 |
| tatttatgtt | tatttattta | ttaaaaaaaa | acaaaaactc | aaaatttctt | ctataaagta | 240 |
| acaaaacttt | tatcgaatac | ctgcagcccg | ggggatgcag | agggacagcc | cccccccaaa | 300 |
| gcccccaggg | atgtaattac | gtccctcccc | cgctaggggg | cagcagcgag | ccgcccgggg | 360 |
| ctccgctccg | gtccggcgct | cccccgcat | ccccgagccg | gcagcgtgcg | gggacagccc | 420 |
| gggcacgggg | aagtggcac | gggatcgctt | tcctctgaac | gcttctcgct | gctctttgag | 480 |
| cctgcagaca | cctgggggga | tacggggaaa | agttgactgt | gcctttcgat | cgaaccatgg | 540 |
| acagttagct | ttgcaaagat | ggataaagtt | ttaaacagag | aggaatcttt | gcagctaatg | 600 |
| gaccttctag | gtcttgaaag | gagtgggaat | tggctccggt | gcccgtcagt | gggcagagcg | 660 |
| cacatcgccc | acagtccccg | agaagttggg | gggaggggtc | ggcaattgaa | ccggtgccta | 720 |
| gagaaggtgg | cgcggggtaa | actgggaaag | tgatgtcgtg | tactggctcc | gcctttttcc | 780 |
| cgagggtggg | ggagaaccgt | atataagtgc | agtagtcgcc | gtgaacgttc | ttttcgcaa | 840 |
| cgggtttgcc | gccagaacac | aggtaagtgc | cgtgtgtggt | tcccgcgggc | ctggcctctt | 900 |
| tacgggttat | ggcccttgcg | tgccttgaat | tacttccacc | tggctgcagt | acgtgattct | 960 |
| tgatcccgag | cttcgggttg | aagtggggtg | ggagagttcg | aggccttgcg | cttaaggagc | 1020 |
| cccttcgcct | cgtgcttgag | ttgaggcctg | gcctgggcgc | tggggccgcc | gcgtgcgaat | 1080 |
| ctggtggcac | cttcgcgcct | gtctcgctgc | tttcgataag | tctctagcca | tttaaaattt | 1140 |
| ttgatgacct | gctgcgacgc | ttttttttctg | gcaagatagt | cttgtaaatg | cgggccaaga | 1200 |
| tctgcacact | ggtatttcgg | tttttgggc | cgcgggcggc | gacggggccc | gtgcgtccca | 1260 |
| gcgcacatgt | tcggcgaggc | ggggcctgcg | agcgcggcca | ccgagaatcg | gacggggta | 1320 |
| gtctcaagct | ggccggcctg | ctctggtgcc | tggcctcgcg | ccgccgtgta | tcgcccgcc | 1380 |
| ctgggcggca | aggctggccc | ggtcggcacc | agttgcgtga | gcggaaagat | ggccgcttcc | 1440 |
| cggccctgct | gcagggagct | caaaatggag | gacgcgcgc | tcgggagagc | gggcgggtga | 1500 |
| gtcacccaca | caaaggaaaa | gggccttttcc | gtcctcagcc | gtcgcttcat | gtgactccac | 1560 |
| ggagtaccgg | gcgccgtcca | ggcacctcga | ttagttctcg | agcttttgga | gtacgtcgtc | 1620 |
| tttaggttgg | ggggaggggt | tttatgcgat | ggagtttccc | cacactgagt | gggtggagac | 1680 |
| tgaagttagg | ccagcttggc | acttgatgta | attctccttg | gaatttgccc | ttttttgagtt | 1740 |
| tggatcttgg | ttcattctca | agcctcagac | agtggttcaa | agtttttttc | ttccatttca | 1800 |
| ggtgtcgtga | gaattctaat | acgactcact | ataggggtgtg | ctgtctcatc | attttggcaa | 1860 |
| agattggcca | ccaagcttgt | cctgcaggag | ggtcgacgcc | tctagacggg | cggccgctcc | 1920 |
| ggatccacgg | gtaccgatca | catatgcctt | taattaaaca | ctagttctat | agtgtcacct | 1980 |
| aaattccctt | tagtgagggt | taatggccgt | aggccgccag | aattgggtcc | agacatgata | 2040 |
| agatacattg | atgagtttgg | acaaaccaca | actagaatgc | agtgaaaaaa | atgctttatt | 2100 |

-continued

```
tgtgaaattt gtgatgctat tgctttattt gtaaccatta taagctgcaa taaacaagtt      2160
aacaacaaca attgcattca ttttatgttt caggttcagg gggaggtgtg ggaggttttt      2220
tcggactcta ggacctgcgc atgcgcttgg cgtaatcatg gtcatagctg tttcctgttt      2280
tccccgtatc cccccaggtg tctgcaggct caaagagcag cgagaagcgt tcagaggaaa      2340
gcgatcccgt gccaccttcc ccgtgcccgg ctgtccccg cacgctgccg gctcggggat      2400
gcgggggggag cgccggaccg gagcggagcc ccgggcggct cgctgctgcc ccctagcggg      2460
ggagggacgt aattacatcc ctgggggctt tgggggggg ctgtccctct caccgcggtg      2520
gagctccagc ttttgttcga attggggccc cccctcgagg gtatcgatga tatctataac      2580
aagaaaatat atatataata agttatcacg taagtagaac atgaaataac aatataatta      2640
tcgtatgagt taaatcttaa aagtcacgta aaagataatc atgcgtcatt ttgactcacg      2700
cggtcgttat agttcaaaat cagtgacact taccgcattg acaagcacgc ctcacgggag      2760
ctccaagcgg cgactgagat gtcctaaatg cacagcgacg gattcgcgct atttagaaag      2820
agagagcaat atttcaagaa tgcatgcgtc aattttacgc agactatctt tctagggtta      2880
atctagctag ccttaagggc gcctattgcg ttgcgctcac tgcccgcttt ccagtcggga      2940
aacctgtcgt gccagctgca ttaatgaatc ggccaacgcg cggggagagg cggtttgcgt      3000
attgggcgct cttccgcttc ctcgctcact gactcgctgc gctcggtcgt tcggctgcgg      3060
cgagcggtat cagctcactc aaaggcggta atacggttat ccacagaatc aggggataac      3120
gcaggaaaga acatgaccaa aatcccttaa cgtgagtttt cgttccactg agcgtcagac      3180
cccgtagaaa agatcaaagg atcttcttga gatccttttt ttctgcgcgt aatctgctgc      3240
ttgcaaacaa aaaaaccacc gctaccagcg gtggtttgtt tgccggatca agagctacca      3300
actctttttc cgaaggtaac tggcttcagc agagcgcaga taccaaatac tgttcttcta      3360
gtgtagccgt agttaggcca ccacttcaag aactctgtag caccgcctac atacctcgct      3420
ctgctaatcc tgttaccagt ggctgctgcc agtggcgata agtcgtgtct taccgggttg      3480
gactcaagac gatagttacc ggataaggcg cagcggtcgg gctgaacggg gggttcgtgc      3540
acacagccca gcttggagcg aacgacctac accgaactga gatacctaca gcgtgagcta      3600
tgagaaagcg ccacgcttcc cgaagggaga aaggcggaca ggtatccggt aagcggcagg      3660
gtcggaacag gagagcgcac gagggagctt ccagggggaa acgcctggta tctttatagt      3720
cctgtcgggt ttcgccacct ctgacttgag cgtcgatttt tgtgatgctc gtcagggggg      3780
cggagcctat ggaaaaacgc cagcaacgcg gcctttttac ggttcctggc cttttgctgg      3840
ccttttgctc acatgagatt atcaaaaagg atcttcacct agatcctttt aaattaaaaa      3900
tgaagtttta atcaatctaa agtatatat gagtaaactt ggtctgacag tcagaagaac      3960
tcgtcaagaa ggcgatagaa ggcgatgcgc tgcgaatcgg gagcggcgat accgtaaagc      4020
acgaggaagc ggtcagccca ttcgccgcca agctcttcag caatatcacg ggtagccaac      4080
gctatgtcct gatagcggtc cgccacaccc agccggccac agtcgatgaa tccagaaaag      4140
cggccatttt ccaccatgat attcggcaag caggcatcgc catgggtcac gacgagatcc      4200
tcgccgtcgg gcatgctcgc cttgagcctg gcgaacagtt cggctggcgc gagccctga      4260
tgctcttcgt ccagatcatc ctgatcgaca agaccggctt ccatccgagt acgtgctcgc      4320
tcgatgcgat gtttcgcttg gtggtcgaat gggcaggtag ccggatcaag cgtatgcagc      4380
cgccgcattg catcagccat gatggatact ttctcggcag gagcaaggtg agatgacagg      4440
agatcctgcc ccggcacttc gcccaatagc agccagtccc ttcccgcttc agtgacaacg      4500
```

```
tcgagcacag ctgcgcaagg aacgcccgtc gtggccagcc acgatagccg cgctgcctcg    4560
tcttgcagtt cattcagggc accggacagg tcggtcttga caaaaagaac cgggcgcccc    4620
tgcgctgaca gccggaacac ggcggcatca gagcagccga ttgtctgttg tgcccagtca    4680
tagccgaata gcctctccac ccaagcggcc ggagaacctg cgtgcaatcc atcttgttca    4740
atcataatat tattgaagca tttatcaggg ttcgtctcgt cccggtctcc tcccaatgca    4800
tgtcaatatt ggccattagc catattattc attggttata tagcataaat caatattggc    4860
tattggccat tgcatacgtt gtatctatat cataata                             4897
```

<210> SEQ ID NO 63
<211> LENGTH: 4
<212> TYPE: PRT
<213> ORGANISM: Homo sapiens

<400> SEQUENCE: 63

Thr Glu Asp Ser
1

<210> SEQ ID NO 64
<211> LENGTH: 7
<212> TYPE: PRT
<213> ORGANISM: Homo sapiens

<400> SEQUENCE: 64

Thr Ala Pro Asp Ala Ala Phe
1               5

<210> SEQ ID NO 65
<211> LENGTH: 6
<212> TYPE: PRT
<213> ORGANISM: Homo sapiens

<400> SEQUENCE: 65

Ser Glu Lys Val Gly Glu
1               5

<210> SEQ ID NO 66
<211> LENGTH: 4
<212> TYPE: PRT
<213> ORGANISM: Homo sapiens

<400> SEQUENCE: 66

Gly Ser Glu Arg
1

<210> SEQ ID NO 67
<211> LENGTH: 5
<212> TYPE: PRT
<213> ORGANISM: Homo sapiens

<400> SEQUENCE: 67

Gly Leu Lys Pro Gly
1               5

<210> SEQ ID NO 68
<211> LENGTH: 7
<212> TYPE: PRT
<213> ORGANISM: Homo sapiens

<400> SEQUENCE: 68

Lys Gly Gly His Arg Ser Asn

<210> SEQ ID NO 69
<211> LENGTH: 239
<212> TYPE: PRT
<213> ORGANISM: Homo sapiens

<400> SEQUENCE: 69

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
            100                 105                 110

Thr Val Ser Ala Gly Gly Gly Gly Ser Gly Gly Gly Gly Ser Gly Gly
        115                 120                 125

Gly Gly Ser Asp Ile Val Met Thr Gln Ser Gln Lys Phe Met Ser Thr
130                 135                 140

Ser Val Gly Asp Arg Val Ser Val Thr Cys Lys Ala Ser Gln Asn Val
145                 150                 155                 160

Arg Thr Asn Val Ala Trp Tyr Gln Gln Lys Pro Gly Gln Ser Pro Lys
                165                 170                 175

Ala Leu Ile Tyr Ser Ala Ser Tyr Arg Tyr Ser Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys Gln Gln Tyr Asn Ser
    210                 215                 220

Tyr Pro Arg Thr Phe Gly Gly Gly Thr Lys Leu Glu Ile Lys Arg
225                 230                 235

<210> SEQ ID NO 70
<211> LENGTH: 239
<212> TYPE: PRT
<213> ORGANISM: Homo sapiens

<400> SEQUENCE: 70

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Leu Ser Asn Val Gln Ser
65                  70                  75                  80

Glu Asp Leu Ala Asp Tyr Phe Cys Gln Gln Tyr Asn Ser Tyr Pro Arg

```
                  85                  90                  95

Thr Phe Gly Gly Gly Thr Lys Leu Glu Ile Lys Arg Gly Gly Gly
                100                 105                 110

Ser Gly Gly Gly Gly Ser Gly Gly Gly Ser Gln Val Gln Leu Lys
                115                 120                 125

Gln Ser Gly Ala Glu Leu Val Arg Pro Gly Ala Ser Val Lys Leu Ser
130                 135                 140

Cys Lys Ala Ser Gly Tyr Thr Phe Thr Asp Tyr Tyr Ile Asn Trp Val
145                 150                 155                 160

Lys Gln Arg Pro Gly Gln Gly Leu Glu Trp Ile Ala Arg Ile Tyr Pro
                165                 170                 175

Gly Ser Gly Asn Thr Tyr Tyr Asn Glu Lys Phe Lys Gly Lys Ala Thr
                180                 185                 190

Leu Thr Ala Glu Lys Ser Ser Thr Ala Tyr Met Gln Leu Ser Ser
                195                 200                 205

Leu Thr Ser Glu Asp Ser Ala Val Tyr Phe Cys Ala Arg Gly Val Tyr
                210                 215                 220

Tyr Phe Asp Tyr Trp Gly Gln Gly Thr Thr Leu Thr Val Ser Ala
225                 230                 235

<210> SEQ ID NO 71
<211> LENGTH: 239
<212> TYPE: PRT
<213> ORGANISM: Homo sapiens

<400> SEQUENCE: 71

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ser Gly Asn Thr Tyr Tyr Asn Glu Lys Phe
50                  55                  60

Lys Gly Lys Ala Thr Leu Thr Ala Glu Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
                100                 105                 110

Thr Val Ser Ser Gly Gly Gly Ser Gly Gly Gly Ser Gly Gly
                115                 120                 125

Gly Gly Ser Asp Ile Val Met Thr Gln Ser Gln Lys Phe Met Ser Thr
130                 135                 140

Ser Val Gly Asp Arg Val Ser Val Thr Cys Lys Ala Ser Gln Asn Val
145                 150                 155                 160

Arg Thr Asn Val Ala Trp Tyr Gln Gln Lys Pro Gly Gln Ser Pro Lys
                165                 170                 175

Ala Leu Ile Tyr Ser Ala Ser Tyr Arg Tyr Ser Gly Val Pro Asp Arg
                180                 185                 190

Phe Thr Gly Ser Gly Ser Gly Thr Asp Phe Thr Leu Thr Ile Ser Asn
                195                 200                 205

Val Gln Ser Glu Asp Leu Ala Asp Tyr Phe Cys Gln Gln Tyr Asn Ser
                210                 215                 220
```

Tyr Pro Arg Thr Phe Gly Gly Gly Thr Lys Leu Glu Ile Lys Arg
225                 230                 235

<210> SEQ ID NO 72
<211> LENGTH: 239
<212> TYPE: PRT
<213> ORGANISM: Homo sapiens

<400> SEQUENCE: 72

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Leu Ser Asn Val Gln Ser
65                  70                  75                  80

Glu Asp Leu Ala Asp Tyr Phe Cys Gln Gln Tyr Asn Ser Tyr Pro Arg
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gln Val Gln Leu Lys
            115                 120                 125

Gln Ser Gly Ala Glu Leu Val Arg Pro Gly Ala Ser Val Lys Leu Ser
    130                 135                 140

Cys Lys Ala Ser Gly Tyr Thr Phe Thr Asp Tyr Tyr Ile Asn Trp Val
145                 150                 155                 160

Lys Gln Arg Pro Gly Gln Gly Leu Glu Trp Ile Ala Arg Ile Tyr Pro
                165                 170                 175

Gly Ser Gly Asn Thr Tyr Tyr Asn Glu Lys Phe Lys Gly Lys Ala Thr
            180                 185                 190

Leu Thr Ala Glu Lys Ser Ser Ser Thr Ala Tyr Met Gln Leu Ser Ser
        195                 200                 205

Leu Thr Ser Glu Asp Ser Ala Val Tyr Phe Cys Ala Arg Gly Val Tyr
    210                 215                 220

Tyr Phe Asp Tyr Trp Gly Gln Gly Thr Thr Leu Thr Val Ser Ser
225                 230                 235

<210> SEQ ID NO 73
<211> LENGTH: 244
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Ser Trp Val Arg Gln Ala Pro Gly Lys Gly Leu Glu Trp Val
        35                  40                  45

Ser Ser Ile Val Pro Ser Gly Gly Phe Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                85                  90                  95
Ala Arg Leu Gln Thr Gly Ser Trp Arg Val His Ala Phe Asp Ile Trp
            100                 105                 110
Gly Gln Gly Thr Met Val Thr Val Ser Ser Gly Gly Gly Gly Ser Gly
        115                 120                 125
Gly Gly Gly Ser Gly Gly Gly Ser Asp Ile Gln Met Thr Gln Ser
    130                 135                 140
Pro Thr Ser Leu Ser Ala Phe Val Gly Asp Arg Val Thr Ile Thr Cys
145                 150                 155                 160
Gln Ala Ser Gln Asp Ile Gly Asn Tyr Leu Asn Trp Tyr Gln Gln Lys
                165                 170                 175
Ser Gly Glu Pro Pro Lys Leu Leu Val Tyr Asp Ala Ser Phe Leu Lys
            180                 185                 190
Lys Gly Val Pro Ser Arg Phe Ser Gly Ser Gly Ser Gly Thr Gln Tyr
        195                 200                 205
Phe Leu Thr Ile Tyr Ser Leu Gln Pro Glu Asp Phe Ala Thr Tyr Phe
    210                 215                 220
Cys Gln His Ser Asp Asn Leu Ser Val Thr Phe Gly Gly Gly Thr Lys
225                 230                 235                 240
Val Glu Val Lys

<210> SEQ ID NO 74
<211> LENGTH: 244
<212> TYPE: PRT
<213> ORGANISM: Homo sapiens

<400> SEQUENCE: 74

Asp Ile Gln Met Thr Gln Ser Pro Thr Ser Leu Ser Ala Phe Val Gly
1               5                   10                  15
Asp Arg Val Thr Ile Thr Cys Gln Ala Ser Gln Asp Ile Gly Asn Tyr
            20                  25                  30
Leu Asn Trp Tyr Gln Gln Lys Ser Gly Glu Pro Pro Lys Leu Leu Val
        35                  40                  45
Tyr Asp Ala Ser Phe Leu Lys Lys Gly Val Pro Ser Arg Phe Ser Gly
    50                  55                  60
Ser Gly Ser Gly Thr Gln Tyr Phe Leu Thr Ile Tyr Ser Leu Gln Pro
65                  70                  75                  80
Glu Asp Phe Ala Thr Tyr Phe Cys Gln His Ser Asp Asn Leu Ser Val
                85                  90                  95
Thr Phe Gly Gly Gly Thr Lys Val Glu Val Lys Gly Gly Gly Gly Ser
            100                 105                 110
Gly Gly Gly Gly Ser Gly Gly Gly Ser Glu Val Gln Leu Leu Glu
        115                 120                 125
Ser Gly Gly Gly Leu Val Gln Pro Gly Gly Ser Leu Arg Leu Ser Cys
    130                 135                 140
Ala Ala Ser Gly Phe Thr Phe Ser Asn Tyr Leu Met Ser Trp Val Arg
145                 150                 155                 160
Gln Ala Pro Gly Lys Gly Leu Glu Trp Val Ser Ser Ile Val Pro Ser
                165                 170                 175
Gly Gly Phe Thr His Tyr Ala Asp Ser Val Lys Gly Arg Phe Thr Leu
            180                 185                 190
Ser Arg Asp Asn Ser Lys Asn Thr Leu Tyr Leu Gln Met Asn Ser Leu
        195                 200                 205
```

```
Arg Ala Glu Asp Thr Ala Val Tyr Tyr Cys Ala Arg Leu Gln Thr Gly
    210                 215                 220

Ser Trp Arg Val His Ala Phe Asp Ile Trp Gly Gln Gly Thr Met Val
225                 230                 235                 240

Thr Val Ser Ser

<210> SEQ ID NO 75
<211> LENGTH: 244
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Ser Trp Val Arg Gln Ala Pro Gly Lys Gly Leu Glu Trp Val
        35                  40                  45

Ser Ser Ile Val Pro Ser Gly Gly Phe Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gln Thr Gly Ser Trp Arg Val His Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Thr Ser Leu Ser Ala Phe Val Gly Asp Arg Val Thr Ile Thr Cys
145                 150                 155                 160

Gln Ala Ser Gln Asp Ile Gly Asn Tyr Leu Asn Trp Tyr Gln Gln Lys
                165                 170                 175

Ser Gly Glu Pro Pro Lys Leu Leu Val Tyr Asp Ala Ser Phe Leu Lys
            180                 185                 190

Lys Gly Val Pro Ser Arg Phe Ser Gly Ser Gly Ser Gly Thr Gln Tyr
        195                 200                 205

Phe Leu Thr Ile Tyr Ser Leu Gln Pro Glu Asp Phe Ala Thr Tyr Phe
    210                 215                 220

Cys Gln His Ser Asp Ser Leu Ser Val Thr Phe Gly Gly Gly Thr Lys
225                 230                 235                 240

Val Glu Val Lys

<210> SEQ ID NO 76
<211> LENGTH: 244
<212> TYPE: PRT
<213> ORGANISM: Homo sapiens

<400> SEQUENCE: 76

Asp Ile Gln Met Thr Gln Ser Pro Thr Ser Leu Ser Ala Phe Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Ser Gly Glu Pro Pro Lys Leu Leu Val
        35                  40                  45
```

```
Tyr Asp Ala Ser Phe Leu Lys Lys Gly Val Pro Ser Arg Phe Ser Gly
        50                  55                  60

Ser Gly Ser Gly Thr Gln Tyr Phe Leu Thr Ile Tyr Ser Leu Gln Pro
65                  70                  75                  80

Glu Asp Phe Ala Thr Tyr Phe Cys Gln His Ser Asp Ser Leu Ser Val
                85                  90                  95

Thr Phe Gly Gly Gly Thr Lys Val Glu Val Lys Gly Gly Gly Gly Ser
                100                 105                 110

Gly Gly Gly Gly Ser Gly Gly Gly Ser Glu Val Gln Leu Leu Glu
            115                 120                 125

Ser Gly Gly Gly Leu Val Gln Pro Gly Gly Ser Leu Arg Leu Ser Cys
        130                 135                 140

Ala Ala Ser Gly Phe Thr Phe Ser Asn Tyr Leu Met Ser Trp Val Arg
145                 150                 155                 160

Gln Ala Pro Gly Lys Gly Leu Glu Trp Val Ser Ser Ile Val Pro Ser
                165                 170                 175

Gly Gly Phe Thr His Tyr Ala Asp Ser Val Lys Gly Arg Phe Thr Ile
                180                 185                 190

Ser Arg Asp Asn Ser Lys Asn Thr Leu Tyr Leu Gln Met Asn Ser Leu
                195                 200                 205

Arg Ala Glu Asp Thr Ala Val Tyr Tyr Cys Ala Arg Leu Gln Thr Gly
        210                 215                 220

Ser Trp Arg Val His Ala Phe Asp Ile Trp Gly Gln Gly Thr Met Val
225                 230                 235                 240

Thr Val Ser Ser

<210> SEQ ID NO 77
<211> LENGTH: 210
<212> TYPE: PRT
<213> ORGANISM: Homo sapiens

<400> SEQUENCE: 77

Met Ala Leu Pro Val Thr Ala Leu Leu Leu Pro Leu Ala Leu Leu Leu
1               5                   10                  15

His Ala Ala Arg Pro Glu Gly Ile Cys Arg Asn Arg Val Thr Asn Asn
                20                  25                  30

Val Lys Asp Val Thr Lys Leu Val Ala Asn Leu Pro Lys Asp Tyr Met
            35                  40                  45

Ile Thr Leu Lys Tyr Val Pro Gly Met Asp Val Leu Pro Ser His Cys
50                  55                  60

Trp Ile Ser Glu Met Val Val Gln Leu Ser Asp Ser Leu Thr Asp Leu
65                  70                  75                  80

Leu Asp Lys Phe Ser Asn Ile Ser Glu Gly Leu Ser Asn Tyr Ser Ile
                85                  90                  95

Ile Asp Lys Leu Val Asn Ile Val Asp Asp Leu Val Glu Cys Val Lys
                100                 105                 110

Glu Asn Ser Ser Lys Asp Leu Lys Lys Ser Phe Lys Ser Pro Glu Pro
            115                 120                 125

Arg Leu Phe Thr Pro Glu Glu Phe Phe Arg Ile Phe Asn Arg Ser Ile
        130                 135                 140

Asp Ala Phe Lys Asp Phe Val Val Ala Ser Glu Thr Ser Asp Cys Val
145                 150                 155                 160

Val Ser Ser Thr Leu Ser Pro Glu Lys Asp Ser Arg Val Ser Val Thr
                165                 170                 175
```

```
Lys Pro Phe Met Leu Pro Pro Val Ala Ala Ser Ser Leu Arg Asn Asp
            180                 185                 190

Ser Ser Ser Ser Asn Arg Lys Ala Lys Asn Pro Pro Gly Asp Ser Ser
        195                 200                 205

Leu His
    210

<210> SEQ ID NO 78
<211> LENGTH: 182
<212> TYPE: PRT
<213> ORGANISM: Homo sapiens

<400> SEQUENCE: 78

Met Ala Leu Pro Val Thr Ala Leu Leu Leu Pro Leu Ala Leu Leu Leu
1               5                   10                  15

His Ala Ala Arg Pro Glu Gly Ile Cys Arg Asn Arg Val Thr Asn Asn
            20                  25                  30

Val Lys Asp Val Thr Lys Leu Val Ala Asn Leu Pro Lys Asp Tyr Met
        35                  40                  45

Ile Thr Leu Lys Tyr Val Pro Gly Met Asp Val Leu Pro Ser His Cys
    50                  55                  60

Trp Ile Ser Glu Met Val Val Gln Leu Ser Asp Ser Leu Thr Asp Leu
65                  70                  75                  80

Leu Asp Lys Phe Ser Asn Ile Ser Glu Gly Leu Ser Asn Tyr Ser Ile
                85                  90                  95

Ile Asp Lys Leu Val Asn Ile Val Asp Asp Leu Val Glu Cys Val Lys
            100                 105                 110

Glu Asn Ser Ser Lys Asp Leu Lys Lys Ser Phe Lys Ser Pro Glu Pro
        115                 120                 125

Arg Leu Phe Thr Pro Glu Glu Phe Phe Arg Ile Phe Asn Arg Ser Ile
    130                 135                 140

Asp Ala Phe Lys Asp Phe Val Val Ala Ser Glu Thr Ser Asp Cys Val
145                 150                 155                 160

Val Ser Ser Thr Leu Ser Pro Glu Lys Gly Lys Ala Lys Asn Pro Pro
                165                 170                 175

Gly Asp Ser Ser Leu His
            180

<210> SEQ ID NO 79
<211> LENGTH: 210
<212> TYPE: PRT
<213> ORGANISM: Mus musculus

<400> SEQUENCE: 79

Met Ala Leu Pro Val Thr Ala Leu Leu Leu Pro Leu Ala Leu Leu Leu
1               5                   10                  15

His Ala Ala Arg Pro Lys Glu Ile Cys Gly Asn Pro Val Thr Asp Asn
            20                  25                  30

Val Lys Asp Ile Thr Lys Leu Val Ala Asn Leu Pro Asn Asp Tyr Met
        35                  40                  45

Ile Thr Leu Asn Tyr Val Ala Gly Met Asp Val Leu Pro Ser His Cys
    50                  55                  60

Trp Leu Arg Asp Met Val Ile Gln Leu Ser Leu Ser Leu Thr Thr Leu
65                  70                  75                  80

Leu Asp Lys Phe Ser Asn Ile Ser Glu Gly Leu Ser Asn Tyr Ser Ile
                85                  90                  95
```

```
Ile Asp Lys Leu Gly Lys Ile Val Asp Leu Val Leu Cys Met Glu
            100                 105                 110

Glu Asn Ala Pro Lys Asn Ile Lys Glu Ser Pro Lys Arg Pro Glu Thr
            115                 120                 125

Arg Ser Phe Thr Pro Glu Glu Phe Ser Ile Phe Asn Arg Ser Ile
130             135                 140

Asp Ala Phe Lys Asp Phe Met Val Ala Ser Thr Ser Asp Cys Val
145             150                 155                 160

Leu Ser Ser Thr Leu Gly Pro Glu Lys Asp Ser Arg Val Ser Val Thr
                165                 170                 175

Lys Pro Phe Met Leu Pro Pro Val Ala Ala Ser Leu Arg Asn Asp
            180                 185                 190

Ser Ser Ser Ser Asn Arg Lys Ala Ala Lys Ala Pro Glu Asp Ser Gly
                195                 200                 205

Leu Gln
    210

<210> SEQ ID NO 80
<211> LENGTH: 238
<212> TYPE: PRT
<213> ORGANISM: Homo sapiens

<400> SEQUENCE: 80

Glu Val Lys Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Asn Gln Ala Pro Gly Lys Gly Leu Lys Trp Met
        35                  40                  45

Gly Trp Ile Asn Thr Glu Thr Gly Glu Pro Ser Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Asp Tyr Gly Asp Tyr Phe Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Val Leu Ser Gln Ser Pro Ala Ile Met Ser
    130                 135                 140

Ala Ser Pro Gly Glu Lys Val Thr Ile Ser Cys Ser Ala Ser Ser Ser
145                 150                 155                 160

Val Ser Tyr Met Tyr Trp Tyr Gln Gln Lys Pro Gly Ser Ser Pro Lys
                165                 170                 175

Pro Trp Ile Tyr Arg Thr Ser Asn Leu Ala Ser Gly Val Pro Ala Arg
            180                 185                 190

Phe Ser Gly Ser Gly Ser Gly Thr Ser Tyr Ser Leu Thr Leu Ser Ser
        195                 200                 205

Met Glu Ala Glu Asp Ala Ala Thr Tyr Tyr Cys Gln Gln Tyr His Ser
    210                 215                 220

Tyr Pro Pro Thr Phe Gly Ala Gly Thr Lys Leu Glu Leu Lys
225                 230                 235
```

<210> SEQ ID NO 81
<211> LENGTH: 242
<212> TYPE: PRT
<213> ORGANISM: Homo sapiens

<400> SEQUENCE: 81

Glu Val Lys Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Asn Gln Ala Pro Gly Lys Gly Leu Lys Trp Met
        35                  40                  45

Gly Trp Ile Asn Thr Glu Thr Gly Glu Pro Ser Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Asp Tyr Gly Asp Tyr Phe Asp Tyr Trp Gly Gln Gly Thr Thr
            100                 105                 110

Leu Thr Val Ser Ser Ser Ser Gly Gly Gly Ser Gly Gly Gly
        115                 120                 125

Gly Gly Ser Ser Arg Ser Ser Leu Asp Ile Val Leu Ser Gln Ser Pro
130                 135                 140

Ala Ile Met Ser Ala Ser Pro Gly Glu Lys Val Thr Ile Ser Cys Ser
145                 150                 155                 160

Ala Ser Ser Ser Val Ser Tyr Met Tyr Trp Tyr Gln Gln Lys Pro Gly
                165                 170                 175

Ser Ser Pro Lys Pro Trp Ile Tyr Arg Thr Ser Asn Leu Ala Ser Gly
            180                 185                 190

Val Pro Ala Arg Phe Ser Gly Ser Gly Ser Gly Thr Ser Tyr Ser Leu
        195                 200                 205

Thr Leu Ser Ser Met Glu Ala Glu Asp Ala Ala Thr Tyr Tyr Cys Gln
    210                 215                 220

Gln Tyr His Ser Tyr Pro Pro Thr Phe Gly Ala Gly Thr Lys Leu Glu
225                 230                 235                 240

Leu Lys

<210> SEQ ID NO 82
<211> LENGTH: 238
<212> TYPE: PRT
<213> ORGANISM: Homo sapiens

<400> SEQUENCE: 82

Asp Ile Val Leu Ser Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

```
Phe Gly Ala Gly Thr Lys Leu Glu Leu Lys Gly Gly Gly Ser Gly
                100                 105                 110

Gly Gly Gly Ser Gly Gly Gly Ser Glu Val Lys Leu Val Glu Ser
            115                 120                 125

Gly Pro Glu Leu Lys Pro Gly Glu Thr Val Lys Ile Ser Cys Lys
130                 135                 140

Ala Ser Gly Tyr Thr Phe Thr Asp Tyr Ser Met His Trp Val Asn Gln
145                 150                 155                 160

Ala Pro Gly Lys Gly Leu Lys Trp Met Gly Trp Ile Asn Thr Glu Thr
                165                 170                 175

Gly Glu Pro Ser Tyr Ala Asp Asp Phe Lys Gly Arg Phe Ala Phe Ser
            180                 185                 190

Leu Glu Thr Ser Ala Ser Thr Ala Tyr Leu Gln Ile Asn Asn Leu Lys
        195                 200                 205

Asn Glu Asp Thr Ala Thr Tyr Phe Cys Ala Thr Asp Tyr Gly Asp Tyr
210                 215                 220

Phe Asp Tyr Trp Gly Gln Gly Thr Thr Leu Thr Val Ser Ser
225                 230                 235

<210> SEQ ID NO 83
<211> LENGTH: 242
<212> TYPE: PRT
<213> ORGANISM: Homo sapiens

<400> SEQUENCE: 83

Asp Leu Val Leu Ser Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
                20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

Phe Gly Ala Gly Thr Lys Leu Glu Leu Lys Ser Ser Gly Gly Gly Gly
                100                 105                 110

Ser Gly Gly Gly Gly Gly Ser Ser Arg Ser Ser Leu Glu Val Lys
            115                 120                 125

Leu Val Glu Ser Gly Pro Glu Leu Lys Lys Pro Gly Glu Thr Val Lys
130                 135                 140

Ile Ser Cys Lys Ala Ser Gly Tyr Thr Phe Thr Asp Tyr Ser Met His
145                 150                 155                 160

Trp Val Asn Gln Ala Pro Gly Lys Gly Leu Lys Trp Met Gly Trp Ile
                165                 170                 175

Asn Thr Glu Thr Gly Glu Pro Ser Tyr Ala Asp Asp Phe Lys Gly Arg
            180                 185                 190

Phe Ala Phe Ser Leu Glu Thr Ser Ala Ser Thr Ala Tyr Leu Gln Ile
        195                 200                 205

Asn Asn Leu Lys Asn Glu Asp Thr Ala Thr Tyr Phe Cys Ala Thr Asp
210                 215                 220

Tyr Gly Asp Tyr Phe Asp Tyr Trp Gly Gln Gly Thr Thr Leu Thr Val
```

-continued

```
                225                 230                 235                 240

Ser Ser

<210> SEQ ID NO 84
<211> LENGTH: 238
<212> TYPE: PRT
<213> ORGANISM: Homo sapiens

<400> SEQUENCE: 84

Glu Val Lys Leu Val Glu Ser Gly Pro Glu Leu Lys Lys Pro Gly Glu
1               5                   10                  15

Thr Val Lys Leu Ser Cys Lys Ala Ser Gly Tyr Thr Phe Thr Asp Tyr
            20                  25                  30

Ser Met His Trp Val Asn Gln Ala Pro Gly Lys Gly Leu Lys Trp Met
        35                  40                  45

Gly Trp Ile Asn Thr Glu Thr Gly Glu Pro Ser Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Asp Tyr Gly Asp Tyr Phe Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Ala Ile Met Ser
    130                 135                 140

Ala Ser Pro Gly Glu Lys Val Thr Ile Ser Cys Ser Ala Ser Ser Ser
145                 150                 155                 160

Val Ser Tyr Met Tyr Trp Tyr Gln Gln Lys Pro Gly Gln Pro Pro Arg
                165                 170                 175

Leu Leu Ile Tyr Leu Val Ser Asn Leu Glu Ser Gly Val Pro Ala Arg
            180                 185                 190

Phe Ser Gly Ser Gly Ser Gly Thr Asp Phe Thr Leu Asn Ile His Pro
        195                 200                 205

Val Glu Glu Glu Asp Ala Ala Thr Tyr Tyr Cys Gln Gln Tyr His Ser
    210                 215                 220

Tyr Pro Pro Thr Phe Gly Ala Gly Thr Lys Leu Glu Ile Lys
225                 230                 235

<210> SEQ ID NO 85
<211> LENGTH: 242
<212> TYPE: PRT
<213> ORGANISM: Homo sapiens

<400> SEQUENCE: 85

Glu Val Lys Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Asn Gln Ala Pro Gly Lys Gly Leu Lys Trp Met
        35                  40                  45

Gly Trp Ile Asn Thr Glu Thr Gly Glu Pro Ser Tyr Ala Asp Asp Phe
    50                  55                  60

Lys Gly Arg Phe Ala Phe Ser Leu Glu Thr Ser Ala Ser Thr Ala Tyr
65                  70                  75                  80
```

Leu Gln Ile Asn Asn Leu Lys Asn Glu Asp Thr Ala Thr Tyr Phe Cys
                85                  90                  95

Ala Thr Asp Tyr Gly Asp Tyr Phe Asp Tyr Trp Gly Gln Gly Thr Thr
            100                 105                 110

Leu Thr Val Ser Ser Ser Gly Gly Gly Ser Gly Gly Gly Gly
            115                 120                 125

Gly Gly Ser Ser Arg Ser Ser Leu Asp Ile Val Leu Thr Gln Ser Pro
130                 135                 140

Ala Leu Met Ser Ala Ser Pro Gly Glu Lys Val Thr Ile Ser Cys Ser
145                 150                 155                 160

Ala Ser Ser Ser Val Ser Tyr Met Tyr Trp Tyr Gln Gln Lys Pro Gly
            165                 170                 175

Gln Pro Pro Arg Leu Leu Ile Tyr Leu Val Ser Asn Leu Glu Ser Gly
            180                 185                 190

Val Pro Ala Arg Phe Ser Gly Ser Gly Ser Gly Thr Asp Phe Thr Leu
            195                 200                 205

Asn Ile His Pro Val Glu Glu Glu Asp Ala Ala Thr Tyr Tyr Cys Gln
            210                 215                 220

Gln Tyr His Ser Tyr Pro Pro Thr Phe Gly Ala Gly Thr Lys Leu Glu
225                 230                 235                 240

Ile Lys

<210> SEQ ID NO 86
<211> LENGTH: 238
<212> TYPE: PRT
<213> ORGANISM: Homo sapiens

<400> SEQUENCE: 86

Asp Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Gln Pro Pro Arg Leu Leu Ile Tyr
            35                  40                  45

Leu Val Ser Asn Leu Glu Ser Gly Val Pro Ala Arg Phe Ser Gly Ser
        50                  55                  60

Gly Ser Gly Thr Asp Phe Thr Leu Asn Ile His Pro Val Glu Glu Glu
65                  70                  75                  80

Asp Ala Ala Thr Tyr Tyr Cys Gln Gln Tyr His Ser Tyr Pro Pro Thr
            85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Glu Val Lys Leu Val Glu Ser
            115                 120                 125

Gly Pro Glu Leu Lys Lys Pro Gly Glu Thr Val Lys Ile Ser Cys Lys
130                 135                 140

Ala Ser Gly Tyr Thr Phe Thr Asp Tyr Ser Met His Trp Val Asn Gln
145                 150                 155                 160

Ala Pro Gly Lys Gly Leu Lys Trp Met Gly Trp Leu Asn Thr Glu Thr
            165                 170                 175

Gly Glu Pro Ser Tyr Ala Asp Asp Phe Lys Gly Arg Phe Ala Phe Ser
            180                 185                 190

Leu Glu Thr Ser Ala Ser Thr Ala Tyr Leu Gln Ile Asn Asn Leu Lys
            195                 200                 205

```
Asn Glu Asp Thr Ala Thr Tyr Phe Cys Ala Thr Asp Tyr Gly Asp Tyr
        210                 215                 220

Phe Asp Tyr Trp Gly Gln Gly Thr Leu Thr Val Ser Ser
225                 230                 235

<210> SEQ ID NO 87
<211> LENGTH: 242
<212> TYPE: PRT
<213> ORGANISM: Homo sapiens

<400> SEQUENCE: 87

Asp Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Gln Pro Pro Arg Leu Leu Ile Tyr
        35                  40                  45

Leu Val Ser Asn Leu Glu Ser Gly Val Pro Ala Arg Phe Ser Gly Ser
    50                  55                  60

Gly Ser Gly Thr Asp Phe Thr Leu Asn Ile His Pro Val Glu Glu
65                  70                  75                  80

Asp Ala Ala Thr Tyr Tyr Cys Gln Gln Tyr His Ser Tyr Pro Pro Thr
                85                  90                  95

Phe Gly Ala Gly Thr Lys Leu Glu Leu Lys Ser Ser Gly Gly Gly Gly
            100                 105                 110

Ser Gly Gly Gly Gly Gly Ser Ser Arg Ser Ser Leu Glu Val Lys
        115                 120                 125

Leu Val Glu Ser Gly Pro Glu Leu Lys Lys Pro Gly Glu Thr Val Lys
    130                 135                 140

Ile Ser Cys Lys Ala Ser Gly Tyr Thr Phe Thr Asp Tyr Ser Met His
145                 150                 155                 160

Trp Val Asn Gln Ala Pro Gly Lys Gly Leu Lys Trp Met Gly Trp Leu
                165                 170                 175

Asn Thr Glu Thr Gly Glu Pro Ser Tyr Ala Asp Asp Phe Lys Gly Arg
            180                 185                 190

Phe Ala Phe Ser Leu Glu Thr Ser Ala Ser Thr Ala Tyr Leu Gln Ile
        195                 200                 205

Asn Asn Leu Lys Asn Glu Asp Thr Ala Thr Tyr Phe Cys Ala Thr Asp
    210                 215                 220

Tyr Gly Asp Tyr Phe Asp Tyr Trp Gly Gln Gly Thr Thr Leu Thr Val
225                 230                 235                 240

Ser Ser

<210> SEQ ID NO 88
<211> LENGTH: 486
<212> TYPE: PRT
<213> ORGANISM: Homo sapiens

<400> SEQUENCE: 88

Met Ala Leu Pro Val Thr Ala Leu Leu Leu Pro Leu Ala Leu Leu Leu
1               5                   10                  15

His Ala Ala Arg Pro Asp Ile Val Leu Ser Gln Ser Pro Ala Ile Met
            20                  25                  30

Ser Ala Ser Pro Gly Glu Lys Val Thr Ile Ser Cys Ala Ser Ser
        35                  40                  45
```

```
Ser Val Ser Tyr Met Tyr Trp Tyr Gln Gln Lys Pro Gly Ser Ser Pro
    50                  55                  60
Lys Pro Trp Ile Tyr Arg Thr Ser Asn Leu Ala Ser Gly Val Pro Ala
65                  70                  75                  80
Arg Phe Ser Gly Ser Gly Ser Gly Thr Ser Tyr Ser Leu Thr Leu Ser
                85                  90                  95
Ser Met Glu Ala Glu Asp Ala Ala Thr Tyr Tyr Cys Gln Gln Tyr His
            100                 105                 110
Ser Tyr Pro Pro Thr Phe Gly Ala Gly Thr Lys Leu Glu Leu Lys Ser
        115                 120                 125
Ser Gly Gly Gly Gly Ser Gly Gly Gly Gly Ser Ser Arg Ser
130                 135                 140
Ser Leu Glu Val Lys Leu Val Glu Ser Gly Pro Glu Leu Lys Lys Pro
145                 150                 155                 160
Gly Glu Thr Val Lys Ile Ser Cys Lys Ala Ser Gly Tyr Thr Phe Thr
                165                 170                 175
Asp Tyr Ser Met His Trp Val Asn Gln Ala Pro Gly Lys Gly Leu Lys
            180                 185                 190
Trp Met Gly Trp Ile Asn Thr Glu Thr Gly Glu Pro Ser Tyr Ala Asp
        195                 200                 205
Asp Phe Lys Gly Arg Phe Ala Phe Ser Leu Glu Thr Ser Ala Ser Thr
    210                 215                 220
Ala Tyr Leu Gln Ile Asn Asn Leu Lys Asn Glu Asp Thr Ala Thr Tyr
225                 230                 235                 240
Phe Cys Ala Thr Asp Tyr Gly Asp Tyr Phe Asp Tyr Trp Gly Gln Gly
                245                 250                 255
Thr Thr Leu Thr Val Ser Ser Thr Thr Thr Pro Ala Pro Arg Pro Pro
            260                 265                 270
Thr Pro Ala Pro Thr Ile Ala Ser Gln Pro Leu Ser Leu Arg Pro Glu
        275                 280                 285
Ala Cys Arg Pro Ala Ala Gly Gly Ala Val His Thr Arg Gly Leu Asp
    290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
            340                 345                 350
Thr Thr Gln Glu Glu Asp Gly Cys Ser Cys Arg Phe Pro Glu Glu Glu
        355                 360                 365
Glu Gly Gly Cys Glu Leu Arg Val Lys Phe Ser Arg Ser Ala Asp Ala
    370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
            420                 425                 430
Tyr Asn Glu Leu Gln Lys Asp Lys Met Ala Glu Ala Tyr Ser Glu Ile
        435                 440                 445
```

-continued

```
Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```